US010105373B2

(12) United States Patent
Sharma et al.

(10) Patent No.: US 10,105,373 B2
(45) Date of Patent: Oct. 23, 2018

(54) FUSED TRITERPENE COMPOUNDS AND USES THEREOF

(71) Applicant: PIRAMAL ENTERPRISES LIMITED, Mumbai (IN)

(72) Inventors: Rajiv Sharma, Fremont, CA (US); Namdev Narayan Borhade, Mumbai (IN); Narayan Subhash Chakor, Pune (IN); Hitesh Devchandbhai Mistry, Mumbai (IN)

(73) Assignee: PIRAMAL ENTERPRISES LIMITED, Mumbai (IN)

( * ) Notice: Subject to any disclaimer, the term of this patent is extended or adjusted under 35 U.S.C. 154(b) by 0 days.

(21) Appl. No.: 15/318,973

(22) PCT Filed: Jun. 24, 2015

(86) PCT No.: PCT/IB2015/054725
§ 371 (c)(1),
(2) Date: Dec. 14, 2016

(87) PCT Pub. No.: WO2015/198232
PCT Pub. Date: Dec. 30, 2015

(65) Prior Publication Data
US 2017/0119795 A1 May 4, 2017

Related U.S. Application Data

(60) Provisional application No. 62/016,757, filed on Jun. 25, 2014.

(51) Int. Cl.
*A61K 31/58* (2006.01)
*A61K 45/06* (2006.01)
*C07J 71/00* (2006.01)
*C07J 63/00* (2006.01)

(52) U.S. Cl.
CPC .............. *A61K 31/58* (2013.01); *A61K 45/06* (2013.01); *C07J 63/008* (2013.01); *C07J 71/0047* (2013.01); *C07J 71/0063* (2013.01)

(58) Field of Classification Search
None
See application file for complete search history.

(56) References Cited

U.S. PATENT DOCUMENTS

| 8,324,264 | B1 | 12/2012 | Eldridge et al. |
| 2013/0274256 | A1 | 10/2013 | Eldridge et al. |

FOREIGN PATENT DOCUMENTS

| CN | 103936814 A | 7/2014 |
| CN | 1039368144 A | 7/2014 |
| WO | WO-2012/027965 | 3/2012 |
| WO | WO-2012/028100 | 3/2012 |
| WO | WO-2012/064744 | 5/2012 |
| WO | WO-2012/100732 | 8/2012 |
| WO | WO-2012/100734 | 8/2012 |
| WO | WO-2012/139775 | 10/2012 |
| WO | WO-2013/029338 | 3/2013 |
| WO | WO-2013/085890 | 6/2013 |
| WO | WO-2013/160418 | 10/2013 |
| WO | WO-2014/028669 | 2/2014 |

OTHER PUBLICATIONS

Liang et al., European Journal of Medicinal Chemistry (2011), 46, pp. 2100-2021 (CAS SciFinder abstract).*
Biochem. Pharmacol. 2013, vol. 85, pp. 1579-1587.
Blood and Marrow Transplantation, 2012, vol. 18, S56-S61.
Cancer research, 2011, vol. 71, pp. 1263-1271.
Cell, 2006, pp. 1121-1133.
Cellular and Molecular Immunology, 2010, vol. 7, pp. 182-189.
Chen et al., Synthesis and biological evaluation of ursolic acid derivatives as novel inhibitors of glycogen phosphorylase, Journal of China Pharmaceutical University, vol. 37, 2006, pp. 397-402.
EMBO Mol. Med. 2011, vol. 3, No. 11, pp. 637-651.
Fu et al., Tryptophan hydroxylase 1 (Tph-1)-targeted bone anabolic agents for osteoporosis, Journal of Medicinal Chemistry, vol. 57, published online on May 20, 2014, pp. 4692-4709.
Immunological Reviews, 2008, vol. 223, pp. 87-113.
International Immunopharmacology, 2011, vol. 11, pp. 536-542.
International Search Report and Written Opinion for PCT Application No. PCT/IB2015/054725 dated Aug. 18, 2015, 13 pages.
J. Bio. Chem. 2011, vol. 286, No. 26, pp. 22707-22710.
Journal of Clinical Investigation, 2006, pp. 1310-1316.
Journal of Experimental Medicine, 2008, vol. 205, pp. 1517-1522.
Journal of Experimental Pharmacology, 2012, vol. 4, pp. 141-148.
Journal of Medicinal Chemistry, 2014, vol. 57, pp. 4692-4709.
Liang et al., Identification of pentacyclic triterpenes derivatives as potent inhibitors against glycogen phosphorylase based on 3D-QSAR studies, Europeans Journal of Medicinal Chemistry, vol. 46, 2011, pp. 2011-2021.
Nuclear Receptor Signaling, 2009, vol. 7, pp. 1-32.
Nutr. Food Res., 2008, vol. 52, pp. 26-42.
Respiratory Research, 2010, pp. 1-11.
Yasue et al., Syntheses of nitrogen-containing triterpenes. II. Ring-A fused triterpenes containing nitrogen, Yakugaku Zasshi, vol. 94, 1974, pp. 461-465.
Boruah et al., "Synthesis of β-formylsteroidal enamides and their conversion into germinal dichlorides", Indian Journal of Chemistry, vol. 38B, 1999, 274-282.

(Continued)

*Primary Examiner* — Brian J Davis
(74) *Attorney, Agent, or Firm* — Foley & Lardner LLP

(57) ABSTRACT

The present invention discloses fused triterpene compounds, represented by the compounds of Formula I (as described herein), processes for their preparation, pharmaceutical compositions comprising the said compounds, their use as retinoid-related orphan receptors gamma (RORγ) modulators and/or interleukin-17 (IL-17) inhibitors and methods for their use in the treatment of a disease or a disorder mediated by RORγ and/or IL-17.

22 Claims, No Drawings

(56) References Cited

OTHER PUBLICATIONS

Chem. Abs. AN:1971:125870 Trudy Kishinevksii Politekhnicheskii Institut No. 13, pp. 153-166 (1968), from Ref. Zh. Khim. Abstr. No. 5ZH771 (1970).
Chem. Abs. AN: 2014:1195417 & CN-A-103 936 814 (Jul. 23, 2014).
EP Search Report for Application No. 15811513.9 dated Nov. 7, 2017. (12 pages).
Zheng-Hui et al, "Synthesis of Enamides via CuI-Catalyzed Reductive Acylation of Ketoximes with $NaHSO_3$", Journal of Organic Chemistry, 2011, 76(1):339-341.

\* cited by examiner

FUSED TRITERPENE COMPOUNDS AND USES THEREOF

CROSS-REFERENCE TO RELATED APPLICATIONS

This application is a U.S. national stage application of International Patent Application No. PCT/IB2015/054725, filed on Jun. 24, 2015, which claims priority to U.S. Provisional Application No. 62/016,757, filed on Jun. 25, 2014, the contents of each of these applications is incorporated herein by reference in their entirety.

FIELD OF INVENTION

The present invention relates to fused triterpene compounds, represented by the compounds of Formula I (as described herein), processes for their preparation, pharmaceutical compositions comprising the said compounds, their use as retinoid-related orphan receptors gamma (RORγ) modulators and/or interleukin-17 (IL-17) inhibitors and methods for their use in the treatment of a disease or a disorder mediated by RORγ and/or IL-17.

BACKGROUND OF INVENTION

Nuclear receptors (NR) are ligand-regulated transcription factors that play diverse role in the expression of target genes associated with physiological processes such as cell differentiation, development, metabolism and immunity. All members of the nuclear receptors super family are multi domain proteins. Majority of the nuclear receptors contain the four functional domains, namely N-terminal "A/B domain", DNA-binding domain or "C domain", highly variable hinge or "D domain", and C-terminal ligand-binding domain (LBD) or "E domain" Several NRs contain a highly variable C-terminal F domain.

Retinoid-related orphan receptors (RORs) are the subfamily of nuclear receptors. The ROR subfamily contains three isoforms, namely RORalpha (RORα), RORbeta (RORβ) and RORgamma (RORγ), which are also referred to as NR1F1, NR1F2 and NR1F3 respectively. The RORα, RORβ and RORγ function as ligand dependent transcription factors and recent research studies suggest that RORs may be potential therapeutic targets for treatment of various diseases. Each of the ROR are encoded by a distinct gene RORA, RORB and RORC respectively and each ROR gene generates several isoforms, differing only in their N-terminal "A/B domain" Retinoid-related orphan receptors contain four principle domains as shared by the majority of the nuclear receptors. The RORs display significant sequence similarity. For RORα (α1-4), four isoforms have been identified, and RORβ gene is expressed in only one isoform in humans, whereas for RORγ, two isoforms have been identified namely RORγ1 and RORγ2. The isoform "RORγ2" is also known as RORγt.

RORγt is exclusively detected in a few distinct cell types of the immune system, for instance, in thymus (Journal of Experimental Pharmacology, 2012, 4, 141-148; Nuclear Receptor Signaling, 2009, 7, 1-32) while RORγ1 is expressed in many tissues, including thymus, lung, liver, kidney, skeletal muscle, adipose tissue and skin. The RORγt has been identified as a key regulator of T helper 17 (Th17) cells differentiation. It is reported that RORs have critical regulatory roles in thymopoiesis, development of secondary lymphoid tissues, and Th17 cell differentiation are highly relevant to a variety of immune responses and inflammatory disorders, including autoimmune diseases and asthma (Nuclear Receptor Signaling, 2009, 7, 1-32; International Immunopharmacology, 2011, 11, 536-542).

Th17 cells are a subset of T helper cells producing interleukin-17 (IL-17). They are developmentally distinct from Th1 and Th2 cells, which are the other two subsets of T helper cells. Th17 cells have been shown to play a critical role in several inflammatory disease and autoimmune diseases (Immunological Reviews, 2008, 223, 87-113). In addition, the studies have shown that Th17 cells have key pro-inflammatory roles in cancer and a variety of autoimmune diseases such as experimental autoimmune encephalomyelitis (EAE), collagen-induced arthritis (CIA), inflammatory bowel disease (IBD) and graft versus host disease (Cancer research, 2011, 71, 1263-1271; Cell, 2006, 1121-1133; Journal of Clinical Investigation, 2006, 1310-1316; Blood and Marrow Transplantation, 2012, 18, S56-S61).

Th17 cells/IL-17 plays a key role in the pathogenesis of asthma. In asthmatic patients, both RORγt and IL-17A expression levels have been shown to be increased in sputum, lung, and bronchoalveolar lavage (BAL) fluids and peripheral blood and these levels directly correlate with disease severity. In addition to IL-17A, a recent study have shown that a cytokine of the IL-17 family namely IL-17F, may have a crucial role in allergic airway inflammation and hence, have key implications in airway diseases, such as asthma (Respiratory Research, 2010, 1-11).

The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Journal of Experimental Medicine, 2008, 205, 1517-1522; Cellular and Molecular Immunology, 2010, 7, 182-189). Also, during the disease process Th17 cells are activated and are responsible for recruiting other inflammatory cells types, particularly neutrophils, to mediate pathology in the target tissues.

Several studies suggest that RORγt plays a vital role in metabolic disorders and autoimmune diseases (Journal of Experimental Pharmacology, 2012, 4, 141-148). Metabolic disorders are the disorders or defects that occur when the body is unable to properly metabolise carbohydrates, lipids, proteins, or nucleic acids. Most metabolic disorders are caused by genetic mutations that result in missing or dysfunctional enzymes that are needed for the cell to perform metabolic processes. Examples of metabolic disorders include obesity, excessive body fat, hyperlipidemia, hyperlipoproteinemia, hyperglycemia, hypercholesterolemia, hyperinsulinemia, insulin resistance, glucose intolerance, and diabetes mellitus particularly type 2 diabetes. RORs were shown to affect the expression of several genes involved in steroid, bile acid, and xenobiotic metabolism, suggesting that RORs are promising targets for the treatment of obesity-associated insulin resistance and metabolic disease (EMBO Mol. Med. 2011, 3(11), 637-651.

It is reiterated here that RORγt has also been shown to play a critical role in the differentiation of Th17 cells (Cell, 2006, 1121-1133, International Immunopharmacology, 2011, 11, 536-542). RORγt deficiency results in diminished Th17 activity and severely reduced expression of IL-17.

Various PCT published patent applications, WO2014028669, WO2013160418, WO2013085890, WO2013029338, WO2012100732, WO2012100734, WO2012139775, WO2012027965, WO2012028100 and WO2012064744 disclose compounds which are reported to be modulators of RORγ.

Pentacyclic triterpenes have a range of unique and potentially usable biological effects. In fact, there is a growing interest in the elucidation of the biological roles of the triterpenoid compounds. From biological point of view, the most important pentacyclic triterpenoid type compounds are ursane, oleanane, lupine and taraxasterane. Among these triterpenoid compounds, ursolic acid is known to possess a wide range of biological activities including anti-oxidative, anti-inflammatory and anticancer activities (Nutr. Food Res., 2008, 52, 26-42 and Biochem. Pharmacol. 2013, 85, 1579-1587). It is also reported that ursolic acid suppresses IL-17 production by selectively antagonizing the function of RORγt protein (J. Bio. Chem. 2011, 286(26), 22707-22710). A variety of structure modifications of UA has also been conducted. Three series of UA derivatives and their inhibitory activity on serotonin biosynthesis using RBL2H3 cells were evaluated (Journal of Medicinal Chemistry, 2014, 57, 4692-4709).

Thus, in consideration of various roles of RORγ and IL-17 in the pathogenesis of various diseases or disorders, compounds that modulate the activity of RORγ and inhibit IL-17 expression, will have therapeutic potential in treating diseases or disorders mediated or implicated by RORγ or IL-17. The inventors of the present invention have developed the compounds that function as modulators of RORγ and inhibitors of IL-17. Accordingly, the compounds of the present invention find use in the treatment of diseases mediated by RORγ or IL-17.

SUMMARY OF THE INVENTION

In one aspect, the present invention relates to a compound of Formula I (as described herein) or a stereoisomer, a tautomer, a pharmaceutically acceptable salt, a pharmaceutically acceptable solvate, a prodrug, an N-oxide, a S-oxide or a carboxylic acid isostere thereof.

In another aspect, the present invention relates to processes for the preparation of the compound of Formula I or pharmaceutically acceptable salts thereof.

In further aspect, the present invention relates to a compound of Formula I or a stereoisomer, a tautomer, a pharmaceutically acceptable salt or a pharmaceutically acceptable solvate thereof, for use in the treatment of a disease or a disorder mediated by RORγ.

In yet another aspect, the present invention relates to a compound of Formula I or a stereoisomer, a tautomer, a pharmaceutically acceptable salt or a pharmaceutically acceptable solvate thereof, for use in the treatment of a disease or a disorder mediated by IL-17.

In another aspect the present invention relates to pharmaceutical composition comprising a compound of Formula I or a stereoisomer, a tautomer, a pharmaceutically acceptable salt or a pharmaceutically acceptable solvate thereof and at least one pharmaceutically acceptable excipient.

In another aspect, the present invention relates to a method for the treatment of a disease or a disorder mediated by RORγ or IL-17 comprising administering to a subject in need thereof, a therapeutically effective amount of a compound of Formula I or a stereoisomer, a tautomer, a pharmaceutically acceptable salt or a pharmaceutically acceptable solvate thereof.

In yet another aspect, the present invention relates to a method of modulating the activity of RORγ receptor, comprising contacting the RORγ receptor with the compound of Formula I or a stereoisomer, a tautomer, a pharmaceutically acceptable salt or a pharmaceutically acceptable solvate thereof.

In yet another aspect, the present invention relates to a method of inhibiting IL-17, comprising administering to a subject in need thereof, a therapeutically effective amount of the compound of Formula I or a stereoisomer, a tautomer, a pharmaceutically acceptable salt or a pharmaceutically acceptable solvate thereof.

In another aspect, the present invention relates to use of the compound of Formula I or a stereoisomer, a tautomer, a pharmaceutically acceptable salt or a pharmaceutically acceptable solvate thereof, in combination with at least one therapeutically active agent, for the treatment of a disease or a disorder mediated by RORγ and/or IL-17.

In yet another aspect, the present invention relates to use of the compound of Formula I or a stereoisomer, a tautomer, a pharmaceutically acceptable salt or a pharmaceutically acceptable solvate thereof, in the manufacture of medicaments for the treatment of a disease or a disorder mediated by RORγ and/or IL-17.

These and other objectives and advantages of the present invention will be apparent to those skilled in the art from the following description.

DETAILED DESCRIPTION OF THE INVENTION

In the first aspect, the present invention relates to a compound of Formula I,

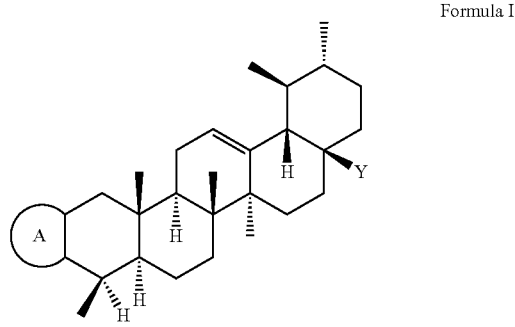

Formula I or a stereoisomer, a tautomer, a pharmaceutically acceptable salt, a pharmaceutically acceptable solvate, a prodrug, an N-oxide, a S-oxide or a carboxylic acid isostere thereof;

Y is —COOR'; wherein R' is hydrogen or $(C_1-C_6)$alkyl, wherein $(C_1-C_6)$alkyl is unsubstituted or substituted with $(C_6-C_{10})$aryl;

Ring A is 5- to 14-membered heteroaryl selected from the group consisting of pyrimidinyl, pyridyl, quinazolinyl, pyrazolyl and thiazolyl;

wherein, said pyrimidinyl, pyridyl, quinazolinyl, pyrazolyl or thiazolyl is unsubstituted or substituted with one or more groups of R; wherein R is selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, 3- to 10-membered heterocyclyl, $(C_6-C_{10})$aryl, 5- to 14-membered heteroaryl, cyano, amino, —O—$(C_6-C_{10})$aryl, —$OR^a$, —$C(O)R^a$, —$C(O)OR^a$, —CH=NOH, —$C(O)NH_2$, —$C(O)NR^aR^b$, —$SR^a$, —$S(O)_mR^a$, —$S(O)_mNR^aR^b$, —$S(O)(NH)R^a$, —N[(C$_1$-C$_6$)alkyl]R$^a$, —N[(C$_1$-C$_6$)alkyl]$_2$, —NHR$^a$, —N(R$^a$)—C(O)R$^a$, —N(R$^a$)—C(O)NR$^a$R$^b$ and —NR$^a$R$^b$;

or two R groups present on adjacent carbon atoms of the ring A combine together to form an optionally substituted unsaturated or saturated carbocycle optionally containing one or two heteroatoms independently selected from the group consisting of N, O and S;

R$^a$ and R$^b$ are independently selected from the group consisting of hydrogen, halogen, hydroxy, (C$_1$-C$_6$)alkyl, halo(C$_1$-C$_6$)alkyl, (C$_3$-C$_{10}$)cycloalkyl, 3- to 10-membered heterocyclyl, (C$_6$-C$_{10}$)aryl, 5- to 14-membered heteroaryl; or R$^a$ and R$^b$ together with the nitrogen to which they are attached, can combine to form a 3- to 10-membered saturated or unsaturated heterocyclyl which contains one or two heteroatoms independently selected from the group consisting of N, O and S;

m is 1 or 2;

provided that when ring A is pyrimidinyl, then one of the R groups is other than hydrogen;

provided that when ring A is pyrazolyl and R is attached on nitrogen atom of pyrazolyl ring then R is selected from the group consisting of

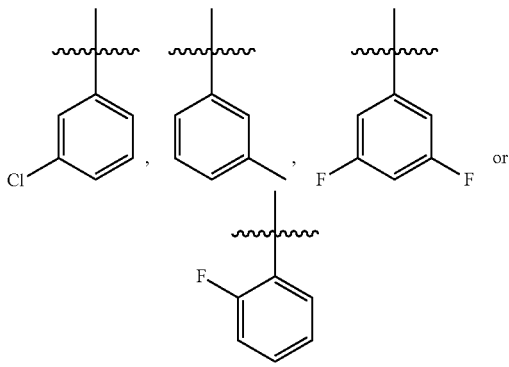

wherein

⌇ is point of attachment to nitrogen atom of pyrazolyl ring;

wherein:
(C$_1$-C$_6$)alkyl is unsubstituted or substituted with one or more groups independently selected from the group consisting of halogen, hydroxy, (C$_1$-C$_6$)alkyl, halo(C$_1$-C$_6$)alkyl, (C$_2$-C$_8$)alkenyl, (C$_2$-C$_8$)alkynyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —NH(C$_1$-C$_6$)alkyl, —N[(C$_1$-C$_6$)alkyl]$_2$, —C(O)(C$_1$-C$_6$)alkyl, —C(O)OR$^a$, —C(O)NH$_2$, —C(O)NR$^a$R$^b$, —C(O)N[(C$_1$-C$_6$)alkyl]$_2$ and —C(O)NHS(O)$_2$(C$_1$-C$_6$)alkyl;

(C$_3$-C$_{10}$)cycloalkyl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)haloalkyl, amino and cyano;

carbocycle is 3- to 12-membered ring which is unsubstituted or substituted with one or more groups independently selected from the group consisting of (C$_1$-C$_6$)alkyl, halo(C$_1$-C$_6$)alkyl, hydroxy, halogen, (C$_1$-C$_6$)alkoxy, halo(C$_1$-C$_6$)alkoxy, (C$_6$-C$_{10}$)aryl, (C$_3$-C$_{10}$)cycloalkyl, heterocyclyl, heteroaryl, cyano, amino, —C(O)O(C$_1$-C$_6$)alkyl, —C(O)NR$^a$R$^b$ and —S(O)$_2$R$^a$; wherein R$^a$ and R$^b$ are as defined above;

(C$_6$-C$_{10}$)aryl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)O(C$_1$-C$_6$)alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

Definitions

Unless otherwise indicated, the following definitions are set forth to illustrate and define the meaning and scope of various terms used to describe the invention herein and the appended claims. These definitions should not be interpreted in the literal sense as they are not general definitions and are relevant only for this application.

The terms "a", "an" and "the" refer to "one or more" when used in the subject specification. Thus, for example, reference to "a compound" may include a plurality of such compounds, or reference to "a disease" or "a condition" includes a plurality of diseases or disorders.

Also, use of "(s)" as part of a term, includes reference to the term singly or in plurality, for example the term salt(s) may indicate a single salt or more than one salt of the compound of Formula I.

As used herein the term "or" is generally employed in its sense including "and/or" unless the content clearly dictates otherwise.

A symbol ( ⌇ ) or (—) is used to indicate a point of attachment to the atom, for example —COOH is attached through the carbon atom.

Unless indicated otherwise, the term "optionally substituted" means "substituted or unsubstituted," and therefore, the generic structural Formulae described herein encompasses compounds containing the specified optional substituent as well as compounds that do not contain the optional substituent. For example, the phrase "heterocyclyl is optionally substituted with one or more groups" encompasses unsubstituted heterocyclic ring, and heterocyclic ring substituted with one or more groups as described therein.

Within the context of the present invention, the term "(C$_1$-C$_6$)alkyl" or "alkyl", as used herein, alone or as part of a substituent group refers to an aliphatic group, including straight or branched chain alkyl group. A straight-chain or branched chain alkyl has six or fewer carbon atoms in its backbone, for instance, C$_1$-C$_6$ for straight chain and C$_3$-C$_6$ for branched chain. Representative examples of alkyl groups containing from one to six carbon atoms include, but are not limited to, methyl, ethyl, propyl, butyl, pentyl, hexyl, isopropyl, isobutyl, 1-methylbutyl, secondary butyl, tertiary butyl, tertiary pentyl, neopentyl, 3-methylbutyl, 3,3-dimethylbutyl, 2-methylpentyl and 3-methylpentyl.

Furthermore, the alkyl groups can be unsubstituted or substituted with one or more groups, preferably one to three groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —N[$(C_1-C_6)$alkyl]$_2$, —C(O)$(C_1-C_6)$alkyl, —O—$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl. Representative examples of substituted alkyl include, but are not limited to, hydroxymethyl, 2-chlorobutyl, trifluoromethyl, aminoethyl and benzyl.

Within the context of the present application, the term "$(C_2-C_8)$alkenyl" or "alkenyl", as used herein, alone or as part of a substituent group, refers to an unsaturated straight or branched chain hydrocarbon radical containing at least one carbon-carbon double bond (two adjacent sp$^2$ carbon atoms). For example, the term "$(C_2-C_8)$alkenyl" refers to an alkenyl group having two to eight carbon atoms. Depending upon the placement of double bond and substituents if any, the geometry of the double bond may be entgegen (E), or zusammen (Z), cis or trans. Examples of alkenyl include, but are not limited to, vinyl, allyl or 2-propenyl. Unless indicated otherwise, the alkenyl groups can be unsubstituted or substituted with one or more of the same or different groups independently selected from the group consisting of $(C_1-C_6)$alkyl, halogen, haloalkyl, hydroxy, —O$(C_1-C_6)$alkyl, amino, nitro and cyano.

Within the context of the present application, and as used herein, the term "$(C_2-C_8)$alkynyl" or "alkynyl" refers to an unsaturated, branched or straight chain having from two to eight carbon atoms and at least one carbon-carbon triple bond (two adjacent sp carbon atoms). Examples of alkynyl include, but are not limited to, ethynyl, 1-propynyl, 3-propynyl and 4-butynyl. The alkynyl groups can be unsubstituted or substituted with one or more of the same or different groups such as $(C_1-C_6)$alkyl, halogen, haloalkyl, hydroxy, —O$(C_1-C_6)$alkyl, amino, nitro or cyano.

Within the context of the present application and as used herein, the term "halo$(C_1-C_6)$alkyl" or "haloalkyl" refers to radicals wherein one or more of the hydrogen atoms of the $(C_1-C_6)$alkyl group are substituted with one or more halogens. A monohalo$(C_1-C_6)$alkyl radical, for example, can have one chlorine, bromine, iodine or fluorine atom. Dihalo and polyhalo$(C_1-C_6)$alkyl radicals can have two or more of the same or different halogen atoms. Representative examples of halo$(C_1-C_6)$alkyl include, but are not limited to, chloromethyl, dichloromethyl, trichloromethyl, dichloroethyl, dichloropropyl, fluoromethyl, difluoromethyl, trifluoromethyl, pentafluoroethyl, heptafluoropropyl, difluorochloromethyl, dichlorofluoromethyl, difluoroethyl and difluoropropyl.

Within the context of the present application and as used herein, the term "alkoxy" or "—O—$(C_1-C_6)$alkyl" refers to $(C_1-C_6)$alkyl having an oxygen radical attached thereto. Representative examples of "—O—$(C_1-C_6)$alkyl" groups include, but are not limited to, methoxy, ethoxy, propoxy, isopropoxy, isobutoxy and tert-butoxy. The alkoxy or "—O—$(C_1-C_6)$alkyl" is unsubstituted or substituted with one or more groups independently selected from the group consisting of $(C_1-C_6)$alkyl, hydroxy, halogen, amino and cyano.

Within the context of the present application and as used herein, the term "halo$(C_1-C_6)$alkoxy" or "haloalkoxy" refers to radicals wherein one or more hydrogen atoms of the $(C_1-C_6)$alkoxy group are substituted with one or more halogens. Representative examples of halo$(C_1-C_6)$alkoxy groups include, but are not limited to, difluoromethoxy (—OCHF$_2$), trifluoromethoxy (—OCF$_3$) and trifluoroethoxy (—OCH$_2$CF$_3$).

As used herein, the term "$(C_3-C_{10})$cycloalkyl" or "cycloalkyl" whether used alone or as part of a substituent group, refers to a saturated or partially unsaturated cyclic hydrocarbon radical including 1, 2 or 3 rings and including a total of 3 to 10 carbon atoms forming the rings. The term cycloalkyl includes bridged, fused and spiro ring systems. For example, $(C_3-C_{10})$cycloalkyl refers to a cycloalkyl group having 3 to 10 (both inclusive) carbon atoms preferably, can refer to cycloalkyl group having 3 to 8 (both inclusive) carbon atoms i.e. $(C_3-C_8)$-cycloalkyl. Representative examples of cycloalkyl include, but are not limited to, cyclopropyl, cyclobutyl, cyclopentyl, cyclohexyl, 1,2,3,3a-tetrahydropentalene, adamantyl, norbornyl, tetrahydronaphthalene bicyclo[2.1.0]pentane, bicyclo[4.2.0]octane, bicyclo[2.2.1]heptyl, bicyclo[2.2.1]hept-2-ene, spiro[3.3]heptane, and the like. Unless stated otherwise, $(C_3-C_{10})$cycloalkyl can be unsubstituted or substituted with one or more groups independently selected from the group consisting of $(C_1-C_6)$alkyl, halogen, halo$(C_1-C_6)$alkyl, hydroxy, —O$(C_1-C_6)$alkyl, halo$(C_1-C_6)$alkoxy, $(C_3-C_{10})$cycloalkyl, $(C_6-C_{10})$aryl, heterocyclyl, heteroaryl, amino and cyano.

Within the context of the present application and as used herein, the term "carbocycle" or "carbocyclic ring" refers to a saturated, partially unsaturated, unsaturated or aromatic 3- to 12-membered ring system whose ring atoms are all carbon, and that said carbocycle has a single point of attachment to the rest of the molecule. The carbocycle can be monocyclic or bicyclic ring system optionally containing 1 to 4 heteroatoms independently selected from oxygen, nitrogen and sulphur. If the carbocycle is a bicyclic ring system, then any one ring in the said bicyclic ring system is a 3- to 7-membered ring. Representative examples of carbocycle include, but are not limited to, cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl.

Within the context of the present application and as used herein, the term "$(C_6-C_{10})$aryl" or "aryl" refers to monocyclic or bicyclic hydrocarbon groups having 6 to 10 carbon atoms in which the carbocyclic ring(s) present have a conjugated pi electron system, which can be optionally substituted by one or more groups. Representative examples of $(C_6-C_{10})$aryl include, but are not limited to, phenyl and naphthyl.

Furthermore, the aryl group can be unsubstituted or substituted with one or more groups. A substituted aryl refers to a $(C_6-C_{10})$ aryl substituted with one or more groups, preferably 1 to 7 groups and more preferably 1 to 3 groups independently selected from the group consisting of $(C_1-C_6)$alkyl, $(C_2-C_8)$alkenyl, $(C_2-C_8)$alkynyl, halogen, halo$(C_1-C_6)$alkyl, hydroxy, —O—$(C_1-C_6)$alkyl, halo$(C_1-C_6)$alkoxy, $(C_3-C_{10})$cycloalkyl, $(C_6-C_{10})$aryl, heterocyclyl, heteroaryl, amino and cyano. Aryl groups can be substituted in any desired position. For example, in monosubstituted phenyl, the substituent can be located in the 2-position, the 3-position, the 4-position or the 5-position. If the phenyl carries two substituents, they can be located in 2,3-position, 2,4-position, 2,5-position, 2,6-position, 3,4-position or 3,5-position. Examples of monosubstituted phenyl groups include, but are not limited to 2-fluorophenyl, 2-ethoxyphenyl, 2-ethylphenyl, 4-morpholinophenyl, (4-ethylpiperazin-1-yl)phenyl or 4-(2-dimethylaminoethyl)phenyl. Examples of disubstituted phenyl groups include, but not limited to, 2,6-difluorophenyl or 3,5-difluorophenyl.

Within the context of the present application and as used herein, the terms "heterocyclyl" or "heterocyclic" whether used alone or as part of a substituent group, refers to a 3- to 10-membered ring system, which include a saturated or partially unsaturated monocyclic, bicyclic or tricyclic ring system containing 1 to 4 heteroatoms independently selected from oxygen, nitrogen and sulfur. Saturated heterocyclic ring systems do not contain any double bond, whereas partially unsaturated heterocyclic ring systems, can contain at least one double bond, but do not form an aromatic system containing a heteroatom. The oxidized form of the ring nitrogen and sulfur atom contained in the heterocyclyl to provide the corresponding N-oxide, S-oxide or S,S-dioxide is also encompassed in the scope of the present invention. Representative examples of heterocyclyls include, but are not limited to, azetidinyl, acridinyl, benzodioxolyl, benzo[d][1,3]dioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazolyl, imidazolyl, tetrahydroisoquinolinyl, piperidinyl, piperazinyl, homopiperazinyl, 2-oxoazepinyl, azepinyl, pyrrolyl, 4-piperidonyl, pyrrolidinyl, pyridinyl, pyrimidinyl, oxazolyl, oxazolinyl, oxazolidinyl, triazolyl, isooxazolyl, isoxazo lidinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, thienyl, morpholinyl, thiomorpholinyl, thiomorpholinyl sulfoxide, furyl, tetrahydrofuryl, tetrahydropyranyl, chromanyl and isochromanyl. Furthermore, the heterocyclyl groups can be unsubstituted or substituted with one or more groups, preferably with 1-7 groups, more preferably with 1-3 groups independently selected from the group consisting of $(C_1-C_6)$alkyl, halogen, halo$(C_1-C_6)$alkyl, hydroxy, $(C_1-C_6)$alkoxy, halo$(C_1-C_6)$alkoxy, amino, cyano, —C(O)—NR$^a$R$^b$ and —S(O)$_m$R$^a$; wherein R$^a$ and R$^b$ are as defined above.

Within the context of the present application and as used herein, the term "heteroaryl" whether used alone or as part of a substituent group, refers to 5- to 14-membered aromatic monocyclic or bicyclic ring system containing one to four identical or different heteroatoms independently selected from oxygen, nitrogen and sulfur atom. Representative examples of heteroaryls include, but are not limited to, pyrrole, pyrazole, imidazole, pyrazine, furan, thiophene, oxazole, oxadiazole, thiazole, benzimidazole, benzoxazole, benzothiazole, benzofuran, indole, indazole, isoindole, isoquinoline, isooxazole, triazine, purine, pyridine, quinoline, oxadiazole, thiene, pyridazine, pyrimidine, isothiazole, quinoxaline (benzopyrazine), tetrazole, pyrido[2,3-b]pyrazine. The oxidized form of the ring nitrogen and sulfur atom contained in the heteroaryl to provide the corresponding N-oxide, S-oxide or S,S-dioxide is also encompassed in the scope of the present invention.

Furthermore, the heteroaryl groups can be unsubstituted or substituted with one or more groups; preferably 1 to 7 groups and more preferably 1 to 3 groups independently selected from halogen, hydroxy, $(C_1-C_6)$alkyl, halo$(C_1-C_6)$alkyl, $(C_1-C_6)$alkoxy, halo$(C_1-C_6)$alkoxy, $(C_3-C_{10})$cycloalkyl, $(C_6-C_{10})$aryl, heterocyclyl, heteroaryl, amino, cyano, —C(O)—O$(C_1-C_6)$alkyl, —C(O)NR$^a$R$^b$ and —S(O)$_m$R$^a$; wherein R$^a$, R$^b$ and m are as defined above.

Within the context of the present invention and as used herein, the term "heteroatom" includes nitrogen (N), oxygen (O), and sulfur (S). Any heteroatom with unsatisfied valency is assumed to have a hydrogen atom to satisfy the valency.

Within the context of the present invention and as used herein, the term "halogen" or "halo" refers to a fluorine, chlorine, bromine, or iodine atom.

Within the context of the present invention and as used herein, the term "amino" refers to the group "NH$_2$" which can be unsubstituted or substituted with one or more substituents. Representative examples of substituents include, but are not limited to, $(C_1-C_6)$alkyl or $(C_6-C_{10})$aryl.

Within the context of the present invention and as used herein, the term "compound of Formula I", "compounds of Formula I", and "compounds of the present invention" interchangeably throughout this application, include all stereoisomeric and tautomeric forms and mixtures thereof in all ratios, pharmaceutically acceptable salts, solvates, prodrugs, N-oxides, S-oxides or carboxylic acid isosteres thereof. Further, in the context of the present invention, reference to the compounds of Formula I may include reference to the compounds represented herein by the compounds of Formula Ia and/or the compounds Formula A and/or the compounds of Formula B and/or the compounds of Formula Ib and/or the compounds of Formula Ic. The compound(s) of the present invention can also be referred to herein as "the active compound" or "the active ingredient".

Within the context of the present invention and as used herein, the term "stereoisomer" is a general term used for all the isomers of individual compounds (compounds of Formula I in the present invention) that differ only in the orientation of their atoms in space. The term stereoisomer includes mirror image isomers (enantiomers), mixtures of mirror image isomers (racemates, racemic mixtures), geometric (cis/trans or E/Z) isomers, and isomers of compounds with more than one chiral center that are not mirror images of one another (diastereoisomers).

Within the context of the present invention and as used herein, the term "tautomer" refers to the coexistence of two (or more) compounds that differ from each other only in the position of one (or more) mobile atoms and in electron distribution, for example, keto-enol tautomers.

Within the context of the present invention and as used herein, the term "pharmaceutically acceptable" means that the carrier, diluent, excipients, and/or salt must be compatible with the other ingredients of the Formulation or composition, and not deleterious to the recipient thereof. As used herein, the term "pharmaceutically acceptable carrier" refers to a material that is non-toxic, inert, solid, semi-solid or liquid filler, diluent, encapsulating material or Formulation auxiliary or excipient of any type which is suitable for a subject, preferably a mammal, more preferably a human, and is suitable for delivering an active agent to the target site without affecting the activity of the agent.

Within the context of the present invention and as used herein, the term "pharmaceutically acceptable salt(s)" includes a salt or salts of the active compound i.e. the compound of Formula I, which retain the desired biological activity of the subject compound, and the salts are prepared using suitable acids or bases, depending on the particular substituents found on the compounds described herein.

Within the context of the present invention and as used herein, the term "solvate(s)" or "pharmaceutically acceptable solvate(s)" refers to a compound formed by the interaction of a solute (in this invention, a compound of Formula I or a pharmaceutically acceptable salt thereof) and a solvent. Such solvents for the purpose of the invention may not interfere with the biological activity of the solute. Preferably, the solvent used is a pharmaceutically acceptable solvent. Examples of suitable pharmaceutically acceptable solvents include, without limitation, water, ethanol and acetic acid or mixtures thereof. Most preferably, the solvent used is water and the solvates obtained are referred to as hydrates. Examples for suitable solvates are the mono- or di-hydrates or alcoholates of the compounds of the present invention.

Within the context of the present invention and as used herein, the term "prodrug(s)" refers to any pharmacologically inactive or less active compound which, when metabolized or chemically transformed in vivo by a chemical or physiological process, e.g., a prodrug on being brought to the physiological pH or through enzyme action is converted to the parent compound e.g. the compound of Formula I of the present invention. For example, in the context of the present invention prodrugs can be esters of the compound of Formula I in respect of which on metabolism, the ester group is cleaved to form the parent compound of Formula I that imparts therapeutic activity. Representative examples of esters include lower alkyl esters, such as the methyl or ethyl ester; carboxy-lower alkyl esters, such as the carboxymethyl ester; nitrooxy or nitrosooxy-lower alkyl esters, such as the 4-nitrooxybutyl or 4-nitrosooxybutyl ester; and the like.

Within the context of the present invention and as used herein, the term "N-oxide" refers to the oxide of the nitrogen atom of a nitrogen-containing heteroaryl or heterocycle. N-oxide can be formed in presence of an oxidizing agent for example peroxide such as m-chloroperbenzoic acid or hydrogen peroxide. N-oxide refers to an amine oxide, also known as amine-N-oxide, and is a chemical compound that contains N→O bond.

Within the context of the present invention and as used herein "S-oxide" refers to the oxide of the sulfur atom (S-oxide) or dioxide of the sulfur atom (S,S-dioxide) of a sulfur-containing heteroaryl or heterocycle. S-oxide and S,S-dioxides can be formed in the presence of an oxidizing agent for example peroxide such as m-chloro-perbenzoic acid or oxone.

Within the context of the present invention and as used herein, the term "a carboxylic acid isostere" refers to a functional group or a moiety that elicits similar physical, biological and/or chemical properties as that of carboxylic acid moiety. Representative examples of carboxylic acid isostere include, but are not limited to:

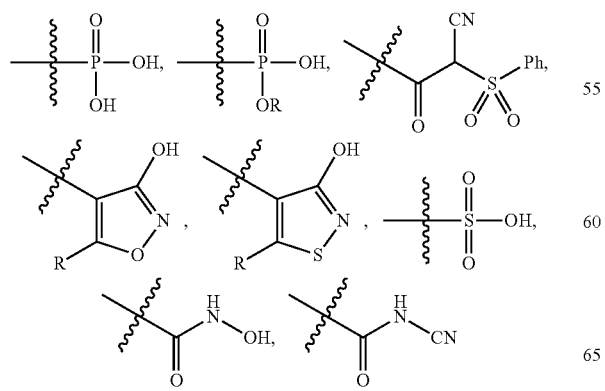

-continued

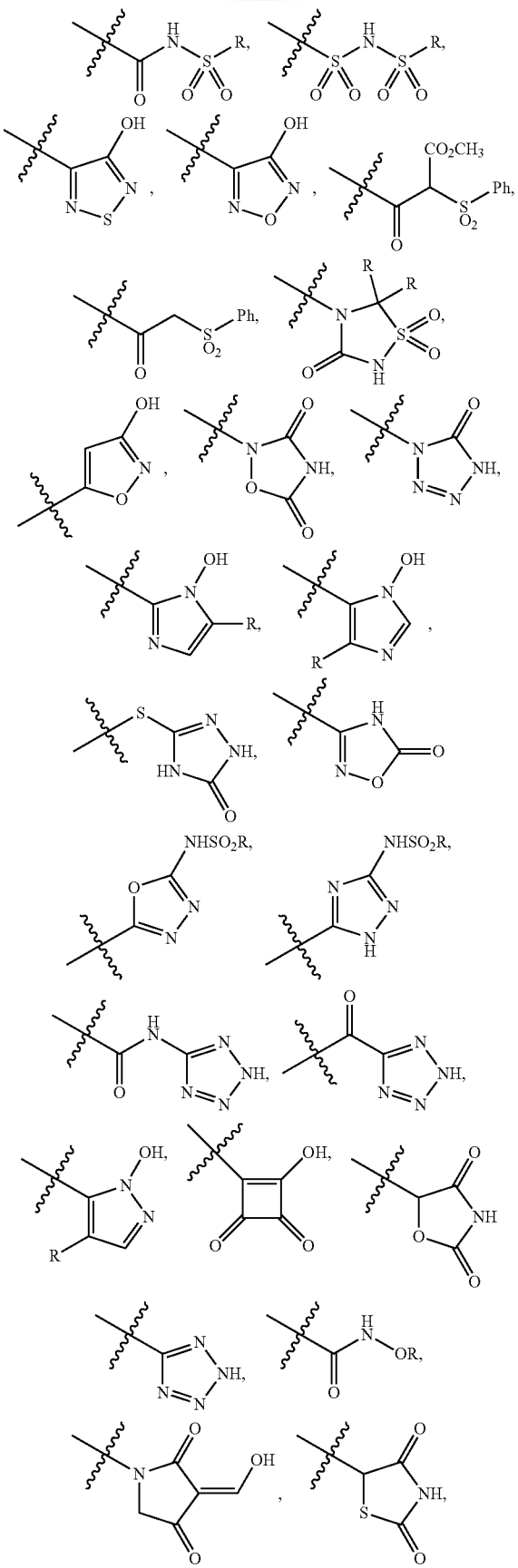

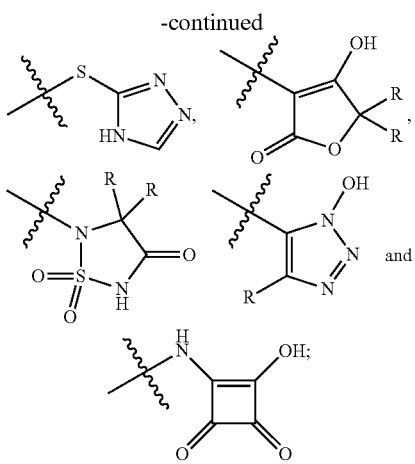

wherein R is hydrogen
or $(C_1-C_3)$alkyl.

Within the context of the present invention and as used herein the phrase "RORγ" refers to all isoforms encoded by the RORC gene which include RORγ1 and RORγt (RORγ2).

Within the context of the present invention and as used herein the phrase "RORγ modulator" refers to a compound that inhibits, either directly or indirectly, the activity of RORγ. RORγ modulators include antagonists and inverse agonists of RORγ.

Within the context of the present invention and as used herein the term "contacting" refers to bringing a compound of the invention or a pharmaceutically acceptable salt thereof and RORγ receptor together in such a manner that the compound can affect the activity of RORγ, either directly or indirectly. Contacting can be accomplished in vitro (i.e., in an artificial environment e.g., without limitation, in a test tube or culture medium) or in vivo (i.e., within a living organism such as, without limitation, a mouse, rat or rabbit or any other animal).

The term, "disease or disorder mediated by RORγ" refers to a disease or disorder in a subject caused due to the uncontrolled expression or dysfunction of the RORγ and/or Th-17 cells.

Within the context of the present invention and as used herein the term "IL-17 inhibitor" means the compounds referred to herein decreases the production of IL-17 in a subject. Alternatively, said term means that the compounds of the present invention referred to herein can block the action or function of IL-17 in a subject.

The term "disease(s) or disorder(s) mediated by IL-17" encompasses all diseases, disorders and medical conditions in which pro-inflammatory cytokine IL-17 plays a role, whether directly or indirectly, including the causation, development, progression, persistence or pathology of the disease or disorder.

Within the context of the present invention and as used herein the term "subject" refers to an animal, preferably a mammal, and most preferably a human. The term "mammal" refers to warm-blooded vertebrate animals of the class 'mammalia', including humans, characterized by a covering of hair on the skin and, in the female, milk-producing mammary glands for nourishing the young. The term mammal includes, but is not limited to, cows, horses, pigs, dogs, cats and humans. In the context of the present invention, the term "mammal" is used interchangeably with the term "patient" or "subject". In the context of the present invention the phrase "a subject in need thereof" means a subject (patient) in need of the treatment for the disease or disorder that is mediated by RORγ and/or IL-17. Alternatively, the phrase "a subject in need thereof" means a subject (patient) diagnosed having a disease or disorder that is mediated by RORγ and/or IL-17.

Within the context of the present invention and as used herein the term, "therapeutically effective amount" means an amount of the compound of the present invention or a composition comprising the compound of the present invention, sufficient to significantly induce a positive modification in the condition (a disease or a disorder) to be treated, but low enough to avoid undue or severe side effects within the scope of sound medical judgment. The therapeutically effective amount of the compounds of the present invention or pharmaceutically acceptable salts thereof or composition containing the said compounds will vary with the particular condition being treated, the age and physical condition of the patient (subject in need of the treatment), the severity of the condition being treated/prevented, the duration of the treatment, the nature of concurrent therapy, the specific compound or composition employed, the particular pharmaceutically acceptable carrier utilized.

Within the context of the present invention and as used herein the terms "treatment", "treat" and "treating" refer to alleviate, slow the progression, attenuation or cure of existing disease or condition as described herein. Treatment also includes treating the symptoms of the disease or condition.

The term "compound(s) for use" as used herein embrace any one or more of the following: (1) use of the compound(s), (2) method of use of the compound(s), (3) use in the treatment of, (4) the use for the manufacture of pharmaceutical composition/medicament for treatment/treating or (5) method of treatment/treating/reducing/inhibiting comprising administering an effective amount of the compound to a subject in need thereof. In this context the term "compound(s)" refer(s) to the compounds of Formula I or stereoisomers, tautomers, pharmaceutically acceptable salts, pharmaceutically acceptable solvates, prodrugs, S-oxides, N-oxides or a carboxylic acid isostere thereof. Preferably, the term "compound(s)" refer(s) to the compounds of Formula I or stereoisomers, tautomers, pharmaceutically acceptable salts or pharmaceutically acceptable solvates thereof.

The term "optionally substituted" means "substituted or unsubstituted," and therefore, the generic structural formulae described herein encompasses compounds containing the specified optional substituent as well as compounds that do not contain the optional substituent.

EMBODIMENTS

The invention encompasses all the compounds described by the Formula I without limitation, however, for the purposes of further illustrations, preferred aspects and elements of the invention are discussed herein the form of the following embodiments.

In an embodiment, the present invention relates to a compound of Formula I or a stereoisomer, a tautomer or a pharmaceutically acceptable salt, a pharmaceutically acceptable solvate, a prodrug, an N-oxide, a S-oxide or a carboxylic acid isostere thereof;
wherein: Y is —COOH; and Ring A is as defined in the first aspect of the invention as described herein above.

In another embodiment, the present invention relates to a compound of Formula I or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOR'; wherein R' (C$_1$-C$_6$)alkyl, wherein (C$_1$-C$_6$)alkyl is unsubstituted or substituted with (C$_6$-C$_{10}$)aryl; and Ring A is 5- to 14-membered heteroaryl selected from the group consisting of pyrimidinyl, pyridyl, quinazolinyl, pyrazolyl, and thiazolyl; wherein said pyrimidinyl, pyridyl, quinazolinyl, pyrazolyl, or thiazolyl is unsubstituted or substituted with one or more groups of R as defined above.

In another embodiment, the present invention relates to a compound of Formula I or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or (C$_1$-C$_6$)alkyl, wherein the (C$_1$-C$_6$)alkyl is unsubstituted or substituted with (C$_6$-C$_{10}$)aryl and Ring A is pyrimidinyl or pyridyl, wherein said pyrimidinyl or pyridyl is unsubstituted or substituted with one or more groups of R as defined above; provided that when ring A is pyrimidinyl, one of the R groups is other than hydrogen.

In another embodiment, the present invention relates to a compound of Formula I or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOH; and

Ring A is pyrimidinyl or pyridyl, wherein said pyrimidinyl and pyridyl is unsubstituted or substituted with one or more groups of R as defined above; provided that when ring A is pyrimidinyl, one of the R groups is other than hydrogen.

In an embodiment, the present invention relates to a compound of Formula I or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or (C$_1$-C$_6$)alkyl, wherein (C$_1$-C$_6$)alkyl is unsubstituted or substituted with (C$_6$-C$_{10}$)aryl; and Ring A is selected from the group consisting of quinazolinyl, pyrazolyl and thiazolyl, wherein said quinazolinyl, pyrazolyl and thiazolyl is unsubstituted or substituted with one or more groups of R as defined above;

provided that when ring A is pyrazolyl and R is attached on nitrogen atom of pyrazolyl ring then R is selected from the group consisting of

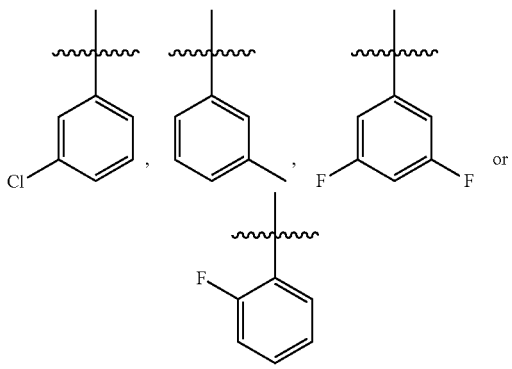

wherein
⸺ is point of attachment to nitrogen atom of pyrazolyl ring.

In an embodiment, the present invention relates to a compound of Formula I or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOH; and

Ring A is selected from the group consisting of quinazolinyl, pyrazolyl and thiazolyl, wherein said quinazolinyl, pyrazolyl and thiazolyl is unsubstituted or substituted with one or more groups of R as defined above;

provided that when ring A is pyrazolyl and R is attached on nitrogen atom of pyrazolyl ring then R is selected from the group consisting of

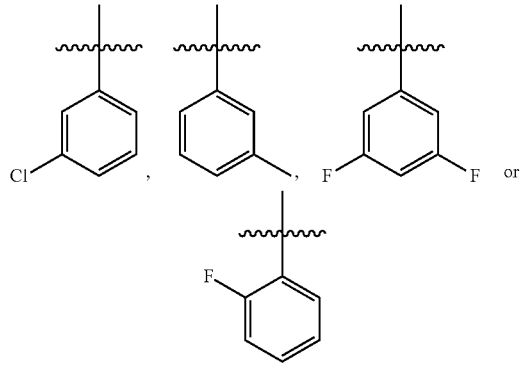

wherein
⸺ is point of attachment to nitrogen atom of pyrazolyl ring.

According to an embodiment, the present invention relates to a compound of Formula I, or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or (C$_1$-C$_6$)alkyl, wherein (C$_1$-C$_6$)alkyl is unsubstituted or substituted with (C$_6$-C$_{10}$)aryl;

Ring A is 5- to 14-membered heteroaryl selected from the group consisting of

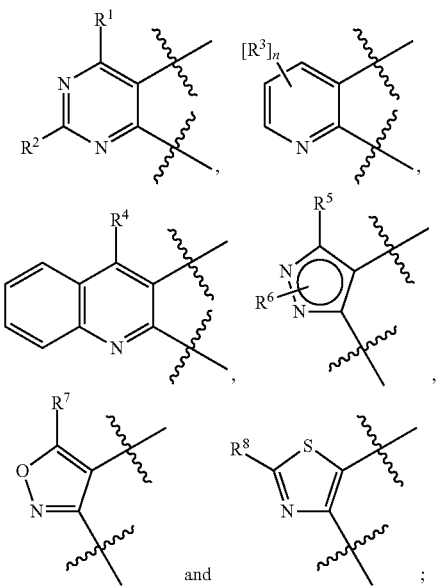

provided that when Ring A is

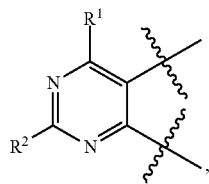

then one of the $R^1$ or $R^2$ is other than hydrogen;

provided that when Ring A is pyrazolyl and $R^6$ is attached on nitrogen atom of pyrazolyl ring then $R^6$ is selected from the group consisting of

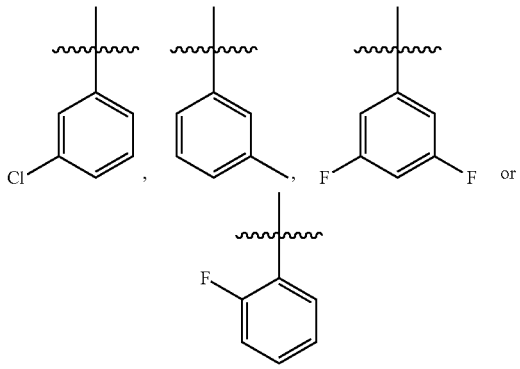

wherein
↧ is point of attachment to nitrogen atom of pyrazolyl ring;
wherein:
$R^1$ is independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, 3- to 10-membered heterocyclyl, $(C_6-C_{10})$aryl, 5- to 14-membered heteroaryl, cyano, amino, —C(O)NH$_2$, —C(O)NR$^a$R$^b$, —SR$^a$, —S(O)$_m$R$^a$, —S(O)$_m$NR$^a$R$^b$, —N[$(C_1-C_6)$alkyl]R$^a$, —N [$(C_1-C_6)$alkyl]$_2$, —NHR$^a$, —N(R$^a$)—C(O)R$^a$, —N(R$^a$)— C(O)NR$^a$R$^b$ and —NR$^a$R$^b$; wherein R$^a$ and R$^b$ are hydrogen or $(C_1-C_6)$alkyl; or R$^a$ and R$^b$ together with the nitrogen atom to which they are attached, can combine to form an unsaturated or saturated 3- to 10-membered heterocyclyl containing 1, 2 or 3 heteroatoms independently selected from the group consisting of N, O and S;
$R^2$ is independently selected from the group consisting of hydrogen, halogen, hydroxy, $(C_1-C_6)$alkyl, halo$(C_1-C_6)$alkyl, $(C_3-C_6)$cycloalkyl, —O—$(C_1-C_6)$alkyl, —O—$(C_1-C_6)$haloalkyl, 3- to 10-membered heterocyclyl, $(C_6-C_{10})$aryl, 5- to 14-membered heteroaryl, cyano, amino, —SR$^a$, —S(O)$_m$R$^a$, —S(O)$_m$NR$^a$R$^b$, —N(R$^a$)—C(O)R$^a$, —N[$(C_1-C_6)$alkyl]R$^a$, —N[$(C_1-C_6)$alkyl]$_2$, —NHR$^a$ and —NR$^a$R$^b$; wherein R$^a$ and R$^b$ are independently selected from the group consisting of hydrogen, $(C_1-C_6)$alkyl, $(C_3-C_{10})$cycloalkyl or $(C_6-C_{10})$aryl; or R$^a$ and R$^b$ combine together with the nitrogen atom to which they are attached, can combine to form an unsaturated or saturated heterocyclyl which contains 1, 2 or 3 heteroatoms independently selected from the group consisting of N, O and S;
$R^3$ at each occurrence is independently selected from the group consisting of hydrogen, halogen, hydroxy, cyano, $(C_1-C_6)$alkyl, halo$(C_1-C_6)$alkyl, —O—$(C_1-C_6)$alkyl, —O—$(C_1-C_6)$haloalkyl, $(C_3-C_6)$cycloalkyl, 3- to 10-membered heterocyclyl, $(C_6-C_{10})$aryl, 5- to 14-membered heteroaryl, —COOH, —CH$_2$OH, —C(O)R$^a$, —C(O)OR$^a$, —CH=N—OH and —C(O)NR$^a$R$^b$; wherein R$^a$ and R$^b$ are independently selected from the group consisting of hydrogen, hydroxy, $(C_1-C_6)$alkyl, —O—$(C_1-C_6)$alkyl, heterocyclyl and heteroaryl; or R$^a$ and R$^b$ together with the nitrogen atom to which they are attached, can combine to form heteroaryl containing 1, 2 or 3 heteroatoms independently selected from the group consisting of N, O and S;
or two $R^3$ groups present on adjacent carbon atoms of the heteroaryl can combine to form a heterocyclyl or a heteroaryl, containing 1, 2 or 3 heteroatoms independently selected from the group consisting of N, O and S;
$R^4$ is independently selected from the group consisting of hydrogen, halogen, hydroxy, $(C_1-C_6)$alkyl, $(C_1-C_6)$haloalkyl, —O—$(C_1-C_6)$alkyl, —O—$(C_6-C_{10})$aryl, amino, —NH$(C_1-C_6)$alkyl, —N[$(C_1-C_6)$alkyl]R$^a$ and —NR$^a$R$^b$; wherein R$^a$ and R$^b$ are hydrogen or $(C_1-C_6)$alkyl;
$R^5$ is hydrogen, $(C_1-C_6)$alkyl, $(C_6-C_{10})$aryl, heteroaryl or —S(R$^a$)$_m$, wherein R$^a$ is as defined above;
$R^6$ is hydrogen or $(C_6-C_{10})$aryl;
$R^7$ is hydrogen or $(C_1-C_6)$alkyl;
$R^8$ is —NR$^a$R$^b$; wherein R$^a$ and R$^b$ are hydrogen or $(C_1-C_6)$alkyl;
m is 1 or 2;
n is 0, 1, 2 or 3;
wherein said
$(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —C(O)$(C_1-C_6)$alkyl, —C(O)O $(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;
$(C_3-C_{10})$cycloalkyl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, amino and cyano;
carbocycle is 3- to 12-membered ring which is unsubstituted or substituted with one or more groups independently selected from the group consisting of $(C_1-C_6)$alkyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heteroaryl, heterocyclyl, cyano, amino, —C(O)O$(C_1-C_6)$alkyl, —C(O)NR$^a$R$^b$ and —S(O)$_2$R$^a$; wherein R$^a$ and R$^b$ are as defined above;
$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)O$(C_1-C_6)$alkyl, —C(O) NR$^a$R$^b$ and —S(O)$_2$R$^a$; wherein R$^a$ and R$^b$ are as defined above;
heterocyclyl is 3- to 10-membered ring which is unsubstituted or substituted with one or more groups independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$ cycloalkyl, (C₆-C₁₀)aryl, heterocyclyl, heteroaryl, cyano, amino, —C(O)ORᵃ, —C(O)NRᵃRᵇ and —S(O)₂Rᵃ; wherein Rᵃ and Rᵇ are as defined above;

heteroaryl is 5- to 14-membered ring, which is unsubstituted or substituted with one or more groups independently selected from the group consisting of halogen, hydroxy, (C₁-C₆)alkyl, halo(C₁-C₆)alkyl, —O—(C₁-C₆)alkyl, —O—(C₁-C₆)haloalkyl, heterocyclyl, heteroaryl, cyano, amino, —C(O)NRᵃRᵇ and —S(O)₂Rᵃ; wherein Rᵃ and Rᵇ are as defined above;

and halogen is selected from chlorine, bromine, iodine and fluorine.

According to an embodiment, the present invention relates to a compound of Formula I, or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOH;

Ring A is 5- to 14-membered heteroaryl selected from the group consisting of

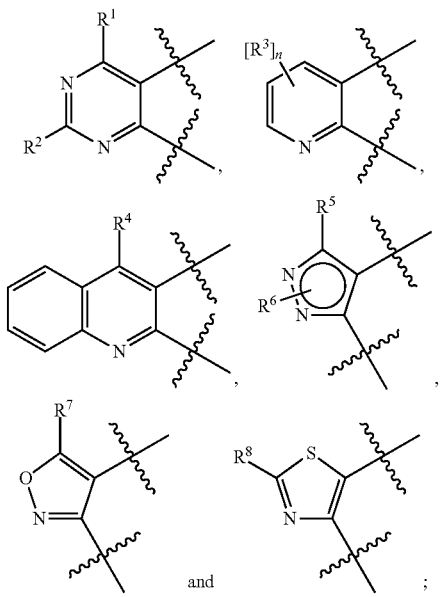

provided that when Ring A is

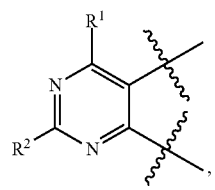

then one of the R¹ or R² is other than hydrogen;

provided that when Ring A is pyrazolyl and R⁶ is attached on nitrogen atom of pyrazolyl ring then R⁶ is selected from the group consisting of

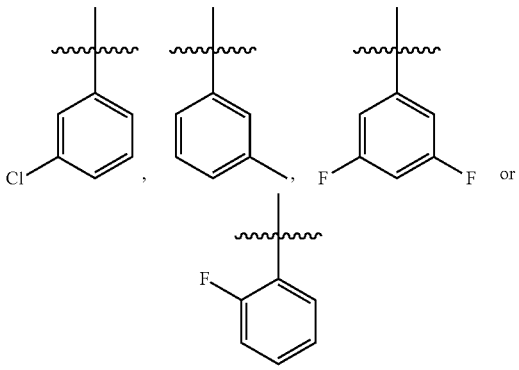

wherein
⸱ is point of attachment to nitrogen atom of pyrazolyl ring;
wherein:

R¹ is independently selected from the group consisting of hydrogen, halogen, hydroxy, (C₁-C₆)alkyl, halo(C₁-C₆)alkyl, —O—(C₁-C₆)alkyl, —O—(C₁-C₆)haloalkyl, (C₃-C₁₀)cycloalkyl, 3- to 10-membered heterocyclyl, (C₆-C₁₀)aryl, 5- to 14-membered heteroaryl, cyano, amino, —C(O)NH₂, —C(O)NRᵃRᵇ, —SRᵃ, —S(O)ₘRᵃ, —S(O)ₘNRᵃRᵇ, —N[(C₁-C₆)alkyl]Rᵃ, —N[(C₁-C₆)alkyl]₂, —NHRᵃ, —N(Rᵃ)—C(O)Rᵃ, —N(Rᵃ)—C(O)NRᵃRᵇ and —NRᵃRᵇ; wherein Rᵃ and Rᵇ are hydrogen or (C₁-C₆)alkyl; or Rᵃ and Rᵇ together with the nitrogen atom to which they are attached, can combine to form an unsaturated or saturated 3- to 10-membered heterocyclyl containing 1, 2 or 3 heteroatoms independently selected from the group consisting of N, O and S;

R² is independently selected from the group consisting of hydrogen, halogen, hydroxy, (C₁-C₆)alkyl, halo(C₁-C₆)alkyl, (C₃-C₆)cycloalkyl, —O—(C₁-C₆)haloalkyl, 3- to 10-membered heterocyclyl, (C₆-C₁₀)aryl, 5- to 14-membered heteroaryl, cyano, amino, —SRᵃ, —S(O)ₘRᵃ, —S(O)ₘNRᵃRᵇ, —N(Rᵃ)—C(O)Rᵃ, —N[(C₆)alkyl]Rᵃ, —N[(C₁-C₆)alkyl]₂, —NHRᵃ and —NRᵃRᵇ; wherein Rᵃ and Rᵇ are independently selected from the group consisting of hydrogen, (C₁-C₆)alkyl, (C₃-C₁₀)cycloalkyl or (C₆-C₁₀)aryl; or Rᵃ and Rᵇ combine together with the nitrogen atom to which they are attached, can combine to form an unsaturated or saturated heterocyclyl which contains 1, 2 or 3 heteroatoms independently selected from the group consisting of N, O and S;

R³ at each occurrence is independently selected from the group consisting of hydrogen, halogen, hydroxy, cyano, (C₁-C₆)alkyl, halo(C₁-C₆)alkyl, —O—(C₁-C₆)haloalkyl, (C₃-C₆)cycloalkyl, heterocyclyl, (C₆-C₁₀)aryl, heteroaryl, —COOH, —CH₂OH, —C(O)Rᵃ, —C(O)ORᵃ, —CH=N—OH and —C(O)NRᵃRᵇ; wherein Rᵃ and Rᵇ are selected from the group consisting of hydrogen, hydroxy, (C₁-C₆)alkyl, heterocyclyl and heteroaryl; or Rᵃ and Rᵇ together with the nitrogen atom to which they are attached, can combine to form an unsaturated or saturated heterocyclyl containing 1, 2 or 3 heteroatoms independently selected from the group consisting of N, O and S; or two R³ groups present on adjacent carbon atoms of the heteroaryl can combine to form an unsaturated or saturated heteroaryl containing 1, 2 or 3 heteroatoms independently selected from the group consisting of N, O and S;

R⁴ is independently selected from the group consisting of hydrogen, halogen, hydroxy, (C₁-C₆)alkyl, (C₁-C₆)

haloalkyl, —O—(C<sub>6</sub>-C<sub>10</sub>)aryl, amino, —NHR<sup>a</sup>, N[(C<sub>1</sub>-C<sub>6</sub>)alkyl]R<sup>a</sup>, —N(R<sup>a</sup>)—C(O)R<sup>a</sup> and NR<sup>a</sup>R<sup>b</sup>; wherein R<sup>a</sup> and R<sup>b</sup> are hydrogen or (C<sub>1</sub>-C<sub>6</sub>)alkyl;

R$^5$ is selected from the group consisting of hydrogen, (C$_1$-C$_6$)alkyl, (C$_6$-C$_{10}$)aryl, heteroaryl and —SR$^a$, wherein R$^a$ is as defined above;

R$^6$ is hydrogen or (C$_6$-C$_{10}$)aryl;

R$^7$ is hydrogen or (C$_1$-C$_6$)alkyl;

R$^8$ is —NR$^a$R$^b$; wherein R$^a$ and R$^b$ are hydrogen or (C$_1$-C$_6$)alkyl;

m is 1 or 2;

n is 0, 1, 2 or 3;

wherein said (C$_1$-C$_6$)alkyl is unsubstituted or substituted with one or more groups independently selected from the group consisting of halogen, hydroxy, (C$_1$-C$_6$)alkyl, halo(C$_1$-C$_6$)alkyl, (C$_2$-C$_8$)alkenyl, (C$_2$-C$_8$)alkynyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —NH(C$_1$-C$_6$)alkyl, —C(O)(C$_1$-C$_6$)alkyl, —C(O)O(C$_1$-C$_6$)alkyl, —C(O)NH$_2$, —C(O)NH(C$_1$-C$_6$)alkyl, —C(O)N[(C$_1$-C$_6$)alkyl]$_2$ and —C(O)NHS(O)$_2$(C$_1$-C$_6$)alkyl;

(C$_3$-C$_{10}$)cycloalkyl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)haloalkyl, amino and cyano;

carbocycle is 3- to 12-membered ring which is unsubstituted or substituted with one or more groups independently selected from the group consisting of (C$_1$-C$_6$)alkyl, halo(C$_1$-C$_6$)alkyl, hydroxy, halogen, (C$_1$-C$_6$)alkoxy, halo(C$_1$-C$_6$)alkoxy, (C$_6$-C$_{10}$)aryl, (C$_3$-C$_{10}$)cycloalkyl, heteroaryl, heterocyclyl, cyano, amino, —C(O)O(C$_1$-C$_6$)alkyl, —C(O)NR$^a$R$^b$ and S(O)$_2$R$^a$; wherein R$^a$ and R$^b$ are as defined above;

(C$_6$-C$_{10}$)aryl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)O(C$_1$-C$_6$)alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, heterocyclyl, heteroaryl, cyano, amino, —C(O)NR$^a$R$^b$ and —S(O)$_2$R$^a$; wherein R$^a$ and R$^b$ are as defined above and halogen is selected from chlorine, bromine, iodine and fluorine.

In an embodiment of the present invention, the compound of Formula I encompasses a compound of Formula Ia

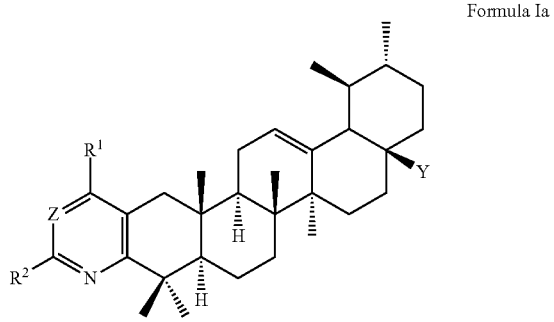

Formula Ia or a stereoisomer, a tautomer or a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or (C$_1$-C$_6$)alkyl, wherein (C$_1$-C$_6$)alkyl is unsubstituted or substituted with (C$_6$-C$_{10}$)aryl;

R$^1$ is independently selected from the group consisting of hydrogen, halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, 3- to 10-membered heterocyclyl, (C$_6$-C$_{10}$)aryl, 5- to 14-membered heteroaryl, cyano, amino, —C(O)NH$_2$, —C(O)NR$^a$R$^b$, —SR$^a$, —S(O)$_m$R$^a$, —S(O)$_m$NR$^a$R$^b$, —N[(C$_1$-C$_6$)alkyl]R$^a$, —N[(C$_1$-C$_6$)alkyl]$_2$, —NHR$^a$, —N(R$^a$)—C(O)R$^a$, —N(R$^a$)—C(O)NR$^a$R$^b$ and —NR$^a$R$^b$; wherein R$^a$ and R$^b$ are hydrogen or (C$_1$-C$_6$)alkyl; or R$^a$ and R$^b$ together with the nitrogen atom to which they are attached, can combine to form an unsaturated or saturated 3- to 10-membered heterocyclyl containing 1, 2 or 3 heteroatoms independently selected from the group consisting of N, O and S;

R$^2$ is independently selected from the group consisting of hydrogen, halogen, hydroxy, (C$_1$-C$_6$)alkyl, halo(C$_1$-C$_6$)alkyl, (C$_3$-C$_6$)cycloalkyl, —O—(C$_1$-C$_6$)haloalkyl, 3- to 10-membered heterocyclyl, (C$_6$-C$_{10}$)aryl, 5- to 14-membered heteroaryl, cyano, amino, —SR$^a$, —S(O)$_m$R$^a$, —S(O)$_m$NR$^a$R$^b$, —N(R$^a$)—C(O)R$^a$, —N[(C$_1$-C$_6$)alkyl]R$^a$, —N[(C$_1$-C$_6$)alkyl]$_2$, —NHR$^a$ and —NR$^a$R$^b$; wherein R$^a$ and R$^b$ are independently selected from the group consisting of hydrogen, (C$_1$-C$_6$)alkyl, (C$_3$-C$_{10}$)cycloalkyl or (C$_6$-C$_{10}$)aryl; or R$^a$ and R$^b$ combine together with the nitrogen atom to which they are attached, can combine to form an unsaturated or saturated heterocyclyl which contains 1, 2 or 3 heteroatoms independently selected from the group consisting of N, O and S;

R$^3$ at each occurrence is independently selected from the group consisting of hydrogen, halogen, hydroxy, cyano, (C$_1$-C$_6$)alkyl, halo(C$_1$-C$_6$)alkyl, —O—(C$_1$-C$_6$)haloalkyl, (C$_3$-C$_6$)cycloalkyl, heterocyclyl, (C$_6$-C$_{10}$)aryl, heteroaryl, —COOH, —CH$_2$OH, —C(O)R$^a$, —C(O)OR$^a$, —CH=N—OH and —C(O)NR$^a$R$^b$, wherein R$^a$ and R$^b$ are selected from the group consisting of hydrogen, hydroxy, (C$_1$-C$_6$)alkyl, heterocyclyl and heteroaryl; or R$^a$ and R$^b$ together with the nitrogen atom to which they are attached, can combine to form an unsaturated or saturated heterocyclyl containing 1, 2 or 3 heteroatoms independently selected from the group consisting of N, O and S;

Z is —CR$^3$ or N;

when Z is N, one of the R$^1$ or R$^2$ is other than hydrogen;

when Z is —CR$^3$; R$^1$, R$^2$ and R$^3$ are as defined above; or R$^2$ and R$^3$ present on adjacent carbon atoms of the heteroaryl can combine to form a 3- to 6-membered saturated or unsaturated heterocyclyl containing one or two heteroatoms independently selected from the group consisting of O, N and S;

m is 1 or 2;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —N[$(C_1-C_6)$alkyl]$_2$, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;

$(C_3-C_{10})$cycloalkyl is unsubstituted or substituted with one or more groups independently selected from the group consisting of halogen, hydroxy, $(C_1-C_6)$alkyl, halo$(C_1-C_6)$alkyl, —O—$(C_1-C_6)$haloalkyl, amino and cyano;

carbocycle is 3- to 12-membered ring which is unsubstituted or substituted with one or more groups independently selected from the group consisting of $(C_1-C_6)$alkyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heteroaryl, heterocyclyl, cyano, amino, —C(O)O$(C_1-C_6)$alkyl, —C(O)NR$^a$R$^b$ and S(O)$_2$R$^a$; wherein R$^a$ and R$^b$ are as defined above;

$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)O$(C_1-C_6)$alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

In an embodiment of the present invention, the compound of Formula Ia encompasses a compound of Formula A

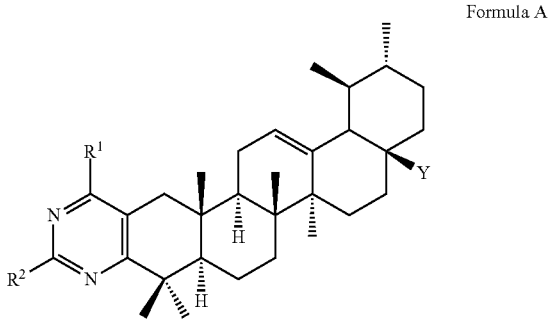

Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or $(C_1-C_6)$alkyl, wherein $(C_1-C_6)$alkyl is unsubstituted or substituted with $(C_6-C_{10})$aryl and one of R$^1$ or R$^2$ is other than hydrogen;

R$^1$ is independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, 3- to 10-membered heterocyclyl, $(C_6-C_{10})$aryl, 5- to 14-membered heteroaryl, cyano, amino, —C(O)NH$_2$, —C(O)NR$^a$R$^b$, —SR$^a$, —S(O)$_m$R$^a$, —S(O)$_m$NR$^a$R$^b$, —N[$(C_1-C_6)$alkyl]R$^a$, —N[$(C_1-C_6)$alkyl]$_2$, —NHR$^a$, —N(R$^a$)—C(O)R$^a$, —N(R$^a$)—C(O)NR$^a$R$^b$ and —NR$^a$R$^b$; wherein R$^a$ and R$^b$ are hydrogen or $(C_1-C_6)$alkyl; or R$^a$ and R$^b$ together with the nitrogen atom to which they are attached, can combine to form an unsaturated or saturated 3- to 10-membered heterocyclyl containing 1, 2 or 3 heteroatoms independently selected from the group consisting of N, O and S;

R$^2$ is independently selected from the group consisting of hydrogen, halogen, hydroxy, $(C_1-C_6)$alkyl, halo$(C_1-C_6)$alkyl, $(C_3-C_6)$cycloalkyl, —O—$(C_1-C_6)$alkyl, —O—$(C_1-C_6)$haloalkyl, 3- to 10-membered heterocyclyl, $(C_6-C_{10})$aryl, 5- to 14-membered heteroaryl, cyano, amino, —SR$^a$, —S(O)$_m$R$^a$, —S(O)$_m$NR$^a$R$^b$, —N(R$^a$)—C(O)R$^a$, —N[$(C_1-C_6)$alkyl]R$^a$, —N[$(C_1-C_6)$alkyl]$_2$, —NHR$^a$ and —NR$^a$R$^b$; wherein R$^a$ and R$^b$ are independently selected from the group consisting of hydrogen, $(C_1-C_6)$alkyl, $(C_3-C_{10})$cycloalkyl or $(C_6-C_{10})$aryl; or R$^a$ and R$^b$ combine together with the nitrogen atom to which they are attached, can combine to form an unsaturated or saturated heterocyclyl which contains 1, 2 or 3 heteroatoms independently selected from the group consisting of N, O and S; and m is 1 or 2;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —N[$(C_1-C_6)$alkyl]$_2$, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;

$(C_3-C_{10})$cycloalkyl is unsubstituted or substituted with one or more groups independently selected from the group consisting of halogen, hydroxy, $(C_1-C_6)$alkyl, halo($C_1$-$C_6$)alkyl, —O—($C_1$-$C_6$)alkyl, —O—($C_1$-$C_6$) haloalkyl, amino and cyano;

carbocycle is 3- to 12-membered ring which is unsubstituted or substituted with one or more groups independently selected from the group consisting of ($C_1$-$C_6$) alkyl, halo($C_1$-$C_6$)alkyl, hydroxy, halogen, ($C_1$-$C_6$) alkoxy, halo($C_1$-$C_6$)alkoxy, ($C_6$-$C_{10}$)aryl, ($C_3$-$C_{10}$) cycloalkyl, heteroaryl, heterocyclyl, cyano, amino, —C(O)O($C_1$-$C_6$)alkyl, —C(O)NR$^a$R$^b$ and S(O)$_2$R$^a$; wherein R$^a$ and R$^b$ are as defined above;

($C_6$-$C_{10}$)aryl is unsubstituted or substituted with one or more groups independently selected from the group consisting of halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —C(O)O($C_1$-$C_6$)alkyl, —C(O) NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$) cycloalkyl, ($C_6$-$C_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, ($C_1$-$C_6$)alkyl, halo($C_1$-$C_6$)alkyl, —O—($C_1$-$C_6$)alkyl, —O—($C_1$-$C_6$)haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

R$^1$ is halogen or hydroxy; and

R$^2$ is hydrogen or —SR$^a$; wherein R$^a$ is hydrogen or ($C_1$-$C_6$)alkyl.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

R$^1$ is hydroxy; and

R$^2$ is hydrogen, halogen, hydroxy, ($C_1$-$C_6$)alkyl, halo($C_1$-$C_6$)alkyl, or —O($C_1$-$C_6$)alkyl.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl; R$^1$ and R$^2$ are hydroxy.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

R$^1$ is NR$^a$R$^b$; wherein R$^a$ and R$^b$ are hydrogen or ($C_1$-$C_6$) alkyl; wherein ($C_1$-$C_6$)alkyl is unsubstituted or substituted with 3- to 10-membered heterocyclyl; or R$^a$ and R$^b$ together with the nitrogen atom to which they are attached, can combine to form an unsubstituted or substituted heterocyclyl containing 1, 2 or 3 heteroatoms independently selected from the group consisting of N, O and S, and R$^2$ is hydrogen.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl; R$^1$ is, —N[($C_1$-$C_6$)alkyl]R$^a$, —N[($C_1$-$C_6$)alkyl]$_2$, —NH($C_3$-$C_{10}$)cycloalkyl, —NHR$^a$, —N(R$^a$)—C(O)R$^a$;

wherein R$^a$ is hydrogen or ($C_1$-$C_6$)alkyl; wherein ($C_1$-$C_6$) alkyl is unsubstituted or substituted with 3- to 10-membered heterocyclyl containing 1, 2 or 3 heteroatoms independently selected from the group consisting of N, O and S, and R$^2$ is hydrogen.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

R$^1$ is NR$^a$R$^b$; wherein R$^a$ and R$^b$ are selected from hydrogen, halogen, ($C_1$-$C_6$)alkyl and halo($C_1$-$C_6$)alkyl; wherein ($C_1$-$C_6$)alkyl is unsubstituted or substituted with 3- to 10-membered heterocyclyl;

R$^a$ and R$^b$ together with the nitrogen atom to which they are attached, can combine to form a heterocyclyl which contains 1, 2 or 3 heteroatoms independently selected from the group consisting of N, O and S, and R$^2$ is ($C_1$-$C_6$)alkyl.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

R$^1$ is NR$^a$R$^b$;

wherein R$^a$ and R$^b$ together with the nitrogen atom to which they are attached, can combine to form a heterocyclyl which contains 1, 2 or 3 heteroatoms independently selected from the group consisting of N, O and S, and R$^2$ is ($C_1$-$C_6$)alkyl.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

R¹ is —N[(C₁-C₆)alkyl]-N[(C₁-C₆)alkyl]₂, —NH(C₃-C₁₀)cycloalkyl, —NH(C₆-C₁₀)aryl or —NHRᵃ; wherein Rᵃ is hydrogen or (C₁-C₆)alkyl; and R² is (C₁-C₆)alkyl.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)alkyl, wherein (C₁-C₆)alkyl is unsubstituted or substituted with (C₆-C₁₀)aryl;
R¹ is hydrogen and R² is (C₃-C₁₀)cycloalkyl which is unsubstituted or substituted with one or more groups independently selected from the group consisting of (C₁-C₆)alkyl, halogen, halo(C₁-C₆)alkyl, hydroxy, —O(C₁-C₆)alkyl, amino and cyano.

In another embodiment, the compound of Formula Ia encompasses a compound of Formula A or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)alkyl, wherein (C₁-C₆)alkyl is unsubstituted or substituted with (C₆-C₁₀)aryl;
R¹ is hydrogen and R² is (C₁-C₆)alkyl, (C₁-C₆)haloalkyl, (C₆-C₁₀)aryl, heterocyclyl or heteroaryl;
wherein said (C₁-C₆)alkyl is unsubstituted or substituted with (C₁-C₆)alkyl, —O(C₆-C₁₀)aryl or (C₆-C₁₀)aryl; aryl is unsubstituted or substituted with one or more groups wherein (C₆-C₁₀) independently selected from the group consisting of halogen, hydroxy, (C₁-C₆)alkyl, halo(C₁-C₆)alkyl, —O(C₁-C₆)alkyl, (C₃-C₁₀)cycloalkyl, —O—(C₆-C₁₀)aryl, heterocyclyl, heteroaryl, cyano and amino.

In another embodiment, the compound of Formula Ia encompasses a compound of Formula A or a stereoisomer, a tautomer or a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)alkyl, wherein (C₁-C₆)alkyl is unsubstituted or substituted with (C₆-C₁₀)aryl;
R¹ is hydrogen and R² is —N[(C₁-C₆)alkyl]Rᵃ, —NH(C₃-C₁₀)cycloalkyl, —NH(C₆-C₁₀)aryl, —NHRᵃ, —NRᵃRᵇ; wherein Rᵃ and Rᵇ are hydrogen or (C₁-C₆)alkyl; or Rᵃ and Rᵇ together with the nitrogen atom to which they are attached; can combine to form an optionally substituted heterocyclyl containing 1, 2 or 3 heteroatoms independently selected from the group consisting of N, O and S.

In another embodiment, the compound of Formula Ia encompasses a compound of Formula A or a stereoisomer, a tautomer or a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)alkyl, wherein (C₁-C₆)alkyl is unsubstituted or substituted with (C₆-C₁₀)aryl;
R¹ is hydrogen and R² is NRᵃRᵇ; wherein Rᵃ and Rᵇ are independently selected from the group consisting of hydrogen, (C₁-C₆)alkyl and halo(C₁-C₆)alkyl; wherein (C₁-C₆)alkyl is unsubstituted or substituted with 3- to 10-membered heterocyclyl; or Rᵃ and Rᵇ together with the nitrogen atom to which are attached, can combine to form a heterocycle containing one or two heteroatoms independently selected from the group consisting of N, O and S.

In another embodiment, the compound of Formula Ia encompasses a compound of Formula A or a stereoisomer, a tautomer or a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)alkyl, wherein (C₁-C₆)alkyl is unsubstituted or substituted with (C₆-C₁₀)aryl;
R¹ is hydrogen and R² is SRᵃ or —S(O)₂Rᵃ; wherein Rᵃ is (C₁-C₆)alkyl or —O(C₁-C₆)alkyl.

In an embodiment of the present invention, the compound of Formula Ia encompasses a compound of Formula B

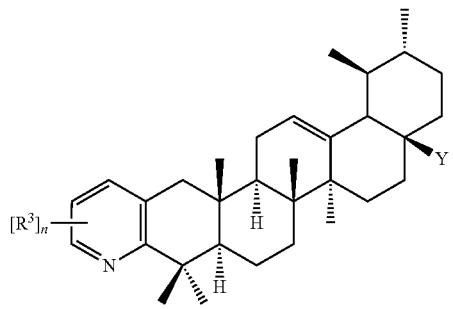

Formula B or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)alkyl, wherein (C₁-C₆)alkyl is unsubstituted or substituted with (C₆-C₁₀)aryl;
R³ at each occurrence is independently selected from the group consisting of hydrogen, halogen, hydroxy, cyano, (C₁-C₆)alkyl, halo(C₁-C₆)alkyl, —O—(C₁-C₆)alkyl, —O—(C₁—C₆)haloalkyl, (C₃-C₆)cycloalkyl, (C₆-C₁₀)aryl, heteroaryl, 3- to 10-membered heterocyclyl, —COOH, —CH₂OH, —C(O)Rᵃ, —C(O)ORᵃ, —CH=N—OH and —C(O)NRᵃRᵇ; wherein Rᵃ and Rᵇ are selected from the group consisting of hydrogen, hydroxy, (C₁-C₆)alkyl, heterocyclyl and heteroaryl; or Rᵃ and Rᵇ together with the nitrogen atom to which they are attached, can combine to form heteroaryl; or
two R³ groups present on adjacent carbon atoms of the heteroaryl ring can combine to form a heteroayrl containing one or two heteroatoms independently selected from the group consisting of N, O and S;
n is 1 or 2;
wherein said
(C₁-C₆)alkyl is unsubstituted or substituted with one or more groups independently selected from the group consisting of halogen, hydroxy, (C₁-C₆)alkyl, halo(C₁-C₆)alkyl, (C₂-C₈)alkenyl, (C₂-C₈)alkynyl, —O—(C₁-C₆)haloalkyl, (C₃-C₁₀)cycloalkyl, (C₆-C₁₀)aryl, heterocyclyl, heteroaryl, cyano, amino, —NH(C₁-C₆)alkyl, —C(O)(C₁-C₆)alkyl, —C(O)O(C₁-C₆)alkyl, —C(O)NH₂, —C(O)NH(C₁-C₆)alkyl, —C(O)N[(C₁-C₆)alkyl]₂ and —C(O)NHS(O)₂(C₁-C₆)alkyl;
(C₃-C₁₀)cycloalkyl is unsubstituted or substituted with one or more groups independently selected from the group consisting of halogen, hydroxy, (C₁-C₆)alkyl, halo(C₁-C₆)alkyl, —O—(C₁-C₆)haloalkyl, amino and cyano;
carbocycle is 3- to 12-membered ring which is unsubstituted or substituted with one or more groups independently selected from the group consisting of (C₁-C₆)

alkyl, halo(C₁-C₆)alkyl, hydroxy, halogen, (C₁-C₆)
  alkoxy, halo(C₁-C₆)alkoxy, (C₆-C₁₀)aryl, (C₃-C₁₀)
  cycloalkyl, heteroaryl, heterocyclyl, cyano, amino,
  —C(O)O(C₁-C₆)alkyl, —C(O)NR$^a$R$^b$ and —S(O)₂R$^a$;
  wherein R$^a$ and R$^b$ are as defined above;
(C₆-C₁₀)aryl is unsubstituted or substituted with one or
  more groups independently selected from the group
  consisting of halogen, hydroxy, (C₁-C₆)alkyl, halo(C₁-
  C₆)alkyl, —O—(C₁-C₆)alkyl, —O—(C₁-C₆)haloalkyl,
  (C₃-C₁₀)cycloalkyl, (C₆-C₁₀)aryl, heterocyclyl, heteroaryl, cyano, amino, —C(O)O(C₁-C₆)alkyl, —C(O)
  NR$^a$R$^b$ and —S(O)₂R$^a$; wherein R$^a$ and R$^b$ are as
  defined above;
heterocyclyl is 3- to 10-membered ring which is unsubstituted or substituted with one or more groups independently selected from the group consisting of hydrogen, halogen, hydroxy, (C₁-C₆)alkyl, halo(C₁-C₆)alkyl,
  —O—(C₁-C₆)alkyl, —O—(C₁-C₆)haloalkyl, (C₃-C₁₀)
  cycloalkyl, (C₆-C₁₀)aryl, heterocyclyl, heteroaryl,
  cyano, amino, —C(O)OR$^a$, —C(O)NR$^a$R$^b$ and
  —S(O)₂R$^a$; wherein R$^a$ and R$^b$ are as defined above;
heteroaryl is 5- to 14-membered ring, which is unsubstituted or substituted with one or more groups independently selected from the group consisting of halogen,
  hydroxy, (C₁-C₆)alkyl, halo(C₁-C₆)alkyl, —O—(C₁-
  C₆)alkyl, —O—(C₁-C₆)haloalkyl, heterocyclyl, heteroaryl, cyano, amino, —C(O)NR$^a$R$^b$ and —S(O)₂R$^a$;
  wherein R$^a$ and R$^b$ are as defined above;
and halogen is selected from chlorine, bromine, iodine
  and fluorine.

In another embodiment, the compound of Formula Ia encompasses a compound of Formula B or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)
  alkyl, wherein (C₁-C₆)alkyl is unsubstituted or substituted
  with (C₆-C₁₀)aryl;
R³ at each occurrence is independently selected from the
  groups consisting of hydrogen, halogen, (C₁-C₆)alkyl,
  halo(C₁-C₆)alkyl, —C(O)R$^a$ and —CH₂OH; wherein R$^a$
  is hydrogen or (C₁-C₆)alkyl; and n is 1 or 2.

In another embodiment, the compound of Formula Ia encompasses a compound of Formula B or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)
  alkyl, wherein (C₁-C₆)alkyl is unsubstituted or substituted
  with (C₆-C₁₀)aryl;
R³ at each occurrence is independently selected from one or
  more groups consisting of halogen, cyano, —O—(C₁-C₆)
  alkyl, (C₁-C₆)haloalkyl, —COOH, —C(O)OR$^a$, —C(O)
  R$^a$ and —CH=N—OH, wherein R$^a$ is hydrogen or (C₁-
  C₆)alkyl and n is 1 or 2.

In another embodiment, the compound of Formula Ia encompasses a compound of Formula B or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)
  alkyl, wherein (C₁-C₆)alkyl is unsubstituted or substituted
  with (C₆-C₁₀)aryl;
n is 2,
R³ is halogen or —C(O)NR$^a$R$^b$; wherein R$^a$ and R$^b$ are
  hydrogen or (C₁-C₆)alkyl.

In another embodiment, the compound of Formula Ia encompasses a compound of Formula B or a stereoisomer, a tautomer, a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)
  alkyl, wherein (C₁-C₆)alkyl is unsubstituted or substituted
  with (C₆-C₁₀)aryl;
n is 2; and
two R³ groups present on adjacent carbon atoms of a
  heteroaryl ring can combine to form a 3- to 6-membered
  saturated or unsaturated heterocyclyl containing 1, 2 or 3
  heteroatoms independently selected from the group consisting of N, O and S, which is unsubstituted or substituted
  with one or more groups independently selected from the
  group consisting of hydrogen, halogen, hydroxy, (C₁-C₆)
  alkyl, halo(C₁-C₆)alkyl, —O—(C₁-C₆)alkyl, —O—(C₁-
  C₆)haloalkyl, (C₃-C₁₀)cycloalkyl, (C₆-C₁₀)aryl, heterocyclyl, heteroaryl, cyano, amino, —C(O)NR$^a$R$^b$ and
  —S(O)₂R$^a$; wherein R$^a$ and R$^b$ are as defined above.

In an embodiment of the present invention, the compound of Formula I encompasses a compound of Formula Ib

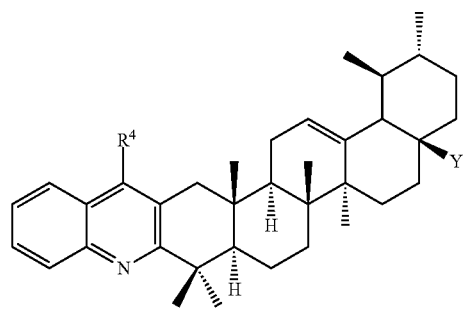

Formula Ib or a stereoisomer, a tautomer or a pharmaceutically acceptable salt, a pharmaceutically acceptable solvate, a prodrug, an N-oxide, a S-oxide or a carboxylic acid isostere thereof;
wherein: Y is —COOR'; wherein R' is hydrogen or (C₁-C₆)
  alkyl, wherein (C₁-C₆)alkyl is unsubstituted or substituted
  with (C₆-C₁₀)aryl;
R⁴ is hydrogen, halogen, hydroxy, (C₁-C₆)alkyl, (C₁-C₆)
  haloalkyl, —O—(C₁-C₆)alkyl, —O—(C₆-C₁₀)aryl,
  amino, —NHR$^a$, —N[(C₁-C₆)alkyl]R$^a$ or —NR$^a$R$^b$;
  wherein R$^a$ and R$^b$ are hydrogen or (C₁-C₆)alkyl;
R$^a$ and R$^b$ are independently selected from the group consisting of hydrogen, (C₁-C₆)alkyl and halo(C₁-C₆)alkyl;
  wherein (C₁-C₆)alkyl is unsubstituted or substituted with
  heterocyclyl containing 1, 2 or 3 heteroatoms independently selected from the group consisting of N, O and S;
wherein said
  (C₁-C₆)alkyl is unsubstituted or substituted with one or
    more groups independently selected from the group
    consisting of halogen, hydroxy, (C₁-C₆)alkyl, halo(C₁-
    C₆)alkyl, (C₂-C₈)alkenyl, (C₂-C₈)alkynyl, —O—(C₁-
    C₆)haloalkyl, (C₃-C₁₀)cycloalkyl, (C₆-C₁₀)aryl, heterocyclyl, heteroaryl, cyano, amino, —NH(C₁-C₆)
    alkyl, —C(O)(C₁-C₆)alkyl, —C(O)O(C₁-C₆)alkyl,
    —C(O)NH₂, —C(O)NH(C₁-C₆)alkyl, —C(O)N[(C₁-
    C₆)alkyl]₂ and —C(O)NHS(O)₂(C₁-C₆)alkyl;
  (C₆-C₁₀)aryl is unsubstituted or substituted with one or
    more groups independently selected from the group
    consisting of halogen, hydroxy, (C₁-C₆)alkyl, halo(C₁-
    C₆)alkyl, —O—(C₁-C₆)alkyl, —O—(C₁-C₆)haloalkyl, ($C_3$-$C_{10}$)cycloalkyl, ($C_6$-$C_{10}$)aryl, heterocyclyl, heteroaryl, cyano, amino, —C(O)O($C_1$-$C_6$)alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

and halogen is selected from chlorine, bromine, iodine and fluorine.

In an embodiment, the compound of Formula I encompasses a compound of Formula Ib or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl; R$^4$ is hydrogen, halogen or —NR$^a$R$^b$; wherein R$^a$ and R$^b$ are hydrogen or ($C_1$-$C_6$)alkyl.

In an embodiment, the compound of Formula I encompasses a compound of Formula Ib or a stereoisomer, a tautomer, a pharmaceutically acceptable salt, a pharmaceutically acceptable solvate, a prodrug, an N-oxide, a S-oxide or a carboxylic acid isostere thereof;

wherein: Y is —COOR'; wherein R' is hydrogen or ($C_1$-$C_6$) alkyl, wherein ($C_1$-$C_6$)alkyl is unsubstituted or substituted with ($C_6$-$C_{10}$)aryl; R$^4$ is —O—($C_1$-$C_6$)alkyl, —O—($C_6$-$C_{10}$)aryl or —NH($C_1$-$C_6$)alkyl;

wherein said ($C_1$-$C_6$)alkyl is unsubstituted or substituted with one or more groups independently selected from the group consisting of halogen, hydroxy, ($C_1$-$C_6$)alkyl, halo($C_1$-$C_6$)alkyl, ($C_2$-$C_8$)alkenyl, ($C_2$-$C_8$)alkynyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —NH($C_1$-$C_6$)alkyl, —C(O)($C_1$-$C_6$)alkyl, —C(O)O($C_1$-$C_6$)alkyl, —C(O)NH$_2$, —C(O)NH($C_1$-$C_6$)alkyl, —C(O)N[($C_1$-$C_6$)alkyl]$_2$ and —C(O)NHS(O)$_2$($C_1$-$C_6$)alkyl.

In another embodiment, the compound of Formula I encompasses a compound of Formula Ic Formula Ic

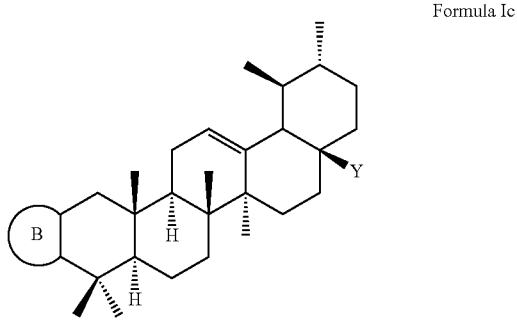

or a stereoisomer, a tautomer, a pharmaceutically acceptable salt, a pharmaceutically acceptable solvate, a prodrug, an N-oxide, a S-oxide or a carboxylic acid isostere thereof;

wherein, Y is —COOR'; wherein R' is hydrogen or ($C_1$-$C_6$) alkyl, wherein ($C_1$-$C_6$)alkyl is unsubstituted or substituted with ($C_6$-$C_{10}$)aryl;

Ring B is a 5-membered heteroaryl selected from the group consisting of

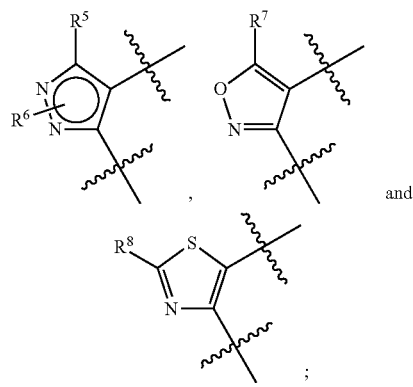

and provided that when Ring B is pyrazolyl and R$^6$ is attached on nitrogen atom of pyrazolyl ring then R$^6$ is selected from the group consisting of

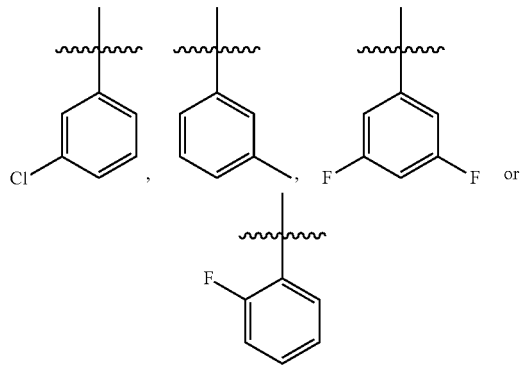

wherein

₤ is point of attachment to nitrogen atom of pyrazolyl ring;

R$^5$ is hydrogen, ($C_1$-$C_6$)alkyl, —O—($C_1$-$C_6$)alkyl, ($C_6$-$C_{10}$) aryl, heteroaryl or —S(R$^a$)$_m$, wherein R$^a$ is hydrogen or ($C_1$-$C_6$)alkyl;

R$^6$ is hydrogen or ($C_6$-$C_{10}$)aryl,

R$^7$ is hydrogen, ($C_1$-$C_6$)alkyl or —O—($C_1$-$C_6$)alkyl;

R$^8$ is —NR$^a$R$^b$; wherein R$^a$ and R$^b$ are hydrogen or ($C_1$-$C_6$) alkyl;

wherein:

($C_1$-$C_6$)alkyl is unsubstituted or substituted with one or more groups independently selected from the group consisting of halogen, hydroxy, ($C_1$-$C_6$)alkyl, halo($C_1$-$C_6$)alkyl, ($C_2$-$C_8$)alkenyl, ($C_2$-$C_8$)alkynyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —NH($C_1$-$C_6$) alkyl, —C(O)($C_1$-$C_6$)alkyl, —C(O)O($C_1$-$C_6$)alkyl, —C(O)NH$_2$, —C(O)NH($C_1$-$C_6$)alkyl, —C(O)N[($C_1$-$C_6$)alkyl]$_2$ and —C(O)NHS(O)$_2$($C_1$-$C_6$)alkyl;

($C_6$-$C_{10}$)aryl is unsubstituted or substituted with one or more groups independently selected from the group consisting of halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —C(O)O($C_1$-$C_6$)alkyl, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

In an embodiment, the compound of Formula I encompasses a compound of Formula Ic or a stereoisomer, a tautomer, a pharmaceutically acceptable salt, a pharmaceutically acceptable solvate, a prodrug, an N-oxide, a S-oxide or a carboxylic acid isostere thereof;

wherein, Y is —COOH;

Ring B is a 5-membered heteroaryl selected from the group consisting of

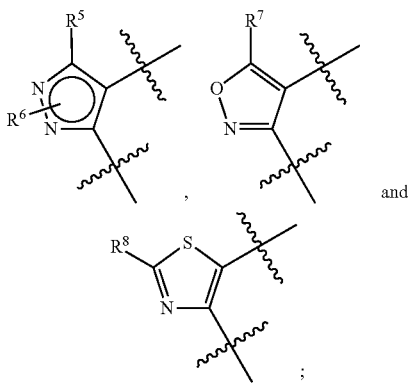

provided that when Ring B is pyrazolyl and R$^6$ is attached on nitrogen atom of pyrazolyl ring then R$^6$ is selected from the group consisting of

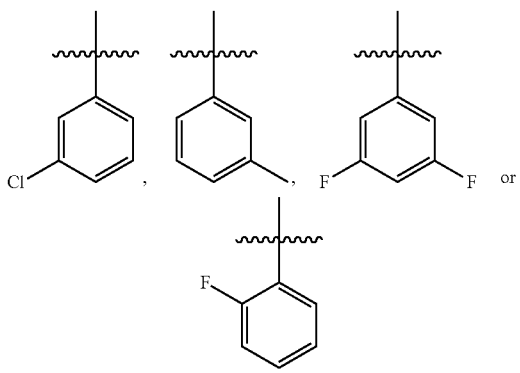

wherein

ξ is point of attachment to nitrogen atom of pyrazolyl ring;

R$^5$ is hydrogen, $(C_1-C_6)$alkyl, —O—$(C_1-C_6)$alkyl, $(C_6-C_{10})$aryl, heteroaryl or —S(R$^a$)$_m$, wherein R$^a$ is hydrogen or $(C_1-C_6)$alkyl;

R$^6$ is hydrogen or $(C_6-C_{10})$aryl;

R$^7$ is hydrogen, $(C_1-C_6)$alkyl and —O—$(C_1-C_6)$alkyl;

R$^8$ is —NR$^a$R$^b$; wherein R$^a$ and R$^b$ are hydrogen or $(C_1-C_6)$alkyl;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;

$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)O$(C_1-C_6)$alkyl, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

In an embodiment, the compound of Formula I encompasses a compound of Formula Ic or a stereoisomer, a tautomer, a pharmaceutically acceptable salt, a pharmaceutically acceptable solvate, a prodrug, an N-oxide, a S-oxide or a carboxylic acid isostere thereof;

wherein, Y is —COOR'; wherein R' is hydrogen or $(C_1-C_6)$alkyl, wherein $(C_1-C_6)$alkyl is unsubstituted or substituted with $(C_6-C_{10})$aryl;

Ring B is

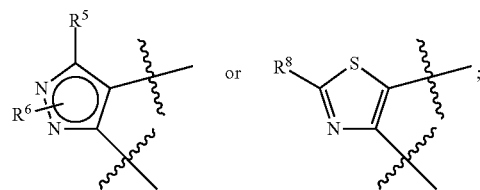

provided that when Ring B is pyrazolyl and R$^6$ is attached on nitrogen atom of pyrazolyl ring then R$^6$ is selected from the group consisting of

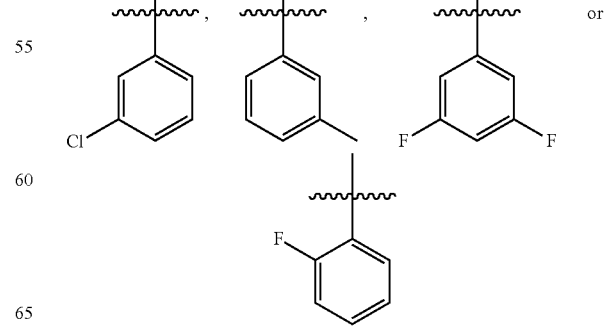

wherein

† is point of attachment to nitrogen atom of pyrazolyl ring;

$R^5$ is hydrogen, $(C_1-C_6)$alkyl, $(C_6-C_{10})$aryl, heteroaryl or —$S(R^a)_m$, wherein $R^a$ is hydrogen or $(C_1-C_6)$alkyl;

$R^6$ is hydrogen or $(C_6-C_{10})$aryl;

$R^8$ is —$NR^aR^b$; wherein $R^a$ and $R^b$ are hydrogen or $(C_1-C_6)$alkyl;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;

$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)O$(C_1-C_6)$alkyl, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —C(O)NR$^a$R$^b$ and —S(O)$_2$R$^a$; wherein R$^a$ and R$^b$ are as defined above and halogen is selected from chlorine, bromine, iodine and fluorine.

In an embodiment, the compound of Formula I encompasses a compound of Formula Ic or a stereoisomer, a tautomer, a pharmaceutically acceptable salt, a pharmaceutically acceptable solvate, a prodrug, an N-oxide, a S-oxide or a carboxylic acid isostere thereof;

wherein, Y is —COOR'; wherein R' is hydrogen or $(C_1-C_6)$alkyl, wherein $(C_1-C_6)$alkyl is unsubstituted or substituted with $(C_6-C_{10})$aryl;

Ring B is

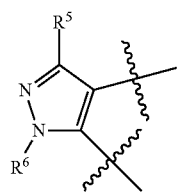

provided that when Ring B is pyrazolyl and $R^6$ is attached on nitrogen atom of pyrazolyl ring then $R^6$ is selected from the group consisting of

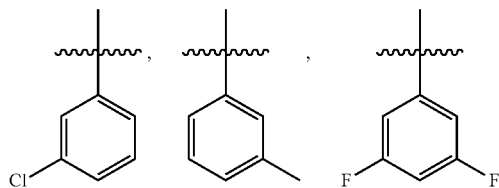

-continued

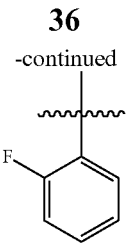

wherein

† is point of attachment to nitrogen atom of pyrazolyl ring;

$R^5$ is hydrogen, $(C_1-C_6)$alkyl, $(C_6-C_{10})$aryl, heteroaryl or —$S(R^a)_m$, wherein $R^a$ is hydrogen or $(C_1-C_6)$alkyl;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;

$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})_{aryl}$, heterocyclyl, heteroaryl, cyano, amino, —C(O)O$(C_1-C_6)$alkyl, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —C(O)NR$^a$R$^b$ and —S(O)$_2$R$^a$; wherein R$^a$ and R$^b$ are as defined above and halogen is selected from chlorine, bromine, iodine and fluorine.

In an embodiment, the compound of Formula I encompasses a compound of Formula Ic or a stereoisomer, a tautomer, a pharmaceutically acceptable salt, a pharmaceutically acceptable solvate, a prodrug, an N-oxide, a S-oxide or a carboxylic acid isostere thereof;

wherein, Y is —COOR'; wherein R' is hydrogen or $(C_1-C_6)$alkyl, wherein $(C_1-C_6)$alkyl is unsubstituted or substituted with $(C_6-C_{10})$aryl;

Ring B is

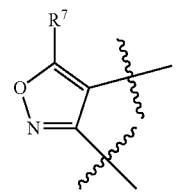

$R^7$ is hydrogen, $(C_1-C_6)$alkyl or —O—$(C_1-C_6)$alkyl;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$alkyl, —O—$(C_1-C_6)$haloalkyl, $(C_3-C_{10})$cycloalkyl, ($C_6$-$C_{10}$)aryl, heterocyclyl, heteroaryl, cyano, amino, —NH($C_1$-$C_6$)alkyl, —N[($C_1$-$C_6$)alkyl]$_2$, —C(O)($C_1$-$C_6$)alkyl, —C(O)O($C_1$-$C_6$)alkyl, —C(O)NH$_2$, —C(O)NH($C_1$-$C_6$)alkyl, —C(O)N[($C_1$-$C_6$)alkyl]$_2$ and —C(O)NHS(O)$_2$($C_1$-$C_6$)alkyl;

and halogen is selected from chlorine, bromine, iodine and fluorine.

In an embodiment, the present invention relates to a compound of Formula I,

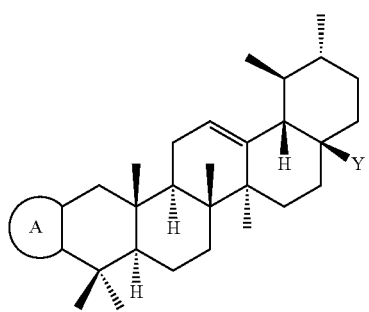

Formula I or a stereoisomer, a tautomer, a pharmaceutically acceptable salt, a pharmaceutically acceptable solvate, a prodrug, an N-oxide, a S-oxide or a carboxylic acid isostere thereof for use in the treatment of a disease or a disorder mediated by RORγ or IL-17;

Y is —COOR'; wherein R' is hydrogen or ($C_1$-$C_6$)alkyl, wherein ($C_1$-$C_6$)alkyl is unsubstituted or substituted with ($C_6$-$C_{10}$)aryl;

Ring A is 5- to 14-membered heteroaryl selected from the group consisting of pyrimidinyl, pyridyl, quinazolinyl, pyrazolyl, isoxazolyl and thiazolyl;

wherein, said pyrimidinyl, pyridyl, quinazolinyl, pyrazolyl, isoxazolyl or thiazolyl is unsubstituted or substituted with one or more groups of R; wherein R is selected from the group consisting of hydrogen, halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$)cycloalkyl, 3- to 10-membered heterocyclyl, ($C_6$-$C_{10}$)aryl, 5- to 14-membered heteroaryl, cyano, amino, —O—($C_6$-$C_{10}$)aryl, —OR$^a$, —C(O)R$^a$, —C(O)OR$^a$, —CH=NOH, —C(O)NH$_2$, —C(O)NR$^a$R$^b$, —SR$^a$, —S(O)$_m$R$^a$, —S(O)$_m$NR$^a$R$^b$, —S(O)(NH)R$^a$, —N[($C_1$-$C_6$)alkyl]R$^a$, —N[($C_1$-$C_6$)alkyl]$_2$, —NHR$^a$, —N(R$^a$)—C(O)R$^a$, —N(R$^a$)—C(O)NR$^a$R$^b$ and —NR$^a$R$^b$;

or two R groups present on adjacent carbon atoms of the ring A combine together to form an optionally substituted unsaturated or saturated carbocycle optionally containing one or two heteroatoms independently selected from the group consisting of N, O and S;

R$^a$ and R$^b$ are independently selected from the group consisting of hydrogen, halogen, hydroxy, ($C_1$-$C_6$)alkyl, halo($C_1$-$C_6$)alkyl, —O—($C_1$-$C_6$)alkyl, ($C_3$-$C_{10}$)cycloalkyl, 3- to 10-membered heterocyclyl, ($C_6$-$C_{10}$)aryl, 5- to 14-membered heteroaryl; or R$^a$ and R$^b$ together with the nitrogen to which they are attached, can combine to form a 3- to 10-membered saturated or unsaturated heterocyclyl which contains one or two heteroatoms independently selected from the group consisting of N, O and S;

m is 1 or 2;

wherein:
($C_1$-$C_6$)alkyl is unsubstituted or substituted with one or more groups independently selected from the group consisting of halogen, hydroxy, ($C_1$-$C_6$)alkyl, halo($C_1$-$C_6$)alkyl, ($C_2$-$C_8$)alkenyl, ($C_2$-$C_8$)alkynyl, —O—($C_1$-$C_6$)alkyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —NH($C_1$-$C_6$)alkyl, —C(O)($C_1$-$C_6$)alkyl, —C(O)OR$^a$, —C(O)NH$_2$, —C(O)NR$^a$R$^b$, —C(O)N[($C_1$-$C_6$)alkyl]$_2$ and —C(O)NHS(O)$_2$($C_1$-$C_6$)alkyl;

($C_3$-$C_{10}$)cycloalkyl is unsubstituted or substituted with one or more groups independently selected from the group consisting of halogen, hydroxy, ($C_1$-$C_6$)alkyl, halo($C_1$-$C_6$)alkyl, —O—($C_1$-$C_6$)alkyl, —O—($C_1$-$C_6$) haloalkyl, amino and cyano;

carbocycle is 3- to 12-membered ring which is unsubstituted or substituted with one or more groups independently selected from the group consisting of ($C_1$-$C_6$) alkyl, halo($C_1$-$C_6$)alkyl, hydroxy, halogen, ($C_1$-$C_6$) alkoxy, halo($C_1$-$C_6$)alkoxy, ($C_6$-$C_{10}$)aryl, ($C_3$-$C_{10}$) cycloalkyl, heteroaryl, heterocyclyl, cyano, amino, —C(O)O($C_1$-$C_6$)alkyl, —C(O)NR$^a$R$^b$ and —S(O)$_2$R$^a$; wherein R$^a$ and R$^b$ are as defined above;

($C_6$-$C_{10}$)aryl is unsubstituted or substituted with one or more groups independently selected from the group consisting of halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$)cycloalkyl, ($C_6$-$C_{10}$)aryl, heterocyclyl, heteroaryl, cyano, amino, —C(O)O($C_1$-$C_6$)alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, ($C_1$-$C_6$)alkyl, halo($C_1$-$C_6$)alkyl, —O—($C_1$-$C_6$)alkyl, —O—($C_1$-$C_6$)haloalkyl, ($C_3$-$C_{10}$) cycloalkyl, ($C_6$-$C_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, ($C_1$-$C_6$)alkyl, halo($C_1$-$C_6$)alkyl, —O—($C_1$-$C_6$)alkyl, —O—($C_1$-$C_6$)haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

The compounds of Formula I as described herein encompass one or more embodiments of the present invention. Accordingly, the embodiments of the present invention described herein are illustrative of the present invention and are not intended to limit to the specific embodiments exemplified. Thus, the invention contemplates all possible combinations and permutations of the various independently described embodiments.

Representative compounds of Formula I encompassed in accordance with the present invention include:

(1S,2R,4aS,6aS,6bR,8aR,14aR,14bR,16bS)-ethyl 13-hydroxy-11-mercapto-1,2,6a, 6b,9,9, 14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-hydroxy-11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-ethyl 13-hydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,
  12,14a-octamethyl-1,2,3,4,4a,5,6,6a,6b,7,8,8a,9,14,14a,
  14b,15,16b-octadecahydrochryseno[1,2-g]quinoline-4a-
  carboxylic acid;
(1S,2R,4aS,6aS,6bR,8aR,14aR,14bR,16bS)-1,2,6a,6b,9,9,
  14a-heptamethyl-1,2,3,4,4a, 5,6,6a,6b,7,8,8a,9,14,14a,
  14b,15,16b-octadecahydrochryseno[1,2-g]quinoline-4a-
  carboxylic acid;
(1S,2R,4aS,6aS,6bR,8aR,14aR,14bR,16bS)-1,2,6a,6b,9,9,
  14a-heptamethyl-1,2,3,4,4a,5,6,6a,6b,7,8,8a,9,14,14a,
  14b,15,16b-octadecahydrochryseno[1,2-g]quinoline-4a,
  12-dicarboxylic acid;
(1S,2R,4aS,6aS,6bR,8aR,14aR,14bR,16bS)-12-(methoxy-
  carbonyl)-1,2,6a,6b,9,9,14a-heptamethyl-1,2,3,4,4a,5,6,
  6a,6b,7,8,8a,9,14,14a,14b,15,16b-octadecahydrochry-
  seno[1,2-g]quinoline-4a-carboxylic acid;
(1S,2R,4aS,6aS,6bR,8aR,14aR,14bR,16bS)-12-carbamoyl-
  1,2,6a,6b,9,9,14a-heptamethyl-1,2,3,4,4a,5,6,6a,6b,7,8,
  8a,9,14,14a,14b,15,16b-octadecahydrochryseno[1,2-g]
  quinoline-4a-carboxylic acid;
(1S,2R,4aS,6aS,6bR,8aR,14aR,14bR,16bS)-1,2,6a,6b,9,9,
  14a-heptamethyl-12-(methylcarbamoyl)-1,2,3,4,4a,5,6,
  6a,6b,7,8,8a,9,14,14a,14b,15,16b-octadecahydrochry-
  seno [1,2-g]quinoline-4a-carboxylic acid;
(1S,2R,4aS,6aS,6bR,8aR,14aR,14bR,16bS)-12-cyano-11-
  ethoxy-1,2,6a,6b,9,9,14a-heptamethyl-1,2,3,4,4a,5,6,6a,
  6b,7,8,8a,9,14,14a,14b,15,16b-octadecahydrochryseno[1,
  2-g]quinoline-4a-carboxylic acid;
(1S,2R,4aS,6aS,6bR,8aR,14aR,14bR,16bS)-11-chloro-12-
  cyano-1,2,6a,6b,9,9, 14a-heptamethyl-1,2,3,4,4a,5,6,6a,
  6b,7,8,8a,9,14,14a,14b,15,16b-octadecahydrochryseno[1,
  2-g]quinoline-4a-carboxylic acid;
(1S,2R,4aS,6aS,6bR,8aR,15aR,15bR,17bS)-1,2,6a,6b,9,9,
  15a-heptamethyl-1,2,3,4,4a,5,6,6a,6b,7,8,8a,9,15,15a,
  15b,16,17b-octadecahydrochryseno[1,2-g]isoxazolo[5,4-
  b]quinoline-4a-carboxylic acid;
(1S,2R,4aS,6aS,6bR,8aR,14aR,14bR,16bS)-13-hydroxy-1,
  2,6a,6b,9,9,14a-heptamethyl-1,2,3,4,4a,5,6,6a,6b,7,8,8a,
  9,14,14a,14b,15,16b-octadecahydrochryseno[1,2-g]qui-
  nazoline-4a-carboxylic acid;
(1S,2R,4aS,6aS,6bR,8aR,14aR,14bR,16bS)-1,2,6a,6b,9,9,
  14a-heptamethyl-1,2,3,4,4a,5,6,6a,6b,7,8,8a,9,14,14a,
  14b,15,16b-octadecahydrochryseno[1,2-g]quinazoline-
  4a-carboxylic acid;
(1S,2R,4aS,6aS,6bR,8aR,14aR,14bR,16bS)-11,13-dihy-
  droxy-1,2,6a,6b,9,9,14a-heptamethyl-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-1,2,6a,6b,9,9,
  14a-heptamethyl-13-(piperidin-1-yl)-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-1,2,6a,6b,9,9,
  14a-heptamethyl-13-morpholino-1,2,3,4,4a,5,6,6a,6b,7,
  8,8a,9,14,14a,14b,15,16b-octadecahydrochryseno[1,2-g]
  quinazoline-4a-carboxylic acid;
(1S,2R,4aS,6aS,6bR,8aR,14aR,14bR,16bS)-1,2,6a,6b,9,9,
  14a-heptamethyl-13-(4-methylpiperazin-1-yl)-1,2,3,4,4a,
  5,6,6a,6b,7,8,8a,9,14,14a,14b,15,16b-octadecahydro
  chryseno[1,2-g]quinazoline-4a-carboxylic acid;
(1S,2R,4aS,6aS,6bR,8aR,14aR,14bR,16bS)-1,2,6a,6b,9,9,
  14a-heptamethyl-13-(piperazin-1-yl)-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-1,2,6a,6b,9,9,
  14a-heptamethyl-13-(pyrrolidin-1-yl)-1,2,3,4,4a,5,6,6a,
  6b,7,8,8a,9,14,14a,14b,15,16b-octadecahydrochryseno
  [1,2-g]quinazoline-4a-carboxylic acid;
(1S,2R,4aS,6aS,6bR,8aR,14aR,14bR,16bS)-13-methoxy-1,
  2,6a,6b,9,9,14a-hepta methyl-1,2,3,4,4a,5,6,6a,6b,7,8,8a,
  9,14,14a,14b,15,16b-octadecahydrochryseno[1,2-g]qui-
  nazoline-4a-carboxylic acid;
(1S,2R,4aS,6aS,6bR,8aR,14aR,14bR,16bS)-1,2,6a,6b,9,9,
  14a-heptamethyl-13-(methylamino)-1,2,3,4,4a,5,6,6a,6b,
  7,8,8a,9,14,14a,14b,15,16b-octadecahydrochryseno[1,2-
  g]quinazoline-4a-carboxylic acid;
(1S,2R,4aS,6aS,6bR,8aR,14aR,14bR,16bS)-13-(dimethyl-
  amino)-1,2,6a,6b,9,9,14a-heptamethyl-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-1,2,6a,6b,9,9,
  14a-heptamethyl-13-((2-morpholinoethyl)amino)-1,2,3,
  4,4a,5,6,6a,6b,7,8,8a,9,14,14a,14b,15,16b-octadecahydro
  chryseno[1,2-g]quinazoline-4a-carboxylic acid;
(1S,2R,4aS,6aS,6bR,8aR,14aR,14bR,16bS)-13-hydroxy-1,
  2,6a,6b,9,9,11,14a-octa methyl-1,2,3,4,4a,5,6,6a,6b,7,8,
  8a,9,14,14a,14b,15,16b-octadecahydrochryseno[1,2-g]
  quinazoline-4a-carboxylic acid;
(1S,2R,4aS,6aS,6bR,8aR,14aR,14bR,16bS)-13-methoxy-1,
  2,6a,6b,9,9,11,14a-octamethyl-1,2,3,4,4a,5,6,6a,6b,7,8,
  8a,9,14,14a,14b,15,16b-octadecahydrochryseno[1,2-g]
  quinazoline-4a-carboxylic acid;
(1S,2R,4aS,6aS,6bR,8aR,14aR,14bR,16bS)-13-ethoxy-1,2,
  6a,6b,9,9,11,14a-octamethyl-1,2,3,4,4a,5,6,6a,6b,7,8,8a,
  9,14,14a,14b,15,16b-octadecahydrochryseno[1,2-g]qui-
  nazoline-4a-carboxylic acid;
(1S,2R,4aS,6aS,6bR,8aR,14aR,14bR,16bS)-13-(dimethyl-
  amino)-1,2,6a,6b,9,9,11,14a-octamethyl-1,2,3,4,4a,5,6,
  6a,6b,7,8,8a,9,14,14a,14b,15,16b-octadecahydrochry-
  seno[1,2-g]quinazoline-4a-carboxylic acid;
(1S,2R,4aS,6aS,6bR,8aR,14aR,14bR,16bS)-1,2,6a,6b,9,9,
  11,14a-octamethyl-13-(methylamino)-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-13-(diethyl-
  amino)-1,2,6a,6b,9,9,11,14a-octamethyl-1,2,3,4,4a,5,6,
  6a,6b,7,8,8a,9,14,14a,14b,15,16b-octadecahydrochry-
  seno[1,2-g]quinazoline-4a-carboxylic acid;
(1S,2R,4aS,6aS,6bR,8aR,14aR,14bR,16bS)-1,2,6a,6b,9,9,
  11,14a-octamethyl-13-(pyrrolidin-1-yl)-1,2,3,4,4a,5,6,6a,
  6b,7,8,8a,9,14,14a,14b,15,16b-octadecahydrochryseno
  [1,2-g]quinazoline-4a-carboxylic acid;
(1S,2R,4aS,6aS,6bR,8aR,14aR,14bR,16bS)-1,2,6a,6b,9,9,
  11,14a-octamethyl-13-(piperidin-1-yl)-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-1,2,6a,6b,9,9,
  11,14a-octamethyl-13-(4-methylpiperazin-1-yl)-1,2,3,4,
  4a,5,6,6a,6b,7,8,8a,9,14,14a,14b,15,16b-octadecahydro-
  chryseno[1,2-g]quinazoline-4a-carboxylic acid;
(1S,2R,4aS,6aS,6bR,8aR,14aR,14bR,16bS)-13-(cyclohexy-
  lamino)-1,2,6a,6b,9,9,11,14a-octamethyl-1,2,3,4,4a,5,6,
  6a,6b,7,8,8a,9,14,14a,14b,15,16b-octadecahydrochry-
  seno[1,2-g]quinazoline-4a-carboxylic acid;
(1S,2R,4aS,6aS,6bR,8aR,14aR,14bR,16bS)-1,2,6a,6b,9,9,
  11,14a-octamethyl-13-(piperazin-1-yl)-1,2,3,4,4a,5,6,6a,
  6b,7,8,8a,9,14,14a,14b,15,16b-octadecahydrochryseno[1,
  2-g]quinazoline-4a-carboxylic acid;
(1S,2R,4aS,6aS,6bR,8aR,14aR,14bR,16bS)-1,2,6a,6b,9,9,
  11,14a-octamethyl-13-morpholino-1,2,3,4,4a,5,6,6a,6b,7,
  8,8a,9,14,14a,14b,15,16b-octadecahydrochryseno[1,2-g]
  quinazoline-4a-carboxylic acid;

(1S,2R,4aS,6aS,6bR,8aR,14aR,14bR,16bS)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-11-((2-carboxyethyl)amino)-1,2,6a,6b, 9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-11-((2-methoxyphenoxy)methyl)-1,2,6a,6b,9,9,14a-heptamethyl-1,2,3,4,4a,5,6,6a,6b,7,8,8a,9,14,14a,14b,15,16b-octadeca hydro chryseno[1,2-g]quinazoline-4a-carboxylic acid;

(1S,2R,4aS,6aS,6bR,8aR,14aR,14bR,16bS)-11-amino-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-11-phenyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-11-morpholino-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-11-(1H-pyrazol-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 11-(ethylthio)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,14a-heptamethyl-11-(methylsulfonyl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR)-11-(ethylsulfonyl)-1,2,6a,6b,9,9,14a-hepta methyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,16aR,16bR,18bS)-1,2,6a,6b,9,9,16a-heptamethyl-1,2,3,4,4a,5,6,6a,6b,7,8,8a,9,16,16a,16b,17,18b-octadecahydrochryseno[1,2-b]acridine-4a-carboxylic acid;

(1S,2R,4aS,6aS,6bR,8aR,16aR,16bR,18bS)-1,2,6a,6b,9,9,16a-heptamethyl-15-((3-morpholinopropyl)amino)-1,2,3,4,4a,5,6,6a,6b,7,8,8a,9,16,16a,16b,17,18b-octadecahydrochryseno[1,2-b]acridine-4a-carboxylic acid;

(1S,2R,4aS,6aS,6bR,8aR,16aR,16bR,18bS)-15-amino-1,2,6a,6b,9,9,16a-heptamethyl-1,2,3,4,4a,5,6,6a,6b,7,8,8a,9,16,16a,16b,17,18b-octadecahydrochryseno[1,2-b]acridine-4a-carboxylic acid;

(1S,2R,4aS,6aS,6bR,8aR,16aR,16bR,18bS)-1,2,6a,6b,9,9,16a-heptamethyl-15-phenoxy-1,2,3,4,4a,5,6,6a,6b,7,8,8a,9,16,16a,16b,17,18b-octadecahydrochryseno[1,2-b]acridine-4a-carboxylic acid;

(1S,2R,4aS,6aS,6bR,8aR,14aR,14bR,16bS)-11-cyclopropyl-1,2,6a,6b,9,9,14a-hepta methyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-hydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl, 11,13-dihydroxy-1,2,6a,6b,9,9,14a heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-ethyl 11,13-dihydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylic acid hydrochloride;

(1S,2R,4aS,6aS,6bR,8aR,14aR,14bR,16bS)-benzyl 1,2,6a,6b,9,9,14a-heptamethyl-13-(4-methylpiperazin-1-yl)-1,2,3,4,4a,5,6,6a,6b,7,8,8a,9,14,14a,14b,15,16b-octadecahydro chryseno[1,2-g]quinazoline-4a-carboxylate;

(1S,2R,4aS,6aS,6bR,8aR,14aR,14bR,16bS)-benzyl 13-(4-((benzyloxy)carbonyl)piperazin-1-yl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,14a-heptamethyl-13-(piperazin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 1,2,6a,6b,9,9,14a-heptamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylate;

(1S,2R,4aS,6aS,6bR,8aR,14aR,14bR,16bS)-benzyl 13-methoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-13-(methylamino)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(dimethylamino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-hydroxy-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-(dimethylamino)-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylic acid hydrochloride;

(1S,2R,4aS,6aS,6bR,8aR,14aR,14bR,16bS)-benzyl 1,2,6a,6b,9,9,11,14a-octamethyl-13-(methylamino)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

1,2,6a,6b,9,9,14a-heptamethyl-13-((2-morpholinoethyl)amino)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-methoxy-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-ethoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(diethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylate;

(1S,2R,4aS,6aS,6bR,8aR,14aR,14bR,16bS)-11-((2-carboxyethyl)amino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 11-((2-methoxyphenoxy)methyl)-1,2,6a, 6b,9,9,14a-heptamethyl-1,2,3,4,4a,5,6,6a,6b,7,8,8a,9,14,14a,14b,15,16b-octadecahydro chryseno[1,2-g]quinazoline-4a-carboxylate;

(1S,2R,4aS,6aS,6bR,8aR,14aR,14bR,16bS)-benzyl 11-amino-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 11-cyclopropyl-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 11-(ethylsulfonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR)-11-(ethylsulfonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 1,2,6a,6b,9,9,11,14a-octamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-13-(4-methylpiperazin-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(cyclohexylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-11-phenyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-11-morpholino-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(4-((benzyloxy)carbonyl) piperazin-1-yl)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-13-morpholino-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-11-(1H-pyrazol-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 11-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate;

(1S,2R,4aS,6aS,6bR,8aR,14aR,14bR,16bS)-benzyl 11-chloro-12-(hydroxymethyl)-1,2,6a,6b,9,9,14a-heptamethyl-1,2,3,4,4a,5,6,6a,6b,7,8,8a,9,14,14a,14b,15,16b octadecahydrochryseno[1,2-g]quinoline-4a-carboxylate;

(1S,4aS,6aS,6bR,8aR,14aR,14bR,16bS)-12-(hydroxymethyl)-1,6a,6b,9,9,14a-hexamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-4a-((benzyloxy)carbonyl)-11-chloro-1,2,6a,6b,9,9,14a-heptamethyl-1,2,3,4,4a,5,6,6a,6b,7,8,8a,9,14,14a,14b,15,16b-octadecahydrochryseno [1,2-g]quinoline-12-carboxylic acid;

(1S,2R,4aS,6aS,6bR,8aR,16aR,16bR,18bS)-benzyl 15-chloro-1,2,6a,6b,9,9,16a-heptamethyl-1,2,3,4,4a,5,6,6a,6b,7,8,8a,9,16,16a,16b,17,18b-octadecahydrochryseno[1,2-b]acridine-4a-carboxylate;

(1S,2R,4aS,6aS,6bR,8aR,16aR,16bR,18bS)-15-amino-1,2,6a,6b,9,9,16a-heptamethyl-1,2,3,4,4a,5,6,6a,6b,7,8,8a,9,16,16a,16b,17,18b-octadecahydrochryseno[1,2-b]acridine-4a-carboxylic acid;

(1S,2R,4aS,6aS,6bR,13aR,13bR)-10-(2-fluorophenyl)-1,2,6a,6b,9,9,13a-heptamethyl-2,3,4,4a,5,6,6a,6b,7,8,8a,9,10,13,13a,13b,14,15b-octadecahydro-1H-chryseno[1,2-f]indazole-4a-carboxylic acid;

(1S,2R,4aS,6aS,6bR,13aR,13bR)-10-(3,5-difluorophenyl)-1,2,6a,6b,9,9,13a-heptamethyl-2,3,4,4a,5,6,6a,6b,7,8,8a,9,10,13,13a,13b,14,15b-octadecahydro-1H-chryseno[1,2-f]indazole-4a-carboxylic acid;

(1S,2R,4aS,6aS,6bR,8aR,14aR,14bR,16bS)benzyl 11chloro12((hydroxyimino)methyl)1,2,6a,6b,9,9,14aheptamethyl1,2,3,4,4a,5,6,6a,6b,7,8,8a,9,14,14a,14b,15,
16boctadecahydrochryseno[1,2-g]quinoline-4a-carboxy-
late;
(1S,2R,4aS,6aS,6bR,8aR,14aR,14bR,16bS)-benzyl
11-chloro-1,2,6a,6b,9,9,14a-heptamethyl-12-(methylcar-
bamoyl)1,2,3,4,4a,5,6,6a,6b,7,8,8a,9,14,14a,14b,15,16b-
octadecahydro chryseno[1,2-g]quinoline-4a-carboxylate;
(1S,2R,4aS,6aS,6bR,8aR,14aR,14bR,16bS)-benzyl 12-car-
bamoyl-11-chloro-1,2,6a,6b,9,9,14a-heptamethyl-1,2,3,
4,4a,5,6,6a,6b,7,8,8a,9,14,14a,14b,15,16b-octadecahy-
drochryseno[1,2-g]quinoline-4a-carboxylate;
(1S,2R,4aS,6aS,6bR,8aR,14aR,14bR,16bS)-1,2,3,4,4a,5,6,
6a,6b,7,8,8a,9,14,14a,14b,15,16b-octadecahydro-1,2,6a,
6b,9,9,14a-heptamethylchryseno[1,2-g]quinoline-4a,12-
dicarboxylic acid;
(1S,2R,4aS,6aS,6bR,8aR,15aR,15bR,17bS)-benzyl,1,2,6a,
6b,9,9,15a-heptamethyl-1,2,3,4,4a,5,6,6a,6b,7,8,8a,9,15,
15a,15b,16,17b-octadecahydrochryseno[1,2-g]isoxazolo
[5,4-b]quinoline-4a-carboxylate;
(1S,2R,4aS,6aS,6bR,8aR,14aR,14bR,16bS)-benzyl
11-chloro-12-cyano-1,2,6a,6b,9,9,14a-heptamethyl-1,2,3,
4,4a,5,6,6a,6b,7,8,8a,9,14,14a,14b,15,16b-octadecahy-
drochryseno[1,2-g]quinoline-4a-carboxylate;
(1S,2R,4aS,6aS,6bR,8aR,14aR,14bR,16bS)-benzyl
12-cyano-11-ethoxy-1,2,6a,6b,9,9,14a-heptamethyl-1,2,
3,4,4a,5,6,6a,6b,7,8,8a,9,14,14a,14b,15,16b-octadecahy-
drochryseno[1,2-g]quinoline-4a-carboxylate;
(1S,2R,4aS,6aS,6bR,8aR,16aR,16bR,18bS)-benzyl 1,2,6a,
6b,9,9,16a-heptamethyl-15-((3-morpholinopropyl)
amino)-1,2,3,4,4a,5,6,6a,6b,7,8,8a,9,16,16a,16b,17,18b-
octadecahydro chryseno[1,2-b]acridine-4a-carboxylate;
(1S,2R,4aS,6aS,6bR,8aR,16aR,16bR,18bS)-benzyl 1,2,6a,
6b,9,9,16a-heptamethyl-15-phenoxy-1,2,3,4,4a,5,6,6a,
6b,7,8,8a,9,16,16a,16b,17,18b-octadecahydrochryseno[1,
2-b]acridine-4a-carboxylate;
(1S,2R,4aS,6aS,6bR,13aR,13bR)-10-(3-chlorophenyl)-1,2,
6a,6b,9,9,13a-heptamethyl-2,3,4,4a,5,6,6a,6b,7,8,8a,9,
10,13,13a,13b,14,15b-octadecahydro-1H-chryseno[1,2-f]
indazole-4a-carboxylic acid;
(1S,2R,6aS,6bR,8aR,13aR,13bR)-methyl1,2,6a,6b,9,9,13a-
heptamethyl-12-(methylthio)-2,3,4,4a,5,6,6a,6b,7,8,8a,9,
11,13,13a,13b,14,15b-octadecahydro-1H-chryseno [1,2-
f]indazole-4a-carboxylate;
(1S,2R,6aS,6bR,8aR,13aR,13bR)-benzyl 12-(4-methoxy-
phenyl)-1,2,6a,6b,9,9,13a-heptamethyl-2,3,4,4a,5,6,6a,
6b,7,8,8a,9,11,12,12a,13,13a,13b,14,15b-icosahydro-1H-
chryseno[1,2-f]indazole-4a-carboxylate;
(1S,2R,4aS,6aS,6bR,13aR,13bR)-1,2,6a,6b,9,9,13a-hep-
tamethyl-10-(m-tolyl)-2,3,4,4a,5,6,6a,6b,7,8,8a,9,10,13,
13a,13b,14,15b-octadecahydro-1H-chryseno[1,2-f]inda-
zole-4a-carboxylic acid;
(1S,2R,6aS,6bR,8aR,13aR,13bR)-1,2,6a,6b,9,9,13a-hep-
tamethyl-1,2,3,4,4a,5,6,6a,6b,7,8,8a, 9,13,13a,13b,14,
15b-octadecahydropiceno[3,2-c]isoxazole-4a-carboxylic
acid;
(1S,2R,6aS,6bR,8aR,13aR,13bR)-benzyl 11-amino-1,2,6a,
6b,9,9,13a-heptamethyl-1,2,3,4,4a, 5,6,6a,6b,7,8,8a,9,13,
13a,13b,14,15b-octadecahydropiceno[3,2-d]thiazole-4a-
carboxylate;
or a stereoisomer, a tautomer, a pharmaceutically acceptable
salt or a solvate thereof;

The compounds of the present invention also include all
stereoisomeric and tautomeric forms and mixtures thereof in
all ratios and their pharmaceutically acceptable salts, phar-
maceutically acceptable solvates, prodrugs, N-oxides, S-ox-
ides or carboxylic acid isosteres thereof.

According to another aspect, the present invention pro-
vides processes for synthesis of the compounds of Formula
I or pharmaceutically acceptable salts thereof.

Thus, the compound(s) of Formula I can be prepared by
various methods including using methods well known to a
person skilled in the art. Examples of processes for the
present compounds are described as follows, and are par-
ticularly illustrated in Schemes 1, 2, 3 and 4. It will be
appreciated by persons skilled in the art that within certain
of the processes described herein, the order of the reaction
steps employed can be varied and will depend inter alia on
factors such as the nature of functional groups present in a
particular substrate (starting compounds and/or an interme-
diate) and the protecting group strategy (if any) to be
adopted.

One or more of the reagents, reactants and intermediates
used in the following processes are either commercially
available or can be prepared according to standard proce-
dures known in the art.

In the following schemes and the description of the
processes, the starting compounds and the intermediates
used for the synthesis of compounds of the present invention
are referred to by the symbols 1a, 1b, 1c, 1d, 1e, 1f, 1g, 1h,
1h, 1i, 1j and 1k, for the ease of reference.

Unless stated otherwise, throughout the process descrip-
tion, the corresponding substituent groups in the various
formulae representing starting compounds and/or interme-
diates have the same meaning as that of the compound of
Formula I as described in one or more embodiments of the
invention.

Processes for the preparation of the compounds of For-
mula 1 in one or more embodiments as described above, are
depicted in schemes 1, 2, 3 and 4, as presented herein below.

The compounds of the present invention were purified by
either flash chromatography (ISCO Combiflash® chroma-
tography instrument from Teledyne Isco, Inc.) or silica gel
column chromatography. Mass spectrometry (MS) was per-
formed using a Esquire 4000 Mass spectrometer (from
Bruker Daltonics), Nuclear magnetic resonance spectros-
copy (NMR) was performed using a Bruker Avance NMR
spectrometer (for the $^1$H NMR spectra acquired at 300 MHz
and 500 MHz) and the chemical shifts were reported in δ
(ppm).

The procedure(s) followed for the preparation of the
compounds of Formula I, designated as compounds 1A, 1B,
2A, 2B, 3A, 3B, 4A, 4B and so on, wherein Y is —COOR';
wherein R' is hydrogen or ($C_1$-$C_6$)alkyl, wherein ($C_1$-$C_6$)
alkyl is unsubstituted or substituted with ($C_6$-$C_{10}$) aryl, is
depicted in the following schemes and described herein as
follows.

Procedure A
Scheme 1
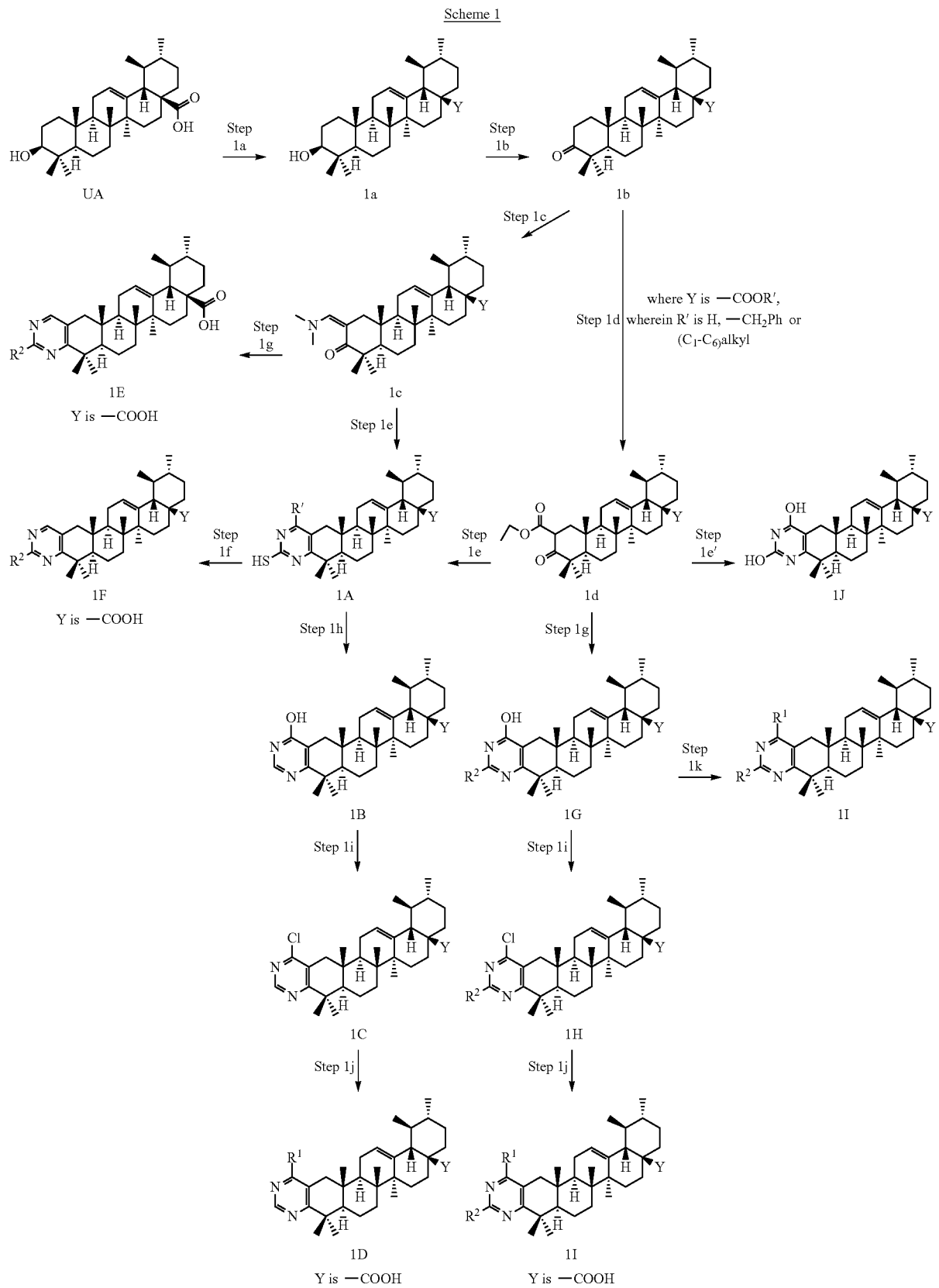

The reaction steps as outlined in the above Scheme 1 are described herein below:

Step 1a:

In this step of the process ursolic acid (UA) is converted to its corresponding ester (compound 1a) by treating UA with bromomethyl benzene in the presence of a base such as potassium carbonate, cesium carbonate and sodium hydride and a solvent such as dimethylformamide (DMF) or acetone at room temperature to obtain intermediate compound 1a.

Step 1b:

The intermediate compound 1b is prepared by Swern oxidation reaction using an oxidising agent such as pyridinium chlorochromate, 2-iodoxybenzoic acid, Dess-Martin periodinane (commercially available) in the presence of a solvent such as DCM, DMSO acetone or acetonitrile at room temperature to obtain intermediate compound 1b.

Step 1c:

In this step, the intermediate compound 1b is treated with 1,1-dimethoxy-N,N-dimethylmethanamine in the presence of a solvent such as toluene or DCM at a temperature in the range of 100-125° C. to obtain the intermediate compound 1c.

Step 1d:

In this step, the intermediate compound 1c is treated with 2-methylpropan-2-olate in the presence of a base such as sodium ethoxide, potassium tert-butoxide or sodium hydride and a solvent such as tetrahydrofuran (THF), DMF, ethanol, methanol or tert-butanol at a temperature in the range of 80–90° C. to obtain intermediate compound 1d.

Step 1e:

In this step, the intermediate compound 1d is treated with thiourea in the presence of a base such as sodium alkoxide, potassium tert-butoxide, sodium ethoxide or sodium hydride and a solvent such as ethanol, methanol or THF at a temperature in the range of 100-125° C. to obtain compound 1A (wherein $R^1$ is OH)

The compound 1A (wherein $R^1$ is H) is prepared by treating the intermediate compound 1c by treatment with thiourea in the presence of base such as sodium alkoxide, potassium tert-butoxide, sodium ethoxide or sodium hydride and a solvent such as ethanol, methanol or THF at a temperature in the range of 100-125° C.

Step 1e':

The compound 1d is converted to the compound 1J by following the procedure of step 1e using urea in place of thiourea to obtain the compound ester compound. The ester compound is subjected to hydrogenation using Pd/C as catalyst to obtain corresponding acid designated as compound 1J.

Step 1f:

In this step, the compound 1A ($R^1$ is H) is subjected to S-alkylation using an alkyl halide such as methyl iodide or ethyl iodide in the presence of a base such as potassium tert-butoxide, cesium carbonate, sodium hydride or triethylamine) and a solvent such as DCM, DMF, acetonitrile (ACN) or toluene to obtain ester compound. The ester compound is subjected to hydrogenation using Pd/C as catalyst to obtain corresponding acid compound 1F ($R^2$ is —$SR^a$, $R^a$ is alkyl group).

The ester compound obtained by alkylation reaction is subjected to oxidation using m-chloroperoxybenzoic acid (mCPBA) in the presence of a solvent such as DCM or DMSO at room temperature to obtain the ester compound 1F (wherein $R^2$ is —$SO_2R^a$ $R^a$ is ($C_1$-$C_6$)alkyl group). The ester compound is subjected to hydrogenation using Pd/C as catalyst to obtain corresponding acid compound 1F.

Step 1g:

The compound 1G is prepared from intermediate compound 1d by Pinner pyrimidine reaction using substituted amidine salt in the presence of base such as such as sodium ethoxide, sodium methoxide or potassium tert-butoxide and a solvent such as ethanol, methanol or THF) to obtain the desired ester compound. The ester compound is subjected to hydrogenation using Pd/C as catalyst to obtain corresponding acid compound 1G.

The compound 1E is prepared from the intermediate compound 1c by following the Pinner pyrimidine reaction as described above to obtain the corresponding ester compound. The ester compound is subjected to hydrogenation using Pd/C as catalyst to obtain corresponding acid designated as compound 1E.

Step 1h:

The compound 1A (wherein $R^1$ is OH) is subjected to reduction using Raney-Ni in the presence of a solvent such as ethanol, methanol or ethyl acetate at a temperature range of 40-60° C. to obtain the corresponding ester compound. The benzyl ester compound is subjected to hydrogenation using Pd/C as catalyst to obtain corresponding acid designated as compound 1B.

Step 1i:

The compound 1B is subjected to chlorination reaction using phosphorus oxychloride ($POCl_3$) in the presence of solvent such as DCM, DMF or chloroform at a temperature in the range of 100-125° C. to obtain the ester compound. The ester compound is subjected to hydrogenation using Pd/C as catalyst to obtain acid compound 1C.

The compound 1H is prepared from the compound 1G by the chlorination reaction using chlorinating agent followed by hydrogenation reaction using Pd/C as catalyst to obtain compound 1H.

Step 1j:

The compound 1C is treated with an organic amine reagent such as dimethylamine, methane amine, diethyl amine, pyrrolidine, piperidine, 1-methylpiperazine, cyclohexyl amine, tert-butyl piperazine-1-carboxylate or morpholine in presence of a solvent such as ethanol, methanol, ethyl acetate, THF, DCM, DMF or DMSO to obtain desired amino ester compound. The amino ester compound is subjected to hydrogenation using Pd/C as catalyst to obtain compound 1D.

The compound 1I (wherein $R^1$ and $R^2$ are independently selected from the group consisting of heterocyclyl, heteroaryl, amino, —$NH(C_1$-$C_6)$alkyl, —$N[(C_1$-$C_6)$alkyl]$R_a$, —$N[(C_1$-$C_6)$alkyl]_2$, —$NH(C_3$-$C_{10})$cycloalkyl, —$NHR_a$ and $NR_aR_b$) is prepared from compound 1H by following the same procedure using an organic amine reagent followed by hydrogenation using Pd/C as catalyst to obtain compound H.

Step 1k:

In this step, O-alkylation of the compound 1G using an alkylhalide such as methyl iodide or ethyl iodide in the presence of a base such as potassium tert-butoxide, cesium carbonate, sodium hydrideor triethylamine and a solvent such as DCM, DMF, ACN or toluene to obtain ester compound. The ester compound is subjected to hydrogenation using Pd/C as catalyst to obtain corresponding compound 1I.

Procedure B
Scheme 2
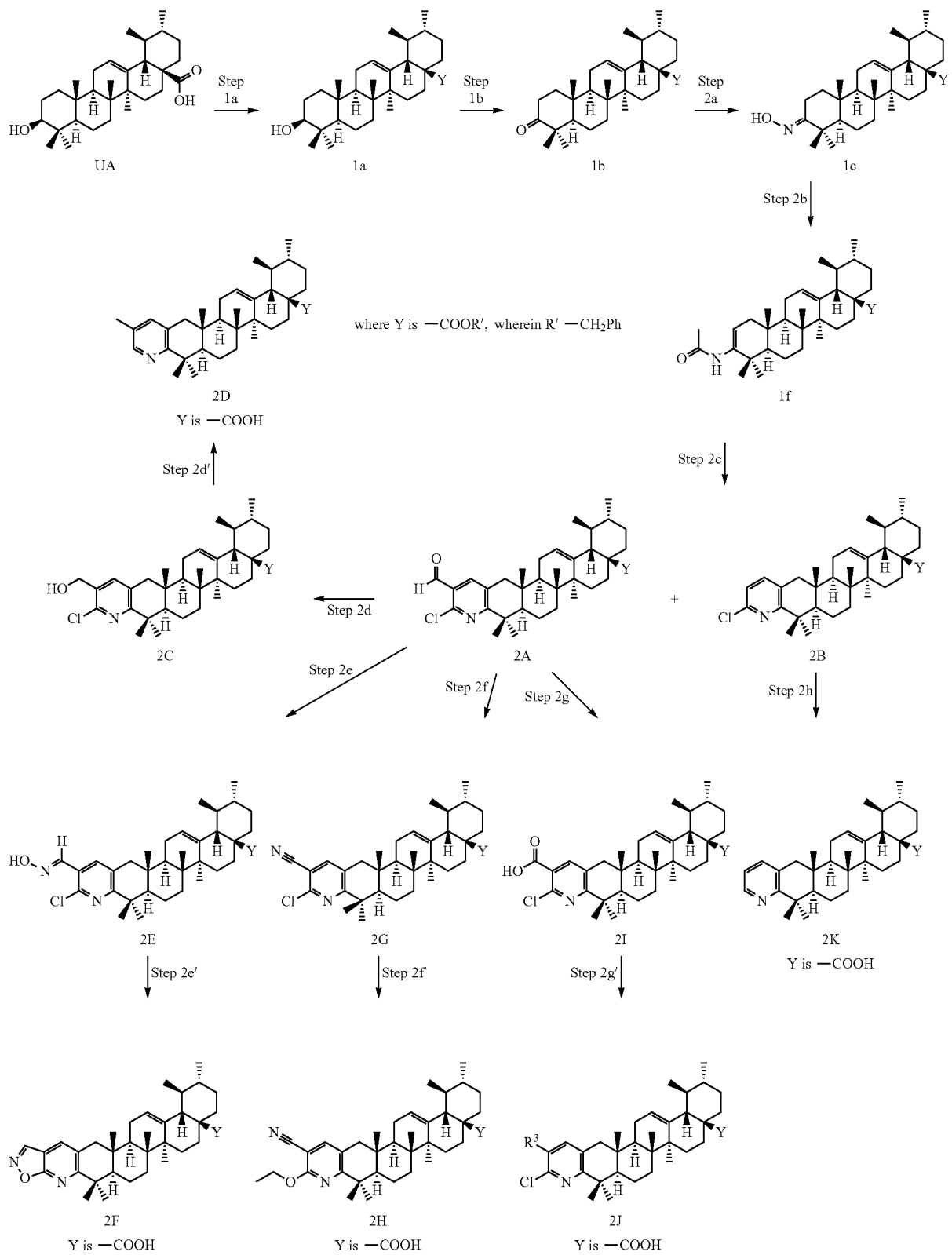

The reaction steps as outlined in the above scheme 2 are described herein below:

The compounds 1a and 1b are prepared by following the procedure of steps 1a and 1b as provided under scheme 1.

Step 2a:

The intermediate compound 1b is treated with hydroxylamine hydrochloride in presence of a solvent such as methanol, DCM, dichloroethane (DCE) or a mixture thereof at reflux temperature to obtain the intermediate compound 1e (wherein R' is as defined in the step 1a of the scheme 1).

Step 2b:

The intermediate compound 1e is converted to ene-amide compound if (wherein R' is as defined) using acetic anhydride, copper iodide, sodium bisulphite solution and a solvent such as DCE or DCM at a temperature in the range of 100-125 V, according to the method described in G. Zheng-Hui et al, Journal of Organic Chemistry, 2011. vol. 76 (1), 339-341).

Step 2c:

The intermediate compound if is subjected to Vilsmeier reaction, according to the method described in Indian Journal of Chemistry, vol. 38B, 1999, 274-282, using POCl₃ in the presence of solvent such as DMF or DCM to obtain a mixture of compound 2A and compound 2B. The compounds 2A and 2B are separated by column chromatography.

Step 2d:

The compound 2A is subjected to reduction using a reducing agent such as sodium borohydride or lithium aluminium hydride in the presence of a solvent such as ethanol, methanol or THF to obtain an ester compound. The ester compound is subjected to hydrogenation using Pd/C as catalyst to obtain compound 2D (Step 2d').

Step 2e:

The compound 2A is converted into the compound 2E using hydroxyl amine hydrochloride, a base such as triethylamine and a solvent such as methanol or ethanol.

Step 2e':

The compound 2E is subjected to alkylation using a base such as potassium carbonate in the presence of a solvent such as DMF or dioxane at a temperature in the range of 70-80 V to obtain an ester compound. The ester compound is subjected to hydrogenation using Pd/C as catalyst to obtain the corresponding acid compound 2F.

Step 2f:

The compound 2A is treated with ammonia in presence of catalytic amount of solid iodine and solvent (for example THF) at room temperature followed by hydrogenation using Pd/C as catalyst to obtain compound 2G.

Step 2f':

The benzyl ester of compound 2G is subjected to alkylation reaction using sodium alkoxide such as sodium ethoxide or sodium methoxide at reflux temperature followed by hydrogenation using Pd/C as catalyst to obtain compound 2H.

Step 2g:

The compound 2A is subjected to alkylation using a base such as potassium carbonate in the presence of a catalytic amount of solid iodine and methanol as solvent at room temperature followed by hydrolysis using lithium hydroxide in the presence of a solvent such as methanol, THF, or a mixture thereof at room temperature followed by hydrogenation using Pd/C as catalyst to obtain compound 21.

Step 2g':

The compound 21 is treated with a coupling agent such as CDI, BOP, PyBOP, N,N'-dicyclohexylcarbodiimide, HATU in presence of a base such as diisopropyl ethyl amine or triethyl amine and a solvent such as methanol, DCM, THF, acetonitrile, DMF or DMSO at room temperature followed by treatment with a base ammonia, ammonium hydroxide or methylamine at room temperature to obtain amide compound. The amind compound is subjected to hydrogenation using Pd/C as catalyst to obtain acid compound 1J (wherein $R^3$ is —$C(O)NR^aR^b$; wherein $R^a$ and $R^b$ are as defined herein).

Step 2h:

The compound 2B is subjected to hydrogenation reaction using Pd—C as catalyst to obtain compound 2K.

Procedure C

Scheme 3

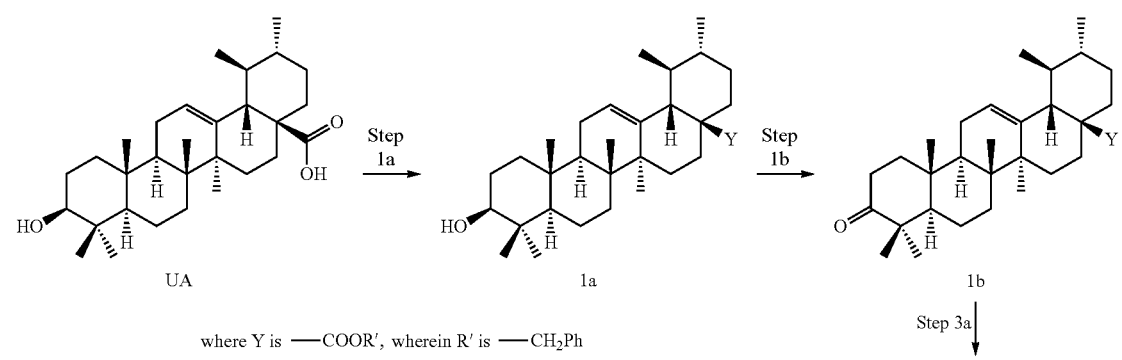

where Y is —COOR', wherein R' is —CH₂Ph

Step 3a

-continued

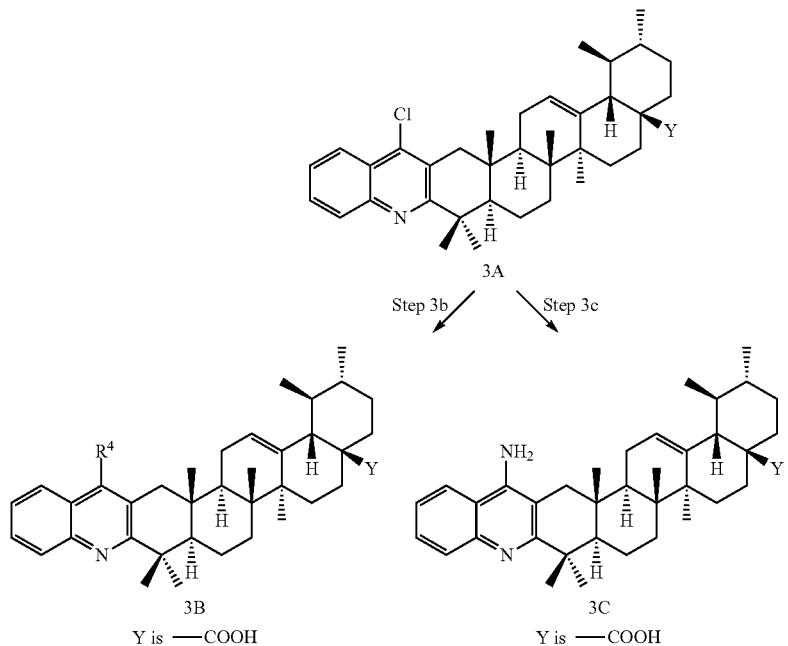

The reaction steps as outlined in the above Scheme 3 are described herein below:
The compounds 1a and 1b are prepared by following the procedure of steps 1a and 1b as provided under scheme 1.
Step 3a:

Compound 3A is prepared by heating the mixture of the compound 1b, 2-aminobenzoic acid and a chlorinating reagent such as POCl$_3$, thionyl chloride or oxalyl chloride in the presence of catalytic amount of DMF at a temperature range of 90–110° C. The compound 3A is subjected to hydrogenation using Pd/C in presence of a base such as triethylamine and solvent such as methanol, ethyl acetate or THF to obtain corresponding acid compound 3B (wherein R$^4$ is H).

Step 3b

The compound 3A is treated with 3-morpholinopropan-1-amine in the presence of phenol at temperature in the range of 120–125° C. to obtain amine compound. The amine compound obtained is subjected to hydrogenation using Pd/C as catalyst to obtain a corresponding acid compound designated as compound 3B (wherein R$^4$ is amino alkyl morpholine group).

A mixture of the compound 3A and phenol is heated to 60-80° C. in presence of a base such as 4-hydroxypyrrolidine-2-carboxylic acid, diethylamine or diisopropylethyl amine at a temperature in the range of 120-125° C. to obtain amine compound. The amine compound is subjected to hydrogenation using Pd/C as catalyst to obtain corresponding acid compound designated as compound 3B. (wherein R$^4$ is phenoxy group).

Step 3c.

The compound 3A is treated with ammonia in the presence of phenol to obtain ester compound. The ester compound is subjected to hydrogenation using Pd/C as catalyst to obtain corresponding acid compound designated as compound 3C.

Procedure D
Scheme 4
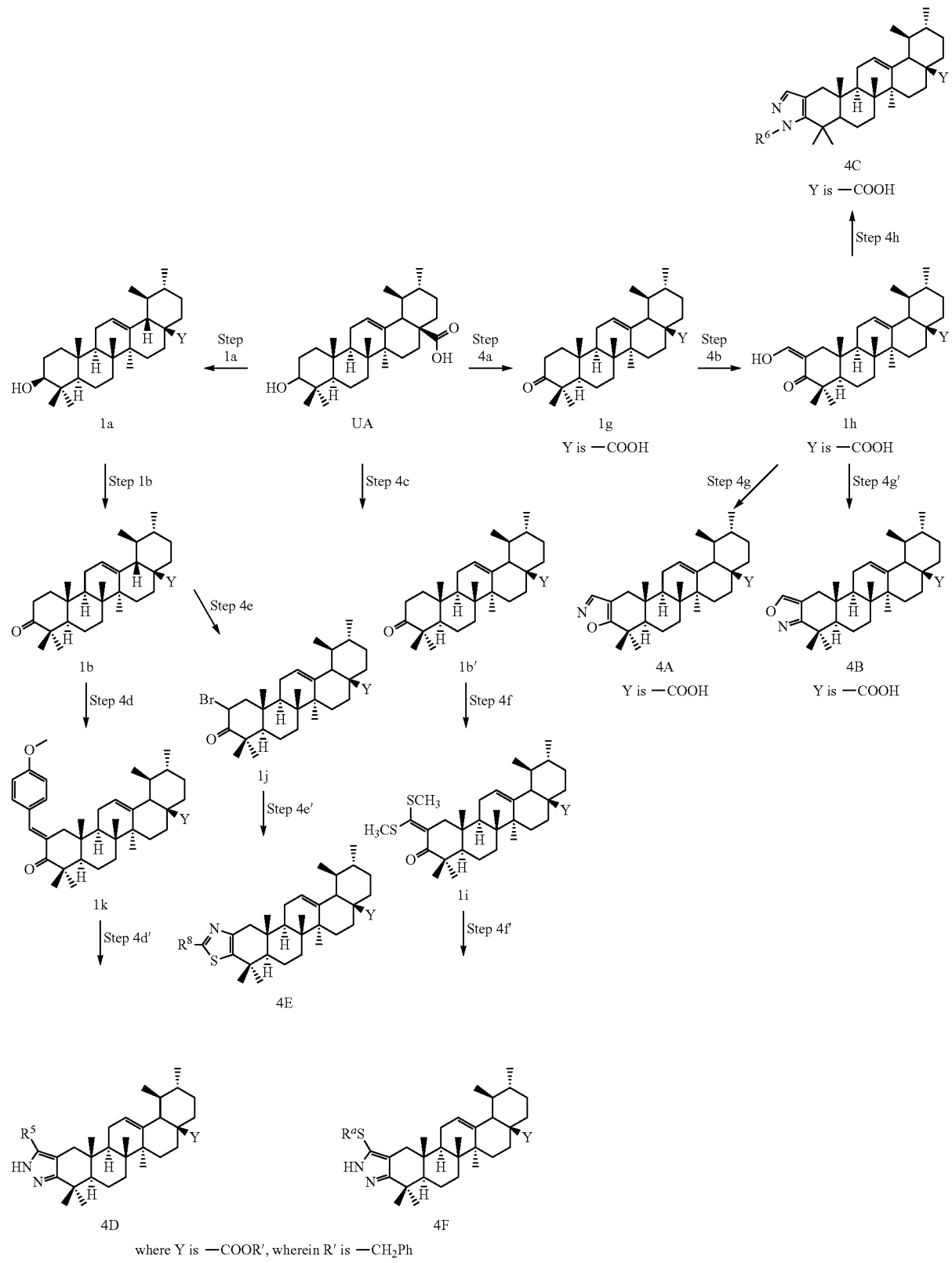
where Y is —COOR', wherein R' is —CH$_2$Ph

The reaction steps as outlined in the above Scheme 4 are described herein below:

The compounds 1a and 1b are prepared by following the procedure of steps 1a and 1b as provided under scheme 1.

Step 4a

Ursolic acid (UA) is treated with Jones reagent to obtain intermediate compound 1g.

Step 4b

The intermediate compound 1g is treated with ethyl formate in the presence of a base such as sodium methoxide, sodium ethoxide or potassium tert-butoxide and a solvent such as THF to obtain intermediate compound 1h.

Step 4c

Ursolic acid (UA) is converted to its alkyl ester using an alkylhalide such as methyl iodide or ethyl iodide in the presence of a base such as potassium tert-butoxide, cesium carbonate, sodium hydride or triethylamine and a solvent such as DCM, DMF, ACN or toluene to obtain intermediate compound 1b'.

Step 4d and 4d'

The intermediate compound 1b is treated 4-methoxybenzaldehyde in the presence of a base such as sodium hydride and a solvent such as DMF or THF at room temperature to obtain compound 1k. The intermediate compound 1k is cyclised using hydrazine in the presence of a solvent such as ethanol, dioxane or THF) at a temperature range of 100-120° C. to obtain compound 4D (wherein $R^5$ is as defined herein).

Step 4e and 4e'

The intermediate compound 1b is treated with pyridinium tribromide in the presence of a solvent such as methylenedichloride or DCE) at room temperature to obtain compound 1j. The compound 1j is treated with thiourea in the presence of a solvent such as ethanol to obtain compound 4E (wherein $R^8$ is as defined herein).

Step 4f and 4f'

The intermediate compound 1b' is treated with carbon disulphide and a base such as sodium hydride in the presence of a solvent such as DMF or DCM followed by treatment with an alkyl halide such as methyl iodide or ethyl iodide to obtain compound 1i. The compound 1i is cyclised using hydrazine at a temperature in the range of 100–120° C. to obtain compound 4F (wherein $R^a$ is (C$_1$-C$_6$)alkyl group).

Step 4g:

The compound 1h is treated with hydroxylamine hydrochloride in the presence of a solvent such as ethanol to obtain compound 4A.

Step 4g':

The compound 1h is treated with hydroxylamine hydrochloride in the presence of pyridine to obtain compound 4B.

Step 4h

The compound 1h is treated with substituted hydrazine reagent such as 3-chloro phenyl hydrazine hydrate, 3,5-difluorophenyl hydrazine hydrochloride, (2-fluorophenyl) hydrazine hydrochloride or (3-methylphenyl)hydrazine hydrochloride in the presence of a solvent such as ethanol, methanol or acetonitrile under reflux condition to obtain compound 4C (wherein $R^6$ is as defined herein above).

The compounds of Formula I in one or more embodiments as described above can be converted into their pharmaceutically acceptable salts by following procedure known to persons skilled in the art.

In an embodiment, the compounds of Formula I in their free base form are converted to their corresponding pharmaceutically acceptable salts. The pharmaceutically acceptable salt of the compounds of Formula I are prepared with relatively non-toxic acids or bases, depending on the particular substituents found on the compound described herein. When the compounds of the present invention contain an acidic group they can form an addition salt with a suitable base. For example, pharmaceutically acceptable base addition salts of the compounds of the present invention may include their alkali metal salts such as sodium, potassium, calcium, magnesium, ammonium or an organic base addition salt. Examples of pharmaceutically acceptable organic base addition salts of the compounds of the present invention include those derived from organic bases like lysine, arginine, guanidine, diethanolamine, choline, tromethamine, metformin or other organic bases known to the person skilled in the art.

When the compounds of Formula I of the present invention contain one or more basic groups, they can form an addition salt with an inorganic or an organic acid. Examples of pharmaceutically acceptable acid addition salts include those derived from inorganic acids like boric acid, perchloric acid, hydrochloric acid, hydrobromic acid, hydrofluoric acid, hydriodic acid, nitric acid, carbonic acid, monohydrogencarbonic acid, phosphoric acid, monohydrogenphosphoric acid, dihydrogenphosphoric acid, sulfuric acid, monohydrogensulfuric acid, phosphorous acids or other inorganic acids known to the person skilled in the art. Furthermore, examples of pharmaceutically acceptable acid addition salts include the salts derived from organic acids such as acetic acid, propionic acid, isobutyric acid, oxalic acid, malic acid, tartaric acid, citric acid, ascorbic, maleic acid, malonic acid, benzoic acid, succinic acid, suberic acid, fumaric acid, mandelic acid, phthalic acid, benzenesulfonic acid, toluenesulfonic acid, methanesulfonic acid, glucuronic acid, galacturonic acid, naphthoic acid, camphoric acid or other organic acids known to the person skilled in the art. Certain specific compounds of the present invention contain both basic and acidic functionalities that allow the compounds to be converted into either base or acid addition salts.

The pharmaceutically acceptable salts of the present invention can be synthesized from the subject compound i.e. the compound of Formula I, which contains a basic or acidic moiety by conventional chemical methods. Generally, the salts are prepared by contacting the free base or acid with a desired salt-forming inorganic or organic acid or a base in a suitable solvent or dispersant or by anion exchange or cation exchange with other salts. Suitable solvents used for the preparation of the pharmaceutically acceptable salts are, for example, ethyl acetate, ethers, alcohols, acetone, or mixtures of these solvents.

The compound of Formula I can be regenerated from their corresponding salts by contacting the said salt with an appropriate base or acid depending on the type of salt and isolating the parent compound in the conventional manner. The corresponding salts of the compounds differ from their parent compounds with respect to certain physical properties, for example solubility.

Those skilled in the art will recognize that the compounds of Formula I of the present invention contain asymmetric or chiral centers, and therefore exist in different stereoisomeric forms, as racemic mixtures of enantiomers, mixtures of diastereomers or enantiomerically or optically pure compounds. The term "chiral" refers to molecules which have the property of non-superimposability of the mirror image cohort, while the term "achiral" refers to molecules which are superimposable on their mirror image partner. It is intended that all stereoisomeric forms of the compounds of the invention, including but not limited to, diastereomers and enantiomers, as well as mixtures thereof such as racemic mixtures, geometric isomers form part of the present invention.

When the compounds of Formula I of the present invention contain one chiral center, the compounds exist in two enantiomeric forms and the present invention includes both enantiomers and mixtures of enantiomers, such as the specific 50:50 mixture referred to as a racemic mixtures. The enantiomers can be resolved by methods known to those skilled in the art, such as formation of diastereoisomeric salts which may be separated, for example, by crystallization (CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form.

Alternatively, specific enantiomers can be synthesized by asymmetric synthesis using optically active reagents, substrates, catalysts or solvents, or by converting one enantiomer into the other by asymmetric transformation. Designation of a specific absolute configuration at a chiral carbon of the compounds of the present invention is understood to mean that the designated enantiomeric form of the compounds is in enantiomeric excess (ee) or in other words is substantially free from the other enantiomer. For example, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. Enantiomeric excess, as used herein, is the presence of a particular enantiomer at greater than 50% in an enantiomeric mixture. In a particular embodiment when a specific absolute configuration is designated, the enantiomeric excess of depicted compounds is at least about 90%. When a compound of Formula I of the present invention has two or more chiral carbons it can have more than two optical isomers and can exist in diastereoisomeric forms. For example, when there are two chiral carbons, the compound can have up to 4 optical isomers and 2 pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs may be separated by methods known to those skilled in the art, for example chromatography or crystallization and the individual enantiomers within each pair may be separated by conventional techniques known to those skilled in the art. The present invention includes each diastereoisomer of such compounds and mixtures thereof.

In one embodiment, the compounds of Formula I exists as tautomers, and it is intended to encompass all the tautomeric forms of the compounds within the scope of the present invention.

The present invention furthermore includes all the solvates of the compounds of Formula I. Certain compounds of the present invention can exist in unsolvated forms as well as solvated forms, including hydrated forms. For example, hydrates and the solvates of the compounds of the present invention can be formed with other solvents of crystallisation, selected from alcohols such as methanol, ethanol, 1-propanol or 2-propanol; ethers such as diethyl ether, isopropyl ether or tetrahydrofuran; esters such as methyl acetate or ethyl acetate, ketone such as acetone or mixtures thereof.

Various polymorphs of the compounds of Formula I can be prepared by crystallization of the compounds under different conditions. The different conditions are, for example, using different solvents or their mixtures for crystallization; crystallization at different temperatures; various modes of cooling, ranging from very fast to very slow cooling during crystallizations. Polymorphs can also be obtained by heating or melting the compound followed by gradual or fast cooling. The presence of polymorphs can be determined by infra-red (IR) spectroscopy, solid probe nuclear magnetic resonance (NMR) spectroscopy, differential scanning calorimetry, powder X-ray diffraction or such other techniques.

Furthermore, the present invention also includes prodrugs of the compounds of Formula I. The prodrugs of the compounds of the present invention are derivatives of the aforesaid compounds of the invention which upon administration to a subject in need thereof undergoes chemical conversion by metabolic or chemical processes to release the parent drug in vivo from which the prodrug is derived. The preferred prodrugs are pharmaceutically acceptable ester derivatives e.g., alkyl esters, cycloalkyl esters, alkenyl esters, benzyl esters, mono- or di-substituted alkyl esters convertible by solvolysis under conditions to the parent carboxylic acid, and those conventionally used in the art.

The present invention also relates to N-oxides of the compounds of Formula I.

The present invention also relates to S-oxides of the compounds of Formula I.

In another further aspect, the present invention relates to pharmaceutical compositions that contain a therapeutically effective amount of at least one compound of Formula I or its pharmaceutically acceptable salt in addition to a customary pharmaceutically acceptable carrier or excipient. The pharmaceutical compositions according to the present invention are prepared in a manner known and familiar to one skilled in the art. Pharmaceutically acceptable inert inorganic and/or organic carriers and/or additives can be used in addition to the compound of Formula I and/or its pharmaceutically acceptable salts. The pharmaceutical compositions according to the present invention can be administered orally, for example in the form of pills, tablets, coated tablets, capsules, granules or elixirs. Administration, however, can also be carried out rectally, for example in the form of suppositories, or parenterally, for example intravenously, intramuscularly or subcutaneously, in the form of injectable sterile solutions or suspensions, or topically, for example in the form of solutions or transdermal patches, or in other ways, for example in the form of aerosols or nasal sprays.

For the production of oral dosages form of the compounds of Formula I such as pills, tablets, coated tablets, hard gelatin capsules or granules it is possible to use, for example, lactose, corn starch or derivatives thereof, gum arabic, magnesia or glucose, etc. Carriers for soft gelatin capsules and suppositories are, for example, fats, waxes, natural or hardened oils, etc. Suitable carriers for the production of solutions, for example injection solutions, or of emulsions or syrups are, for example, water, sodium chloride solution or alcohols, for example, ethanol, propanol or glycerol, sugar solutions, such as glucose solutions or mannitol solutions, or a mixture of the various solvents which have been mentioned.

Further, the pharmaceutical composition of the present invention also contains additives such as, for example, fillers, antioxidants, emulsifiers, preservatives, flavours, solubilisers or colourants. The pharmaceutical composition of the present invention can also contain more than one compound of Formula I and/or its pharmaceutically acceptable salts.

The pharmaceutical compositions can further contain one or more other therapeutically or prophylactically active agents.

The pharmaceutical compositions normally contain about 1 to 99%, for example, about 10 to 80%, or from about 10% to about 30% by weight of the compounds of Formula I or their pharmaceutically acceptable salts. The amount of the active ingredient i.e. the compound of Formula I or its pharmaceutically acceptable salt in the pharmaceutical compositions may, for example, vary from about 1 to 500 mg. The desirable dosage of the compounds of Formula I can be selected over a wide range. The daily dosage to be administered is selected to achieve the desired therapeutic effect in subjects being treated for the disease or disorder as described herein. A dosage of about 0.05 to 100 mg/kg/day of the compounds of Formula I or its pharmaceutically acceptable salt can be administered depending on the body weight of the recipient (subject) per day. If required, higher or lower daily dosages can also be administered. Actual dosage levels of the active ingredient i.e. the compound of Formula I or its pharmaceutically acceptable salt contained in the pharmaceutical composition of this present invention can be varied so as to obtain an amount of the active ingredient, which is effective to achieve the desired therapeutic response for a particular patient, composition, and mode of administration without being toxic to the patient. The selected dosage level can be readily determined by a skilled medical practitioner in the light of the relevant circumstances, including the condition (diseases or disorder) to be treated, the chosen route of administration depending on a number of factors, such as age, weight and physical health and response of the individual patient, pharmacokinetics, severity of the disease and the like, factors known in the medical art.

In one aspect of the present invention, the compounds of Formula I are RORγ modulators.

In one aspect of the present invention, the compounds of Formula I are IL-17 inhibitors.

In an embodiment of the present invention, the compounds of Formula I are used to reduce the differentiation of Th17 cells by inhibiting the IL-17 production in Th17 cells.

In an aspect of the present invention, the compounds of Formula I are used in the treatment of a disease or a disorder mediated by RORγ.

In another aspect of the present invention, the compounds of Formula I are used in the treatment of a disease or a disorder mediated by IL-17.

In an embodiment of the present invention, the compounds of Formula I are used for inhibition of Th17 cells in a mammal.

In an aspect, the present invention relates to a method for the treatment of a disease or a disorder mediated by RORγ, comprising administering to a subject in need thereof a therapeutically effective amount of a compound of Formula I or a stereoisomer, a tautomer, a pharmaceutically acceptable salt or a pharmaceutically acceptable solvate thereof.

In another aspect, the present invention relates to a method for the treatment of a disease or a disorder mediated by IL-17, comprising administering to a subject in need thereof a therapeutically effective amount of a compound of Formula I or a stereoisomer, a tautomer, a pharmaceutically acceptable salt or a pharmaceutically acceptable solvate thereof.

In another aspect, the present invention relates to use of the compound of Formula I or a stereoisomer, a tautomer, a pharmaceutically acceptable salt or a pharmaceutically acceptable solvate thereof, for the treatment of a disease or a disorder mediated by RORγ.

In yet another aspect, the present invention relates to use of the compound of Formula I or a stereoisomer, a tautomer, a pharmaceutically acceptable salt or a pharmaceutically acceptable solvate thereof, for the treatment of a disease or a disorder mediated by IL-17.

In an embodiment, the present invention relates to use of the compound of Formula I or a stereoisomer, a tautomer, a pharmaceutically acceptable salt or a pharmaceutically acceptable solvate thereof for the treatment of a disease or a disorder mediated by RORγ.

In an embodiment, the present invention relates to use of the compound of Formula I or a stereoisomer, a tautomer, a pharmaceutically acceptable salt or a pharmaceutically acceptable solvate thereof for the treatment of a disease or a disorder mediated by IL-17.

According to an aspect, the present invention relates to use of the compounds of Formula I or a stereoisomer, a tautomer, a pharmaceutically acceptable salt or a pharmaceutically acceptable solvate thereof in the manufacture of a medicament, for the treatment of a disease or a disorder mediated by RORγ.

According to an aspect, the present invention relates to use of the compounds of Formula I or a stereoisomer, a tautomer, a pharmaceutically acceptable salt or a pharmaceutically acceptable solvate thereof, in the manufacture of a medicament for the treatment of a disease or a disorder mediated by IL-17.

In an embodiment, the disease or disorder mediated by RORγ is an autoimmune disease or disorder, an inflammatory disorder or a metabolic disorder.

According to another embodiment, the disease or disorders mediated by RORγ or IL-17 is selected from respiratory diseases such as asthma, chronic obstructive pulmonary disease (COPD) and bronchitis; allergic diseases such as allergic rhinitis and atopic dermatitis; arthritis; multiple sclerosis; psoriasis; cystic fibrosis; lung allograph rejection, Crohn's disease, inflammatory bowel diseases (IBD); irritable bowel syndrome (IBS); colitis and ulcerative colitis.

In an embodiment of the present invention, the disease or disorders mediated by RORγ or IL-17 is an autoimmune disease(s)/disorder(s) or an inflammatory disease(s)/disorder(s); which can be selected from the group consisting of: inflammatory bowel disease, rheumatoid arthritis, juvenile rheumatoid arthritis, psoriatic arthritis, osteoarthritis, refractory rheumatoid arthritis, chronic non-rheumatoid arthritis, ankylosing spondylitis, osteoporosis/bone resorption, chronic graft-versus-host disease, acute graft-versus-host disease, multiple sclerosis, systemic lupus erythematosus, Celiac Sprue, idiopathic thrombocytopenic thrombotic purpura, myasthenia gravis, Sjogren's syndrome, scleroderma, asthma, bronchitis, epidermal hyperplasia, Crohn's disease, atherosclerosis, septic shock syndrome, coronary heart disease, vasculitis, ulcerative colitis, psoriasis, adult respiratory distress syndrome, myolitis, polymyolitis, dermatomyolitis, polyarteritis nodossa, Wegener's granulomatosis, arteritis, polymyalgia rheumatica, sarcoidosis, sclerosis, primary biliary sclerosis, sclerosing cholangitis, dermatitis, atopic dermatitis, Still's disease, chronic obstructive pulmonary disease, Guillain-Barre disease, Type I diabetes mellitus, Graves' disease, Addison's disease, Raynaud's phenomenon, autoimmune hepatitis, psoriatic epidermal hyperplasia, and delayed type hypersensitivity in skin disorders.

In an embodiment, autoimmune disease that can be treated by the compound of present invention is selected from alopecia areata, autoimmune hemolytic anemia, autoimmune hepatitis, dermatomyositis, diabetes (type 1), some forms of juvenile idiopathic arthritis, glomerulonephritis, Graves' disease, Guillain-Barre syndrome, idiopathic thrombocytopenic purpura, myasthenia gravis, some forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjogren's syndrome, systemic lupus erythematosus, Pernicious anemia (Addison's disease), some forms of thyroiditis (Hashimoto's thyroiditis or chronic lymphocytic thyroiditis), some forms of uveitis, vitiligo and granulomatosis with polyangiitis (Wegener's granulomatosis).

According to another embodiment, the inflammatory disorders are selected from the group consisting of arthritis, asthma, atherosclerosis, celiac disease, chronic prostatitis, colitis, Crohn's disease, dermatitis, diverticulitis, glomerulonephritis, hepatitis, hypersensitivities, inflammatory bowel diseases (IBD), interstitial cystitis, irritable bowel syndrome (IBS), lupus erythematous, nephritis, Parkinson's disease, pelvic inflammatory disease, reperfusion injury, rheumatoid arthritis, sarcoidosis, transplant rejection, ulcerative colitis and vasculitis.

In another embodiment, the arthritis that can be treated by the compound of present invention includes rheumatoid arthritis, juvenile rheumatoid arthritis, osteoarthritis, gouty arthritis, pseudogout arthritis, lupus arthritis, septic arthritis and spondyloarthropathies (ankylosing spondylitis, reactive arthritis (Reiter's syndrome), psoriatic arthritis and enteropathic arthritis).

In an embodiment of present invention, the disease or disorder mediated by RORγ or IL-17 is metabolic disorder.

In an embodiment, the metabolic disorder is selected from diabetes, obesity, cardiovascular disease, hypertension, ketoacidosis, insulin resistance, glucose intolerance, hyperglycemia, hypertriglylceridemia, polycystic ovary syndrome, hypercholesterolemia, hyperlipoproteinemia, dyslipidemia, metabolic syndrome, syndrome X, hyperlipidemia, diabetic neuropathy, diabetic retinopathy, edema and related disorders associated with abnormal plasma lipoprotein, triglycerides or pancreatic beta cell degeneration.

In an embodiment of present invention, the compound of Formula I can be used for the treatment of cancer.

According to another embodiment, the cancers include, but are not limited to, thyroid carcinoma, cardiac sarcoma, lung carcinoma, gastrointestinal carcinoma, genitourinary tract carcinoma, liver carcinoma, mantle cell lymphoma, bone sarcoma, sarcoma of the nervous system, gynaecological carcinoma, haematological cancer, adrenal gland neuroblastoma, skin cancer, astrocytic cancer, breast cancer, colorectal cancer, endometrial cancer, head and neck cancer and oral cancer.

In an embodiment, the present invention relates to compounds of Formula I or a stereoisomer, a tautomer, a pharmaceutically acceptable salt, a pharmaceutically acceptable solvate, a prodrug, an N-oxide, a S-oxide or a carboxylic acid isostere thereof, for use in the treatment of autoimmune disease or a disorder.

In an embodiment the present invention relates to compounds of Formula I or a stereoisomer, a tautomer, a pharmaceutically acceptable salt, a pharmaceutically acceptable solvate, a prodrug, an N-oxide, a S-oxide or a carboxylic acid isostere thereof, for use in the treatment of inflammatory disease or a disorder.

In an embodiment the present invention relates to compounds of Formula I or a stereoisomer, a tautomer, a pharmaceutically acceptable salt, a pharmaceutically acceptable solvate, a prodrug, an N-oxide, a S-oxide or a carboxylic acid isostere thereof, for use in the treatment of cancer.

In an embodiment the present invention relates to compounds of Formula I or a stereoisomer, a tautomer, a pharmaceutically acceptable salt, a pharmaceutically acceptable solvate, a prodrug, an N-oxide, a S-oxide or a carboxylic acid isostere thereof, for use in the treatment of metabolic disease or a disorder.

In an embodiment the present invention relates to method of modulating the activity of RORγ receptor comprising contacting the RORγ receptor with at least one compound of Formula I or a pharmaceutically acceptable salt thereof in an amount effective to modulate the activity of RORγ, or a pharmaceutical composition as described herein.

In an embodiment the present invention relates to method of inhibiting IL-17 expression in a subject, comprising administering to a subject in need thereof, a therapeutically effective amount of compound of Formula I or a pharmaceutically acceptable salt or a pharmaceutically acceptable solvate thereof, or a pharmaceutical composition as described herein.

In an embodiment the present invention relates to method of inhibiting Th17 differentiation in a subject comprising administering to a subject in need thereof, a therapeutically effective amount of compound of Formula I or a pharmaceutically acceptable salt or a pharmaceutically acceptable solvate thereof, or a pharmaceutical composition as described herein.

In an embodiment the present invention relates to use of the compound of Formula I or a stereoisomer, a tautomer, a pharmaceutically acceptable salt or a pharmaceutically acceptable solvate thereof, in the manufacture of a medicament for the treatment of a disease or a disorder mediated by RORγ and/or IL-17.

The present invention furthermore relates to pharmaceutical compositions that contain a therapeutically effective amount of at least one compound of Formula I in addition to a customary pharmaceutically acceptable carrier, and to a process for the production of a pharmaceutical composition, which includes bringing at least one compound of Formula I, into a suitable administration form using a pharmaceutically suitable excipient and, if appropriate, further suitable active compounds, additives or auxiliaries.

In an embodiment the present invention relates to pharmaceutical compositions comprising one or more or a stereoisomer, a tautomer, a pharmaceutically acceptable salt or a pharmaceutically acceptable solvate thereof, and at least one pharmaceutically acceptable excipient.

In another embodiment the present invention relates to pharmaceutical compositions comprising one or more compounds of Formula I or a stereoisomer, a tautomer, a pharmaceutically acceptable salt or a pharmaceutically acceptable solvate thereof, and at least one therapeutically active agent.

In yet another embodiment the present invention relates to pharmaceutical compositions comprising one or more compounds of Formula I or a stereoisomer, a tautomer, a pharmaceutically acceptable salt or a pharmaceutically acceptable solvate thereof, at least one therapeutically active agent and at least one pharmaceutically acceptable excipient.

In an embodiment, the present invention relates to a pharmaceutical composition for use in the treatment of a disease or a disorder mediated by RORγ or IL-17, comprising the compounds of Formula I or pharmaceutically acceptable salts thereof and a pharmaceutically acceptable excipient.

In an embodiment, the present invention relates to a pharmaceutical composition for use in the treatment of a disease or a disorder mediated by RORγ or IL-17, comprising the compounds of Formula I or pharmaceutically acceptable salts thereof at least one therapeutically active agent and at least one pharmaceutically acceptable excipient.

The term "pharmaceutically acceptable" as used herein in the present invention means that the carrier, diluents, excipients, and/or salt must be compatible with the other ingredients of the Formulation, and not deleterious to the recipient thereof.

The term "pharmaceutically acceptable excipient" as used herein means a non-toxic, inert, solid, semi-solid, diluent, encapsulating material or Formulation auxiliary of any type. Some examples of materials which can serve as pharmaceutically acceptable excipient are sugars such as lactose, glucose, and sucrose; starches such as corn starch and potato starch; cellulose and its derivatives such as sodium carboxymethyl cellulose, ethyl cellulose and cellulose acetate; malt; gelatin; talc; as well as other non-toxic compatible lubricants such as sodium lauryl sulfate and magnesium stearate, as well as coloring agents, releasing agents, coating agents, sweetening, flavoring and perfuming agents; preservatives and antioxidants can also be present in the composition, according to the judgment of the Formulator.

The therapeutically active agents used in combination with one or more compounds of Formula I or its pharmaceutically acceptable salt can be selected from $β_2$-adrenoreceptor agonists (for example, but not limited to, bambuterol, formoterol, levosalbutamol, salmeterol and salbutamol), S1P1 agonist (for example, but not limited to, fingolimod, siponimod (phase III, Novartis) and RPC-1063 (phase III, Receptos)), $H_1$ receptor antagonist, anti-inflammatory agents (e.g. corticosteroids (for example, fluticasone) and non-steroidal antiinflammatory agent, NSAID (for example, but not limited to, diclofenac, indomethacin, sulindac, mefenamic acid, piroxicam, ibuprofen, naproxen, ketoprofen, phenylbutazone, aspirin, diflunisal, nimesulide, celecoxib, valdecoxib, etorcoxib and meloxicam)), anticholinergic agents (for example, but not limited to, ipratropium, tiotropium and oxitropium), anti-diabetic agents (for example, but not limited to alogliptin, anagliptin, sitagliptin, saxagliptin, vildagliptin, denagliptin, Dutogliptin, Tenelgliptin, Trelagliptin (SYR-472, phase III), gemigliptin ($LC_{15}$-0444, phase III), omarigliptin (MK-3102, phase III), pioglitazone, rosiglitazone, balaglitazone (DRF-2593, phase III), lobeglitazone (CKD-501, phase III), saroglitazar, farglitazar (GI-262570, Phase III), ragaglitazar (DRF-2725, phase III)), TNF-α inhibitor (for example, but not limited to, etanercept, infliximab, adalimumab, certolizumab and golimumab), COX-1/COX-2 inhibitor (such as celecoxib and rofecoxib), LTD4 receptor antagonist (for example, but not limited to, montelukast, zafirlukast, tipelukast and pranlukast), phosphodiesterase type IV (PDE-IV) inhibitor (for example, but not limited to, rolipram, ibudilast, luteolin, cilomilast and roflumilast), insulin-like growth factor type I (IGF-1) inhibitor, kinase inhibitor (for example, imatinib, gefitinib, erlotinib, sorafenib, dasatinib, sunitinib, nilotinib, lapatinib, pazopanib, vandetanib, vemurafenib and crizotinib) and mTOR inhibitor (such as, rapamycin, sirolimus, temsirolimus, everolimus, deforolimus, cyclosporin and tacrolimus).

It is understood that modifications that do not substantially affect the activity of the various embodiments of this invention are included within scope of the invention disclosed herein. Accordingly, the following examples are intended to illustrate but not to limit scope of the present invention.

EXAMPLES

The following abbreviations or terms are used herein:

LIST OF ABBREVIATIONS

| | | | |
|---|---|---|---|
| L | Liter | dd | Doublet of doublet |
| min | Minute(s) | m | Multiplet |
| mL | Milliliter | $K_2CO_3$ | Potassium carbonate |
| μL | Microliter | ACN | Acetonitrile |
| g | Gram | DMSO-$d_6$ | Deuterated dimethylsulfoxide |
| mg | Milligram | ESI | Electrospray ionisation |
| μg | Microgram | MS | Mass spectrometry |
| nM | Nanomolar | $^1$H NMR | Proton nuclear magnetic resonance |
| DMF | N,N-Dimethylformamide | NaH | Sodium hydride |
| DMSO | Dimethylsulfoxide | MeOH | Methanol |
| THF | Tetrahydrofuran | $POCl_3$ | Phosphorous trichloride |
| MHz | Megahertz | $Na_2S_2O_3$ | Sodium thiosulfate |
| mmol | Milimolar | DCM | Dichloromethane |
| h | Hour(s) | $NaHCO_3$ | Sodium bicarbonate |
| HCl | Hydrochloric acid | $Na_2SO_4$ | Sodium sulfate |
| ° C. | Degree Celsius | Pd/C | Palladium on carbon |
| N | Normal | CDI | 1,1'-Carbonyldiimidazole |
| d | Doublet | $NaH_2PO_4$ | Sodium dihydrogen phosphate |
| PCC | Pyridinium chlorochromate | LiHMDS | Lithium bis(trimethylsilyl)amide |
| PyBOP | Benzotriazolyloxy-tris[pyrrolidino]-phosphonium hexafluorophosphate | | |
| HATU | 1-[Bis(dimethylamino)methylene]-1H-1,2,3-triazolo[4,5-b]-pyridinium 3-oxid hexafluorophosphate | | |

Ursolic acid is used as starting material for preparation of compounds of the present invention. Ursolic acid is obtained from commercial source such as Sigma Aldrich.

Example 1

(1S,2R,4aS,6aS,6bR,8aR,14aR,14bR,16bS)-ethyl 13-hydroxy-11-mercapto-1,2,6a,6b,9,9,14a-heptamethyl-1,2,3,4,4a,5,6,6a,6b,7,8,8a,9,14,14a,14b,15,16b-octadecahydrochryseno [1,2-g]quinazoline-4a-carboxylate (Compound 1)

Step 1

Synthesis of (1S,2R,4aS,6aS,6bR,8aR,10S,12aR,12bR,14bS)-benzyl 10-hydroxy-1,2,6a,6b,9,9,12a-heptamethyl-1,2,3,4,4a,5,6,6a,6b,7,8,8a,9,10,11,12,12a,12b,13,14b-icosa hydropicene-4a-carboxylate To a suspension of (1S,2R,4aS,6aS,6bR,8aR,10S,12aR,12bR,14bS)-10-hydroxy-1,2,6a,6b,9,9,12a-heptamethyl-1,2,3,4,4a,5,6,6a,6b,7,8,8a,9,10,11,12,12a,12b,13,14b-icosa hydropicene-4a-carboxylic acid (50g, 109 mmol) in DMF (500 mL) was added potassium carbonate salt (40 g, 289 mmol) under nitrogen atmosphere followed by addition of bromomethyl benzene (16.90 mL, 142 mmol) to the mixture. The reaction mixture was stirred for 6 h at room temperature and on completion of reaction the reaction mixture was poured into cold water (5 L). The separated solid material was collected and washed with acetonitrile (500 mL) to afford pure title compound 2 (58 g) as white solid.

Yield: 97%; $^1$H NMR (300 MHz, DMSO-d$_6$): δ 0.54 (s, 3H), 0.66 (s, 3H), 0.82 (s, 3H), 0.90 (d, J=9.0 Hz, 6H), 1.0 (s, 3H), 0.99-1.07 (m, 3H), 1.42-2.15 (m, 23H), 2.98 (bs, 1H), 4.31 (bs, 1H), 4.94 (d, J=12.0 Hz, 1H), 5.04 (d, J=12.0 Hz, 1H), 5.13 (s, 1H), 7.32 (bs, 5H); MS (ES+): 547.8 (M+1).

Step 2

Synthesis of (1S,2R,4aS,6aS,6bR,8aR,12aR,12bR, 14bS)-benzyl 1,2,6a,6b,9,9,12a-heptamethyl-10-oxo-1,2,3,4,4a,5,6,6a,6b,7,8,8a,9,10,11,12,12a,12b, 13,14b-icosahydropicene-4a-carboxylate To a solution of the compound as obtained in step 1, (1S,2R,4aS,6aS,6bR,8aR,10S,12aR,12bR,14bS)-benzyl 10-hydroxy-1,2,6a,6b,9,9,12a-heptamethyl-1,2,3,4,4a,5,6, 6a,6b,7,8,8a,9,10,11,12,12a,12b,13,14b-icosahydropicene-4a-carboxylate (26 g, 47.5 mmol) in DCM (400 mL) was added pyridinium chlorochromate (PCC) (15.37 g, 71.3 mmol) at room temperature under nitrogen atmosphere. The reaction mixture was stirred for 4 h and diethyl ether (400 mL) was added to the reaction mixture. The mixture was stirred at room temperature for 0.5 h. The reaction mixture was decanted and the sticky solid was washed with diethyl ether (150 mL). The organic wash was passed through celite, the filtrate was collected and concentrated under vacuum to obtain a solid which was washed with acetonitrile (200 mL) to afford pure title compound (23 g) as white solid.

Yield: 90%; $^1$H NMR (300 MHz, DMSO-d$_6$): δ 0.58 (s, 3H), 0.88 (d, J=6.3 Hz, 3H), 0.92 (d, J=8.1 Hz, 9H), 0.97 (s, 3H), 1.0 (s, 3H), 1.15-2.30 (m, 23H), 4.94 (d, J=12.6 Hz, 1H), 5.10 (d, J=12.6 Hz, 1H), 5.15 (s, 1H), 7.32-7.35 (bs, 5H); MS (ES+): 545.3 [M+1].

Step 3

Synthesis of (4aR,6aR,6bS,8aS,11R,12S,12aS,14aR, 14bR)-8a-benzyl 2-ethyl 4,4,6a,6b,11,12,14b-heptamethyl-3-oxo-1,2,3,4,4a,5,6,6a,6b,7,8,8a,9,10,11, 12,12a,14,14a, 14b-icosahydropicene-2,8a-dicarboxylate To a solution of the compound as obtained in step 2, (1S,2R,4aS,6aS,6bR,12aR)-benzyl 1,2,6a,6b,9,9,12a-heptamethyl-10-oxo-1,2,3,4,4a,5,6,6a,6b,7,8,8a,9,10,11,12,12a, 12b,13,14b-icosahydropicene-4a-carboxylate (20 g, 36.7 mmol) in THF (100 mL) was added 2-methylpropan-2-olate, potassium tertiary butoxide (6.18 g, 55.1 mmol) in THF (100 mL) under nitrogen atmosphere at room temperature. The reaction mixture was refluxed to 85° C. for 1.5 h followed by addition of diethyl carbonate (11.18 mL, 92 mmol) to the reaction mixture. The reaction mixture was stirred for 16 h at same temperature. After the completion of reaction, the reaction mixture was acidified using 1NHCl and the mixture was concentrated under vacuum to obtain a residue. The residue obtained was diluted with DCM (150 mL) and washed with water (3×150 mL), brine (2×150 mL), dried over Na$_2$SO$_4$, concentrated under vacuum and purified by Combiflash chromatography (0-7% ethyl acetate/petroleum ether) to afford pure titled compound (8.0 g) as white solid.

Yield: 35%; $^1$H NMR (300 MHz, DMSO-d$_6$): δ 0.59 (s, 3H), 0.83 (bs, 6H), 0.91 (s, 3H), 1.03 (d, J=8.10 Hz, 6H), 1.11 (s, 3H), 1.23 (t, J=6.0 Hz, 3H), 1.29-2.27 (m, 21H), 4.15 (q, 2H), 4.97-5.0 (m, 2H), 5.19 (bs, 1H), 7.31-7.36 (m, 5H), 12.36 (s, 1H); MS (ES+):616.87 [M+1].

Step 4

Synthesis of (1S,2R,4aS,6aS,6bR,8aR,14aR,14bR, 16bS)-ethyl 13-hydroxy-11-mercapto-1,2,6a, 6b,9,9, 14a-heptamethyl-1,2,3,4,4a,5,6,6a,6b,7,8,8a,9,14, 14a,14b,15,16b-octadeca hydrochryseno[1,2-g] quinazoline-4a-carboxylate To a solution of the compound obtained in step 3, (4aR, 6aR,6bS,8aS,11R,12S,12aS,14aR,14bR)-8a-benzyl 2-ethyl4,4,6a,6b,11,12,14b-hepta methyl-3-oxo-1,2,3,4,4a, 5,6,6a,6b,7,8,8a,9,10,11,12,12a,14,14a,14b-icosahydropicene-2,8a-dicarboxylate (0.700 g, 1.135 mmol) in ethanol (15 mL) was added thiourea (0.130 g, 1.702 mmol) followed by addition of sodium ethoxide (0.116 g, 1.702 mmol) at room temperature under nitrogen atmosphere. The reaction mixture was refluxed at 120° C. for 12 h. After the completion of reaction, the reaction mixture was concentrated under vacuum, diluted with DCM (20 mL) and washed with water (3×20 mL), brine (2×15 mL) dried over Na$_2$SO$_4$, concentrated under vacuum and purified by Combiflash chromatography (0-5% methanol/dichloromethane) to afford pure compound 1 (0.065 g) as white solid.

Yield: 10%; $^1$H NMR (300 MHz, DMSO-d$_6$): δ 0.78 (s, 3H), 0.83 (d, J=5.0 Hz, 3H), 0.92 (s, 3H), 1.05 (s, 3H), 1.14 (s, 3H), 1.24 (s, 6H), 1.28-2.20 (m, 20H), 2.20 (d, J=10 Hz, 1H), 4.96 (d, J=15 Hz, 1H), 5.01 (d, J=15 Hz, 1H), 5.20 (s, 1H), 7.32-7.38 (m, 5H), 11.66 (s, 1H), 12.34 (s, 1H); MS (ES+): 629.5 [M+1].

Example 2

(1S,2R,4aS,6aS,6bR,8aR,14aR,14bR,16bS)-benzyl 13-hydroxy-11-mercapto-1,2,6a,6b,9,9,14a-heptamethyl-1,2,3,4,4a,5,6,6a,6b,7,8,8a,9,14,14a,14b,15, 16b-octadecahydrochryseno[1,2-g]quinazoline-4a-carboxylate (Compound 2)

The title compound was prepared in an analogous manner as step 4 of example 1 involving the reaction of the compound, (4aR,6aR,6bS,8aS,11R,12S,12aS,14aR,14bR)-8a-benzyl 2-ethyl4,4,6a,6b,11,12,14b-heptamethyl-3-oxo-1,2, 3,4,4a,5,6,6a,6b,7,8,8a,9,10,11,12,12a,14,14a,14b-icosahydropicene-2,8a-dicarboxylate (the compound obtained in step 3) (0.700 g, 1.135 mmol) in ethanol (15 mL) with thiourea (0.130 g, 1.702 mmol) in presence of potassium tertiary butoxide (0.116 g, 1.702 mmol) to afford the title compound 2 (0.070 g) as white solid. Yield: 10%; $^1$H NMR (500 MHz, DMSO-d$_6$): δ 0.74 (s, 3H), 0.78 (s, 3H), 0.85 (d, J=5.0 Hz, 3H), 0.92 (s, 3H), 1.06 (s, 3H), 1.12-1.15 (m, 6H), 1.25 (m, 3H), 1.43-2.0 (m, 20H), 2.17 (d, J=10 Hz, 1H), 3.98 (q, J=5 Hz, 2H), 5.21 (s, 1H), 11.66 (s, 1H), 12.34 (s, 1H); MS (ES+):567.7 [M+1].

Example 3

(1S,2R,4aS,6aS,6bR,8aR,14aR,14bR,16bS)-benzyl 13-hydroxy-1,2,6a,6b,9,9,14a-hepta methyl-1,2,3,4, 4a,5,6,6a,6b,7,8,8a,9,14,14a,14b,15,16b-octadecahydrochryseno[1,2-g]quinazoline-4a-carboxylate (Compound 3)

To a solution of the compound obtained in example 2, (1S,2R,4aS,6aS,6bR,8aR,14aR,14bR,16bS)-ethyl 13-hydroxy-11-mercapto-1,2,6a,6b,9,9,14a-heptamethyl-1,2,3,4, 4a,5,6,6a,6b,7,8,8a,9,14,14a,14b,15,16b-octadecahydrochryseno [1,2-g]quinazoline-4a-carboxylate (3.8 g, 6.04 mmol) in ethanol (10 mL) was added Raney-Ni (2.5 g, 3.04 mmol) at room temperature under nitrogen atmosphere and the reaction mixture was heated at 50° C. under hydrogen atmosphere for 12 h. The reaction mixture was filtered and concentrated under vacuum. The residue obtained was diluted with DCM (25 mL), washed with water (3×25 mL), brine (3×20 mL) and dried over $Na_2SO_4$ to obtain the crude material. The crude material obtained was purified by Combiflash chromatography (0-5% methanol/dichloromethane) to afford the title compound 3 (2.5 g).

Yield: 70%; $^1$H NMR (300 MHz, DMSO-$d_6$): δ 0.76 (d, J=3.0 Hz, 3H), 0.83 (d, J=6.0 Hz, 3H), 0.91 (s, 3H), 1.07 (d, J=3.0 Hz, 3H), 1.09 (bs, 3H), 1.13 (bs, 3H), 1.21 (s, 3H), 1.28-2.28 (m, 20H), 2.63 (d, J=18 Hz, 1H), 4.95 (d, J=12 Hz, 1H), 5.04 (d, J=12 Hz, 1H), 5.20 (s, 1H), 7.34 (bs, 5H), 8.0 (s, 1H), 12.15 (s, 1H); MS (ES+):597.4 [M+1].

Example 4

(1S,2R,4aS,6aS,6bR,8aR,14aR,14bR,16bS)-13-hydroxy-1,2,6a,6b,9,9,14a-heptamethyl-1,2,3,4,4a,5,6, 6a,6b,7,8,8a,9,14,14a,14b,15,16b-octadecahydrochryseno[1,2-g]quinazoline-4a-carboxylic acid (Compound 4)

To a solution of the compound as obtained in example 3 (0.040 g, 0.064 mmol) in methanol (3.00 mL) and THF (1.00 mL) was added Pd/C (0.030 g, 0.282 mmol) at room temperature under nitrogen atmosphere. The reaction mixture was continued under hydrogen atmosphere for 24 h. After the completion of the reaction, the reaction mixture was filtered, concentrated under vacuum and purified by Combiflash chromatography (0-5% methanol/dichloromethane) to afford the title compound 4 (0.01 g).

Yield: 31%; $^1$H NMR (500 MHz, DMSO-$d_6$): δ 0.83 (d, J=5.0 Hz, 6H), 0.84 (d, J=5.0 Hz, 3H), 0.92 (s, 3H), 1.08 (s, 3H), 1.11 (s, 3H), 1.16 (s, 3H), 1.43-1.98 (m, 19H), 2.14 (d, J=10 Hz, 1H), 2.65 (d, J=15 Hz, 1H), 5.20 (s, 1H), 8.0 (s, 1H), 11.98 (s, 1H), 12.17 (s, 1H); MS (ES+): 507.3 [M+1].

Example 5

(1S,2R,4aS,6aS,6bR,8aR,14aR,14bR,16bS)-benzyl 13-chloro-1,2,6a,6b,9,9,14a-heptamethyl-1,2,3,4,4a, 5,6,6a,6b,7,8,8a,9,14,14a,14b,15,16b-octadecahydrochryseno[1,2-g]quinazoline-4a-carboxylate (Compound 5)

To a solution of the compound as obtained in example 3 (2.5 g, 4.19 mmol) in DMF (0.05 mL, 4.19 mmol) was added $POCl_3$ (10 mL, 107 mmol) at room temperature under nitrogen atmosphere. The reaction mixture was refluxed at 120° C. for 5 h. The reaction mixture was concentrated under vacuum, diluted with DCM (10 mL), washed with saturated $NaHCO_3$ (2×10 mL), brine (2×10 mL), and dried over $Na_2SO_4$. The reaction mixture was further concentrated under vacuum to obtain the crude material. The crude material obtained was purified by Combiflash chromatography (0-5% ethyl acetate/petroleum ether) to afford the title compound 5 (2.0 g).

Yield: 78%; $^1$H NMR (300 MHz, DMSO-$d_6$): δ 0.76 (s, 3H), 0.79 (s, 3H), 0.84 (d, J=6.0 Hz, 3H), 0.91 (s, 3H), 1.08 (s, 3H), 1.13 (s, 3H), 1.22 (s, 3H), 1.38-2.91 (m, 21H), 4.95 (d, J=9 Hz, 1H), 5.04 (d, J=9 Hz, 1H), 5.21 (s, 1H), 7.33 (bs, 5H), 8.82 (s, 1H), 12.15; MS (ES+):615.29 [M+1].

Example 6

(1S,2R,4aS,6aS,6bR,8aR,14aR,14bR,16bS)-1,2,6a, 6b,9,9,14a-heptamethyl-1,2,3,4,4a,5,6,6a,6b,7,8,8a, 9,14,14a,14b,15,16b-octadecahydrochryseno[1,2-g] quinazoline-4a-carboxylic acid (Compound 6)

The title compound was prepared in an analogous manner as example 4 involving hydrogenation of the compound obtained in example 5, (1S,2R,4aS,6aS,6bR,8aR,14aR, 14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate using Pd/C, to afford the title compound 6 (0.025 g) as white solid.

Yield 62%; $^1$H NMR (500 MHz, DMSO-$d_6$): δ 0.79 (s, 3H), 0.84 (s, 6H), 0.93 (s, 3H), 1.10 (s, 3H), 1.21 (s, 3H), 1.23 (s, 3H), 1.35-2.0 (m, 18H), 2.15 (d, J=10 Hz, 1H), 2.37 (d, J=15 Hz, 1H), 2.75 (d, J=15 Hz, 1H), 5.22 (s, 1H), 8.41 (s, 1H), 8.97 (s, 1H), 12 (s, 1H); MS (ES+):491.6 [M+1].

Example 7

(1S,2R,4aS,6aS,6bR,8aR,14aR,14bR,16bS)-ethyl 13-hydroxy-1,2,6a,6b,9,9,14a-heptamethyl-1,2,3,4, 4a,5,6,6a,6b,7,8,8a,9,14,14a,14b,15,16b-octadecahydrochryseno[1,2-g]quinazoline-4a-carboxylate (Compound 7)

The title compound was prepared in an analogous manner as example 3 involving the reduction of the compound obtained in example 1, (1S,2R,4aS,6aS,6bR,8aR,14aR, 14bR,16bS)-ethyl 13-hydroxy-11-mercapto-1,2,6a,6b,9,9, 14a-heptamethyl-1,2,3,4,4a,5,6,6a,6b,7,8,8a,9,14,14a,14b, 15,16b-octadecahydrochryseno [1,2-g]quinazoline-4a-carboxylate using Raney-Ni, to afford the titled compound 7 (0.02 g) as white solid.

Yield: 20%; $^1$H NMR (500 MHz, DMSO-$d_6$): δ 0.76 (s, 3H), 0.80 (s, 3H), 0.85 (d, J=5.0 Hz, 3H), 0.93 (s, 3H), 1.09 (s, 3H), 1.11 (s, 3H), 1.16 (s, 3H), 1.28 (s, 3H), 1.37-1.98 (m, 19H), 2.18 (d, J=10 Hz, 1H), 2.64 (d, J=15 Hz, 1H), 3.96 (q, J=7 Hz & 5 Hz, 2H), 5.23 (s, 1H), 8.0 (s, 1H), 12.17 (s, 1H); MS (ES+):535.5 [M+1].

Example 8

(1S,2R,4aS,6aS,6bR,8aR,14aR,14bR,16bS)-benzyl, 11,13-dihydroxy-1,2,6a,6b,9,9,14a heptamethyl-1,2, 3,4,4a,5,6,6a,6b,7,8,8a,9,14,14a,14b,15,16b-octadecahydrochryseno[1,2-g]quinazoline-4a-carboxylate (Compound 8)

To a solution of the compound obtained in step 3 of example 1, (4aR,6aR,6bS,8aS,11R,12S,12aS,14aR,14bR)-8a-benzyl 2-ethyl 4,4,6a,6b,11,12,14b-heptamethyl-3-oxo-1,2,3,4,4a,5,6, 6a,6b,7,8,8a,9,10,11,12,12a,14,14a,14b-icosahydropicene-2,8a-dicarboxylate (0.700 g, 1.135 mmol) in ethanol (15.00 mL) was added urea (0.082 g, 1.362 mmol) followed by addition of potassium tertiary butoxide (0.116 g, 1.702 mmol) at room temperature under nitrogen atmosphere and the reaction mixture was refluxed at 120° C. for 24 h. The reaction mixture was concentrated under vacuum, diluted with DCM (20 mL), washed with water (3×20 mL), brine (2×15 mL), and dried over $Na_2SO_4$ and purified by combiflash chromatography (0-5% methanol/dichloromethane) to afford the title compound 8 (0.1 g).

Yield: 15%; $^1$H NMR (500 MHz, DMSO-$d_6$): δ 0.55 (s, 3H), 0.69 (s, 3H), 0.82-0.84 (m, 6H), 0.89 (s, 3H), 0.97 (s, 3H), 1.00 (s, 3H), 1.07-2.19 (m, 21H), 4.95 (d, J=15 Hz, 1H), 5.04 (d, J=15 Hz, 1H), 5.15 (bs, 1H), 7.31-7.37 (m, 5H), 8.22 (s, 1H), 10.49 (bs, 1H); MS (ES+):613.12 [M+1].

Example 9

(1S,2R,4aS,6aS,6bR,8aR,14aR,14bR,16bS)-ethyl 11,13-dihydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (Compound 9)

The title compound was prepared in an analogous manner as example 8 involving the reaction of the compound obtained in step 3 of example 1, (4aR,6aR,6bS,8aS,11R,12S,12aS,14aR,14bR)-8a-benzyl 2-ethyl 4,4,6a,6b,11,12,14b-heptamethyl-3-oxo-1,2,3,4,4a,5,6,6a,6b,7,8,8a,9,10,11,12,12a,14,14a,14b-icosahydropicene-2,8a-dicarboxylate with urea in presence of sodium ethoxide in place of potassium tertiary butoxide, to afford the title compound 9 (0.2 g) as white solid.

Yield: 32%; $^1$H NMR (500 MHz, DMSO-$d_6$): δ 0.69 (s, 3H), 0.82 (d, J=5.0 Hz, 3H), 0.89 (s, 3H), 0.92 (s, 6H), 1.03 (s, 3H), 1.08 (s, 3H), 1.39 (t, J=5 Hz, 3H), 1.26-2.16 (m, 21H), 3.98 (q, J=5 Hz, 2H), 5.15 (s, 1H), 8.22 (s, 1H), 10.46 (s, 1H); MS (ES+):551.5 [M+1].

Example 10

(1S,2R,4aS,6aS,6bR,8aR,14aR,14bR,16bS)-11,13-dihydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid (Compound 10)

The title compound was prepared in an analogous manner as example 5 involving hydrogenation of the compound obtained in example 8, (1S,2R,4aS,6aS,6bR,8aR,14aR,14bR,16bS)-benzyl, 11,13-dihydroxy-1,2,6a,6b,9,9,14a heptamethyl-1,2,3,4,4a,5,6,6a,6b,7,8,8a,9,14,14a,14b,15,16b-octadecahydrochryseno[1,2-g]quinazoline-4a-carboxylate using Pd/C, to afford the title compound 10 (0.3 g) as white solid. Yield: 28%; $^1$H NMR (500 MHz, DMSO-$d_6$): δ 0.75 (s, 3H), 0.82 (d, J=5 Hz, 3H), 0.89 (s, 3H), 0.92 (bs, 6H), 1.03 (s, 3H), 1.08 (s, 3H), 1.23-2.12 (m, 20H), 5.13 (s, 1H), 8.22 (s, 1H), 10.49 (s, 1H), 11.95 (s, 1H); MS (ES+): 523.50 [M+1].

Example 11

(1S,2R,4aS,6aS,6bR,8aR,14aR,14bR,16bS)-benzyl 1,2,6a,6b,9,9,14a-heptamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylate (Compound 11)

To a solution of the compound as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b, 7,8,8a,9,14,14a,14b,15,16b-octadecahydrochryseno[1,2-g]quinazoline-4a-carboxylate (0.1 g, 0.163 mmol) in ethanol (5 mL), was added piperidine (0.1 mL, 1.010 mmol) at room temperature under nitrogen atmosphere. The reaction mixture was refluxed for 12 h. After the completion of reaction, the reaction mixture was concentrated under vacuum, diluted with DCM (10 mL), washed with water (2×10 mL), brine (2×10 mL) and dried over Na$_2$SO$_4$ to afford the title compound 11 (0.1 g) as white solid.

Yield: 93%; $^1$H NMR (300 MHz, DMSO-$d_6$): δ 0.60 (d, J=9.0 Hz, 6H), 0.84 (d, J=6.0 Hz, 3H), 0.91 (s, 3H), 1.09 (s, 3H), 1.20 (d, J=12.0 Hz, 6H), 1.34-3.12 (m, 31H), 4.94 (d, J=12.0 Hz, 1H), 5.04 (d, J=12.0 Hz, 1H), 5.21 (bs, 1H), 7.30-7.35 (m, 5H), 8.5 (s, 1H); MS (ES+): 664.5 [M+1].

Example 12

(1S,2R,4aS,6aS,6bR,8aR,14aR,14bR,16bS)-1,2,6a,6b,9,9,14a-heptamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylic acid (Compound 12)

To a solution of the compound as obtained in example 11 (0.1 g, 0.151 mmol) in THF (2 mL) and MeOH (10 mL), was added Pd/C (0.05 g, 0.470 mmol) at room temperature and the reaction mixture was stirred under hydrogen atmosphere for 2 h. The reaction mixture was filtered and concentrated under vacuum to obtain a residue. The residue obtained was suspended in DCM (10 mL), the mixture was washed with water (2×10 mL), brine (2×10 mL), dried over Na$_2$SO$_4$ and concentrated under vacuum to obtain the crude material. The crude material obtained was washed with acetonitrile (3×2 mL) to afford the title compound 12 (0.03 g) as white solid.

Yield 38%; $^1$H NMR (300 MHz, DMSO-$d_6$): δ 0.65 (s, 3H), 0.79 (s, 3H), 0.84 (d, J=6.0 Hz, 3H), 0.91 (s, 3H), 1.10 (s, 3H), 1.18 (d, J=12.0 Hz, 6H), 1.34-3.12 (m, 31H), 5.20 (bs, 1H), 8.5 (s, 1H), 11.99 (s, 1H); MS (ES+):574.5 [M+1].

Example 13

(1S,2R,4aS,6aS,6bR,8aR,14aR,14bR,16bS)-benzyl 1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylate (Compound 13)

To a solution of the compound as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (0.1 g, 0.163 mmol) in ethanol (5 mL), was added morpholine (0.085 mL, 0.975 mmol) at room temperature under nitrogen atmosphere and the reaction mixture was refluxed for 12 h at the same temperature. The reaction mixture was concentrated under vacuum, diluted with DCM (10 mL), washed with water (2×10 mL), brine (2×10 mL), dried over Na$_2$SO$_4$ and concentrated under vacuum to afford the title compound 13 (0.1 g) as white solid.

Yield 92%; $^1$H NMR (300 MHz, DMSO-$d_6$): δ 0.60 (d, J=9.0 Hz, 6H), 0.84 (d, J=6.0 Hz, 3H), 0.91 (s, 3H), 1.09 (s, 3H), 1.17 (d, J=3.0 Hz, 6H), 1.34-2.41 (m, 22H), 3.0-3.70 (m, 8H), 4.94 (d, J=12.0 Hz, 1H), 5.04 (d, J=12.0 Hz, 1H), 5.21 (bs, 1H), 7.30-7.35 (m, 5H), 8.55 (s, 1H); MS (ES+): 666.5 [M+1].

Example 14

(1S,2R,4aS,6aS,6bR,8aR,14aR,14bR,16bS)-1,2,6a,
6b,9,9,14a-heptamethyl-13-morpholino-1,2,3,4,4a,5,
6,6a,6b,7,8,8a,9,14,14a,14b,15,16b-octadecahydro-
chryseno[1,2-g]quinazoline-4a-carboxylic acid
(Compound 14)

The title compound was prepared in an analogous manner as example 12 involving hydrogenation of compound as obtained in example 13, (1S,2R,4aS,6aS,6bR,8aR,14aR,14bR,16bS)-benzyl 1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylate using Pd/C, to afford title compound 14 (0.03 g) as white solid. Yield 41%; $^1$H NMR (300 MHz, DMSO-$d_6$): δ 0.66 (s, 3H), 0.79 (s, 3H), 0.85 (d, J=6.0 Hz, 3H), 0.91 (s, 3H), 1.09 (s, 3H), 1.19 (s, 3H), 1.38 (s, 3H), 1.40-2.42 (m, 21H), 3.10-3.70 (m, 8H), 5.20 (bs, 1H), 8.55 (s, 1H), 11.98 (s, 1H); MS (ES+):576.5 [M+1].

Example 15

(1S,2R,4aS,6aS,6bR,8aR,14aR,14bR,16bS)-1,2,6a,
6b,9,9,14a-heptamethyl-13-morpholino-1,2,3,4,4a,5,
6,6a,6b,7,8,8a,9,14,14a,14b,15,16b-octadecahydro-
chryseno[1,2-g]quinazoline-4a-carboxylic acid
hydrochloride (Compound 15)

To a solution of the compound as obtained in example 14, (1S,2R,4aS,6aS,6bR,8aR,14aR,14bR,16bS)-1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylic acid (0.1 g, 0.174 mmol) in diethyl ether (5.0 mL) was added hydrogen chloride solution in diethyl ether (2.0M, 2 mL, 4.00 mmol) at 0° C. under nitrogen atmosphere. The reaction mixture was stirred for 12 h at room temperature. After the completion of reaction, the reaction mixture was filtered, obtained solid was washed with diethyl ether (3×5 mL) and dried under vacuum to afford pure title compound 15 (0.07 g) as white solid.

Yield: 65%; $^1$H NMR (300 MHz, DMSO-$d_6$): δ 0.72 (s, 3H), 0.80 (s, 3H), 0.86 (s, 3H), 0.93 (s, 3H), 1.10 (s, 3H), 1.28-1.37 (m, 6H), 1.53-2.38 (m, 21H), 3.55-3.69 (m, 6H), 4.0 (bs, 2H), 5.20 (s, 1H), 8.69 (s, 1H), 11.96 (s, 1H), 14.19 (bs, 1H); MS (ES+):576.5 [M+1].

Example 16

(1S,2R,4aS,6aS,6bR,8aR,14aR,14bR,16bS)-benzyl
1,2,6a,6b,9,9,14a-heptamethyl-13-(4-methylpiper-
azin-1-yl)-1,2,3,4,4a,5,6,6a,6b,7,8,8a,9,14,14a,14b,
15,16b-octadecahydro chryseno[1,2-g]quinazoline-
4a-carboxylate (Compound 16)

To a solution of the compound as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b, 7,8,8a,9,14,14a,14b,15,16b-octadecahydrochryseno[1,2-g]quinazoline-4a-carboxylate (0.1 g, 0.163 mmol) in ethanol (5 mL) was added 1-methylpiperazine (0.109 mL, 0.975 mmol) at room temperature under nitrogen atmosphere and the reaction mixture was refluxed for 12 h. The reaction mixture was concentrated, diluted with DCM (10 mL), washed with water (2×10 mL), brine (2×10 mL), dried over Na$_2$SO$_4$ and concentrated under vacuum to obtain the title compound 16 (0.1 g).

Yield 91%; $^1$H NMR (300 MHz, DMSO-$d_6$): δ 0.60 (d, J=9.0 Hz, 3H), 0.85 (d, J=6.0 Hz, 3H), 0.91 (s, 3H), 1.09 (s, 3H), 1.17 (d, J=3.0 Hz, 3H), 1.34 (s, 3H), 1.35-3.20 (m, 35H), 4.94 (d, J=12.0 Hz, 1H), 5.04 (d, J=12.0 Hz, 1H), 5.22 (bs, 1H), 7.30-7.34 (m, 5H), 8.5 (s, 1H); MS (ES+):679.6 [M+1].

Example 17

(1S,2R,4aS,6aS,6bR,8aR,14aR,14bR,16bS)-1,2,6a,
6b,9,9,14a-heptamethyl-13-(4-methyl piperazin-1-
yl)-1,2,3,4,4a,5,6,6a,6b,7,8,8a,9,14,14a,14b,15,16b-
octadecahydrochryseno[1,2-g]quinazoline-4a-
carboxylic acid (Compound 17)

The title compound was prepared in an analogous manner as example 12 involving hydrogenation of the compound as obtained in example 16, (1S,2R,4aS,6aS,6bR,8aR,14aR,14bR,16bS)-benzyl 1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylate using Pd/C, to afford title compound 17 (0.03 g) as white solid. Yield 35%; $^1$H NMR (300 MHz, DMSO-$d_6$): δ 0.65 (s, 3H), 0.79 (s, 3H), 0.85 (d, J=6.0 Hz, 3H), 0.92 (s, 3H), 1.10 (s, 3H), 1.19 (bs, 6H), 1.38-3.10 (m, 32H), 5.20 (s, 1H), 8.52 (s, 1H), 11.98 (s, 1H); MS (ES+):588.87 [M+1].

Example 18

(1S,2R,4aS,6aS,6bR,8aR,14aR,14bR,16bS)-benzyl
13-(4-((benzyloxy)carbonyl)piperazin-1-yl)-1,2,6a,
6b,9,9,14a-heptamethyl-1,2,3,4,4a,5,6,6a,6b,7,8,8a,
9,14,14a,14b,15,16b-octadeca hydrochryseno[1,2-g]
quinazoline-4a-carboxylate (Compound 18)

To a solution of the compound as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (0.100 g, 0.163 mmol) in ethanol (10 mL), was added benzyl piperazine-1-carboxylate (0.188 mL, 0.975 mmol) at room temperature under nitrogen atmosphere and the reaction mixture was refluxed for 12 h. The reaction mixture was concentrated, diluted with DCM (10 mL), washed with water (2×10 mL), brine (2×10 mL), dried over Na$_2$SO$_4$ and concentrated under vacuum to obtain the title compound 18 (0.05 g, yield 39%) which was used for next reaction without purification.

Example 19

(1S,2R,4aS,6aS,6bR,8aR,14aR,14bR,16bS)-1,2,6a,
6b,9,9,14a-heptamethyl-13-(piperazin-1-yl)-1,2,3,4,
4a,5,6,6a,6b,7,8,8a,9,14,14a,14b,15,16b-octadecahy-
drochryseno[1,2-g]quinazoline-4a-carboxylic acid
(Compound 19)

The title compound was prepared in an analogous manner as example 12 involving hydrogenation of the compound as obtained in example 18, (1S,2R,4aS,6aS,6bR,8aR,14aR,14bR,16bS)-benzyl 13-(4-((benzyloxy)carbonyl)piperazin-1-yl)-1,2,6a,6b,9,9,14a-heptamethyl-1,2,3,4,4a,5,6,6a,6b,7,8,8a,9,14,14a,14b,15,16b-octadeca hydrochryseno[1,2-g]quinazoline-4a-carboxylate using Pd/C, to afford the title compound 19 (0.02 g) as white solid.

Yield: 40%; $^1$H NMR (300 MHz, DMSO-$d_6$): δ 0.64 (s, 3H), 0.79 (s, 3H), 0.85 (d, J=6.0 Hz, 3H), 0.91 (s, 3H), 1.09

(s, 3H), 1.18 (bs, 3H), 1.37-3.10 (m, 33H), 5.20 (s, 1H), 8.52 (s, 1H), 11.99 (s, 1H); MS (ES+):589.4 [M+1]

Example 20

(1S,2R,4aS,6aS,6bR,8aR,14aR,14bR,16bS)-benzyl 1,2,6a,6b,9,9,14a-heptamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylate (Compound 20)

To a solution of the compound as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (0.100 g, 0.163 mmol) in ethanol (5 mL), was added pyrrolidine (0.081 mL, 0.975 mmol) at room temperature under nitrogen atmosphere and the reaction mixture was refluxed for 12 h. The reaction mixture was concentrated under vacuum, diluted with DCM (10 mL), washed with water (2×10 mL), brine (2×10 mL), dried over Na$_2$SO$_4$ and concentrated under vacuum to obtain the title compound 20 (0.1 g) as white solid.

Yield 95%; $^1$H NMR (300 MHz, DMSO-d$_6$): δ 0.59 (s, 3H), 0.65 (s, 3H), 0.83 (d, J=6.0 Hz, 3H), 0.91 (s, 3H), 1.08 (s, 3H), 1.15 (bs, 6H), 1.31-3.57 (m, 29H), 4.94 (d, J=12.0 Hz, 1H), 5.04 (d, J=12.0 Hz, 1H), 5.19 (bs, 1H), 7.32-7.35 (m, 5H), 8.30 (s, 1H); MS (ES+): 650.5 [M+1].

Example 21

(1S,2R,4aS,6aS,6bR,8aR,14aR,14bR,16bS)-1,2,6a,6b,9,9,14a-heptamethyl-13-(pyrrolidin-1-yl)-1,2,3,4,4a,5,6,6a,6b,7,8,8a,9,14,14a,14b,15,16b-octadecahydrochryseno[1,2-g]quinazoline-4a-carboxylic acid (Compound 21)

The title compound was prepared in an analogous manner as example 12 involving hydrogenation of the compound as obtained in example 20, (1S,2R,4aS,6aS,6bR,8aR,14aR,14bR,16bS)-benzyl 1,2,6a,6b,9,9,14a-heptamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylate using Pd/C, to afford the title compound 21 (0.04 g) as white solid.

Yield 46%; $^1$H NMR (300 MHz, DMSO-d$_6$): δ 0.68 (s, 3H), 0.79 (s, 3H), 0.84 (d, J=6.0 Hz, 3H), 0.91 (s, 3H), 1.09 (s, 3H), 1.16 (bs, 6H), 1.34-3.57 (m, 29H), 5.19 (bs, 1H), 8.30 (s, 1H), 11.99 (s, 1H); MS (ES+):550.5 [M+1].

Example 22

(1S,2R,4aS,6aS,6bR,8aR,14aR,14bR,16bS)-benzyl 13-methoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (Compound 22)

To a solution of the compound 5 as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (0.1 g, 0.163 mmol) in methanol (10 mL), was added sodium methoxide (0.088 g, 1.625 mmol) at room temperature under nitrogen atmosphere and the reaction mixture was continued for 12 h. The reaction mixture was concentrated, diluted with DCM (10 mL), washed with water (2×10 mL), brine (2×10 mL), dried over Na$_2$SO$_4$ and concentrated under vacuum to obtain the title compound 22 (0.8 g).

Yield: 85%; $^1$H NMR (300 MHz, DMSO-d$_6$): δ 0.60 (s, 3H), 0.75 (s, 3H), 0.82 (d, J=6.0 Hz, 3H), 0.91 (s, 3H), 1.06 (s, 3H), 1.19 (s, 6H), 1.21-2.03 (m, 19H), 2.19 (d, J=12.0 Hz, 1H), 2.70 (d, J=18.0 Hz, 1H), 3.87 (s, 3H), 4.94 (d, J=12.0 Hz, 1H), 5.04 (d, J=12.0 Hz, 1H), 5.20 (s, 1H), 7.30-7.35 (m, 5H), 8.57 (s, 1H); MS (ES+):611.5 [M+1].

Example 23

(1S,2R,4aS,6aS,6bR,8aR,14aR,14bR,16bS)-13-methoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid (Compound 23)

The title compound was prepared in an analogous manner as example 12 involving hydrogenation of the compound as obtained in example 22, (1S,2R,4aS,6aS,6bR,8aR,14aR,14bR,16bS)-benzyl 13-methoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate using Pd/C, to afford the title compound 23 (0.03 g) as white solid.

Yield 35%; $^1$H NMR (300 MHz, DMSO-d$_6$): δ 0.79-0.84 (m, 6H), 0.91 (s, 3H), 1.08 (s, 3H), 1.18 (s, 6H), 1.34 (s, 3H), 1.5-2.16 (m, 20H), 2.70 (d, J=18.0 Hz, 1H), 3.89 (s, 3H), 5.19 (s, 1H), 8.57 (s, 1H), 11.98 (s, 1H); MS (ES+):521.5 [M+1].

Example 24

(1S,2R,4aS,6aS,6bR,8aR,14aR,14bR,16bS)-benzyl 1,2,6a,6b,9,9,14a-heptamethyl-13-(methylamino)-1,2,3,4,4a,5,6,6a,6b,7,8,8a,9,14,14a,14b,15,16b-octadecahydrochryseno[1,2-g]quinazoline-4a-carboxylate (Compound 24)

To a solution of the compound 5 as obtained in example 5, (1S,2R,4aS,6aS,6bR,8aR,14aR,14bR,16bS)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (0.07 g, 0.114 mmol) in ethanol (15 mL) was added 4-dimethylaminopyridine (DMAP) (0.014 g, 0.114 mmol) followed by methanamine (2M in THF, 2 mL) at room temperature under nitrogen atmosphere and the reaction was stirred at room temperature for 30 h. The reaction mixture was concentrated, diluted with DCM (10 mL), washed with water (3×10 mL), brine (2×10 mL), dried over Na$_2$SO$_4$ and concentrated under vacuum to obtain a crude material. The crude material obtained was washed with acetonitrile (3×3 mL) to obtain the title compound 24 (0.05 g) as white solid.

Yield: 72%; $^1$H NMR (300 MHz, DMSO-d$_6$): δ 0.62 (s, 3H), 0.76 (s, 3H), 0.82 (d, J=6.0 Hz, 3H), 0.91 (s, 3H), 1.08 (bs, 9H), 1.22-2.41 (m, 21H), 2.79 (d, J=6.0 Hz, 3H), 4.95 (d, J=12.0 Hz, 1H), 5.04 (d, J=12.0 Hz, 1H), 5.23 (s, 1H), 6.67 (bs, 1H), 7.33-7.35 (m, 5H), 8.29 (s, 1H); MS (ES+): 610.9 [M+1].

Example 25

(1S,2R,4aS,6aS,6bR,8aR,14aR,14bR,16bS)-1,2,6a,6b,9,9,14a-heptamethyl-13-(methylamino)-1,2,3,4,4a,5,6,6a,6b,7,8,8a,9,14,14a,14b,15,16b-octadecahydrochryseno[1,2-g]quinazoline-4a-carboxylic acid (Compound 25)

The title compound was prepared in an analogous manner as example 12 involving hydrogenation of the compound as obtained in example 24, (1S,2R,4aS,6aS,6bR,8aR,14aR, 14bR,16bS)-benzyl 1,2,6a,6b,9,9,14a-heptamethyl-13-(methylamino)-1,2,3,4,4a,5,6,6a,6b,7,8,8a,9,14,14a,14b,15, 16b-octadecahydrochryseno[1,2-g]quinazoline-4a-carboxylate using Pd/C, to afford the title compound 25 (0.03 g) as white solid.

Yield: 70%; $^1$H NMR (300 MHz, DMSO-d$_6$): δ 0.79-0.83 (m, 9H), 0.92 (s, 3H), 1.08-1.14 (m, 9H), 1.28-2.30 (m, 21H), 2.79 (d, J=3.0 Hz, 3H), 5.23 (s, 1H), 6.68 (s, 1H), 8.29 (s, 1H), 11.97 (s, 1H); MS (ES+):520.9 [M+1].

Example 26

(1S,2R,4aS,6aS,6bR,8aR,14aR,14bR,16bS)-benzyl 13-(dimethylamino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (Compound 26)

To a solution of the compound 5 as obtained in example 5, (1S,2R,4aS,6aS,6bR,8aR,14aR,14bR,16bS)-benzyl13-chloro-1,2,6a,6b,9,9,14a-heptamethyl-1,2,3,4,4a,5,6,6a,6b, 7,8,8a,9,14,14a,14b,15,16b-octadecahydrochryseno[1,2-g] quinazoline-4a-carboxylate (0.07 g, 0.114 mmol) in ethanol (15 mL), was added dimethylamine (0.072 mL, 0.569 mmol, 40% solution in water) at room temperature under nitrogen atmosphere and the reaction mixture was refluxed at 120° C. for 12 h. The reaction mixture was concentrated under vacuum, diluted with DCM (10 mL), washed with water (3×10 mL), brine (2×10 mL), dried over Na$_2$SO$_4$ and concentrated to obtain the title compound 26 (0.05 g) as white solid.

Yield: 70%; $^1$H NMR (300 MHz, DMSO-d$_6$): δ 0.60 (d, J=6.0 Hz, 6H), 0.84 (d, J=6.0 Hz, 3H), 0.92 (s, 3H), 1.10 (s, 3H), 1.17 (bs, 6H), 1.34-2.35 (m, 21H), 2.88 (s, 6H), 4.95 (d, J=12.0 Hz, 1H), 5.04 (d, J=12.0 Hz, 1H), 5.21 (bs, 1H), 7.32 (bs, 5H), 8.43 (s, 1H); MS (ES+):625.0 [M+1].

Example 27

(1S,2R,4aS,6aS,6bR,8aR,14aR,14bR,16bS)-13-(dimethylamino)-1,2,6a,6b,9,9,14a-hepta methyl-1,2,3,4,4a,5,6,6a,6b,7,8,8a,9,14,14a,14b,15,16b-octadecahydrochryseno[1,2-g]quinazoline-4a-carboxylic acid (Compound 27)

The title compound was prepared in an analogous manner as example 12 involving hydrogenation of the compound as obtained in example 26, (1S,2R,4aS,6aS,6bR,8aR,14aR, 14bR,16bS)-benzyl 13-(dimethylamino)-1,2,6a,6b,9,9,14a-heptamethyl-1,2,3,4,4a,5,6,6a,6b,7,8,8a,9,14,14a,14b,15, 16b-octadecahydrochryseno[1,2-g]quinazoline-4a-carboxylate to afford the title compound 27 (0.03 g) as white solid.

Yield: 70%; $^1$H NMR (300 MHz, DMSO-d$_6$): δ 0.65 (s, 3H), 0.80 (s, 3H), 0.85 (d, J=6.0 Hz, 3H), 0.92 (s, 3H), 1.10 (s, 3H), 1.18 (s, 6H), 1.38-2.36 (m, 21H), 2.89 (bs, 6H), 5.20 (bs, 1H), 8.44 (s, 1H), 11.98 (s, 1H); MS (ES+):535.0 [M+1].

Example 28

(1S,2R,4aS,6aS,6bR,8aR,14aR,14bR,16bS)-benzyl 1,2,6a,6b,9,9,14a-heptamethyl-13-((2-morpholinoethyl)amino)-1,2,3,4,4a,5,6,6a,6b,7,8,8a,9,14,14a, 14b,15,16b-octadecahydrochryseno[1,2-g]quinazoline-4a-carboxylate (Compound 28)

To a solution of the compound 5 as obtained in example 5, (1S,2R,4aS,6aS,6bR,8aR,14aR,14bR,16bS)-benzyl13-chloro-1,2,6a,6b,9,9,14a-heptamethyl-1,2,3,4,4a,5,6,6a,6b, 7,8,8a,9,14,14a,14b,15,16b-octadecahydrochryseno[1,2-g] quinazoline-4a-carboxylate (0.07 g, 0.114 mmol) in ethanol (15 mL), was added 2-morpholinoethanamine (0.075 mL, 0.569 mmol) at room temperature under nitrogen atmosphere and the reaction mixture was refluxed at 120° C. for 24 h. The reaction mixture was concentrated, diluted with DCM (10 mL), washed with water (3×10 mL), brine (2×10 mL), dried over Na$_2$SO$_4$ and concentrated under vacuum to obtain the crude material. The crude material obtained was washed with acetonitrile (3×3 mL) to obtain the pure title compound 28 (0.054 g) as white solid.

Yield: 54%; $^1$H NMR (300 MHz, DMSO-d$_6$): δ 0.62 (s, 3H), 0.75 (s, 3H), 0.83 (d, J=6.0 Hz, 3H), 0.91 (s, 3H), 1.08 (s, 3H), 1.23 (s, 6H), 1.32-2.44 (m, 25H), 3.33-3.55 (m, 8H), 4.95 (d, J=12.0 Hz, 1H), 5.06 (d, J=12.0 Hz, 1H), 5.23 (bs, 1H), 6.63 (bs, 1H), 7.33 (bs, 5H), 8.27 (s, 1H); MS (ES+): 710.0 [M+1].

Example 29

(1S,2R,4aS,6aS,6bR,8aR,14aR,14bR,16bS)-1,2,6a, 6b,9,9,14a-heptamethyl-13-((2-morpholinoethyl) amino)-1,2,3,4,4a,5,6,6a,6b,7,8,8a,9,14,14a,14b,15, 16b-octadecahydrochryseno [1,2-g]quinazoline-4a-carboxylic acid (Compound 29)

The title compound was prepared in an analogous manner as example 12 involving hydrogenation of the compound as obtained in example 28, (1S,2R,4aS,6aS,6bR,8aR,14aR, 14bR,16bS)-benzyl 1,2,6a,6b,9,9,14a-heptamethyl-13-((2-morpholinoethyl)amino)-1,2,3,4,4a,5,6,6a,6b,7,8,8a,9,14, 14a,14b,15,16b-octadecahydro chryseno[1,2-g]quinazoline-4a-carboxylate to afford the title compound 29 (0.054 g) as white solid.

Yield: 54%; $^1$H NMR (300 MHz, DMSO-d$_6$): δ 0.62 (s, 3H), 0.75 (s, 3H), 0.83 (d, J=6.0 Hz, 3H), 0.91 (s, 3H), 1.08 (s, 3H), 1.23 (s, 6H), 1.32-2.44 (m, 25H), 3.33-3.55 (m, 8H), 4.95 (d, J=12.0 Hz, 1H), 5.06 (d, J=12.0 Hz, 1H), 5.23 (bs, 1H), 6.63 (bs, 1H), 7.33 (bs, 5H), 8.27 (s, 1H); MS (ES+): 710.0 [M+1].

Example 30

(1S,2R,4aS,6aS,6bR,8aR,14aR,14bR,16bS)-benzyl 13-hydroxy-1,2,6a,6b,9,9,11,14a-octa methyl-1,2,3, 4,4a,5,6,6a,6b,7,8,8a,9,14,14a,14b,15,16b-octadecahydrochryseno[1,2-g]quinazoline-4a-carboxylate (Compound 30)

To a solution of the compound, (4aR,6aR,6bS,8aS,11R, 12S,12aS,14aR,14bR)-8a-benzyl 2-ethyl 4,4,6a,6b,11,12, 14b-heptamethyl-3-oxo-1,2,3,4,4a,5,6,6a,6b,7,8,8a,9,10,11, 12,12a,14,14a,14b-icosahydropicene-2,8a-dicarboxylate as obtained in step 3 of example 1 (0.5 g, 0.811 mmol) in ethanol (15 mL) was added acetimidamide hydrochloride (0.268 g, 2.84 mmol) followed by addition of sodium ethoxide (0.331 g, 4.86 mmol) at room temperature under nitrogen atmosphere. The reaction mixture was refluxed at 120° C. for 16 h. On completion of reaction the mixture was concentrated under vacuum. The residue obtained was diluted with DCM (15 mL), washed with NaH$_2$PO$_4$ solution (3×15 mL), brine (3×15 mL), dried over Na$_2$SO$_4$ and concentrated under vacuum. The crude material obtained was purified by Combiflash chromatography (0-5% methanol/ dichloromethane) to afford pure title compound 30 (0.1 g) as a white solid.

Yield: 20%; $^1$H NMR (300 MHz, DMSO-d$_6$): δ 0.60 (s, 3H), 0.75 (s, 3H), 0.83 (d, J=6.3 Hz, 3H), 0.94 (s, 3H), 1.06 (s, 3H), 1.08 (s, 3H), 1.11 (s, 3H), 1.22-1.92 (m, 21H), 2.20 (s, 3H), 2.57-2.63 (m, 1H), 4.97 (d, J=12.6 Hz, 1H), 5.05 (d, J=12.6 Hz, 1H), 5.20 (bs, 1H), 7.31-7.36 (m, 5H), 12.08 (s, 1H); MS (ES+): 611.87 [M+1]

Example 31

(1S,2R,4aS,6aS,6bR,8aR,14aR,14bR,16bS)-13-hydroxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid
(Compound 31)

To a solution of the compound 30 as obtained in example 30 (0.130 g, 0.213 mmol) in THF (2 mL) and methanol (10 mL) was added Pd/C (0.05 g, 0.047 mmol) at room temperature. The reaction mixture was stirred at room temperature under hydrogen atmosphere for 3 h and on completion of reaction, the reaction mixture was filtered and the filtrate was concentrated under vacuum. The residue obtained was diluted with DCM (10 mL), washed with water (3×10 mL), brine (2×10 mL), dried over Na$_2$SO$_4$ and concentrated under vacuum. The crude material obtained was washed with acetonitrile (3×3 mL) to afford pure title compound 31 (0.05 g) as a white solid.

Yield: 45%; $^1$H NMR (300 MHz, DMSO-d$_6$): δ 0.77 (s, 3H), 0.80 (s, 3H), 0.84 (d, J=6.3 Hz, 3H), 0.92 (s, 3H), 1.05 (s, 3H), 1.08 (s, 3H), 1.14 (s, 3H), 1.19-2.09 (m, 19H), 2.14 (d, J=11.0 Hz, 1H), 2.23 (s, 3H), 2.57-2.63 (m, 1H), 5.20 (bs, 1H), 11.98 (s, 1H), 12.08 (s, 1H); MS (ES+): 521.7 [M+1].

Example 32

(1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate
(Compound 32)

To a solution of the compound 30 as obtained in example 30 (0.09 g, 0.147 mmol) in POCl$_3$ (1.5 ml, 16.09 mmol) was added DMF (1.14411, 0.015 mmol). The reaction mixture was heated at 120° C. under nitrogen atmosphere and maintained for 6 h. On completion of reaction the mixture was diluted with DCM (20 mL) and neutralized to basic pH using NaHCO$_3$ solution (20 ml). The separated organic layer was washed with water (3×15 mL), brine (2×15 mL), dried over Na$_2$SO$_4$ and concentrated under vacuum. The crude material obtained was purified by Combiflash chromatography (0-10% ethyl acetate/petroleum ether) to afford pure title compound 32 (0.068 g) as a white solid.

Yield: 73%; (300 MHz, DMSO-d$_6$): δ 0.61 (s, 3H), 0.76 (s, 3H), 0.82 (d, J=9.0 Hz, 3H), 0.91 (s, 3H), 1.08 (s, 3H), 1.21 (bs, 6H), 1.36-2.81 (m, 24H), 4.96 (d, J=12.6 Hz, 1H), 5.04 (d, J=12.6 Hz, 1H), 5.22 (s, 1H), 7.33-7.36 (m, 5H); MS (ES+): 630.10 [M+1].

Example 33

(1S,2R,4aS,6aS,6bR,8aR,14aR,14bR,16bS)-benzyl 13-methoxy-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate
(Compound 33)

To a solution of the compound 30 as obtained in example 30 (0.150 g, 0.246 mmol) in DMF (5 mL) was added methyl iodide (0.046 mL, 0.737 mmol) followed by addition of K$_2$CO$_3$ (0.170 g, 1.228 mmol). The reaction mixture was stirred at room temperature under nitrogen atmosphere for 12 h. On completion of reaction, the mixture was poured into cold water (35 mL) and the mixture was extracted with DCM (3×15 mL). The separated organic layer was washed with brine (2×35 mL), dried over Na$_2$SO$_4$ and concentrated under vacuum. The crude material obtained was purified using Combiflash chromatography (0-5% methanol/dichloromethane) to afford pure title compound 33 (0.048 g) as a white solid.

Yield: 31%; $^1$H NMR (500 MHz, DMSO-d$_6$): δ 0.62 (s, 3H), 0.77 (s, 3H), 0.83 (d, J=8.5 Hz, 3H), 0.93 (s, 3H), 1.03 (s, 3H), 1.05 (s, 3H), 1.08 (s, 3H), 1.39-2.36 (m, 19H), 2.46 (s, 3H), 2.61-2.65 (m, 1H), 3.4 (s, 3H), 4.97 (d, J=12.6 Hz, 1H), 5.05 (d, J=12.6 Hz, 1H), 5.22 (s, 1H), 7.31-7.37 (m, 5H); MS (ES+): 626 [M+1].

Example 34

(1S,2R,4aS,6aS,6bR,8aR,14aR,14bR,16bS)-13-methoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid
(Compound 34)

The title compound was prepared in an analogous manner as example 31 involving hydrogenation of the compound as obtained in example 33, (1S,2R,4aS,6aS,6bR,8aR,14aR,14bR,16bS)-benzyl 13-methoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate (0.02 g) as a white solid.

Yield: 58%; $^1$H NMR (500 MHz, DMSO-d$_6$): δ 0.70-0.86 (m, 9H), 0.93 (s, 3H), 1.05 (s, 3H), 1.08 (s, 3H), 1.11 (s, 3H), 1.38-1.98 (m, 19H), 2.15 (d, J=11.0 Hz, 1H), 2.45 (s, 3H), 2.61-2.65 (m, 1H), 3.4 (s, 3H), 5.21 (s, 1H), 11.98 (s, 1H); MS (ES+): 536 [M+1].

Example 35

(1S,2R,4aS,6aS,6bR,8aR,14aR,14bR,16bS)-benzyl 13-ethoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate
(Compound 35)

The title compound was prepared in an analogous manner as example 33 involving reaction of the compound as obtained in example 30, (1S,2R,4aS,6aS,6bR,8aR,14aR,14bR,16bS)-benzyl 13-hydroxy-1,2,6a,6b,9,9,11,14a-octamethyl-1,2,3,4,4a,5,6,6a,6b,7,8,8a,9,14,14a, 14b,15,16b-octadecahydrochryseno[1,2-g]quinazoline-4a-carboxylate with ethyl iodide in place of methyl iodide, in presence of K$_2$CO$_3$ and DMF, to afford the title compound 35 (0.048 g) as a white solid.

Yield: 30%; $^1$H NMR (500 MHz, DMSO-d$_6$): δ 0.61 (s, 3H), 0.73 (s, 3H), 0.84 (d, J=6.5 Hz, 3H), 1.0 (s, 3H), 1.06 (d, J=6.5 Hz, 3H), 1.14 (s, 3H), 1.14-2.18 (m, 25H), 2.21 (d, J=11.0 Hz, 1H), 2.62 (d, J=16.5 Hz, 1H), 3.94 (q, J=7.0 Hz, 2H), 4.97 (d, J=12.6 Hz, 1H), 5.05 (d, J=12.6 Hz, 1H), 5.22 (s, 1H), 7.31-7.37 (m, 5H); MS (ES+): 640 [M+1]

Example 36

(1S,2R,4aS,6aS,6bR,8aR,14aR,14bR,16bS)-13-ethoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid (Compound 36)

The title compound was prepared in an analogous manner as example 31 involving hydrogenation of the compound as obtained in example 35, (1S,2R,4aS,6aS,6bR,8aR,14aR,14bR,16bS)-benzyl 13-ethoxy-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate to afford pure title compound 36 (0.034 g) as a white solid.

Yield: 44%; $^1$H NMR (500 MHz, DMSO-d$_6$): δ 0.75 (d, J=12.5 Hz, 6H), 0.81 (d, J=8.0 Hz, 3H), 0.93 (s, 3H), 1.02 (s, 3H), 1.05 (s, 3H), 1.08 (s, 3H), 1.11-2.98 (m, 25H), 2.15 (d, J=11.5 Hz, 1H), 2.62 (d, J=17.0 Hz, 1H), 3.94 (q, J=7.5 Hz, 2H), 5.22 (s, 1H), 11.98 (s, 1H); MS (ES+): 550 [M+1].

Example 37

(1S,2R,4aS,6aS,6bR,8aR,14aR,14bR,16bS)-benzyl 13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate (Compound 37)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate (0.1 g, 0.159 mmol) in ethanol (10 mL) was added dimethylamine (40% in water, 5 mL, 0.159 mmol). The reaction mixture was stirred at room temperature under nitrogen atmosphere for 12 h. On completion of reaction the mixture was concentrated under vacuum and the residue obtained was diluted with DCM (15 mL). The mixture was washed with water (3×15 ml), brine (2×10 mL), dried over Na$_2$SO$_4$ and concentrated under vacuum to afford title compound 37 (0.1 g) as a white solid.

Yield: 99%; $^1$H NMR (500 MHz, DMSO-d$_6$): δ 0.61-0.65 (m, 6H), 0.85 (d, J=6.5 Hz, 3H), 0.93 (s, 3H), 1.10 (s, 3H), 1.14 (bs, 6H), 1.23-2.33 (m, 20H), 2.37 (s, 3H), 2.42-2.45 (m, 1H), 2.86 (s, 6H), 4.96 (d, J=12.6 Hz, 1H), 5.05 (d, J=12.6 Hz, 1H), 5.22 (s, 1H), 7.31-7.37 (m, 5H); MS (ES+): 638.6 [M+1].

Example 38

(1S,2R,4aS,6aS,6bR,8aR,14aR,14bR,16bS)-13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid (Compound 38)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate (0.1 g, 0.157 mmol) in THF (2 mL) and methanol (10 mL) was added Pd/C (0.04 g, 0.038 mmol). The reaction mixture was stirred at room temperature under hydrogen atmosphere for 3 h. On completion of reaction, the mixture was filtered and concentrated under vacuum. The residue obtained was diluted with DCM (10 mL) and the mixture was washed with water (3×10 mL) followed by brine (2×10 mL), dried over Na$_2$SO$_4$ and concentrated under vacuum. The crude material obtained was washed with acetonitrile (3×3 mL) to afford pure title compound 38 (0.07 g) as a white solid.

Yield: 82%; $^1$H NMR (300 MHz, DMSO-d$_6$): δ 0.64 (s, 3H), 0.80 (s, 3H), 0.84 (d, J=6.5 Hz, 3H), 0.91 (s, 3H), 1.09 (s, 3H), 1.16 (bs, 6H), 1.23-2.33 (m, 20H), 2.35 (s, 3H), 2.41 (s, 1H), 2.85 (s, 6H), 5.20 (s, 1H), 12.0 (s, 1H); MS (ES+): 548.5 [M+1].

Example 39

(1S,2R,4aS,6aS,6bR,8aR,14aR,14bR,16bS)-13-(dimethylamino)-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylic acid hydrochloride (Compound 39)

To a solution of the compound as obtained in example 38, (1S,2R,4aS,6aS,6bR,8aR,14aR,14bR,16bS)-13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid (0.1 g, 0.183 mmol) in diethyl ether (5.0 mL) was added hydrogen chloride solution in diethyl ether (2 mL, 4.00 mmol, 2.0M) at 0° C. The reaction mixture was stirred at room temperature under nitrogen atmosphere for 12 h. The reaction mixture was filtered and the solid obtained was washed with diethyl ether (3×5 mL) to afford pure title compound 39 (0.07 g) as a white solid.

Yield: 65%; $^1$H NMR (300 MHz, DMSO-d$_6$): δ 0.71 (s, 3H), 0.79 (s, 3H), 0.86 (d, J=6.0 Hz, 3H), 0.92 (s, 3H), 1.10 (s, 3H), 1.31-1.38 (m, 6H), 1.57-2.33 (m, 21H), 2.63 (s, 3H), 3.67 (s, 6H), 4.08 (bs, 2H), 5.20 (s, 1H), 11.99 (s, 1H), 13.35 (s, 1H); MS (ES+): 590.5 [M+1].

Example 40

(1S,2R,4aS,6aS,6bR,8aR,14aR,14bR,16bS)-benzyl 1,2,6a,6b,9,9,11,14a-octamethyl-13-(methylamino)-1,2,3,4,4a,5,6,6a,6b,7,8,8a,9,14,14a,14b,15,16b-octadecahydrochryseno[1,2-g]quinazoline-4a-carboxylate (Compound 40)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate (0.1 g, 0.159 mmol) in ethanol (10 mL) was added methane amine (40% in water, 5 mL, 0.159 mmol). The reaction mixture was stirred at room temperature under nitrogen atmosphere for 30 h. The reaction mixture was concentrated under vacuum. The residue obtained was diluted with DCM (15 mL), washed with water (3×5 mL), brine (2×10 mL), dried over Na$_2$SO$_4$ and concentrated under vacuum to afford title compound 40 (0.09 g) as a white solid.

Yield: 90%; $^1$H NMR (500 MHz, DMSO-d$_6$): δ 0.63 (s, 3H), 0.76 (bs, 3H), 0.84 (bs, 3H), 0.93 (s, 3H), 1.08 (s, 3H), 1.13 (s, 3H), 1.21 (s, 3H), 1.23-2.23 (m, 20H), 2.31 (s, 3H), 2.36-2.55 (m, 1H), 2.79 (d, J=3.5 Hz, 3H), 4.96 (d, J=12.6 Hz, 1H), 5.05 (d, J=12.6 Hz, 1H), 5.24 (s, 1H), 6.54 (d, J=5.0 Hz, 1H), 7.31-7.37 (m, 5H); MS (ES+): 624.5 [M+1].

Example 41

(1S,2R,4aS,6aS,6bR,8aR,14aR,14bR,16bS)-1,2,6a,6b,9,9,11,14a-octamethyl-13-(methylamino)-1,2,3,4,4a,5,6,6a,6b,7,8,8a,9,14,14a,14b,15,16b-octadecahydrochryseno[1,2-g]quinazoline-4a-carboxylic acid (Compound 41)

The title compound was prepared in an analogous manner as example 38 involving hydrogenation of the compound as obtained in example 40, (1S,2R,4aS,6aS,6bR,8aR,14aR,14bR,16bS)-benzyl 1,2,6a,6b,9,9,11,14a-octamethyl-13-(methylamino)-1,2,3,4,4a,5,6,6a,6b,7,8,8a,9,14,14a,14b,15,16b-octadecahydrochryseno[1,2-g]quinazoline-4a-carboxylate to afford pure title compound 41 (0.06 g) as a white solid.

Yield: 70%; $^1$H NMR (500 MHz, DMSO-$d_6$): δ 0.78 (s, 3H), 0.84 (bs, 6H), 0.91 (s, 3H), 1.07 (s, 3H), 1.12 (bs, 3H), 1.22 (s, 3H), 1.38-2.16 (m, 20H), 2.29 (s, 3H), 2.33-2.39 (m, 1H), 2.77 (d, J=3.5 Hz, 3H), 5.22 (s, 1H), 6.52 (bs, 1H), 1.98 (s, 1H); MS (ES+): 634.5 [M+1].

Example 42

(1S,2R,4aS,6aS,6bR,8aR,14aR,14bR,16bS)-benzyl 13-(diethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate (Compound 42)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate (0.1 g, 0.159 mmol) in ethanol (10 mL) was added diethyl amine (1.0 mL, 9.57 mmol). The reaction mixture was stirred at room temperature under nitrogen atmosphere for 30 h. The reaction mixture was concentrated under vacuum. The residue obtained was diluted with DCM (15 mL), washed with water (3×15 ml), brine (2×10 mL), dried over $Na_2SO_4$ and concentrated under vacuum to afford title compound 42 (0.05 g) as a white solid.

Yield: 47%; $^1$H NMR (300 MHz, DMSO-$d_6$): δ 0.62 (s, 3H), 0.85 (d, J=6.5 Hz, 3H), 0.93 (s, 3H), 1.10-1.10 (m, 9H), 1.16 (bs, 3H), 1.23-2.33 (m, 30H), 2.37 (s, 3H), 4.96 (d, J=12.6 Hz, 1H), 5.05 (d, J=12.6 Hz, 1H), 5.22 (s, 1H), 7.31-7.37 (m, 5H); MS (ES+): 666.6 [M+1].

Example 43

(1S,2R,4aS,6aS,6bR,8aR,14aR,14bR,16bS)-13-(diethylamino)-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylic acid (Compound 43)

The title compound was prepared in an analogous manner as example 38 involving hydrogenation of the compound as obtained in example 42 to afford pure title compound 43 (0.05 g) as a white solid.

Yield: 57%; $^1$H NMR (300 MHz, DMSO-$d_6$): δ 0.62 (s, 3H), 0.73 (s, 3H), 0.85 (d, J=6.5 Hz, 3H), 0.93 (s, 3H), 1.10-1.10 (m, 9H), 1.16 (bs, 3H), 1.23-2.33 (m, 24H), 2.37 (s, 3H), 3.14-3.32 (m, 4H), 5.22 (s, 1H), 11.94 (s, 1H); MS (ES+):576.6 [M+1].

Example 44

(1S,2R,4aS,6aS,6bR,8aR,14aR,14bR,16bS)-benzyl 1,2,6a,6b,9,9,11,14a-octamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylate (Compound 44)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno [1,2-g]quinazoline-4a-carboxylate (0.1 g, 0.159 mmol) in ethanol (10 mL) was added pyrrolidine (1 mL, 12.09 mmol). The reaction mixture was stirred at room temperature under nitrogen atmosphere for 12 h. The reaction mixture was concentrated under vacuum. The residue obtained was diluted with DCM (15 mL), washed with water (3×15 ml), brine (2×10 mL), dried over $Na_2SO_4$ and concentrated under vacuum to afford crude title compound 44 (0.1 g) as a white solid.

Yield: 90%; $^1$H NMR (500 MHz, DMSO-$d_6$): δ 0.61 (s, 3H), 0.66 (s, 3H), 0.85 (d, J=6.5 Hz, 3H), 0.93 (s, 3H), 1.06 (s, 3H), 1.10 (s, 3H), 1.47 (s, 3H), 1.23-2.0 (m, 25H), 2.31 (s, 3H), 3.38-3.59 (m, 4H), 4.96 (d, J=12.0 Hz, 1H), 5.05 (d, J=12.0 Hz, 1H), 5.22 (s, 1H), 7.31-7.37 (m, 5H); MS (ES+):665.5 [M+1].

Example 45

(1S,2R,4aS,6aS,6bR,8aR,14aR,14bR,16bS)-1,2,6a,6b,9,9,11,14a-octamethyl-13-(pyrrolidin-1-yl)-1,2,3,4,4a,5,6,6a,6b,7,8,8a,9,14,14a,14b,15,16b-octadecahydrochryseno[1,2-g]quinazoline-4a-carboxylic acid (Compound 45)

The title compound was prepared in an analogous manner as example 38 involving hydrogenation of the compound as obtained in example 44 to afford pure title compound 45 as a white solid (0.075 g).

Yield: 96%; $^1$H NMR (300 MHz, DMSO-$d_6$): δ 0.67 (s, 3H), 0.79 (s, 3H), 0.85 (d, J=6.3 Hz, 3H), 0.91 (s, 3H), 1.08 (s, 3H), 1.13 (s, 3H), 1.16 (s, 3H), 1.30-2.15 (m, 25H), 2.30 (s, 3H), 3.30-3.35 (m, 2H), 3.55-3.60 (m, 2H), 5.18 (s, 1H), 12.0 (s, 1H); MS (ES+): 574.5 [M+1].

Example 46

(1S,2R,4aS,6aS,6bR,8aR,14aR,14bR,16bS)-benzyl 1,2,6a,6b,9,9,11,14a-octamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylate (Compound 46)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno [1,2-g]quinazoline-4a-carboxylate (0.1 g, 0.159 mmol) in ethanol (10 mL) was added piperidine (1 mL, 10.10 mmol). The reaction mixture was stirred at room temperature under nitrogen atmosphere for 30 h. The reaction mixture was concentrated under vacuum. The residue obtained was diluted with DCM (15 mL), washed with water (3×15 mL), brine (2×10 mL), dried over $Na_2SO_4$ and concentrated under vacuum to afford titled compound 46 (0.1 g) as a white solid.

Yield: 93%; ¹H NMR (500 MHz, DMSO-$d_6$): δ 0.61 (d, J=9.0 Hz, 6H), 0.85 (d, J=6.5 Hz, 3H), 0.93 (s, 3H), 1.11 (s, 3H), 1.16 (s, 3H), 1.18 (s, 3H), 1.34-2.23 (m, 23H), 2.39 (s, 3H), 3.0-3.37 (m, 8H), 4.96 (d, J=12.5 Hz, 1H), 5.05 (d, J=12.5 Hz, 1H), 5.23 (s, 1H), 7.31-7.37 (m, 5H); MS (ES+): 678.5 [M+1].

Example 47

(1S,2R,4aS,6aS,6bR,8aR,14aR,14bR,16bS)-1,2,6a,
6b,9,9,11,14a-octamethyl-13-(piperidin-1-yl)-1,2,3,
4,4a,5,6,6a,6b,7,8,8a,9,14,14a,14b,15,16b-octadeca-
hydrochryseno[1,2-g]quinazoline-4a-carboxylic acid
(Compound 47)

The title compound was prepared in an analogous manner as example 38 involving hydrogenation of the compound as obtained in example 46 to afford pure title compound 47 (0.06 g) as a white solid.

Yield: 86%; ¹H NMR (500 MHz, DMSO-$d_6$): δ 0.64 (s, 3H), 0.79 (s, 3H), 0.84 (d, J=5.7 Hz, 3H), 0.91 (s, 3H), 1.09 (s, 3H), 1.16 (bs, 3H), 1.22 (s, 3H), 1.36-2.32 (m, 23H), 2.37 (s, 3H), 3.0-3.42 (m, 8H), 5.20 (s, 1H), 11.99 (s, 1H); MS (ES+): 588.5 [M+1].

Example 48

(1S,2R,4aS,6aS,6bR,8aR,14aR,14bR,16bS)-benzyl
1,2,6a,6b,9,9,11,14a-octamethyl-13-(4-methylpiper-
azin-1-yl)-1,2,3,4,4a,5,6,6a,6b,7,8,8a,9,14,14a,14b,
15,16b-octadecahydrochryseno[1,2-g]quinazoline-
4a-carboxylate (Compound 48)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6, 6a,6b,7,8,8a,9,14,14a,14b,15,16b-octadecahydrochryseno [1,2-g]quinazoline-4a-carboxylate (0.1 g, 0.159 mmol) in ethanol (10 mL), was added 1-methylpiperazine (1 mL, 0.159 mmol). The reaction mixture was refluxed at 120° C. under nitrogen atmosphere for 12 h. The reaction mixture was concentrated under vacuum. The residue obtained was diluted with DCM (15 mL), washed with water (3×15 ml), brine (2×10 mL), dried over $Na_2SO_4$ and concentrated under vacuum to afford crude title compound 48 (0.07 g) as a white solid. Yield: 60%; ¹H NMR (500 MHz, DMSO-$d_6$): δ 0.60 (s, 3H), 0.62 (s, 3H), 0.86 (d, J=6.0 Hz, 3H), 0.93 (s, 3H), 1.11 (s, 3H), 1.17 (bs, 6H), 1.30-2.04 (m, 27H), 2.22 (s, 3H), 2.40 (s, 3H), 3.0 (bs, 2H), 4.94 (d, J=12.5 Hz, 1H), 5.05 (d, J=12.5 Hz, 1H), 5.23 (s, 1H), 7.31-7.37 (m, 5H); MS (ES+): 693.6 [M+1].

Example 49

(1S,2R,4aS,6aS,6bR,8aR,14aR,14bR,16bS)-1,2,6a,
6b,9,9,11,14a-octamethyl-13-(4-methyl piperazin-1-
yl)-1,2,3,4,4a,5,6,6a,6b,7,8,8a,9,14,14a,14b,15,16b-
octadecahydro chryseno [1,2-g]quinazoline-4a-
carboxylic acid (Compound 49)

The title compound was prepared in an analogous manner as example 38, involving hydrogenation of the compound as obtained in example 48, (1S,2R,4aS,6aS,6bR,8aR,14aR, 14bR,16bS)-benzyl 1,2,6a,6b,9,9,11,14a-octamethyl-13-(4-methylpiperazin-1-yl)-1,2,3,4,4a,5,6,6a,6b,7,8,8a,9,14,14a, 14b,15,16b-octadecahydrochrysenno[1,2-g]quinazoline-4a-carboxylate using Pd/C, to afford pure title compound 49 (0.05 g) as a white solid.

Yield: 57%; ¹H NMR (300 MHz, DMSO-$d_6$): δ 0.64 (s, 3H), 0.79 (s, 3H), 0.85 (d, J=6.3 Hz, 3H), 0.92 (s, 3H), 1.09 (s, 3H), 1.17 (bs, 6H), 1.35-2.23 (m, 29H), 2.38 (bs, 6H), 5.20 (s, 1H), 11.98 (s, 1H); MS (ES+):603.6 [M+1].

Example 50

(1S,2R,4aS,6aS,6bR,8aR,14aR,14bR,16bS)-benzyl
13-(cyclohexylamino)-1,2,6a,6b,9,9,11,14a-octam-
ethyl-1,2,3,4,4a,5,6,6a,6b,7,8,8a,9,14,14a,14b,15,
16b-octadecahydrochryseno[1,2-g]quinazoline-4a-
carboxylate (Compound 50)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6, 6a,6b,7,8,8a,9,14,14a,14b,15,16b-octadecahydrochryseno [1,2-g]quinazoline-4a-carboxylate (0.1 g, 0.159 mmol) in ethanol (10 mL) was added cyclohexyl amine (1 mL, 0.159 mmol). The reaction mixture was refluxed at 120° C. under nitrogen atmosphere for 12 h. The reaction mixture was concentrated under vacuum. The residue was diluted with DCM (15 mL), washed with water (3×15 ml), brine (2×10 mL), dried over $Na_2SO_4$ and concentrated under vacuum to afford crude title compound 50 (0.08 g) as a white solid.

Yield: 70%; ¹H NMR (300 MHz, DMSO-$d_6$): δ 0.60 (s, 3H), 0.73 (s, 3H), 0.82 (d, J=6.3 Hz, 3H), 0.90 (s, 3H), 1.06 (s, 3H), 1.09 (bs, 6H), 1.21-2.00 (m, 30H), 2.26 (s, 3H), 3.94 (bs, 1H), 4.94 (d, J=12.5 Hz, 1H), 5.05 (d, J=12.5 Hz, 1H), 5.23 (s, 1H), 6.10 (d, J=8.10 Hz, 1H), 7.31-7.37 (m, 5H); MS (ES+): 692.6 [M+1].

Example 51

(1S,2R,4aS,6aS,6bR,8aR,14aR,14bR,16bS)-13-(cy-
clohexylamino)-1,2,6a,6b,9,9,11,14a-octamethyl-1,2,
3,4,4a,5,6,6a,6b,7,8,8a,9,14,14a,14b,15,16b-octa-
decahydrochryseno[1,2-g]quinazoline-4a-carboxylic
acid (Compound 51)

The title compound was prepared in an analogous manner as example 38 involving hydrogenation of the compound as obtained in example 50, (1S,2R,4aS,6aS,6bR,8aR,14aR, 14bR,16bS)-benzyl 13-(cyclohexylamino)-1,2,6a,6b,9,9,11, 14a-octamethyl-1,2,3,4,4a,5,6,6a,6b,7,8,8a,9,14,14a,14b, 15,16b-octadecahydrochryseno[1,2-g]quinazoline-4a-carboxylate using Pd/C, to afford pure title compound 51 (0.04 g) as a white solid.

Yield: 61%; ¹H NMR (300 MHz, DMSO-$d_6$): δ 0.77 (s, 3H), 0.82 (s, 3H), 0.91 (s, 3H), 1.07 (s, 3H), 1.11 (bs, 6H), 1.22 (s, 3H), 1.26-2.36 (m, 31H), 2.26 (s, 3H), 3.97 (bs, 1H), 5.23 (s, 1H), 6.11 (d, J=8.10 Hz, 1H), 11.98 (s, 1H); MS (ES+): 602.6 [M+1].

Example 52

(1S,2R,4aS,6aS,6bR,8aR,14aR,14bR,16bS)-benzyl
13-(4-((benzyloxy)carbonyl) piperazin-1-yl)-1,2,6a,
6b,9,9,11,14a-octamethyl-1,2,3,4,4a,5,6,6a,6b,7,8,
8a,9,14,14a,14b,15,16b-octadecahydrochryseno[1,2-
g]quinazoline-4a-carboxylate (Compound 52)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate (0.1 g, 0.159 mmol) in ethanol (10 mL) was added tert-butyl piperazine-1-carboxylate (0.5 mL, 0.159 mmol). The reaction mixture was refluxed at 120° C. under nitrogen atmosphere for 12 h. The reaction mixture was concentrated under vacuum. The residue obtained was diluted with DCM (15 mL), washed with water (3×15 mL), brine (2×10 mL), dried over $Na_2SO_4$ and concentrated under vacuum to afford title compound 52 (0.06 g) as a white solid.

Yield: 48%; $^1H$ NMR (300 MHz, DMSO-$d_6$): δ0.60 (d, J=7.5 Hz, 6H), 0.84 (d, J=6.0 Hz, 3H), 0.91 (s, 3H), 1.08 (s, 3H), 1.15 (bs, 6H), 1.31-2.32 (m, 21H), 2.38 (s, 3H), 3.09-3.54 (m, 8H), 4.91-5.08 (m, 4H), 5.20 (s, 1H), 7.28-7.37 (m, 10H); MS (ES+): 813.6 [M+1].

Example 53

(1S,2R,4aS,6aS,6bR,8aR,14aR,14bR,16bS)-1,2,6a,6b,9,9,11,14a-octamethyl-13-(piperazin-1-yl)-1,2,3,4,4a,5,6,6a,6b,7,8,8a,9,14,14a,14b,15,16b-octadecahydrochryseno[1,2-g]quinazoline-4a-carboxylic acid (Compound 53)

The title compound was prepared in an analogous manner as example 38 involving hydrogenation of the compound as obtained in example 52, (1S,2R,4aS,6aS,6bR,8aR,14aR,14bR,16bS)-benzyl 13-(4-((benzyloxy)carbonyl) piperazin-1-yl)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate using Pd/C, to afford pure title compound 53 (0.05 g) as a white solid.

Yield: 67%; $^1H$ NMR (300 MHz, DMSO-$d_6$): δ 0.64 (s, 3H), 0.79 9s, 3H), 0.85 (d, J=6.0 Hz, 3H), 0.92 (s, 3H), 1.09 (s, 3H), 1.16 (bs, 6H), 1.22-2.38 (m, 28H), 3.09-3.54 (m, 8H), 5.20 (s, 1H); MS (ES+): 589.8 [M+1].

Example 54

(1S,2R,4aS,6aS,6bR,8aR,14aR,14bR,16bS)-benzyl 1,2,6a,6b,9,9,11,14a-octamethyl-13-morpholino-1,2,3,4,4a,5,6,6a,6b,7,8,8a,9,14,14a,14b,15,16b-octadecahydrochryseno[1,2-g]quinazoline-4a-carboxylate (Compound 54)

To a solution of the compound as obtained in example 32, (1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate (0.065 g, 0.103 mmol) in ethanol (10 mL) was added morpholine (0.045 mL, 0.516 mmol). The reaction mixture was at temperature 120° C. under nitrogen atmosphere for 20 h. The reaction mixture was concentrated under vacuum. The residue obtained was diluted with DCM (10 mL), washed with water (3×10 mL), brine (2×10 mL), dried over $Na_2SO_4$ and concentrated under vacuum to afford crude title compound 54 (0.05 g) as a white solid.

Yield: 71%; $^1H$ NMR (500 MHz, DMSO-$d_6$): δ 0.61 (s, 3H), 0.63 (s, 3H), 0.86 (d, J=6.0 Hz, 3H), 0.93 (s, 3H), 1.10 (s, 3H), 1.18 (s, 6H), 1.23-3.00 (m, 24H), 3.03-3.06 (m, 2H), 3.37-3.41 (m, 2H), 3.62-3.65 (m, 2H), 3.72-3.75 (m, 2H), 4.96 (d, J=13.0 Hz, 1H), 5.05 (d, J=13.0 Hz, 1H), 5.23 (s, 1H), 7.31-7.39 (m, 5H); MS (ES+): 681.5 [M+1].

Example 55

(1S,2R,4aS,6aS,6bR,8aR,14aR,14bR,16bS)-1,2,6a,6b,9,9,11,14a-octamethyl-13-morpholino-1,2,3,4,4a,5,6,6a,6b,7,8,8a,9,14,14a,14b,15,16b-octadecahydrochryseno[1,2-g]quinazoline-4a-carboxylic acid (Compound 55)

The title compound was prepared in an analogous manner as example 38 involving hydrogenation of the compound as obtained in example 54, (1S,2R,4aS,6aS,6bR,8aR,14aR,14bR,16bS)-benzyl 1,2,6a,6b,9,9,11,14a-octamethyl-13-morpholino-1,2,3,4,4a,5,6,6a,6b,7,8,8a,9,14,14a,14b,15,16b-octadecahydrochryseno[1,2-g]quinazoline-4a-carboxylate using Pd/C, to afford pure title compound 55 (0.025 g) as a white solid.

Yield: 48%; $^1H$ NMR (500 MHz, DMSO-$d_6$): δ 0.70 (s, 3H), 0.80 (s, 3H), 0.87 (d, J=6.5 Hz, 3H), 0.93 (s, 3H), 1.11 (s, 3H), 1.19 (s, 6H), 1.24-2.23 (m, 21H), 2.46 (s, 3H), 3.04-3.06 (bs, 2H), 3.37 (bs, 2H), 3.63 (bs, 2H), 3.72 (bs, 2H), 5.21 (s, 1H), 12.0 (s, 1H); MS (ES+): 591.1 [M+1].

Example 56

(1S,2R,4aS,6aS,6bR,8aR,14aR,14bR,16bS)-1,2,6a,6b,9,9,11,14a-octamethyl-13-morpholino-1,2,3,4,4a,5,6,6a,6b,7,8,8a,9,14,14a,14b,15,16b-octadecahydrochryseno[1,2-g]quinazoline-4a-carboxylic acid hydrochloride (Compound 56)

To a solution of the compound as obtained in example 55 (0.067 g, 0.114 mmol) in diethyl ether (4 mL) was added hydrochloride solution in ether (2.0 mL, 4.00 mmol, 2.0M)) at 0° C. The mixture was stirred at room temperature under nitrogen atmosphere for 12 h. The reaction mixture was filtered and solid obtained was washed with diethyl ether (3×5 mL) and dried over vacuum to afford pure title compound 56 (0.05 g) as a white solid.

Yield: 70%; $^1H$ NMR (300 MHz, DMSO-$d_6$): δ 0.72 (s, 3H), 0.80 (s, 3H), 0.83 (d, J=6.3 Hz, 3H), 1.10 (s, 3H), 1.30 (s, 3H), 1.36 (bs, 6H), 1.48-2.00 (m, 13H), 2.12 (s, 3H), 2.14 (d, J=10.8 Hz, 1H), 2.60 (s, 3H), 3.35 (bs, 6H), 3.38 (s, 2H), 3.72 (bs, 2H), 5.20 (s, 1H), 12.0 (s, 1H), 13.11 (s, 1H); MS (ES+): 547.45 [M+1].

Example 56A

Synthesis of (1S,2R,4aS,6aS,6bR,8aR,14aR,14bR,16bS)-1,2,6a,6b,9,9,11,14a-octamethyl-13-(morpholine-4-carbonyl)-1,2,3,4,4a,5,6,6a,6b,7,8,8a,9,14,14a,14b,15,16b-octadecahydrochryseno[1,2-g]quinazoline-4a-carboxylic acid (Compound 56A)

Step 1

Synthesis of (1S,2R,4aS,6aS,6bR,14aR)-benzyl 13-cyano-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate To a solution of the compound as obtained in example 32, (1S,2R,4aS,6aS,6bR,8aR,14aR,14bR,16bS)-benzyl 13-chloro-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate (0.5 g, 0.795 mmol) in DMF (8 mL) was added dicyanozinc (0.140 g, 1.192 mmol) followed by addition of tetrakis(triphenylphosphine)palladium(O) (0.080 g, 0.278 mmol) at room temperature under nitrogen atmosphere. The reaction mixture was stirred at temperature 130° C. for 3 h. On completion of reaction the mixture was poured into cold water and filtered. The material obtained was washed with ACN (3×10 mL) and dried over Na$_2$SO$_4$ to afford title pure compound 39A (0.422 g) as a white solid.

Yield: 86%; $^1$H NMR (300 MHz, DMSO-d$_6$): δ 0.62 (s, 3H), 0.77 (s, 3H), 0.79-0.90 (m, 4H), 0.92-1.00 (m, 4H), 1.15-1.20 (m, 5H), 1.18-1.85 (m, 18H), 1.90-2.10 (m, 3H), 2.15-2.30 (m, 1H), 2.62 (s, 3H), 2.80-2.90 (m, 1H), 4.94 (d, J=12.5 Hz, 1H), 5.08 (d, J=12.5 Hz, 1H), 5.24 (s, 1H), 7.28-7.45 (m, 5H); MS (ES+): 620.5[M+1].

Step 2

Synthesis of (1S,2R,4aS,6aS,6bR,14aR)-4a-((benzyloxy)carbonyl)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-13-carboxylic acid To a solution of the compound obtained in step 1, (1S,2R,4aS,6aS,6bR,14aR)-benzyl 13-cyano-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate (0.5 g, 0.807 mmol) in ethanol (10 mL) and THF (2.0 mL) was added 4N solution of sodium hydroxide (5.0 mL) at room temperature. The reaction mixture was heated at 80° C. for 12 h. After the completion of reaction, the reaction mixture was acidified to acidic P$^H$ using 1NHCl solution. The reaction mixture was concentrated under vacuum and the material obtained was diluted with DCM (15 mL) and washed with water (3×10 mL), brine (2×10 mL), dried over Na$_2$SO$_4$ and concentrated under vacuum to afford pure titled compound (0.09 g) as white solid.

Yield: 17.49%; $^1$H NMR (300 MHz, DMSO-d$_6$): δ 0.62 (s, 3H), 0.77 (s, 3H), 0.79-0.90 (m, 4H), 0.92-1.00 (m, 4H), 1.15-1.20 (m, 5H), 1.18-1.85 (m, 18H), 1.90-2.10 (m, 3H), 2.15-2.30 (m, 1H), 2.64 (s, 3H), 2.75-2.85 (m, 1H), 4.95 (d, J=12.5 Hz, 1H), 5.05 (d, J=12.5 Hz, 1H), 5.22 (s, 1H), 7.28-7.45 (m, 5H); MS (ES+): 620.5[M+1].

Step 3

Synthesis of (1S,2R,4aS,6aS,6bR,14aR)-benzyl 1,2,6a,6b,9,9,11,14a-octamethyl-13-(morpholine-4-carbonyl)-1,2,3,4,4a,5,6,6a,6b,7,8,8a,9,14,14a,14b,15,16b-octadecahydrochryseno[1,2-g]quinazoline-4a-carboxylate To a solution of the compound obtained in step 2, (1S,2R,4aS,6aS,6bR,14aR)-4a-((benzyloxy)carbonyl)-1,2,6a,6b,9,9,11,14a-octamethyl-1,2,3,4,4a,5,6,6a,6b,7,8,8a,9,14,14a, 14b,15,16b-octadecahydrochryseno[1,2-g]quinazoline-13-carboxylic acid (0.3 g, 0.470 mmol) in THF (5 mL), was added PyBOP (0.519 g, 1.174 mmol) followed by addition of diisopropylethylamine (DIPEA) (0.287 mL, 1.644 mmol) at room temperature under nitrogen atmosphere. The reaction mixture was stirred for 12 h. After the completion of reaction, the reaction mixture was concentrated and the material obtained was diluted with DCM (20 mL), washed with 1NHCl (3×15 mL), saturated sodium bicarbonate solution (3×15 mL), brine (3×10 mL), dried over Na$_2$SO$_4$ and concentrated under vacuum. The crude material obtained was purified by Combiflash chromatography (0-10% methanol/dichloromethane) to afford pure titled compound (0.220 g) as white solid.

Yield: 66.2%; $^1$H NMR (300 MHz, DMSO-d$_6$): δ 0.62 (s, 3H), 0.74 (s, 3H), 0.86 (d, J=6.3 Hz, 3H), 0.92 (m, 3H), 1.08 (s, 3H), 1.21 (s, 3H), 1.25 (s, 3H), 1.28-2.10 (m, 17H), 2.15-2.28 (m, 3H), 2.45-2.48 (m, 1H), 2.56 (s, 3H), 3.0-3.25 (m, 2H), 3.38-3.48 (m, 1H), 3.49-3.65 (m, 3H), 3.68-3.81 (m, 2H), 4.95 (d, J=12.5 Hz, 1H), 5.03 (d, J=12.5 Hz, 1H), 5.22 (s, 1H), 7.28-7.45 (m, 5H); MS (ES+): 708.5[M+1].

Step 4

Synthesis of (1S,2R,4aS,6aS,6bR,14aR)-1,2,6a,6b,9,9,11,14a-octamethyl-13-(morpholine-4-carbonyl)-1,2,3,4,4a,5,6,6a,6b,7,8,8a,9,14,14a,14b,15,16b-octadecahydrochryseno[1,2-g]quinazoline-4a-carboxylic acid To a solution of the compound as obtained in step 3, (1S,2R,4aS,6aS,6bR,14aR)-benzyl 1,2,6a,6b,9,9,11,14a-octamethyl-13-(morpholine-4-carbonyl)-1,2,3,4,4a,5,6,6a,6b,7,8,8a, 9,14,14a,14b,15,16b-octadecahydrochryseno[1,2-g]quinazoline-4a-carboxylate (0.2 g, 0.282 mmol) in THF (2 mL) and methanol (10 mL) was added Pd/C (75 mg, 0.071 mmol). The reaction mixture was stirred at room temperature under hydrogen atmosphere for 3 h. On completion of reaction, the mixture was filtered and concentrated under vacuum. The residue obtained was diluted with DCM (20 mL) and the mixture was washed with water (3×15 mL) followed by brine (2×10 mL), dried over Na$_2$SO$_4$ and concentrated under vacuum. The crude material obtained was purified by Combiflash chromatography (0-10% methanol/dichloromethane) to afford pure compound titled compound 56A (0.113 g) as a white solid.

Yield: 64.7%; $^1$H NMR (300 MHz, DMSO-d$_6$): δ 0.79 (s, 3H), 0.83 (s, 3H), 0.86 (d, J=6.3 Hz, 3H), 0.92 (m, 3H), 1.09 (s, 3H), 1.22 (s, 3H), 1.26 (s, 3H), 1.28-2.10 (m, 18H), 2.10-2.30 (m, 3H), 2.56 (s, 3H), 2.95-3.21 (m, 2H), 3.35-3.42 (m, 1H), 3.45-3.63 (m, 3H), 3.65-3.85 (m, 2H), 5.21 (s, 1H), 11.99 (s, 1H); MS (ES+): 616.3[M−1].

Example 56B

Synthesis of (1S,2R,4aS,6aS,6bR,8aR,14aR,14bR,16bS)-13-(dimethylcarbamoyl)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid (Compound 56B)

Step 1

Synthesis of (1S,2R,4aS,6aS,6bR,8aR,14aR,14bR,16bS)-benzyl 13-(dimethylcarbamoyl)-1,2,6a,6b,9,9,11,14a-octamethyl-1,2,3,4,4a,5,6,6a,6b,7,8,8a,9,14,14a,14b,15,16b-octadeca hydrochryseno[1,2-g]quinazoline-4a-carboxylate To a solution of the compound obtained in step 2 of example 56A, (1S,2R,4aS,6aS,6bR,8aR,14aR,14bR,16bS)-4a-((benzyloxy)carbonyl)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-13-carboxylic acid (0.3 g, 0.470 mmol) in THF (20 ml), was added dimethylamine (0.177 ml, 1.409 mmol, 40% solution in water), BOP (0.519 g, 1.174 mmol) and DIPEA (0.286 ml, 1.644 mmol). The reaction mixture was stirred for 12 h at room temperature under nitrogen atmosphere. After the completion of reaction, the reaction mixture was concentrated under vacuum, diluted with DCM (10 mL), washed with water (3×10 mL), brine (2×10 mL), dried over $Na_2SO_4$ and concentrated to obtain the crude material. The crude material obtained was purified by Combiflash chromatography to afford the title compound (179 mg) as white solid.

Yield: 57%; $^1$H NMR (300 MHz, DMSO-$d_6$): δ 0.62 (s, 3H), 0.75 (s, 3H), 0.85 (d, 3H), 0.92 (s, 3H), 1.12 (s, 3H), 1.20-1.70 (m, 21H), 1.78-2.10 (m, 4H), 2.13-2.28 (m, 2H), 2.56 (s, 3H), 2.75 (s, 3H), 3.00 (s, 3H), 4.96 (d, J=12.5 Hz, 1H), 5.05 (d, J=12.5 Hz, 1H), 5.21 (s, 1H), 7.32-7.40 (m, 5H); MS (ES+):666.5 [M+1].

Step 2

Synthesis of (1S,2R,4aS,6aS,6bR,8aR,14aR,14bR, 16bS)-13-(dimethylcarbamoyl)-1,2,6a,6b,9,9,11,14a-octamethyl-1,2,3,4,4a,5,6,6a,6b,7,8,8a,9,14,14a,14b, 15,16b-octadecahydrochryseno[1,2-g]quinazoline-4a-carboxylic acid The title compound was prepared in an analogous manner as in step 4 of example 56A involving hydrogenation of the compound as obtained in step 1, (1S,2R,4aS,6aS,6bR,8aR, 14aR,14bR,16bS)-benzyl 13-(dimethylcarbamoyl)-1,2,6a, 6b,9,9,11,14a-octamethyl-1,2,3,4,4a,5,6,6a,6b,7,8,8a,9,14, 14a,14b,15,16b-octadecahydrochryseno[1,2-g]quinazoline-4a-carboxylate to afford the title compound 56B (120 mg).

Yield: 93%; $^1$H NMR (300 MHz, DMSO-$d_6$): δ 0.85 (d, J=5.0 Hz, 6H), 0.92 (d, 3H), 1.06 (s, 3H), 1.15 (s, 3H), 1.22 (s, 3H), 1.23-1.75 (m, 19H), 1.80-2.10 (m, 3H), 2.10-2.30 (m, 2H), 2.56 (s, 3H), 2.72 (s, 3H), 3.0 (s, 3H), 5.20 (s, 1H), 11.98 (s, 1H); MS (ES+): 576.4 [M+1].

Example 57

(1S,2R,4aS,6aS,6bR,8aR,12aR,12bR,14bS,Z)-benzyl 11-((dimethylamino)methylene)-1,2,6a,6b,9,9, 12a-heptamethyl-10-oxo-1,2,3,4,4a,5,6,6a,6b,7,8,8a, 9,10,11,12,12a,12b,13,14b-icosahydropicene-4a-carboxylate (Compound 57)

A mixture of the compound obtained in step 3 of example 1, (1S,2R,4aS,6aS,6bR,8aR,12aR,12bR,14bS)-benzyl 1,2, 6a,6b,9,9,12a-heptamethyl-10-oxo-1,2,3,4,4a,5,6,6a,6b,7,8, 8a,9,10,11,12,12a,12b,13,14b-icosahydropicene-4a-carboxylate (2 g, 3.67 mmol) and 1,1-dimethoxy-N,N-dimethylmethanamine (8.75 g, 73.4 mmol) was heated at 120° C. for 12 h. The excess of 1,1-dimethoxy-N,N-dimethylmethanamine was removed under reduced pressure to afford the title compound 57 (1.87 g, 3.67 mmol, yield: 85%) which was for next reaction without purification.

Example 58

(1S,2R,4aS,6aS,6bR,8aR,14aR,14bR,16bS)-benzyl 1,2,6a,6b,9,9,11,14a-octamethyl-1,2,3,4,4a,5,6,6a, 6b,7,8,8a,9,14,14a,14b,15,16b-octadecahydrochryseno[1,2-g]quinazoline-4a-carboxylate (Compound 58)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a, 12b,13,14b-icosahydropicene-4a-carboxylate (2.00 g, 3.33 mmol), acetimidamide hydrochloride (0.946 g, 10.00 mmol) and sodium ethoxide (0.794 g, 11.67 mmol) in ethanol (10 mL) was refluxed for 18 h. On the completion of reaction, the solvent was evaporated under reduced pressure. The solid obtained was suspended in water (25 mL), the aqueous mixture was neutralised by addition of 2N HCl and extracted with DCM (3×40 mL). The combined organic layer was washed with brine (20 mL), dried over $Na_2SO_4$ and concentrated under reduced pressure. The crude material obtained was purified by column chromatography (15% ethylacetate in hexane) to afford the title compound 58 (467 mg, 0.785 mmol).

Yield: 24%; $^1$H NMR (300 MHz, DMSO-$d_6$): δ 0.61 (s, 3H), 0.73 (s, 3H), 0.81-0.83 (m, 6H), 0.91 (s, 3H), 1.02-1.10 (m, 4H), 1.12-1.20 (m, 3H), 1.21-1.29 (m, 3H), 1.23-1.45 (m, 6H), 1.50-1.70 (m, 5H), 1.80-2.10 (m, 3H), 2.12-2.30 (m, 2H), 2.52 (s, 3H), 2.60-2.75 (m, 1H), 4.97 (d, 1H, J=12.5 Hz), 5.03 (d, 1H, J=12.5 Hz), 5.21 (brs, 1H), 7.20-7.4 (m, 5H), 8.26 (s, 1H); MS (ES+): 595.5 [M+1].

Example 59

(1S,2R,4aS,6aS,6bR,8aR,14aR,14bR,16bS)-1,2,6a, 6b,9,9,11,14a-octamethyl-1,2,3,4,4a,5,6,6a,6b,7,8, 8a,9,14,14a,14b,15,16b-octadecahydrochryseno[1,2-g]quinazoline-4a-carboxylic acid (Compound 59)

To a solution of the compound as obtained in example 58, (1S,2R,4aS,6aS,6bR,8aR,14aR,14bR,16bS)-benzyl 1,2,6a, 6b,9,9,11,14a-octamethyl-1,2,3,4,4a,5,6,6a,6b,7,8,8a,9,14, 14a,14b,15,16b-octadecahydrochryseno[1,2-g]quinazoline-4a-carboxylate (250 mg, 0.420 mmol) in mixture of methanol (7 mL) and THF (3 mL) was added Pd/C (53.7 mg, 0.050 mmol). The reaction mixture was stirred at room temperature under hydrogen atmosphere for 2 h. The reaction mixture was filtered through celite and filtrate was concentrated under reduced pressure to obtain solid which was purified by washing with acetonitrile (15 mL) to afford the title compound 59 (171 mg, 0.339 mmol) as a white solid. Yield: 81%; $^1$H NMR (300 MHz, DMSO-$d_6$): δ 0.76 (s, 3H), 0.78-0.85 (m, 6H), 0.90 (s, 3H), 1.00-1.09 (m, 4H), 1.17 (s, 3H), 1.22 (s, 3H), 1.25-2.30 (m, 19H), 2.52 (s, 3H), 2.66-2.71 (m, 1H), 5.20 (brs, 1H), 8.26 (s, 1H), 11.97 (brs, 1H); MS (ES+): 505.6 [M+1].

Example 60

3-(((1S,2R,4aS,6aS,6bR,8aR,14aR,14bR,16bS)-4a-((benzyloxy)carbonyl)-1,2,6a,6b,9,9,14a-heptamethyl-1,2,3,4,4a,5,6,6a,6b,7,8,8a,9,14,14a,14b,15, 16b-octadecahydrochryseno[1,2-g]quinazolin-11-yl) amino)propanoic acid (Compound 60)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a, 12b,13,14b-icosahydropicene-4a-carboxylate (0.7 g, 1.167 mmol), 3-guanidinopropanoic acid hydrochloride (0.587 g, 3.50 mmol) and sodium ethoxide (0.278 g, 4.08 mmol) in ethanol (10 mL) was refluxed at 90° C. for 18 h. The reaction mixture was cooled to room temperature and solvent was evaporated under reduced pressure. The solid obtained was suspended in water (25 mL), the aqueous mixture was neutralised by addition of 2N HCl, extracted with DCM (3×40 mL) and the combined organic layer was washed with brine, dried over $Na_2SO_4$ and concentrated under vacuum.

The crude material obtained was purified by column chromatography (silica gel, 15% ethyl acetate in hexane) to afford the title compound 60 (350 mg, 0.524 mmol) as a white solid.

Yield: 44.9%; $^1$H NMR (300 MHz, DMSO-d$_6$): δ 0.60 (s, 3H), 0.74 (s, 3H), 0.81 (d, 3H), 0.85-0.92 (m, 4H), 1.00-1.05 (m, 3H), 1.15 (s, 3H), 1.18-1.20 (m, 3H), 1.22-1.41 (m, 5H), 1.43-1.65 (m, 7H), 1.67-1.81 (m, 2H), 1.82-2.05 (m, 4H), 2.08-2.15 (m, 3H), 2.41-2.43 (m, 2H), 3.40-3.42 (m, 2H), 4.93 (d, 1H, J=12.5 Hz), 5.03 (d, 1H, J=12.5 Hz), 5.21 (brs, 1H), 6.71 (t, 1H), 7.28-7.40 (m, 5H), 7.89 (s, 1H), 12.13 (brs, 1H); MS (ES+): 668.2 [M+1].

Example 61

(1S,2R,4aS,6aS,6bR,8aR,14aR,14bR,16bS)-11-((2-carboxyethyl)amino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid (Compound 61)

The title compound was prepared in an analogous manner as example 59 involving hydrogenation of the compound as obtained in example 60, 3-(((1S,2R,4aS,6aS,6bR,8aR,14aR,14bR,16bS)-4a-((benzyloxy)carbonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazolin-11-yl)amino)propanoic acid using Pd/C, to afford pure title compound 61 (195 g, 0.337 mmol).

Yield: 75%; $^1$H NMR (300 MHz, DMSO-d$_6$): δ 0.60 (s, 3H), 0.74 (s, 3H), 0.83 (d, 3H), 0.85-0.92 (m, 4H), 1.00-1.05 (m, 3H), 1.15 (s, 3H), 1.18-1.20 (m, 3H), 1.22-1.41 (m, 5H), 1.43-1.65 (m, 7H), 1.67-1.81 (m, 1H), 1.82-2.05 (m, 3H), 2.08-2.15 (m, 2H), 2.41-2.43 (m, 2H), 3.40-3.42 (m, 2H), 4.93 (d, 1H, J=12.5 Hz), 5.03 (d, 1H, J=12.5 Hz), 5.21 (brs, 1H), 6.71 (t, 1H), 7.28-7.40 (m, 5H), 7.89 (s, 1H), 12.13 (brs, 1H); MS (ES+): 578.8 [M+1].

Example 62

(1S,2R,4aS,6aS,6bR,8aR,14aR,14bR,16bS)-benzyl 11((2-methoxyphenoxy)methyl)-1,2,6a, 6b,9,9,14a-heptamethyl-1,2,3,4,4a,5,6,6a,6b,7,8,8a,9,14,14a, 14b,15,16b-octadecahydro chryseno[1,2-g]quinazoline-4a-carboxylate (Compound 62)

A mixture of A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (0.9 g, 1.652 mmol) and 1,1-dimethoxy-N,N-dimethyl methanamine (3.94 g, 33.0 mmol) was heated at 120° C. for 12 h. The excess reagent 1,1-dimethoxy-N,N-dimethylmethanamine was removed from the mixture under reduced pressure. The solid obtained was dissolved in ethanol (10 mL) and 2-(2-methoxyphenoxy)acetimidamide hydrochloride (0.358 g, 1.652 mmol) and sodium ethoxide (0.112 g, 1.652 mmol) were added to the reaction mixture. The reaction mixture was then refluxed at 90° C. under nitrogen atmosphere for 18 h. The solvent was evaporated from the mixture under reduced pressure. The solid obtained was suspended in water (25 mL) and the aqueous mixture was neutralised using 2NHCl. The aqueous mixture was extracted with DCM (3×40 mL) and the combined organic layer was washed with brine (30 mL), dried over Na$_2$SO$_4$, filtered and concentrated under vacuum. The crude product obtained was purified by column chromatography (silica gel, 15% ethylacetate in hexane) to afford the title compound 62 (500 mg, 0.697 mmol).

Yield: 42.2%; $^1$H NMR (300 MHz, DMSO-d$_6$): δ 0.62 (s, 3H), 0.74 (s, 3H), 0.83 (d, 3H), 0.92 (s, 3H), 1.08-1.09 (m, 4H), 1.14 (s, 3H), 1.18-1.22 (m, 4H), 1.30-2.10 (m, 19H), 2.19-2.32 (m, 1H), 2.30-2.36 (m, 1H), 3.74 (s, 3H), 4.93 (d, 1H, J=12.5 Hz), 5.03 (d, 1H, J=12.5 Hz), 5.21 (brs, 1H), 6.75-6.89 (m, 2H), 6.94-6.98 (m, 2H), 7.28-7.4 (m, 5H), 8.41 (s, 1H); MS (ES+): 717.4 [M+1].

Example 63

(1S,2R,4aS,6aS,6bR,8aR,14aR,14bR,16bS)-11-((2-methoxyphenoxy)methyl)-1,2,6a,6b,9,9,14a-heptamethyl-1,2,3,4,4a,5,6,6a,6b,7,8,8a,9,14,14a,14b,15,16b-octadecahydrochryseno [1,2-g]quinazoline-4a-carboxylic acid (Compound 63)

The title compound was prepared in an analogous manner as example 59 involving hydrogenation of the compound as obtained in example 62 to afford pure title compound 63 (0.673 g, 1.07 mmol).

Yield: 77%; $^1$H NMR (300 MHz, DMSO-d$_6$): δ 0.77 (s, 3H), 0.86-0.87 (m, 6H), 0.89-0.92 (m, 4H), 1.07 (s, 3H), 1.15 (s, 3H), 1.17-1.27 (m, 4H), 1.32-1.39 (m, 6H), 1.49-1.52 (m, 6H), 1.53-1.75 (m, 4H), 1.80-1.92 (m, 2H), 1.94-2.15 (m, 2H), 2.18-2.20 (m, 1H), 2.23-2.42 (m, 2H), 2.73-2.78 (m, 1H), 3.75 (s, 3H), 5.13-5.25 (m, 3H), 6.73-6.91 (m, 2H), 6.92-7.02 (m, 2H), 8.42 (s, 1H); MS (ES+): 627.2 [M+1].

Example 64

(1S,2R,4aS,6aS,6bR,8aR,14aR,14bR,16bS)-benzyl 11-amino-1,2,6a,6b,9,9,14a-heptamethyl-1,2,3,4,4a, 5,6,6a, 6b,7,8,8a,9,14,14a,14b,15,16b-octadecahydrochryseno [1,2-g]quinazoline-4a-carboxylate (Compound 64)

A mixture of the compound as obtained in example 57 (0.7 g, 1.285 mmol) and 1,1-dimethoxy-N,N-dimethylmethanamine (3.06 g, 25.7 mmol) heated at 120° C. for 12 h and excess of 1,1-dimethoxy-N,N-dimethylmethanamine was removed from the mixture under reduced pressure. The solid obtained was dissolved in ethanol (10 mL), guanidine hydrochloride (0.368 g, 3.85 mmol) and sodium ethoxide (0.306 g, 4.50 mmol) were added to the solution. The reaction mixture was refluxed under nitrogen atmosphere for 18 h. The solvent was evaporated from the reaction mixture under reduced pressure. The solid obtained was suspended in water (25 mL) and the aqueous mixture was neutralised using 2NHCl. The reaction mixture was extracted with DCM (3×40 mL) and the combined organic layer was washed with brine (20 mL), dried over anhydrous Na$_2$SO$_4$, filtered, and concentrated under vacuum. The crude product obtained was purified by column chromatography (15% ethylacetae in hexane) to afford the title compound 64 (0.345 g, 0.578 mmol).

Yield: 45%; $^1$H NMR (300 MHz, DMSO-d$_6$): δ 0.61 (s, 3H), 0.74 (s, 3H), 0.81 (s, 3H), 0.83-0.84 (m, 3H), 0.92 (s, 3H), 1.07-1.08 (m, 3H), 1.11-1.14 (m, 3H), 1.22-1.70 (m, 15H), 1.83-2.32 (m, 6H), 4.93 (d, 1H, J=12.5 Hz), 5.03 (d, 1H, J=12.5 Hz), 5.20 (brs, 1H), 6.17 (brs, 2H), 7.28-7.43 (m, 5H), 7.84 (s, 1H); MS (ES+): 596.6 [M+1].

Example 65

(1S,2R,4aS,6aS,6bR,8aR,14aR,14bR,16bS)-11-amino-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid (Compound 65)

The title compound was prepared in an analogous manner as example 59 involving hydrogenation of the compound as obtained in example 64 to afford the title compound 65 (122 mg, 0.242 mmol).

Yield: 72%; $^1$H NMR (300 MHz, DMSO-$d_6$): δ 0.70-0.88 (m, 9H), 0.91 (s, 3H), 1.07-1.12 (m, 6H), 1.17-1.25 (m, 6H), 1.27-1.45 (m, 6H), 1.47-1.70 (m, 6H), 1.72-1.88 (m, 1H), 1.90-2.02 (m, 2H), 2.03-2.18 (m, 2H), 2.45-2.55 (m, 1H), 5.20 (brs, 1H), 6.18 (brs, 2H), 7.94 (s, 1H), 11.99 (brs, 1H); MS (ES+):506.6 [M+1].

Example 66

(1S,2R,4aS,6aS,6bR,8aR,14aR,14bR,16bS)-benzyl 1,2,6a,6b,9,9,14a-heptamethyl-11-phenyl-1,2,3,4,4a,5,6,6a,6b,7,8,8a,9,14,14a,14b,15,16b-octadecahydrochryseno[1,2-g]quinazoline-4a-carboxylate (Compound 66)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (1.100 g, 1.834 mmol), benzimidamide hydrochloride (0.862 g, 5.50 mmol) and sodium ethoxide (0.437 g, 6.42 mmol) in ethanol (10 mL) was refluxed at 90° C. for 18 h. The solvent was evaporated from the reaction mixture under reduced pressure. The solid obtained was suspended in water (25 mL) and the aqueous mixture was neutralised using 2N HCl. The reaction mixture was extracted with DCM (3×30 mL) and the combined organic layer was washed with brine (25 mL), dried over anhydrous Na$_2$SO$_4$, filtered and concentrated under vacuum. The crude product obtained was purified by column chromatography (15% ethyl acetate in hexane) to afford the title compound 66 (390 mg, 0.594 mmol).

Yield: 32.4%; $^1$H NMR (300 MHz, DMSO-$d_6$): δ 0.58 (s, 3H), 0.78 (s, 3H), 0.83 (d, 3H), 0.93 (s, 3H), 0.97 (s, 3H), 1.03 (s, 3H), 1.08-1.10 (m, 1H), 1.20-2.10 (m, 20H), 2.13-2.40 (m, 2H), 2.70-2.80 (m, 1H), 4.92 (d, 1H, J=12.5 Hz), 5.02 (d, 1H, J=12.5 Hz), 5.21 (brs, 1H), 7.25-7.40 (m, 6H), 7.45-7.55 (m, 2H), 8.37-8.39 (m, 2H), 8.49 (s, 1H); MS (ES+): 657.5 [M+1].

Example 67

(1S,2R,4aS,6aS,6bR,8aR,14aR,14bR,16bS)-1,2,6a,6b,9,9,14a-heptamethyl-11-phenyl-1,2,3,4,4a,5,6,6a,6b,7,8,8a,9,14,14a,14b,15,16b-octadecahydrochryseno[1,2-g]quinazoline-4a-carboxylic acid (Compound 67)

The title compound was prepared in an analogous manner as example 59 involving hydrogenation of the compound as obtained in example 66 to afford the title compound 67 (40 mg, 0.071 mmol).

Yield: 46.4%; $^1$H NMR (300 MHz, DMSO-$d_6$): δ 0.79 (d, 3H), 0.82-0.84 (m, 6H), 0.92-1.02 (m, 4H), 1.08 (s, 3H), 1.18 (s, 3H), 1.24 (s, 3H), 1.35-2.18 (m, 19H), 2.76 (m, 1H), 5.23 (s, 1H), 7.48-7.50 (m, 3H), 8.37-8.38 (m, 2H), 8.50 (s, 1H), 11.99 (brs, 1H); MS (ES+):567.8 [M+1].

Example 68

(1S,2R,4aS,6aS,6bR,8aR,14aR,14bR,16bS)-benzyl 1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (Compound 68)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (2.00 g, 3.33 mmol), formamidine acetate salt (1.171 g, 10.00 mmol) and ethanolate sodium (I) salt (0.794 g, 11.67 mmol) in ethanol (10 mL) was refluxed for 18 h. The solvent was evaporated from the reaction mixture under reduced pressure. The solid obtained was suspended in water (25 mL) and aqueous mixture was neutralised using 2N HCl. The reaction mixture was extracted with DCM (3×40 mL), the combined organic layer was washed with brine (30 mL), dried over anhydrous Na$_2$SO$_4$, filtered and concentrated under vacuum. The crude product obtained was purified by column chromatography (silica gel, 15% ethylacetate in hexane) to afford the title compound 68 (700 mg, 1.205 mmol).

Yield: 36.1%; $^1$H NMR (300 MHz, DMSO-$d_6$): δ 0.61 (s, 3H), 0.73 (s, 3H), 0.79-0.82 (m, 4H), 0.83-0.90 (m, 4H), 1.05-1.10 (m, 4H), 1.17-1.23 (m, 5H), 1.27-2.40 (m, 17H), 2.70-2.75 (m, 1H), 4.93 (d, 1H, J=12.5 Hz), 5.06 (d, 1H, J=12.5 Hz), 5.20 (brs, 1H), 7.20-7.45 (m, 5H), 8.38 (s, 1H), 8.95 (s, 1H); MS (ES+): 581 [M+1].

The obtained compound was converted into compound 6 (as obtained in example 6) by following the procedure in an analogous manner as example 59 to afford pure compound 6 (0.455 g, Yield: 67%).

Example 69

(1S,2R,4aS,6aS,6bR,8aR,14aR,14bR,16bS)-benzyl 1,2,6a,6b,9,9,14a-heptamethyl-11-morpholino-1,2,3,4,4a,5,6,6a,6b,7,8,8a,9,14,14a,14b,15,16b-octadecahydrochryseno[1,2-g]quinazoline-4a-carboxylate (Compound 69)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (1 g, 1.667 mmol), morpholine-4-carboximidamide hydrobromide (1.051 g, 5.00 mmol) and sodium ethoxide (0.397 g, 5.83 mmol) in ethanol (8 mL) was refluxed at 90° C. for 18 h. The solvent was removed from the reaction mixture under reduced pressure. The solid obtained was suspended in water (25 mL) and the aqueous mixture was neutralised using 2N HCl. The reaction mixture was extracted with DCM (3×40 mL) and the combined organic layer was washed with brine (35 mL), dried over anhydrous Na$_2$SO$_4$, filtered, and concentrated under vacuum. The crude product was purified by column chromatography (15% ethyl acetate in hexane) to afford the title compound 69 (0.388 g) as a white solid.

Yield: 35%; $^1$H NMR (300 MHz, DMSO-$d_6$): δ 0.78 (d, 3H), 0.81-0.83 (m, 6H), 0.91-1.00 (m, 4H), 1.07 (s, 3H), 1.14 (s, 3H), 1.20 (s, 3H), 1.31-2.13 (m, 19H), 2.60 (m, 1H), 3.61-3.63 (m, 8H), 5.03 (q, 2H), 5.05 (d, J=12.5 Hz, 1H), 5.09 (d, J=12.5 Hz, 1H), 5.21 (brs, 1H), 8.02 (s, 1H); MS (ES+): 666.8 [M+1].

Example 70

(1S,2R,4aS,6aS,6bR,8aR,14aR,14bR,16bS)-1,2,6a, 6b,9,9,14a-heptamethyl-11-morpholino-1,2,3,4,4a,5, 6,6a,6b,7,8,8a,9,14,14a,14b,15,16b-octadecahydrochryseno[1,2-g]quinazoline-4a-carboxylic acid (Compound 70)

The title compound was prepared in an analogous manner as example 59 involving hydrogenation of the compound as obtained in example 69 to afford the title compound 70 (171 mg, 0.297 mmol) as a white solid.

Yield: 65.9%; $^1$H NMR (300 MHz, DMSO-$d_6$): δ 0.78 (d, 3H), 0.81-0.83 (m, 6H), 0.91-1.00 (m, 4H), 1.07 (s, 3H), 1.14 (s, 3H), 1.20 (s, 3H), 1.31-2.13 (m, 19H), 2.60 (m, 1H), 3.61-3.63 (m, 8H), 5.20 (s, 1H), 8.02 (s, 1H), 11.99 (brs, 1H); MS (ES+): 576.9 [M+1].

Example 71

(1S,2R,4aS,6aS,6bR,8aR,14aR,14bR,16bS)-benzyl 1,2,6a,6b,9,9,14a-heptamethyl-11-(1H-pyrazol-1-yl)-1,2,3,4,4a,5,6,6a,6b,7,8,8a,9,14,14a,14b,15,16b-octadecahydrochryseno[1,2-g]quinazoline-4a-carboxylate (Compound 71)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a, 12b,13,14b-icosahydropicene-4a-carboxylate (1.5 g, 2.500 mmol), 1H-pyrazole-1-carboximidamide hydrochloride (1.100 g, 7.50 mmol) and sodium ethoxide (0.596 g, 8.75 mmol) in ethanol (15 mL) was refluxed at 90° C. for 18 h. The solvent was evaporated under reduced pressure. The solid obtained was suspended in water (25 mL) and the aqueous mixture was neutralised using 2N HCl. The reaction mixture was extracted with DCM (3×50 mL), the combined organic layer was washed with brine (40 mL), dried over anhydrous $Na_2SO_4$, filtered and concentrated under vacuum. The crude product obtained was purified by column chromatography (silica gel, 15% ethylacetate in hexane) to afford the title compound 71 (400 mg, 0.618 mmol) as a white solid.

Yield: 24.73%; $^1$H NMR (300 MHz, DMSO-$d_6$): δ 0.65 (s, 3H), 0.78 (s, 3H), 0.85 (s, 3H), 0.89-0.95 (m, 4H), 1.10-1.14 (m, 4H), 1.15-1.17 (m, 1H), 1.23-1.25 (m, 4H), 1.30-1.37 (m, 4H), 1.38-1.50 (m, 4H), 1.46-1.77 (m, 6H), 1.85-1.95 (m, 1H), 2.00-2.10 (m, 2H), 2.21-2.24 (m, 1H), 2.35-2.39 (m, 1H), 2.83-2.86 (m, 1H), 4.96 (d, J=12.5 Hz, 1H), 4.96 (d, J=12.5 Hz, 1H), 5.06 (d, J=12.5 Hz, 1H), 5.21 (brs, 1H), 6.57 (t, 1H), 7.20-7.40 (m, 5H), 7.82 (d, 1H), 8.45 (d, 1H), 8.68 (s, 1H); MS (ES+): 647.9 [M+1].

Example 72

(1S,2R,4aS,6aS,6bR,8aR,14aR,14bR,16bS)-1,2,6a, 6b,9,9,14a-heptamethyl-11-(1H-pyrazol-1-yl)-1,2,3, 4,4a,5,6,6a,6b,7,8,8a,9,14,14a,14b,15,16b-octadecahydrochryseno[1,2-g]quinazoline-4a-carboxylic acid (Compound 72)

The title compound was prepared in an analogous manner as example 59 involving hydrogenation of the compound as obtained in example 71 to afford to afford the title compound 72 (44 mg) as a white solid.

Yield: 65%; $^1$H NMR (300 MHz, DMSO-$d_6$): δ 0.79-0.89 (m, 9H), 0.92-0.96 (m, 4H), 1.07-1.11 (m, 4H), 1.25-1.3 (m, 4H), 1.32-1.36 (m, 1H), 1.40-1.49 (m, 4H), 1.52-2.13 (m, 12H), 2.15-2.20 (m, 2H), 2.32-2.40 (m, 1H), 2.85-2.90 (m, 1H), 5.21 (brs, 1H), 6.57 (t, 1H), 7.82 (d, 1H), 8.64 (d, 1H), 8.68 (s, 1H), 12.02 (brs, 1H); MS (ES+): 557.6 [M+1].

Example 73

(1S,2R,4aS,6aS,6bR,8aR,14aR,14bR,16bS)-benzyl 11-cyclopropyl-1,2,6a,6b,9,9,14a-heptamethyl-1,2,3, 4,4a,5,6,6a,6b,7,8,8a,9,14,14a,14b,15,16b-octadecahydrochryseno[1,2-g]quinazoline-4a-carboxylate (Compound 73)

A mixture of the compound as obtained in example 57, (1S,2R,4aS,6aS,6bR,8aR,12aR,12bR,14bS,Z)-benzyl 11-((dimethylamino)methylene)-1,2,6a,6b,9,9,12a-heptamethyl-10-oxo-1,2,3,4,4a,5,6,6a,6b,7,8,8a,9,10,11,12,12a, 12b,13,14b-icosahydropicene-4a-carboxylate (1.2 g, 2.000 mmol), cyclopropanecarboximidamide hydrochloride (0.965 g, 8.00 mmol) and sodium ethoxide (0.817 g, 12.00 mmol) in ethanol (15 mL) was refluxed at 90° C. for 18 h. The reaction mixture was cooled to room temperature and solvent was evaporated under reduced pressure. The resulting solid was suspended in water (25 mL) and the aqueous mixture was neutralised using 2N HCl. The reaction mixture was extracted with DCM (3×40 mL), the combined organic layer was washed with brine (35 mL), dried over anhydrous $Na_2SO_4$, filtered, and concentrated under vacuum. The crude product obtained was purified by column chromatography (silica gel, 15% ethyl acetate in hexane) to afford the title compound 73 (400 mg, 0.644 mmol) as a white solid.

Yield: 32.2%; $^1$H NMR (300 MHz, DMSO-$d_6$): δ 0.62 (s, 3H), 0.73 (s, 3H), 0.84 (d, 3H), 0.85-1.0 (m, 8H), 1.08 (s, 3H), 1.15 (s, 3H), 1.21 (s, 3H), 1.25-1.80 (m, 13H), 1.82-2.31 (m, 7H), 2.57-2.73 (m, 1H), 4.94 (d, 1H, J=12.5 Hz), 5.08 (d, 1H, J=12.5 Hz), 5.21 (brs, 1H), 7.20-7.42 (m, 5H), 8.20 (s, 1H); MS (ES+): 621.90 [M+1].

Example 74

(1S,2R,4aS,6aS,6bR,8aR,14aR,14bR,16bS)-11-cyclopropyl-1,2,6a,6b,9,9,14a-heptamethyl-1,2,3,4,4a, 5,6,6a,6b,7,8,8a,9,14,14a,14b,15,16b-octadecahydrochryseno[1,2-g]quinazoline-4a-carboxylic acid (Compound 74)

The title compound was prepared in an analogous manner as example 59 involving hydrogenation of the compound as obtained in example 73 to afford the title compound 74 (170 mg, 0.320 mmol) as a white solid.

Yield: 66.3%; $^1$H NMR (300 MHz, DMSO-$d_6$): δ 0.75 (s, 3H), 0.77-0.85 (m, 6H), 0.88-0.99 (m, 8H), 1.00-1.09 (m, 4H), 1.10-1.21 (m, 7H), 1.22-1.42 (m, 5H), 1.41-1.70 (m, 6H), 1.70-2.01 (m, 4H), 2.02-2.19 (m, 2H), 2.20-2.30 (m, 1H), 2.60-2.75 (m, 1H), 5.20 (brs, 1H), 8.21 (s, 1H), 12.06 (brs, 1H); MS (ES+): 531.4 [M+1].

Example 75

(1S,2R,4aS,6aS,6bR,8aR,14aR,14bR,16bS)-benzyl 11-mercapto-1,2,6a,6b,9,9,14a-heptamethyl-1,2,3,4, 4a,5,6,6a,6b,7,8,8a,9,14,14a,14b,15,16b-octadecahydrochryseno[1,2-g]quinazoline-4a-carboxylate (Compound 75)

A mixture of the compound as obtained in example 57, (1S,2R,4aS,6aS,6bR,8aR,12aR,12bR,14bS,Z)-benzyl 11-

((dimethyl amino)methylene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (1.200 g, 2.000 mmol), (1.1 g, 2.019 mmol) and 1,1-dimethoxy-N,N-dimethylmethanamine (0.241 g, 2.019 mmol) was heated at 120° C. for 12 h. At the end of 12 h the excess reagent, 1,1-dimethoxy-N,N-dimethylmethanamine was removed under reduced pressure and resulting solid was dissolved in ethanol (10 mL) followed by addition of thiourea (0.461 g, 6.06 mmol) and sodium ethoxide (0.481 g, 7.07 mmol) under nitrogen atmosphere. The reaction mixture was refluxed at 90° C. for 18 h. The solvent was evaporated from the reaction mixture under reduced pressure. The solid obtained was suspended in water (25 mL) and the aqueous mixture was neutralised using 2N HCl. The reaction mixture was extracted with DCM (3×40 mL), the combined organic layer was washed with brine (25 mL), dried over anhydrous $Na_2SO_4$, filtered and concentrated under vacuum. The crude product obtained was purified by column chromatography (silica gel, 5% methanol in DCM) to afford the title compound 75 (0.433 g, 0.707 mmol) as a white solid.

Yield: 35%; $^1$H NMR (300 MHz, DMSO-$d_6$): δ 0.60 (s, 3H), 0.74 (s, 3H), 0.81 (d, 3H), 0.91 (s, 3H), 1.0-1.10 (m, 5H), 1.13 (s, 3H), 1.19 (s, 3H), 1.21-1.38 (m, 5H), 1.40-1.7 (m, 7H), 1.67-2.15 (m, 5H), 2.15-2.30 (m, 1H), 2.42-2.65 (m, 1H), 4.93 (d, J=12.5 Hz, 1H), 5.03 (d, J=12.5 Hz, 1H), 5.19 (brs, 1H), 7.20-7.45 (m, 5H), 7.70 (s, 1H), 13.59 (s, 1H); MS (ES+): 613.6 [M+1].

Example 76

(1S,2R,4aS,6aS,6bR,8aR,14aR,14bR,16bS)-benzyl 11-(ethylthio)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (Compound 76)

To a solution of compound as obtained in example 75, (1S,2R,4aS,6aS,6bR,8aR,14aR,14bR,16bS)-benzyl 11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (150 mg, 0.245 mmol) in DMF (4 mL) was added $K_2CO_3$ (169 mg, 1.224 mmol) followed by addition of iodoethane (0.079 mL, 0.979 mmol). The reaction mixture was stirred under nitrogen atmosphere at room temperature for 12 h. The reaction mixture was diluted with water (10 mL), extracted with ethyl acetate (3×25 mL), the combined organic layer was washed with brine (10 mL) water (10 mL) dried over anhydrous $Na_2SO_4$, evaporated under reduced pressure to obtain a solid. The solid obtained was purified by column chromatography (10% ethyl acetate in hexane) to afford the title compound 76 (150 mg, 0.234 mmol) as a white solid.

Yield: 96%; $^1$H NMR (300 MHz, DMSO-$d_6$): δ 0.61 (s, 3H), 0.75 (s, 3H), 0.81-0.83 (m, 3H), 0.91-0.95 (m, 4H), 1.05-1.08 (m, 4H), 1.13-1.20 (m, 4H), 1.21-1.27 (m, 4H), 1.28-1.40 (m, 4H), 1.40-1.7 (m, 9H), 1.80-2.1 (m, 3H), 2.15-2.30 (m, 2H), 2.69-2.80 (m, 2H), 3.06 (q, 2H), 4.97 (d, J=12.5 Hz, 1H), 5.07 (d, J=12.5 Hz, 1H), 5.21 (brs, 1H), 7.20-7.45 (m, 5H), 8.23 (s, 1H); MS (ES+): 642 [M+1].

Example 77

(1S,2R,4aS,6aS,6bR,8aR,14aR,14bR,16bS)-benzyl 11-(ethylsulfonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (Compound 77)

To a solution of the compound as obtained in example 76 (150 mg, 0.234 mmol) in DCM (5 mL) was added metachloroperbenzoic acid (202 mg, 1.170 mmol). The reaction mixture was stirred at room temperature under nitrogen atmosphere for 12 h. The reaction mixture was diluted with DCM (15 mL), washed with saturated $NaHCO_3$ (5 mL), brine (5 mL) and dried over anhydrous $Na_2SO_4$, filtered and concentrated under reduced pressure. The crude product obtained was purified by column chromatography (20% ethyl acetate in hexane) to afford the title compound 77 (79 mg, 0.117 mmol) as white solid.

Yield: 50%; $^1$H NMR (300 MHz, DMSO-$d_6$): δ 0.71 (s, 3H), 0.82 (s, 3H), 0.83-0.86 (m, 3H), 0.93-0.96 (m, 3H), 1.10-1.15 (m, 4H), 1.20-1.90 (m, 23H), 2.0-2.10 (m, 3H), 2.30-2.45 (m, 2H), 2.85-2.90 (m, 1H), 3.55 (m, 2H), 4.97 (d, J=12.5 Hz, 1H), 5.07 (d, J=12.5 Hz, 1H), 5.21 (brs, 1H), 7.25-7.45 (m, 5H), 8.5 (s, 1H); MS (ES+): 674 [M+1].

Example 78

(1S,2R,4aS,6aS,6bR,8aR,14aR,14bR)-11-(ethylsulfonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid (Compound 78)

To a solution of the compound as obtained in example 77 (100 mg, 0.149 mmol) in mixture of methanol (3 mL) and THF (1 mL) was added Pd/C (18.98 mg, 0.018 mmol). The reaction mixture was stirred at room temperature under hydrogen atmosphere for 2 h. The reaction mixture was filtered through celite and the filtrate was concentrated under reduced pressure. The solid obtained was purified by washing with acetonitrile (8 mL) to afford the title compound 78 (87 mg) as a white solid.

Yield: 70%; $^1$H NMR (300 MHz, DMSO-$d_6$): δ 0.80 (d, 3H), 0.82-0.84 (m, 6H), 0.92-1.02 (m, 4H), 1.08 (s, 3H), 1.18 (s, 3H), 1.20-1.32 (m, 6H), 1.35-2.18 (m, 19H), 2.85-2.95 (m, 1H), 3.59 (q, 2H), 5.21 (s, 1H), 8.68 (s, 1H), 12.01 (brs, 1H); MS (ES+): 583.7 [M+1].

Example 79

(1S,2R,4aS,6aS,6bR,8aR,14aR,14bR,16bS)-benzyl 1,2,6a,6b,9,9,14a-heptamethyl-11-(methylthio)-1,2,3,4,4a,5,6,6a,6b,7,8,8a,9,14,14a,14b,15,16b-octadecahydrochryseno[1,2-g]quinazoline-4a-carboxylate (Compound 79)

To a solution of compound as obtained in example 75, (1S,2R,4aS,6aS,6bR,8aR,14aR,14bR,16bS)-benzyl 11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate (150 mg, 0.245 mmol) in DMF (4 mL) was added $K_2CO_3$ (169 mg, 1.224 mmol) followed by addition of iodomethane (0.061 mL, 0.979 mmol). The reaction mixture was stirred under nitrogen atmosphere at room temperature for 12 h. The reaction mixture was diluted with water (10 mL), extracted with ethylacetate (3×25 mL), the combined organic layer was washed with brine (15 mL), water (10 ml) dried over $Na_2SO_4$, filtered and evaporated under reduced pressure to obtain a solid. The solid obtained was purified by column chromatography (silica gel, 10% ethyl acetate in hexane) to afford the title compound 79 (108 mg, 0.171 mmol) as a white solid.

Yield: 70%; $^1$H NMR (300 MHz, DMSO-$d_6$): δ 0.61 (s, 3H), 0.75 (s, 3H), 0.83 (d, 3H), 0.91 (s, 3H), 1.07-1.10 (m, 3H), 1.17 (s, 3H), 1.23 (s, 3H), 1.30-1.45 (m, 6H), 1.50-1.70 (m, 6H), 1.80-2.10 (m, 4H), 2.12-2.32 (m, 3H), 2.47 (s, 3H), 2.63-2.75 (m, 2H), 4.93 (d, J=12.5 Hz, 1H), 5.03 (d, J=12.5 Hz, 1H), 5.20 (brs, 1H), 7.21-7.45 (m, 5H), 8.24 (s, 1H); MS (ES+): 628 [M+1].

Example 80

(1S,2R,4aS,6aS,6bR,8aR,14aR,14bR,16bS)-benzyl1, 2,6a,6b,9,9,14a-heptamethyl-11-(methylsulfonyl)-1, 2,3,4,4a,5,6,6a,6b,7,8,8a,9,14,14a,14b,15,16b-octa-decahydrochryseno [1,2-g]quinazoline-4a-carboxylate (Compound 80)

The title compound was prepared in an analogous manner as example 77 involving reaction of the compound as obtained in example 79, (1S,2R,4aS,6aS,6bR,8aR,14aR,14bR,16bS)-benzyl 1,2,6a,6b,9,9,14a-heptamethyl-11-(methylthio)-1,2,3,4,4a,5,6,6a,6b,7,8,8a,9,14,14a,14b,15,16b-octadecahydrochryseno[1,2-g]quinazoline-4a-carboxylate with metachloro perbenzoic acid, to afford the title compound 80 (53 mg) as white solid.

Yield: 63%; $^1$H NMR (300 MHz, DMSO-d$_6$): δ 0.70 (s, 3H), 0.87 (s, 3H), 0.89 (d, 3H), 0.94 (s, 3H), 1.07-1.12 (m, 3H), 1.26 (s, 3H), 1.31 (s, 3H), 1.30-1.39 (m, 3H), 1.50-1.90 (m, 13H), 1.95-2.10 (m, 2H), 2.25-2.45 (m, 2H), 2.70-2.90 (m, 1H), 3.36 (s, 3H), 4.98 (d, J=12.5 Hz, 1H), 5.11 (d, J=12.5 Hz, 1H), 5.31 (brs, 1H), 7.30-7.40 (m, 5H), 8.49 (s, 1H); MS (ES+): 659 [M+1].

Example 81

(1S,2R,4aS,6aS,6bR,8aR,14aR,14bR,16bS)-1,2,6a, 6b,9,9,14a-heptamethyl-11-(methylsulfonyl)-1,2,3,4, 4a,5,6,6a,6b,7,8,8a,9,14,14a,14b,15,16b-octadecahy-drochryseno [1,2-g]quinazoline-4a-carboxylic acid (Compound 81)

The title compound was prepared in an analogous manner as example 78 involving hydrogenation of the compound as obtained in example 80 to afford the title compound 81 (30 mg) as a white solid.

Yield: 69%; $^1$H NMR (300 MHz, DMSO-d$_6$): δ 0.79 (s, 3H), 0.83 (s, 3H), 0.85 (d, 3H), 0.91 (s, 3H), 1.07-1.12 (m, 3H), 1.24 (s, 3H), 1.29 (s, 3H), 1.30-1.90 (m, 16H), 1.95-2.09 (m, 2H), 2.25-2.43 (m, 2H), 2.65-2.95 (m, 2H), 3.37 (s, 3H), 5.21 (brs, 1H), 8.67 (s, 1H); MS (ES+): 570 [M+1].

Example 82

(1S,2R,4aS,6aS,6bR,8aR,14aR,14bR,16bS)-benzyl 11-chloro-1,2,6a,6b,9,9,14a-heptamethyl-1,2,3,4,4a, 5,6,6a,6b,7,8,8a,9,14,14a,14b,15,16b-octadecahydro-chryseno[1,2-g]quinoline-4a-carboxylate (Compound 82)

Step 1

Synthesis of (1S,2R,4aS,6aS,6bR,8aR,12aR,12bR, 14bS,E)-benzyl 10-(hydroxyimino)-1,2,6a,6b,9,9, 12a-heptamethyl-1,2,3,4,4a,5,6,6a,6b,7,8,8a,9,10,11, 12,12a,12b,13,14b-icosahydropicene-4a-carboxylate To a solution of the compound obtained in step 2 of example 1, (1S,2R,4aS,6aS,6bR,8aR,12aR,12bR,14bS)-benzyl 1,2,6a,6b,9,9,12a-heptamethyl-10-oxo-1,2,3,4,4a,5,6,6a,6b,7,8,8a,9,10,11,12,12a,12b,13,14b-icosahydropi-cene-4a-carboxylate (1.10 g, 2.019 mmol) in methanol (25 mL) and dichloromethane (10 mL) was added hydroxyl amine hydrochloride (0.080 g, 2.423 mmol) followed by addition of sodium acetate (0.199 g, 2.423 mmol) at room temperature under nitrogen atmosphere. The reaction mixture was refluxed at 80° C. for 16 h. The reaction mixture was concentrated under vacuum. The residue obtained was diluted with dichloromethane (50 mL), washed with water (3×50 mL) followed by brine (3×50 mL) and concentrated under vacuum. The crude material obtained was purified by Combiflash chromatography (0-5% methanol/dichloromethane) to afford the pure title compound (1.10 g).

Yield: 72%; $^1$H NMR (300 MHz, DMSO-d$_6$): δ 0.58 (s, 3H), 0.80 (d, J=6.3 Hz, 3H), 0.91-0.96 (m, 6H), 1.03 (s, 3H), 1.08 (s, 3H), 1.17-2.20 (m, 25H), 2.86-2.91 (m, 1H), 4.95 (d, J=12.6 Hz, 1H), 5.05 (d, J=12.6 Hz, 1H), 5.15 (s, 1H), 7.31-7.39 (m, 5H), 10.29 9s, 1H); MS (ES+): 560.8 [M+1].

Step 2

Synthesis of (1S,2R,4aS,6aS,6bR,8aR,12aR,12bR, 14bS)-benzyl 10-acetamido-1,2,6a,6b,9,9,12a-hep-tamethyl-1,2,3,4,4a,5,6,6a,6b,7,8,8a,9,12,12a,12b, 13,14b-octadeca hydropicene-4a-carboxylate To a solution of the compound as obtained in above step 1 (3.0 g, 5.36 mmol) in dichloroethane (50 mL) was added acetic anhydride (1.011 mL, 10.72 mmol), followed by addition of copper(I)iodide (0.102 g, 0.536 mmol) and sodium bisulfite (1.673 g, 16.08 mmol) at room temperature under nitrogen atmosphere. The reaction mixture was refluxed at 120° C. for 16 h. The mixture was diluted with ethyl acetate (50 mL) and washed with NaOH (2×100 mL, 2N), water (2×100 mL) and brine (2×100 mL) and the combined organic layer was concentrated under vacuum. The material obtained was purified by Combiflash chroma-tography (0-5% methanol/dichloromethane) to afford pure title compound (1 g). Yield: 72%; $^1$H NMR (300 MHz, DMSO-d$_6$): δ 0.58 (s, 3H), 0.80 (d, J=6.3 Hz, 3H), 0.86-0.90 (m, 9H), 0.97 (s, 3H), 1.0 (s, 3H), 1.22-1.81 (m, 20H), 1.98 (s, 3H), 1.17 (d, J=10.8 Hz, 1H), 4.94 (d, J=12.3 Hz, 1H), 5.03 (d, J=12.6 Hz, 1H), 5.16 (s, 1H), 7.30-7.35 (m, 5H), 8.0 (s, 1H); MS (ES+): 586.6 [M+1].

Step 3

(1S,2R,4aS,6aS,6bR,8aR,14aR,14bR,16bS)-benzyl 11-chloro-1,2,6a,6b,9,9,14a-heptamethyl-1,2,3,4,4a, 5,6,6a,6b,7,8,8a,9,14,14a,14b,15,16b-octadecahydro-chryseno[1,2-g]quinoline-4a-carboxylate To a solution of the compound as obtained in above step 2 (0.2 g, 0.341 mmol) in chloroform (8.0 mL) was added POCl$_3$ (0.573 mL, 6.14 mmol) in DMF (0.740 mL, 9.56 mmol) at 0° C. under nitrogen atmosphere. The reaction mixture was stirred at 0° C. to 10° C. for 2 hr and refluxed at 62° C. for 4 h. The reaction mixture was quenched with chloroform (15 mL), neutralized with sodium bicarbonate solution and the mixture was extracted with chloroform (3×15 mL). The combined organic layer was washed with water (2×15 mL), brine (2×15 mL) and dried over sodium sulphate, filtered and concentrated under vacuum to obtain a crude material which was a mixture of (1S,2R,4aS,6aS, 6bR,8aR,14aR,14bR,16bS)-benzyl 11-chloro-1,2,6a,6b,9,9, 14a-heptamethyl-1,2,3,4,4a,5,6,6a,6b,7,8,8a,9,14,14a,14b, 15,16b-octadeca hydroxyseno[1,2-g]quinoline-4a-carboxylate (10%) and (1S,2R,4aS,6aS,6bR,8aR,14aR, 14bR,16bS)-benzyl 11-chloro-12-formyl-1,2,6a,6b,9,9,14a- heptamethyl-1,2,3,4,4a,5,6,6a,6b, 7,8,8a,9,14,14a,14b,15,16b-octadecahydrochryseno[1,2-g]quinoline-4a-carboxylate (40%).

Step 4

Synthesis of (1S,2R,4aS,6aS,6bR,8aR,14aR,14bR,16bS)-benzyl 11-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate The crude material obtained in step 3 was subjected to Combiflash chromatography (0-10% ethyl acetate/petroleum ether) to afford title compound 82 (0.08 g) as white solid.

Yield: 40%; $^1$H NMR (300 MHz, DMSO-$d_6$): δ 0.62 (s, 3H), 0.76 (s, 3H), 0.83 (d, J=6.0 Hz, 3H), 0.92 (s, 3H), 1.0 (s, 3H), 1.17 (s, 3H), 1.21 (s, 3H), 1.23-1.73 (m, 17H), 2.0 (d, J=17.5 Hz, 1H), 2.21 (d, J=11.5 Hz, 1H), 2.35 (d, J=16 Hz, 1H), 2.74 (d, J=16 Hz, 1H), 4.94 (d, J=12.5 Hz, 1H), 5.06 (d, J=12.5 Hz, 1H), 5.21 (s, 1H), 7.20 (d, J=8.0 Hz, 1H), 7.31-7.38 (m, 5H), 7.45 (d, J=8.0 Hz, 1H); MS (ES+): 614.6 [M+1].

Example 83

(1S,2R,4aS,6aS,6bR,8aR,14aR,14bR,16bS)-benzyl 11-chloro-1,2,6a,6b,9,9,14a-heptamethyl-1,2,3,4,4a,5,6,6a, 6b,7,8,8a,9,14,14a,14b,15,16b-octadecahydrochryseno[1,2-g]quinoline-4a-carboxylate (Compound 83)

The crude material obtained in step 3 of example 82 was subjected to Combiflash chromatography (0-10% ethyl acetate/petroleum ether) to afford title compound 83 (0.02 g) as white solid.

Yield: 10%; $^1$H NMR (300 MHz, DMSO-$d_6$): δ 0.63 (s, 3H), 0.76 (s, 3H), 0.84 (d, J=6.0 Hz, 3H), 0.92 (s, 3H), 1.0 (s, 3H), 1.21 (s, 3H), 1.26 (s, 3H), 1.32-2.0 (m, 18H), 2.22 (d, J=11.5 Hz, 1H), 2.41 (d, J=16.5 Hz, 1H), 2.88 (d, J=16 Hz, 1H), 4.96 (d, J=13.0 Hz, 1H), 5.06 (d, J=12.5 Hz, 1H), 5.22 (s, 1H), 7.30-7.38 (m, 5H), 7.88 (s, 1H), 10.28 (s, 1H); MS (ES+): 642 [M+1].

Example 84

(1S,2R,4aS,6aS,6bR,8aR,14aR,14bR,16bS)-1,2,3,4,4a,5,6,6a,6b,7,8,8a,9,14,14a,14b,15,16b-octadecahydro-1,2,6a, 6b,9,9,14a-heptamethylchryseno[1,2-g]quinoline-4a-carboxylic acid (Compound 84)

To a solution of the compound as obtained in example 83 (0.030 g, 0.049 mmol) in methanol (3.00 mL) and THF (1.00 mL), was added Pd/C (0.030 g, 0.282 mmol) and the mixture was stirred at room temperature under hydrogen atmosphere for 2 h. On completion of reaction the mixture was filtered and the filtrate was concentrated under vacuum to obtain crude material which was purified by Combiflash chromatography (0-5% methanol/dichloromethane). The material obtained was washed with acetonitrile (2×3 mL) to afford the pure title compound 83 (0.01 g).

Yield: 54%; $^1$H NMR (300 MHz, DMSO-$d_6$): δ 0.81 (s, 3H), 0.84 (bs, 6H), 0.92 (s, 3H), 1.10 (s, 3H), 1.21 (s, 3H), 1.23-1.20 (m, 21H), 2.15 (d, J=11.0 Hz, 1H), 2.40 (d, J=15.5 Hz, 1H), 2.71 (d, J=15.5 Hz, 1H), 5.22 (s, 1H), 7.65 (d, J=7.0 Hz, 1H), 7.36 (d, J=7.0 Hz, 1H), 8.39 9s, 1H), 11.98 (s, 1H); MS (ES+): 490.6[M+1].

Example 85

(1S,2R,4aS,6aS,6bR,8aR,14aR,14bR,16bS)-benzyl 11-chloro-12-(hydroxymethyl)-1,2,6a,6b,9,9,14a-heptamethyl-1,2,3,4,4a,5,6,6a,6b,7,8,8a,9,14,14a, 14b,15,16b octadecahydrochryseno[1,2-g]quinoline-4a-carboxylate (Compound 85)

To a solution of the compound as obtained in example 82 (0.060 g, 0.093 mmol) in methanol (4 mL) was added sodium borohydride (0.021 g, 0.560 mmol). The reaction mixture was stirred at room temperature under nitrogen atmosphere for 4 h and on completion of reaction the mixture was concentrated under vacuum. The material obtained was diluted with dichloromethane (5 mL), washed with water (3×5 mL), brine (2×5 mL), dried over $Na_2SO_4$ and concentrated and obtained residue was purified by Combiflash chromatography system (0-5% methanol/dichloromethane) to afford pure title compound 85 (0.05 g) as white solid.

Yield: 83%; $^1$H NMR (300 MHz, DMSO-$d_6$): δ 0.63 (s, 3H), 0.767 (s, 3H), 0.85 (bs, 3H), 0.93 (s, 3H), 1.09 (s, 3H), 1.16 (s, 3H), 1.23 (s, 3H), 1.35-2.40 (m, 16H), 2.75 (d, J=15.6 Hz, 2H), 4.47 (d, J=5.4 Hz, 2H), 4.97 (d, J=13.0 Hz, 1H), 5.06 (d, J=12.3 Hz, 1H), 5.22 (s, 1H), 5.44 (bs, 1H), 7.35 (bs, 5H), 7.52 (s, 1H); MS (ES+): 645[M+1].

Example 86

(1S,2R,4aS,6aS,6bR,8aR,14aR,14bR,16bS)-1,2,3,4,4a,5,6,6a,6b,7,8,8a,9,14,14a,14b,15,16b-octadecahydro-1,2,6a,6b,9,9,12,14a-octamethylchryseno[1,2-g]quinoline-4a-carboxylic acid (Compound 86)

The title compound was prepared in an analogous manner as example 84 involving hydrogenation of the compound obtained in example 82, (1S,2R,4aS,6aS,6bR,8aR,14aR,14bR,16bS)-benzyl 11-chloro-1,2,6a,6b,9,9,14a-heptamethyl-1,2,3,4,4a,5,6,6a,6b,7,8,8a, 9,14,14a,14b,15,16b-octadecahydrochryseno[1,2-g]quinoline-4a-carboxylate to afford the title compound 86 (0.01 g) as white solid.

Yield: 55%; $^1$H NMR (300 MHz, DMSO-$d_6$: δ 0.75-0.92 (bs, 9H), 0.93 (s, 3H), 1.09 (s, 3H), 1.18 (s, 3H), 1.23 (bs, 6H), 1.37-1.39 (m, 20H), 2.67 (d, J=15.6 Hz, 1H), 5.22 (s, 1H), 7.16 (s, 1H), 8.22 (s, 1H), 12.0 (s, 1H); MS (ES+): 504.8[M+1].

Example 87

(1S,2R,4aS,6aS,6bR,8aR,14aR,14bR,16bS)-12-(hydroxymethyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylic acid (Compound 87)

The title compound was prepared in an analogous manner as example 84 involving hydrogenation of the compound, (1S,2R,4aS,6aS,6bR,8aR,14aR,14bR,16bS)-benzyl 11-chloro-12-(hydroxymethyl)-1,2,6a,6b,9,9,14a-heptamethyl-1,2,3,4,4a,5,6,6a,6b,7,8,8a,9,14,14a,14b,15,16b octadecahydrochryseno[1,2-g]quinoline-4a-carboxylate to afford the title compound 87 (0.02 g) as white solid.

Yield: 55%; $^1$H NMR (300 MHz, DMSO-d$_6$): δ 0.75-0.92 (bs, 9H), 0.93 (s, 3H), 1.09 (s, 3H), 1.18 (s, 3H), 1.23 (bs, 6H), 1.37-1.39 (m, 20H), 2.67 (d, J=15.6 Hz, 1H), 5.22 (s, 1H), 7.16 (s, 1H), 8.22 (s, 1H), 12.0 (s, 1H); MS (ES+): 504.8[M+1]

Example 88

(1S,2R,4aS,6aS,6bR,8aR,14aR,14bR,16bS)-benzyl, 11-chloro-12-formyl-1,2,3,4,4a,5,6,6a, 6b,7,8,8a,9, 14,14a,14b,15,16b-octadecahydro-1,2,6a,6b,9,9,14a-heptamethylchryseno[1,2-g]quinoline-4a-carboxylate (Compound 88)

The title compound was prepared in an analogous manner as example 85 involving hydrogenation of the compound 82, (1S,2R,4aS,6aS,6bR,8aR,14aR,14bR,16bS)-benzyl 11-chloro-12-formyl-1,2,6a,6b,9,9,14a-heptamethyl-1,2,3, 4,4a,5,6,6a,6b,7,8,8a,9,14,14a,14b,15,16b-octadecahydrochryseno[1,2-g]quinoline-4a-carboxylate to afford the title compound 88 (0.028 g) as white solid.
Yield: 7%; $^1$H NMR (300 MHz, DMSO-d$_6$): δ 0.79 (s, 3H), 0.83 (bs, 6H), 0.91 (bs, 3H), 1.08 (s, 3H), 1.18 (s, 3H), 1.22 (bs, 3H), 1.37-2.15 (m, 20H), 2.69 (d, J=16 Hz, 1H), 4.42 (d, J=5.4 Hz, 2H), 5.16 (d, J=5.4 Hz, 1H), 5.19 (d, J=4.2 Hz, 1H), 7.26 (s, 1H), 8.30 (s, 1H), 11.99 (s, 1H); MS (ES+): 520.4[M+1].

Example 89

(1S,2R,4aS,6aS,6bR,8aR,14aR,14bR,16bS)-4a-benzyl 12-methyl 11-chloro-1,2,6a, 6b,9,9,14a-heptamethyl-1,2,3,4,4a,5,6,6a,6b,7,8,8a,9,14,14a,14b,15, 16b-octadecahydrochryseno [1,2-g]quinoline-4a,12-dicarboxylate (Compound 89)

To a solution of the compound as obtained in example 82, (1S,2R,4aS,6aS,6bR,8aR,14aR,14bR,16bS)-benzyl 11-chloro-12-formyl-1,2,6a,6b,9,9,14a-heptamethyl-1,2,3, 4,4a,5,6,6a,6b,7,8,8a,9,14,14a,14b,15,16b-octadecahydrochryseno[1,2-g]quinoline-4a-carboxylate (0.5 g, 0.778 mmol) in methanol (20 mL) was added iodine (0.593 g, 2.335 mmol) followed by K$_2$CO$_3$ (0.323 g, 2.335 mmol). The reaction mixture was stirred at room temperature under nitrogen atmosphere for 2.5 h. On completion of reaction the mixture was filtered and the filtrate was concentrated under vacuum. The residue obtained was diluted with dichloromethane (30 mL), washed with saturated Na$_2$S$_2$O$_3$ (2×30 mL), water (2×30 mL) and brine (2×30 mL), dried over Na$_2$SO$_4$ and concentrated under vacuum to afford pure title compound 89 (0.4 g).
Yield: 80%; $^1$H NMR (300 MHz, DMSO-d$_6$): δ 0.61 (s, 3H), 0.75 (s, 3H), 0.83 (d, J=6.3 Hz, 3H), 0.91 (s, 3H), 1.08 (s, 3H), 1.18 (s, 3H), 1.23 (s, 3H), 1.37-1.2.0 (m, 18H), 2.21 (d, J=11.1 Hz, 1H), 2.38 (d, J=16.2 Hz, 1H), 2.81 (d, J=16.2 Hz, 1H), 3.85 (s, 3H), 4.96 (d, J=12.3 Hz, 1H), 5.05 (d, J=12.6 Hz, 1H), 5.21 (s, 1H), 7.33-7.36 (m, 5H), 7.87 (s, 1H); MS (ES+): 672.9[M+1]

Example 90

(1S,2R,4aS,6 aS,6bR,8aR,14aR,14bR,16bS)-4a-((benzyloxy)carbonyl)-11-chloro-1,2,6a,6b,9,9,14a-heptamethyl-1,2,3,4,4a,5,6,6a,6b,7,8,8a,9,14,14a, 14b,15,16b-octadecahydrochryseno [1,2-g] quinoline-12-carboxylic acid (Compound 90)

To a solution of the compound as obtained in example 89 (0.450 g, 0.669 mmol) in methanol (10 mL) and THF (2.00 mL) was added a solution of lithium hydroxide (0.080 g, 3.35 mmol) in water (2.00 mL). The reaction mixture was stirred at room temperature for 12 h. On completion of reaction, the reaction mixture was concentrated under vacuum. The residue obtained was diluted with water (15 mL), pH of mixture was adjusted to about 7 by adding NaH$_2$PO$_4$ and the mixture was extracted with DCM (3×20 mL), brine (2×10 mL), dried over Na$_2$SO$_4$ and concentrated under vacuum to afford pure title compound 90 (0.42 g) as white solid.
Yield: 95%; $^1$H NMR (300 MHz, DMSO-d$_6$): δ 0.62 (s, 3H), 0.75 (s, 3H), 0.83 (d, J=6.3 Hz, 3H), 0.91 (s, 3H), 1.08 (s, 3H), 1.17 (s, 3H), 1.22 (s, 3H), 1.37-1.98 (m, 18H), 2.21 (d, J=10.8 Hz, 1H), 2.37 (d, J=16.2 Hz, 1H), 2.80 (d, J=16.2 Hz, 1H), 4.96 (d, J=12.3 Hz, 1H), 5.05 (d, J=12.6 Hz, 1H), 5.21 (s, 1H), 7.33-7.36 (m, 5H), 7.82 (s, 1H), 13.5 (bs, 1H); MS (ES+): 658.5[M+1].

Example 91

(1S,2R,4aS,6aS,6bR,8aR,14aR,14bR,16bS)-1,2,3,4, 4a,5,6,6a,6b,7,8,8a,9,14,14a,14b,15,16b-octadecahydro-1,2,6a,6b,9,9,14a-heptamethylchryseno[1,2-g] quinoline-4a,12-dicarboxylic acid (Compound 91)

The title compound was prepared in an analogous manner as example 84 involving hydrogenation of the compound obtained in example 89, (1S,2R,4aS,6aS,6bR,8aR,14aR, 14bR,16bS)-4a-((benzyloxy)carbonyl)-11-chloro-1,2,6a,6b, 9, 9,14a-heptamethyl-1,2,3,4,4a,5,6,6a,6b,7,8,8a,9,14,14a, 14b,15,16b-octadecahydrochryseno [1,2-g]quinoline-12-carboxylic acid to afford pure title compound 91 (0.04 g) as white solid. Yield: 54%; $^1$H NMR (300 MHz, DMSO-d$_6$): δ 0.79-0.83 (m, 9H), 0.92 (s, 3H), 1.09 (s, 3H), 1.22-1.26 (bs, 6H), 1.32-2.17 (m, 20), 2.83 (d, J=15.9 Hz, 1H), 5.22 (s, 1H), 8.88 (s, 1H), 9.0 (s, 1H), 12.12 (bs, 1H), 13.5 (bs, 1H); MS (ES+): 534.6[M+1]

Example 92

(1S,2R,4aS,6aS,6bR,8aR,14aR,14bR,16bS)-12-(methoxycarbonyl)-1,2,3,4,4a,5,6,6a,6b,7,8,8a,9,14, 14a,14b,15,16b-octadecahydro-1,2,6a,6b,9,9,14a-heptamethylchryseno[1,2-g]quinoline-4a-carboxylic acid (Compound 92)

The title compound was prepared in an analogous manner as example 84 involving hydrogenation of the compound obtained in example 88, (1S,2R,4aS,6aS,6bR,8aR,14aR, 14bR,16bS)-4a-benzyl 12-methyl-11-chloro-1,2,6a,6b,9,9, 14a-heptamethyl-1,2,3,4,4a,5,6,6a,6b,7,8,8a,9,14,14a,14b, 15,16b-octadecahydrochryseno[1,2-g]quinoline-4a,12-dicarboxylate to afford pure compound 92 (0.05 g) as white solid.
Yield; 65%; $^1$H NMR (300 MHz, DMSO-d$_6$): δ 0.78 (s, 3H), 0.83 (bs, 6H), 0.92 (s, 3H), 1.09 (s, 3H), 1.22 (s, 3H), 1.26 (s, 3H), 1.32-2.17 (m, 20H), 2.85 (d, J=15.9 Hz, 1H), 3.85 (s, 3H), 5.22 (s, 1H), 7.89 (s, 1H), 8.90 (s, 1H), 11.98 (s, 1H); MS (ES+): 548.5[M+1]

Example 93

(1S,2R,4aS,6aS,6bR,8aR,14aR,14bR,16bS)-benzyl 12-carbamoyl-11-chloro-1,2,6a, 6b,9,9,14a-heptamethyl-1,2,3,4,4a,5,6,6a,6b,7,8,8a,9,14,14a,14b,15, 16b-octadecahydrochryseno [1,2-g]quinoline-4a-carboxylate (Compound 93)

To a solution of (1S,2R,4aS,6aS,6bR,8aR,14aR,14bR, 16bS)-4a-((benzyloxy)carbonyl)-11-chloro-1,2,6a,6b,9,9, 14a-heptamethyl-1,2,3,4,4a,5,6,6a,6b,7,8,8a,9,14,14a,14b, 15,16b-octadecahydrochryseno[1,2-g]quinoline-12-carboxylic acid (0.315 g, 0.478 mmol) in THF (15.0 mL) was added CDI (0.155 g, 0.957 mmol) at room temperature under nitrogen atmosphere and the reaction mixture was stirred at room temperature for 12 h. The reaction mixture was concentrated under vacuum to obtain a crude material. To the crude material obtained (0.150 g, 0.212 mmol) in DCM (7.5 mL) was added THF (3.0 mL) followed by ammonium hydroxide (3.0 mL, 19.26 mmol). The reaction mixture was maintained at 0° C. for 2 h. The mixture was then stirred at room temperature for 16 h. After the completion of reaction, the reaction mixture was concentrated under vacuum. The residue obtained was diluted with DCM (10 mL), washed with water (2×10 mL), brine (2×10 mL), dried over $Na_2SO_4$ and concentrated under vacuum to afford pure title compound 93 (0.130 g) as white solid.

Yield: 93%; $^1$H NMR (300 MHz, DMSO-$d_6$): δ 0.62 (s, 3H), 0.76 (s, 3H), 0.83 (d, J=6.0 Hz, 3H), 0.92 (s, 3H), 1.08 (s, 3H), 1.17 (s, 3H), 1.22 (s, 3H), 1.34-2.23 (m, 19H), 2.36 (d, J=16.2 Hz, 1H), 2.76 (d, J=16.2 Hz, 1H), 4.96 (d, J=12.6 Hz, 1H), 5.05 (d, J=12.6 Hz, 1H), 5.22 (bs, 1H), 7.34 (bs, 5H), 7.49 (s, 1H), 7.65 (s, 1H), 7.94 (s, 1H); MS (ES+): 657.7 [M+1]

Example 94

(1S,2R,4aS,6aS,6bR,8aR,14aR,14bR,16bS)-12-carbamoyl-1,2,3,4,4a,5,6,6a,6b,7,8,8a,9,14,14a,14b,15, 16b-octadecahydro-1,2,6a,6b,9,9,14a-heptamethylchryseno[1,2-g]quinoline-4a-carboxylic acid (Compound 94)

The title compound was prepared in an analogous manner as example 84 involving hydrogenation of the compound obtained in example 92, (1S,2R,4aS,6aS,6bR,8aR,14aR, 14bR,16bS)-benzyl 12-carbamoyl-11-chloro-1,2,6a, 6b,9,9, 14a-heptamethyl-1,2,3,4,4a,5,6,6a,6b,7,8,8a,9,14,14a,14b, 15,16b-octadecahydrochryseno [1,2-g]quinoline-4a-carboxylate to afford pure compound 94 (0.045 g) as white solid.

Yield: 35%; $^1$H NMR (300 MHz, DMSO-$d_6$): δ 0.79 (s, 3H), 0.83 (bs, 6H), 0.92 (s, 3H), 1.08 (s, 3H), 1.22 (s, 3H), 1.25 (s, 3H), 1.25-1.42 (m, 12H), 2.75 (d, J=15.9 Hz, 1H), 5.22 (s, 1H), 7.45 (s, 1H), 7.78 (s, 1H), 8.01 (s, 1H), 8.82 (s, 1H), 11.98 (s, 1H); MS (ES+): 533.7 [M+1]

Example 95

(1S,2R,4aS,6aS,6bR,8aR,14aR,14bR,16bS)-benzyl 11-chloro-1,2,6a,6b,9,9,14a-heptamethyl-12-(methylcarbamoyl)1,2,3,4,4a,5,6,6a,6b,7,8,8a,9,14,14a, 14b,15,16b-octadecahydro chryseno[1,2-g]quinoline-4a-carboxylate (Compound 95)

To a solution of (1S,2R,4aS,6aS,6bR,8aR,14aR,14bR, 16bS)-4a-((benzyloxy)carbonyl)-11-chloro-1,2,6a,6b,9,9, 14a-heptamethyl-1,2,3,4,4a,5,6,6a,6b,7,8,8a,9,14,14a,14b, 15,16b-octa decahydrochryseno[1,2-g]quinoline-12-carboxylic acid (0.315 g, 0.478 mmol) in THF (15.0 mL) was added CDI (0.155 g, 0.957 mmol) at room temperature under nitrogen atmosphere and the reaction mixture was stirred at room temperature for 12 h. The reaction mixture was concentrated under vacuum to obtain a crude material. To the crude material obtained (0.150 g, 0.212 mmol) in DCM (7.5 mL) was added THF (5 mL) followed by methanamine solution in ethanol (3.0 mL, 0.212 mmol). The reaction mixture was stirred at room temperature for 12 h. On completion of reaction the mixture was concentrated under vacuum. The residue obtained was diluted with DCM (10 mL), washed with water (3×10 mL), brine (2×10 mL), dried over $Na_2SO_4$ and concentrated under vacuum to afford pure compound 95 (0.08 g) as white solid.

Yield: 88%; $^1$H NMR (300 MHz, DMSO-$d_6$): δ 0.62 (s, 3H), 0.76 (s, 3H), 0.83 (d, J=6.0 Hz, 3H), 0.92 (s, 3H), 1.08 (s, 3H), 1.17 (s, 3H), 1.22 (bs, 6H), 1.34-2.37 (m, 20H), 2.72 (d, J=4.2 Hz, 1H), 4.96 (d, J=12.3 Hz, 1H), 5.05 (d, J=12.6 Hz, 1H), 5.21 (bs, 1H), 7.34 (bs, 5H), 7.64 (s, 1H), 8.45 (s, 1H); MS (ES+): 671.7 [M+1]

Example 96

(1S,2R,4aS,6aS,6bR,8aR,14aR,14bR,16bS)-12-(methylcarbamoyl)-1,2,3,4,4a,5,6,6a,6b,7,8,8a,9,14, 14a,14b,15,16b-octadecahydro-1,2,6a,6b,9,9,14a-heptamethylchryseno[1,2-g]quinoline-4a-carboxylic acid (Compound 96)

The title compound was prepared in an analogous manner as example 85 involving hydrogenation of the compound obtained in example 94, (1S,2R,4aS,6aS,6bR,8aR,14aR, 14bR,16bS)-benzyl 11-chloro-1,2,6a,6b,9,9,14a-heptamethyl-12-(methylcarbamoyl)1,2,3,4,4a,5,6,6a,6b,7,8,8a,9, 14,14a,14b,15,16b-octadecahydro chryseno[1,2-g] quinoline-4a-carboxylate to afford pure titled compound 96 (0.06 g) as white solid.

Yield: 53%; $^1$H NMR (300 MHz, DMSO-$d_6$): δ 0.79 (s, 3H), 0.84 (bs, 6H), 0.92 (s, 3H), 1.09 (s, 3H), 1.21 (bs, 6H), 1.29-2.16 (m, 21H), 2.76 (d, J=4.2 Hz, 3H), 5.21 (s, 1H), 7.74 (s, 1H), 8.49 (d, J=4.5 Hz, 1H), 8.77 (s, 1H), 11.99 (s, 1H); MS (ES+): 54707 [M+1]

Example 97

(1S,2R,4aS,6aS,6bR,8aR,14aR,14bR,16bS)benzyl 11chloro12((hydroxyimino)methyl) 1,2,6a,6b,9,9, 14aheptamethyl1,2,3,4,4a,5,6,6a,6b,7,8,8a,9,14,14a, 14b,15,16boctadecahydrochryseno[1,2-g]quinoline-4a-carboxylate (Compound 97)

To a stirred solution of the compound obtained in example 82, (1S,2R,4aS,6aS,6bR,8aR,14aR,14bR,16bS)-benzyl 11-chloro-12-formyl-1,2,6a,6b,9,9,14a-heptamethyl-1,2,3, 4,4a,5,6,6a,6b,7,8,8a,9,14,14a,14b,15,16b-octadecahydro-chryseno[1,2-g]quinoline-4a-carboxylate (0.220 g, 0.343 mmol) in ethanol (10 mL) was added hydroxylamine hydrochloride (0.071 g, 1.028 mmol) followed by triethyamine (0.143 mL, 1.028 mmol) under nitrogen atmosphere. The reaction mixture was stirred at room temperature for 5 h. On completion of reaction the mixture was concentrated under vacuum. The residue obtained was diluted with DCM (10 mL), washed with water (2×10 mL), dried over $Na_2SO_4$ and concentrated under vacuum. The crude material obtained was purified by Combiflash chromatography (0-15% ethyl acetate/petroleum ether) to afford pure compound 97 (0.15 g) as white solid.

Yield: 69%; $^1$H NMR (300 MHz, DMSO-$d_6$): δ 0.62 (s, 3H), 0.76 (s, 3H), 0.83 (d, J=6.3 Hz, 3H), 0.91 (s, 3H), 1.0 (s, 3H), 1.17 (s, 3H), 1.22 (bs, 6H), 1.48-2.39 (m, 17H), 2.80 (d, J=16.2 Hz, 1H), 4.96 (d, J=12.3 Hz, 1H), 5.05 (d, J=12.3 Hz, 1H), 5.22 (s, 1H), 7.34 (bs, 5H), 7.78 (s, 1H), 8.21 (s, 1H), 11.78 (s, 1H); MS (ES+): 657 [M+1]

Example 98

(1S,2R,4aS,6aS,6bR,8aR,15aR,15bR,17bS)-benzyl, 1,2,6a,6b,9,9,15a-heptamethyl-1,2,3,4,4a,5,6,6a,6b, 7,8,8a,9,15,15a,15b,16,17b-octadecahydrochryseno [1,2-g]isoxazolo[5,4-b]quinoline-4a-carboxylate (Compound 98)

To a solution of the compound obtained in example 97 (0.150 g, 0.228 mmol) in DMF (10 mL) was added $K_2CO_3$ (0.126 g, 0.913 mmol) under nitrogen atmosphere. The reaction mixture was heated at 80° C. for 6 h and on completion of reaction the mixture was diluted with DCM (20 mL), washed with cold water (3×25 mL), brine (3×15 ml), dried over $Na_2SO_4$ and concentrated under vacuum. The crude material obtained was purified by Combiflash chromatography (0-5% ethyl acetate/petroleum ether) to afford pure compound 98 (0.038 g) as white solid.

Yield: 27%; $^1$H NMR (300 MHz, DMSO-$d_6$): δ 0.58 (s, 3H), 0.77 (s, 3H), 0.82 (d, J=6.0 Hz, 3H), 0.91 (s, 3H), 1.05 (s, 3H), 1.15 (s, 3H), 1.24 (bs, 8H), 1.42-2.22 (m, 14H), 2.72 (s, 1H), 2.88 (s, 1H), 4.95 (d, J=12.6 Hz, 1H), 5.05 (d, J=12.6 Hz, 1H), 5.19 (s, 1H), 7.33 (bs, 5H), 7.84 (s, 1H), 12.0 (s, 1H); MS (ES+): 621.5[M+1].

Example 99

(1S,2R,4aS,6aS,6bR,8aR,15aR,15bR,17bS)-1,2,6a, 6b,9,9,15a-heptamethyl-1,2,3,4,4a,5,6,6a,6b,7,8,8a, 9,15,15a,15b,16,17b-octadecahydrochryseno[1,2-g] isoxazolo[5,4b]quinoline-4a-carboxylic acid (Compound 99)

The title compound was prepared in an analogous manner as example 85 involving hydrogenation of the compound obtained in example 98 to afford the pure title compound 99 (0.06 g).

Yield: 20%; $^1$H NMR (300 MHz, DMSO-$d_6$): δ 0.80-0.83 (m, 9H), 0.91 (s, 3H), 1.05 (s, 3H), 1.16 (s, 3H), 1.25-1.32 (m, 8H), 1.51-2.11 (m, 15H), 5.19 (s, 1H), 7.84 (s, 1H), 7.84 (s, 1H), 11.98 (s, 1H), 12.0 (s, 1H); MS (ES+): 531.3[M+1].

Example 100

(1S,2R,4aS,6aS,6bR,8aR,14aR,14bR,16bS)-benzyl 11-chloro-12-cyano-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate (Compound 100)

To a solution of the compound obtained in example 82, (1S,2R,4aS,6aS,6bR,8aR,14aR,14bR,16bS)-benzyl 11-chloro-12-formyl-1,2,6a,6b,9,9,14a-heptamethyl-1,2,3, 4,4a,5,6,6a,6b,7,8,8a,9,14,14a,14b,15,16b-octadecahydrochryseno[1,2-g]quinoline-4a-carboxylate (2.0 g, 3.11 mmol) in THF (20 mL) was added ammonia solution (30%, 18 mL, 3.11 mmol) followed by iodine (1.185 g, 4.67 mmol) at room temperature. The reaction mixture was stirred for 16 h. The reaction mixture was diluted with ethylacetate (50 mL), washed with saturated $Na_2S_2O_3$ (3×25 mL), brine (2×30 mL), dried over $Na_2SO_4$ and concentrated under vacuum. The crude material obtained was washed with acetonitrile (3×10 mL) to afford pure title compound 100 (2.0 g) as white solid.

Yield: 98%; $^1$H NMR (300 MHz, DMSO-$d_6$): δ 0.61 (s, 3H), 0.74 (s, 3H), 0.82 (d, J=6.3 Hz, 3H), 0.91 (s, 3H), 1.07 (s, 3H), 1.18 (s, 3H), 1.22 (s, 3H), 1.48-2.0 (m, 18H), 2.20 (d, J=11.1 Hz, 1H), 2.38 (d, J=16.2 Hz, 1H), 2.79 (d, J=16 Hz, 1H), 4.96 (d, J=12.6 Hz, 1H), 5.03 (d, J=12.6 Hz, 1H), 5.20 (s, 1H), 7.33-7.35 (m, 5H), 8.11 (s, 1H); MS (ES+): 639.5 [M+1].

Example 101

(1S,2R,4aS,6aS,6bR,8aR,14aR,14bR,16bS)-benzyl 12-cyano-11-ethoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate (Compound 101)

To a solution of the compound as obtained in example 100 (0.2 g, 0.313 mmol) in ethanol (15 mL) was added sodium ethoxide (0.055 g, 1.25 mmol) at room temperature under nitrogen atmosphere. The reaction mixture was refluxed at 120° C. for 20 h, The mixture was concentrated and the obtained material was diluted with dichloromethane (20 mL) followed by washing with water (3×20 mL). The mixture was concentrated to obtain the crude material which was purified by Combiflash chromatography (0-5% methanol/dichloromethane) to afford the pure title compound 101 (0.1 g) as white solid.

Yield: 50%; $^1$H NMR (300 MHz, DMSO-$d_6$): δ 0.61 (s, 3H), 0.74 (s, 3H), 0.82 (d, J=6.3 Hz, 3H), 0.91 (s, 3H), 1.07 (s, 3H), 1.18 (s, 3H), 1.23 (s, 3H), 1.31-1.35 (m, 6H), 1.38-2.10 (m, 15H), 2.18-2.30 (m, 2H), 2.68 (d, J=15.9 Hz, 1H), 4.42 (q, J=7.2 Hz, 2H), 4.96 (d, J=12.3 Hz, 1H), 5.03 (d, J=12.3 Hz, 1H), 5.20 (s, 1H), 7.33-7.35 (m, 5H), 7.84 (s, 1H); MS (ES+): 649.8 [M+1]

Example 102

(1S,2R,4aS,6aS,6bR,8aR,14aR,14bR,16bS)-12-cyano-11-ethoxy-1,2,6a,6b,9,9,14a-hepta methyl-1, 2,3,4,4a,5,6,6a,6b,7,8,8a,9,14,14a,14b,15,16b-octadecahydrochryseno[1,2-g]quinoline-4a-carboxylic acid (Compound 102)

The title compound was prepared in an analogous manner as example 85 involving hydrogenation of the compound as obtained in example 101, to afford pure title compound 102 (0.03 g) as white solid.

Yield: 70%; $^1$H NMR (300 MHz, DMSO-$d_6$): δ 0.78-0.82 (m, 9H), 0.91 (s, 3H), 1.16 (s, 3H), 1.19 (s, 3H), 1.24 (s, 3H), 1.34 (bs, 3H), 1.57-2.31 (m, 21H), 2.69 (d, J=15.6 Hz, 1H), 4.42 (q, J=6.9 Hz, 2H), 5.20 (s, 1H), 7.85 (bs, 1H); MS (ES+): 560.5 [M+1]

Example 103

(1S,2R,4aS,6aS,6bR,8aR,14aR,14bR,16bS)-11-chloro-12-cyano-1,2,6a,6b,9,9,14a-hepta methyl-1,2, 3,4,4a,5,6,6a,6b,7,8,8a,9,14,14a,14b,15,16b-octadecahydrochryseno[1,2-g]quinoline-4a-carboxylic acid (Compound 103)

The title compound was prepared in an analogous manner as example 85 involving hydrogenation of the compound obtained in example 100, to afford the pure title compound 103 (0.03 g) as white solid.

Yield: 23%; $^1$H NMR (300 MHz, DMSO-$d_6$): δ 0.78 (s, 3H), 0.82 (s, 3H), 0.91 (s, 3H), 1.08 (s, 3H), 1.19 (s, 3H), 1.24 (bs, 6H), 1.52-1.52 (m, 19H), 2.72-2.83 (m, 2H), 5.20 (s, 1H), 8.11 (s, 1H), 11.98 (s, 1H); MS (ES+): 639.5[M+1]

Example 104

(1S,2R,4aS,6aS,6bR,8aR,16aR,16bR,18bS)-benzyl 15-chloro-1,2,6a,6b,9,9,16a-heptamethyl-1,2,3,4,4a, 5,6,6a,6b,7,8,8a,9,16,16a,16b,17,18b-octadecahydro-chryseno[1,2-b]acridine-4a-carboxylate (Compound 104)

A mixture of the compound as obtained in step 2 of example 1 (2.5 g, 4.84 mmol), 2-aminobenzoic acid (0.663 g, 4.84 mmol) and POCl$_3$ (25 mL, 268 mmol) was heated at 100° C. for 6 h, At the end of 6 h the excess of POCl$_3$ was removed under reduced pressure and resulting solid was neutralized with saturated NaHCO$_3$ (3×50 mL) and extracted with DCM (3×40 mL). The combined organic layer was washed with brine (3×50 mL), water, dried over Na$_2$SO$_4$, filtered and concentrated under reduced pressure. The crude product obtained was purified by column chromatography (10% ethyl acetate in hexane) to afford the title compound 104 (2.68 g) as a white solid.

Yield: 42%; $^1$H NMR (300 MHz, DMSO-d$_6$): δ 0.76 (s, 3H), 0.88 (s, 3H), 0.90-0.98 (m, 3H), 0.98 (s, 3H), 1.10-1.21 (m, 4H), 1.21-1.80 (m, 20H), 1.82-1.90 (m, 1H), 1.95-2.13 (m, 2H), 2.15-2.27 (m, 1H), 2.30-2.41 (m, 2H), 5.03 (d, 1H, J=12.5 Hz), 5.14 (d, 1H, J=12.5 Hz), 5.37 (brs, 1H), 7.30-7.40 (m, 5H), 7.53 (t, 1H, J=7.5, 7.8 Hz), 7.66 (t, 1H, J=7.2, 8.1 Hz), 8.01 (d, 1H, J=8.1 Hz), 8.15 (d, 1H, J=8.4 Hz); MS (ES+): 583.7 [M+1].

Example 105

(1S,2R,4aS,6aS,6bR,8aR,16aR,16bR,18bS)-1,2,6a, 6b,9,9,16a-heptamethyl-1,2,3,4,4a,5,6,6a, 6b,7,8,8a, 9,16,16a,16b,17,18b-octadecahydrochryseno[1,2-b]acridine-4a-carboxylicacid (Compound 105)

To a solution of the compound as obtained in example 104 (40 mg, 0.060 mmol) in methanol (4 mL) was added triethylamine (0.018 ml, 0.132 mmol) followed by addition of 10% Pd/C (10 mg, 9.40 µmol). The reaction mixture was stirred at room temperature under hydrogen atmosphere for 4-5 h. The reaction mixture was filtered through celite pad and the filtrate was concentrated under reduced pressure. The crude product obtained was purified by column chromatography (10% ethyl acetate in hexane) to afford the title compound 105 (17 mg).

Yield: 53%; $^1$H NMR (300 MHz, DMSO-d$_6$): δ 0.91 (s, 3H), 0.93-0.10 (m, 6H), 1.17 (s, 3H), 1.25-1.35 (m, 9H), 1.42 (s, 3H), 1.44 (s, 3H), 1.46-2.38 (m, 14H), 2.6 (d, 1H, J=15.6 Hz,), 5.37 (brs, 1H), 7.44 (t, 1H, J=7.5 Hz), 7.59 (t, 1H, J=7.8 Hz), 7.68 (d, 1H, J=7.5 Hz), 7.99 (d, 1H, J=8.7 Hz); MS (ES+): 540.5 [M+1].

Example 106

(1S,2R,4aS,6aS,6bR,8aR,16aR,16bR,18bS)-benzyl 1,2,6a,6b,9,9,16a-heptamethyl-15-((3-morpholino-propyl)amino)-1,2,3,4,4a,5,6,6a,6b,7,8,8a,9,16,16a, 16b,17,18b-octadecahydro chryseno[1,2-b]acridine-4a-carboxylate (Compound 106)

A mixture of the compound as obtained in example 104 (50 mg, 0.075 mmol) and phenol (708 mg, 7.53 mmol) was heated to 70° C. to get homogeneous solution followed by addition of 3-morpholinopropan-1-amine (33 µl, 0.226 mmol). The reaction mixture was stirred at 125° C. for 6 h. The reaction mixture was cooled to room temperature, diluted with ethyl acetate (30 mL) and washed with 10% NaOH (2×15 mL). The organic layer was washed with brine (10 mL), water (10 mL), dried over anhydrous Na$_2$SO$_4$, filtered and concentrated under reduced pressure. The crude product obtained was purified by column chromatography (1-10% methanol in DCM) to afford the title compound 106 (27 mg).

Yield: 48%; $^1$H NMR (300 MHz, DMSO-d$_6$): 0.65 (s, 3H), 0.73 (s, 3H), 0.86 (d, 3H), 0.90-0.98 (m, 4H), 1.12 (s, 3H), 1.14-1.20 (m, 2H), 1.21-1.30 (m, 5H), 1.31-1.47 (m, 9H), 1.48-1.50 (m, 6H), 1.68-1.80 (m, 3H), 1.88-1.90 (m, 2H), 1.95-2.08 (m, 2H), 2.10-2.39 (m, 8H), 3.40-3.58 (m, 4H), 4.94 (d, 1H, J=12.5 Hz), 5.05 (d, 1H, J=12.5 Hz), 5.26 (brs, 1H) 7.28-7.44 (m, 6H), 7.45-7.60 (m, 1H), 7.70-7.80 (m, 1H), 8.08-8.19 (m, 1H); MS (ES+): 772.6 [M+1].

Example 107

(1S,2R,4aS,6aS,6bR,8aR,16aR,16bR,18115)-1,2,6a, 6b,9,9,16a-heptamethyl-15-((3-morpholino propyl)amino)-1,2,3,4,4a,5,6,6a,6b,7,8,8a,9,16,16a,16b,17, 18b-octadecahydrochryseno[1,2-b]acridine-4a-carboxylic acid (Compound 107)

To a solution of the compound as obtained in example 106 (30 mg, 0.039 mmol) in methanol (3 ml, 0.039 mmol) was added Pd/C (4.96 mg, 4.66 µmol). The reaction mixture was stirred under hydrogen atmosphere at room temperature for 2 h. The reaction mixture was filtered through celite and the filtrate was concentrated under reduced pressure. The solid obtained was purified by washing with acetonitrile (5 ml) to afford the title compound 107 as a white solid (20.61 mg, 0.027 mmol).

Yield: 70%; $^1$H NMR (300 MHz, DMSO-d$_6$): 0.82-0.92 (m, 12H), 1.13-1.38 (m, 11H), 1.39-1.60 (m, 10H), 1.61-2.18 (m, 11H), 2.26 (t, 2H), 2.46-2.61 (m, 4H), 2.84-2.89 (m, 1H), 3.49 (q, 2H, J 7.2 Hz, 6.9 Hz, 13.8 Hz), 3.65-3.90 (m, 4H), 5.35 (brs, 1H), 7.41 (t, 1H, J=7.8 Hz), 7.60 (t, 1H, J=7.5 Hz), 8.05 (d, 1H, J=8.7 Hz), 8.45 (m, 1H); MS (ES+): 682.6 [M+1].

Example 108

(1S,2R,4aS,6aS,6bR,8aR,16aR,16bR,18bS)-benzyl 15-amino-1,2,6a,6b,9,9,16a-heptamethyl-1,2,3,4,4a, 5,6,6a,6b,7,8,8a,9,16,16a,16b,17,18b-octadecahydro-chryseno[1,2-b]acridine-4a-carboxylate (Compound 108)

A mixture of the compound as obtained in example 104 (50 mg, 0075 mmol) and phenol (1 ml) was heated at 80° C. to obtain a homogenous solution. To the homogenous solution ammonia gas was purged for 6 h at 130° C. The reaction mixture was cooled to room temperature, diluted with ethyl acetate (20 ml) and washed with 10% NaOH (5 ml). The organic layer was washed brine (2×10 mL), water (10 mL), dried over anhydrous sodium sulphate, filtered and concentrated under vacuum. The crude product obtained was purified by column chromatography (2% methanol in DCM) to afford the title compound 108 (20 mg).

Yield: 40%; $^1$H NMR (300 MHz, DMSO-d$_6$): δ 0.76 (s, 3H), 0.88 (s, 3H), 0.90-0.98 (m, 3H), 0.98 (s, 3H), 1.10-1.21 (m, 4H), 1.21-1.80 (m, 20H), 1.82-1.90 (m, 1H), 1.95-2.13 (m, 2H), 2.15-2.27 (m, 1H), 2.30-2.41 (m, 2H), 5.03 (d, 1H, J=12.5 Hz), 5.14 (d, 1H, J=12.5 Hz), 5.37 (brs, 1H), 7.30-

7.40 (m, 5H), 7.53 (t, 1H, J=7.5, 7.8 Hz), 7.66 (t, 1H, J=7.2, 8.1 Hz), 8.01 (d, 1H, J=8.1 Hz), 8.15 (d, 1H, J=8.4 Hz); MS (ES+): 645.5 [M+1].

Example 109

(1S,2R,4aS,6aS,6bR,8aR,16aR,16bR,18bS)-15-amino-1,2,6a,6b,9,9,16a-heptamethyl-1,2,3,4,4a,5,6,6a,6b,7,8,8a,9,16,16a,16b,17,18b-octadecahydro-chryseno[1,2-b]acridine-4a-carboxylic acid (Compound 109)

The title compound was prepared in an analogous manner as example 106 involving hydrogenation of the compound as obtained in example 108, to afford the title compound 109 (16 mg) as a white solid.

Yield: 93%; ¹H NMR (300 MHz, DMSO-$d_6$): δ 0.84 (s, 3H), 0.87 (s, 3H), 0.94 (s, 3H), 1.10 (s, 3H), 1.24 (s, 3H), 1.25-1.70 (m, 16H), 1.71-1.80 (m, 1H), 1.83-2.10 (m, 7H), 2.18-2.21 (m, 1H), 2.30-2.40 (m, 1H), 2.72-2.80 (m, 1H), 5.28 (s, 1H), 6.45 (brs, 2H), 7.30-7.32 (m, 1H), 7.53-7.55 (m, 1H), 7.73-7.75 (m, 1H), 8.16-8.18 (m, 1H), 11.99 (brs, 1H); MS (ES+): 555.6 [M+1].

Example 110

(1S,2R,4aS,6aS,6bR,8aR,16aR,16bR,18bS)-benzyl 1,2,6a,6b,9,9,16a-heptamethyl-15-phenoxy-1,2,3,4,4a,5,6,6a,6b,7,8,8a,9,16,16a,16b,17,18b-octadecahydrochryseno[1,2-b]acridine-4a-carboxylate (Compound 110)

A mixture of the compound as obtained in example 104 (100 mg, 0.151 mmol) and phenol (14.17 mg, 0.151 mmol) was heated to 60° C. to get homogeneous solution. To this solution 4-hydroxypyrrolidine-2-carboxylic acid (59.2 mg, 0.452 mmol) was added and the resulting reaction mixture was heated at 110° C. for 6 h. The reaction mixture was diluted with water (10 mL) and extracted with ethyl acetate (30×3 mL). The combined organic layer was washed with 10% NaOH (20 ml), dried over anhydrous $Na_2SO_4$, filtered and concentrated under reduced pressure. The crude product obtained was purified by column chromatography (4% ethyl acetate in petroleum ether) to afford the title compound 110 (72.8 mg, 0.101 mmol) as a white solid.

Yield: 67%; ¹H NMR (300 MHz, DMSO-$d_6$): δ 0.61 (s, 3H), 0.70-0.95 (m, 9H), 1.05-1.10 (m, 4H), 1.12-1.90 (m, 22H), 1.92-2.30 (m, 4H), 4.97 (d, 1H, J=12.5 Hz), 5.02 (d, 1H, J=12.5 Hz), 5.14 (brs, 1H), 7.75-7.85 (m, 2H), 7.02-7.10 (m, 2H), 7.28-7.36 (m, 5H), 7.40-7.50 m, 2H), 7.64-7.66 (m, 2H), 7.96 (m, 1H); MS (ES+): 722.5 [M+1].

Example 111

(1S,2R,4aS,6aS,6bR,8aR,16aR,16bR,18bS)-1,2,6a,6b,9,9,16a-heptamethyl-15-phenoxy-1,2,3,4,4a,5,6,6a,6b,7,8,8a,9,16,16a,16b,17,18b-octadecahydro-chryseno[1,2-b]acridine-4a-carboxylic acid (Compound 111)

To a solution of the compound as obtained in example 110 (50 mg, 0.069 mmol) in a mixture of methanol (5 ml) and THF (2 ml) was added Pd/C (10.10 mg, 9.50 μmol). The reaction mixture was stirred at room temperature under hydrogen atmosphere for 2 h. The reaction mixture was filtered through celite and the filtrate was concentrated under reduced pressure. The solid obtained was purified by washing with acetonitrile (10 mL) to afford the title compound 111 (28.5 mg, 0.045 mmol).

Yield: 57%; ¹H NMR (300 MHz, DMSO-$d_6$): δ 0.76-0.88 (m, 9H), 0.90 (s, 3H), 1.00-1.10 (m, 3H), 1.12-2.05 (m, 23H), 2.05-2.40 (m, 4H), 5.14 (brs, 1H), 6.78-6.83 (m, 2H), 7.0-7.10 (m, 1H), 7.25-7.38 (m, 2H), 7.40-7.50 (m, 1H), 7.61-7.75 (m, 2H), 7.95-8.05 (m, 1H), 11.96 (brs, 1H); MS (ES+): 632.5 [M+1].

Example 112

Synthesis of (1S,2R,6aS,6bR,8aR,13aR,13bR)-methyl1,2,6a,6b,9,9,13a-heptamethyl-12-(methylthio)-2,3,4,4a,5,6,6a,6b,7,8,8a,9,11,13,13a,13b,14,15b-octadecahydro-1H-chryseno [1,2-f]indazole-4a-carboxylate (Compound 112)

Step 1

Synthesis of (1S,2R,6aS,6bR,8aR,12aR,12bR)-methyl 1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate To a solution of (1S,2R,4aS,6aS,6bR,8aR,10S,12aR,12bR,14bS)-10-hydroxy-1,2,6a,6b,9,9,12a-heptamethyl-1,2,3,4,4a,5,6,6a,6b,7,8,8a,9,10,11,12,12a,12b,13,14b-icosa hydropicene-4a-carboxylic acid (10 g, 21.99 mmol) in DMF (40 mL) was added potassium carbonate (6.08 g, 44.0 mmol) followed by addition of methyl iodide (2.063 mL, 33.0 mmol). The reaction mixture was stirred at room temperature overnight. On completion of reaction the reaction mixture was quenched in water (200 mL) and solid obtained was filtered, washed with acetonitrile (100 mL) and dried to afford the title compound (8.7 gm).

Yield: 84%; ¹H NMR (300 MHz, DMSO-$d_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.29-2.31 (m, 1H), 2.46-2.53 (m, 2H), 5.18 (S, 1H), 3.52 (S, 3H). MS (ES+): 469.4 [M+1]

Step 2

Synthesis of (1S,2R,6aS,6bR,8aR,12aR,12bR)-methyl 11-(bis(methylthio)methylene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate To a solution of the compound as obtained in step 1 (1 g, 2.134 mmol) in DMF (5 mL) and THF (9 mL) was added sodium hydride (0.512 g, 21.34 mmol) under inert atmosphere followed by addition of carbon disulphide (1.286 mL, 21.34 mmol) and methyl iodide (1.334 mL, 21.34 mmol) to the reaction mixture. The reaction mixture was stirred at room temperature for 30 min After the completion of reaction, the reaction mixture was quenched in cold water (200 mL). The mixture was extracted with ethylacetate (15 mL), washed with water (10 mL), brine (10 mL), dried over $Na_2SO_4$ and concentrated under vacuum to obtain a crude material. The crude material obtained was purified by column chromatography (0-5% ethyl acetate/petroleum ether) to afford pure title compound (0.7 g) as white solid.

Yield: 57.3%; ¹H NMR (300 MHz, DMSO-$d_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.27 (S, 3H), 2.34 (S, 3H), 2.29-2.31 (m, 1H), 2.91-2.97 (d, 2H), 5.21 (S, 1H), 3.51 (S, 3H); MS (ES+): 573.9 [M+1].

Step 3

A mixture of the compound obtained in step 2 (0.469 g, 1 mmole) and hydrazine (0.5 mL, 10 mmole) was heated overnight at 110° C. On completion of reaction, ethyl acetate (5 mL) was added to the reaction mixture and the organic layer was washed with water (10 mL), brine (10 mL) and dried over $Na_2SO_4$ and concentrated under vacuum to obtain oily material which was purified by Combiflash chromatography (50% ethylacetate/petroluem ether) to afford the pure titled compound 112 (17 mg).

Yield: 3.15%; $^1$H NMR (300 MHz, DMSO-$d_6$): δ 0.80-0.82 (m, 6H), 0.91 (S, 3H), 0.955 (S, 3H), 0.98-1.00 (d, 6H), 1.06 (S, 3H), 1.26-1.32 (m, 5H), 1.44 (m, 5H), 1.49-1.59 (m, 5H), 1.76-1.83 (m, 3H), 1.86-1.95 (m, 3H), 2.11-2.13 (d, 1H), 2.15-2.19 (d, 1H), 2.32 (S, 1H), 3.52 (S, 3H), 5.22 (S, 1H), 12.48 (S, 1H); MS (ES+): 539.7 [M+1].

Example 113

1,2,6a,6b,9,9,13a-heptamethyl-1,2,3,4,4a,5,6,6a,6b, 7,8,8a,9,13,13a,13b,14,15b-octadecahydropiceno[2, 3-d]isoxazole-4a-carboxylic acid (Compound 113)

Step 1

Synthesis of (1S,2R,6aS,6bR,8aR,12aR,12bR)-1,2, 6a,6b,9,9,12a-heptamethyl-10-oxo-1,2,3,4,4a,5,6,6a, 6b,7,8,8a,9,10,11,12,12a,12b,13,14b-icosahydropicene-4a-carboxylic acid To a solution of (1S,2R,4aS,6aS,6bR,8aR,10S,12aR, 12bR,14bS)-10-hydroxy-1,2,6a,6b,9,9,12a-heptamethyl-1, 2,3,4,4a,5,6,6a,6b,7,8,8a,9,10,11,12,12a,12b,13,14b-icosa hydropicene-4a-carboxylic acid (80 gms, 175 mmol) in THF (1 L) was added freshly prepared Jones reagent (chromium (VI) oxide (55 g, 550 mmol) and 150 mL of sulphuric acid, 500 mL water). The reaction mixture was stirred for 15-20 min. and on completion of reaction, the reaction mixture was extracted with ethylacetate (1000 mL), washed with brine (500 mL), dried over $Na_2SO_4$ and concentrated under vacuum to obtain a solid which was triturated with acetonitrile (500 mL) and filtered to afford pure title compound (57 gm).

Yield: 71%; $^1$H NMR (DMSO $d_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.29-2.31 (m, 1H), 2.46-2.53 (m, 2H), 5.18 (S, 1H), 11.98 (S, 1H); MS (ES+): 455.8 [M+1].

Step 2

Synthesis of (1S,2R,6aS,6bR,8aR,12aR,12bR,Z)-11-(hydroxymethylene)-1,2,6a,6b,9,9,12a-heptamethyl-10-oxo-1,2,3,4,4a,5,6,6a,6b,7,8,8a,9,10,11,12,12a, 12b,13,14b-icosahydro picene-4a-carboxylic acid To a solution of the compound obtained in step 1 (1 g, 2.199 mmol) in THF (50 mL) was added sodium methoxide (0.475 g, 8.8 mmol) followed by addition of ethyl formate (0.637 g, 8.6 mmol) under nitrogen atmosphere at 0° C. The reaction mixture was stirred for 16 hrs at room temperature. After the completion of reaction, the mixture was acidified with 10% HCl and extracted with ethylacetate (50 mL), washed with water (30 mL), brine (25 mL), dried over $Na_2SO_4$ and concentrated under vacuum to afford pure title compound (0.78 g) as white solid. Yield: 73.9%; $^1$H NMR (DMSO $d_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 4H), 2.11-2.13 (d, 1H), 2.29-2.35 (m, 1H), 5.3 (S, 1H), 8.59 (S, 1H), 14.90 (S, 1H); MS (ES+):483 [M−1].

Step 3

To a solution of the compound obtained in step 2 (0.15 g, 0.311 mmol) in ethanol (5 mL) was added hydroxylamine hydrochloride (0.022 g, 0.311 mmol) under nitrogen atmosphere at room temperature. The reaction mixture was stirred for 16 hrs at room temperature and on completion of reaction, ethanol was distilled out from the reaction mixture under vacuum and obtained crude material was extracted with ethylacetate (20 mL), washed water (10 mL), brine (10 mL), dried over $Na_2SO_4$ and concentrated under vacuum to obtain a crude material which was purified by column chromatography (30% ethyl acetate/petroleum ether) to afford pure title compound 113 (90 mg) as white solid.

Yield: 60%; $^1$H NMR (DMSO $d_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 4H), 2.11-2.13 (d, 1H), 2.29-2.35 (m, 1H), 5.3 (S, 1H), 8.28 (S, 1H), 11.99 (S, 1H exchangeable); MS (ES+): 480.4 [M+1].

Example 114

(1S,2R,6aS,6bR,8aR,13aR,13bR)-1,2,6a,6b,9,9,13a-heptamethyl-1,2,3,4,4a,5,6,6a,6b,7,8,8a, 9,13,13a, 13b,14,15b-octadecahydropiceno[3,2-c]isoxazole-4a-carboxylic acid (Compound 114)

To a solution of the compound obtained in step 2 of example 113 (0.241 g, 0.499 mmol) in pyridine (2 mL) was added hydroxylamine hydrochloride (0.173 g, 2.496 mmol) and the reaction mixture were heated to reflux overnight. The reaction mixture was quenched in 10% HCl, extracted with ethylacetate (15 mL), washed with water (10 mL), brine (10 mL), dried over $Na_2SO_4$ and concentrated under vacuum. The crude material obtained was purified by Combiflash chromatography (20% ethyl acetate/petroleum ether) to afford pure title compound 114 (44 mg).

Yield: 18.37%; $^1$H NMR (DMSO $d_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.29-2.31 (m, 1H), 2.46-2.53 (m, 2H), 5.15 (S, 1H), 8.49 (S, 1H), 11.98 (S, 1H); MS (ES+): 480 [M+1].

Example 115

(1S,2R,4aS,6aS,6bR,13aR,13bR)-10-(3-chlorophenyl)-1,2,6a,6b,9,9,13a-heptamethyl-2,3,4,4a,5,6,6a, 6b,7,8,8a,9,10,13,13a,13b,14,15b-octadecahydro-1H-chryseno[1,24]indazole-4a-carboxylic acid (Compound 115)

To a solution of the compound obtained in step 2 of example 113 (0.2 g, 0.414 mmol) in ethanol (9 mL) and water (1 mL) was added 3-chloro phenyl hydrazinehydrate (0.082 g, 0.456 mmol) and the reaction mixture was refluxed for 1 h. After the completion of reaction, the reaction mixture was concentrated to obtain crude material which was purified by Combiflash chromatography (20% ethyl acetate/petroleum ether) to afford the title compound 115 (36 mg).

Yield: 14.75%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.6 (m, 1H), 5.15 (S, 1H), 11.98 (S, 1H), 7.32-7.62 (m, 5H); MS (ES+): 601.6 [M+1].

Example 116

(1S,2R,4aS,6aS,6bR,13aR,13bR)-10-(2-fluorophenyl)-1,2,6a,6b,9,9,13a-heptamethyl-2,3,4,4a,5,6,6a,6b,7,8,8a,9,10,13,13a,13b,14,15b-octadecahydro-1H-chryseno[1,2-f]indazole-4a-carboxylic acid (Compound 116)

To a solution of the compound obtained in step 2 of example 113 (0.2 g, 0.414 mmol) in ethanol (9 mL) and water (1 mL) was added 3,5 difluorophenyl hydrazine hydrochloride (0.082 g, 0.456 mmol) and the reaction mixture was refluxed for 1 h. After the completion of reaction, the reaction mixture was concentrated to obtain a crude material which was purified by Combiflash chromatography (5-20% ethyl acetate/petroleum) to afford pure title compound 116 (0.116 gm).

Yield: 47.4%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.6 (m, 1H), 5.21 (S, 1H), 11.97 (S, 1H), 7.27-7.29 (m, 2H) 7.34 (S, 1H) 7.46-7.52 (m, 1H); MS (ES+): 573.6 [M+1].

Example 117

(1S,2R,4aS,6aS,6bR,13aR,13bR)-10-(3,5-difluorophenyl)-1,2,6a,6b,9,9,13a-heptamethyl-2,3,4,4a,5,6,6a,6b,7,8,8a,9,10,13,13a,13b,14,15b-octadecahydro-1H-chryseno[1,2-f]indazole-4a-carboxylic acid (Compound 117)

To a solution of the compound obtained in step 2 of example 113 (0.2 g, 0.414 mmol) in ethanol (9 mL) and water (1 mL) was added (2-fluorophenyl)hydrazine hydrochloride (0.074 g, 0.456 mmol) and the reaction mixture was refluxed for 1 h. After the completion of reaction, the reaction mixture was concentrated and the obtained crude material was purified by Combiflash chromatography (5-20% ethyl acetate/petroleum ether) to afford pure title compound 117 (0.04 gm).

Yield: 16.85%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.6 (m, 1H), 5.21 (S, 1H), 11.97 (S, 1H), 7.31-7.52 (m, 3H) 7.34 (S, 1H) 7.55-7.60 (m, 2H); MS (ES+): 591 [M+1].

Example 118

(1S,2R,4aS,6aS,6bR,13aR,13bR)-1,2,6a,6b,9,9,13a-heptamethyl-10-(m-tolyl)-2,3,4,4a,5,6,6a,6b,7,8,8a,9,10,13,13a,13b,14,15b-octadecahydro-1H-chryseno[1,2-f]indazole-4a-carboxylic acid (Compound 118)

To a solution of the compound obtained in step 2 of example 113 (0.2 g, 0.414 mmol) in ethanol (9 mL) and water (1 mL) was added (3-methylphenyl)hydrazine hydrochloride (0.074 g, 0.456 mmol) and reaction mixture was refluxed for 1 h. After the completion of reaction, the reaction mixture was concentrated under reduced pressure and the crude material obtained was purified by Combiflash chromatography (5-20% ethyl acetate/petroleum ether) to afford the title pure compound 118 (0.035 gm).

Yield: 14.85%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.36 (S, 3H) 2.6 (m, 1H), 5.21 (S, 1H), 11.97 (S, 1H), 7.13-7.39 (m, 5H); MS (ES+): 569.8 [M+1].

Example 119

(1S,2R,6aS,6bR,8aR,13aR,13bR)-benzyl 12-(4-methoxyphenyl)-1,2,6a,6b,9,9,13a-heptamethyl-2,3,4,4a,5,6,6a,6b,7,8,8a,9,11,12,12a,13,13a,13b,14,15b-icosahydro-1H-chryseno[1,2-f]indazole-4a-carboxylate (Compound 119)

Step 1

Synthesis of (1S,2R,6aS,6bR,8aR,12aR,12bR,E)-benzyl 11-(4-methoxybenzylidene)-1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate To a solution of the compound obtained in step 2 of example 1, (1S,2R,4aS,6aS,6bR,8aR,12aR,12bR,14bS)-benzyl 1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (0.272 g, 0.499 mmol) in DMF (1 mL), THF (2 mL) was added 4-methoxybenzaldehyde (0.067 mL, 0.551 mmol) followed by addition sodium hydride (0.200 g, 4.99 mmol). The reaction mixture was stirred at room temperature for overnight. After the completion of reaction, ethylacetate (10 mL) was added to the reaction mixture and the mixture was concentrated to obtain the crude material which was purified by column chromatography (5-10% ethyl acetate/petroleum ether) to afford pure title compound (186 mg).

Yield: 56.2%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.29-2.31 (m, 1H), 2.46-2.53 (m, 2H), 5.19 (S, 1H), 4.9-5.06 (dd, 2H), 3.79 (S, 3H), 7.01-7.04 (d, 2H), 7.3-7.49 (m, 7H), 7.85-7.88 (d, 2H), 9.86 (S, 1H); MS (ES+): 663.9 [M+1].

Step 2

Synthesis of (1S,2R,6aS,6bR,8aR,13aR,13bR)-benzyl 12-(4-methoxyphenyl)-1,2,6a, 6b,9,9,13a-heptamethyl-2,3,4,4a,5,6,6a,6b,7,8,8a,9,11,12,12a,13,13a,13b,14,15b-icosa hydro-1H-chryseno[1,2-f]indazole-4a-carboxylate To a solution of the compound obtained in step 1 (0.186 g, 0.281 mmol) in ethanol (5 mL) and dioxane (5.00 mL) was added hydrazine (0.055 mL, 1.403 mmol) and the reaction mixture was refluxed overnight. After the completion of reaction, the reaction mixture was concentrated under vacuum and the crude material obtained was purified by Combiflash chromatography (60% ethylacetate/petroleum ether) to afford title pure compound 119 (17 mg).

Yield: 8.95%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 4H), 1.76-1.83 (m, 3H), 1.89-1.99 (m, 3H), 2.11-2.13 (d, 1H), 2.29-2.31 (m, 1H), 2.68-2.73 (d, 1H), 5.13 (S, 1H), 5.27 (S, 1H), 6.87-6.98 (d, 2H), 6.81 (S, 1H), 7.06-7.09 (d, 1H), 7.33-7.34 (S, 5H), 8.7 (S, NH), 3.8 (S, 3H), 4.97-5.03 (q, 2H), 4.76-4.78 (S, 1H); MS (ES+): 677 [M+1].

Example 120

(1S,2R,6aS,6bR,8aR,13aR,13bR)-benzyl 11-amino-1,2,6a,6b,9,9,13a-heptamethyl-1,2,3,4,4a, 5,6,6a, 6b,7,8,8a,9,13,13a,13b,14,15b-octadecahydropiceno[3,2-d]thiazole-4a-carboxylate (Compound 120)

Step 1

Synthesis of (1S,2R,6aS,6bR,8aR,12aR,12bR)-benzyl 11-bromo-1,2,6a,6b,9,9,12a-heptamethyl-10-oxo-1,2,3,4,4a,5,6,6a,6b,7,8,8a,9,10,11,12,12a,12b, 13,14b-icosahydropicene-4a-carboxylate To a solution of the compound obtained in step 2 of example 1, (1S,2R,4aS,6aS,6bR,8aR,12aR,12bR,14bS)-benzyl 1,2,6a,6b,9,9,12a-heptamethyl-10-oxo-1,2,3,4,4a,5,6,6a,6b,7,8,8a,9,10,11,12,12a,12b,13,14b-icosahydropicene-4a-carboxylate (0.5 g, 0.918 mmol) in methylenedichloride (10 mL) was added pyridinium tribromide (0.294 g, 0.918 mmol) and the reaction mixture was stirred at room temperature for overnight. After completion of reaction, the reaction mixture was concentrated to afford the title compound (0.45 g, 0.721 mmol).

Yield: 79%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 5H), 1.76-1.83 (m, 3H), 1.89-1.99 (m, 3H), 2.11-2.13 (d, 1H), 2.29-2.31 (m, 1H), 2.6 (m, 2H), 5.16 (S, 1H), 4.9-5.06 (dd, 2H), 7.33 (m 5H); MS (ES+): 623.3 [M+1].

Step 2

Synthesis of (1S,2R,6aS,6bR,8aR,13aR,13bR)-benzyl 11-amino-1,2,6a,6b,9,9,13a-heptamethyl-1,2,3,4, 4a,5,6,6a,6b,7,8,8a,9,13,13a,13b,14,15b-octadecahydropiceno[3,2-d]thiazole-4a-carboxylate To a solution of the compound obtained in step 1 (0.447 g, 0.717 mmol) in ethanol (10 mL) was added thiourea (0.055 g, 0.717 mmol) and the reaction mixture was refluxed for overnight. After the completion of reaction, the reaction mixture was concentrated under vacuum and the crude material obtained was purified by column chromatography (2% dichloromethane/methanol) to afford title pure compound 120 (0.1 g).

Yield: 22.23%; $^1$H NMR (DMSO d$_6$): δ 0.80-0.82 (m, 6H), 0.91 (S, 3H), 0.955 (S, 3H), 0.98-1.00 (d, 6H), 1.06 (S, 3H), 1.26-1.32 (m, 4H), 1.44 (m, 4H), 1.49-1.59 (m, 4H), 1.76-1.83 (m, 3H), 1.89-1.99 (m, 3H), 3.52 (S, 3H), 4.98 (m, 2H), 5.18 (bs, 1H), 6.60 (s, 2H), 7.34 (m, 5H); MS (ES+): 601 [M+1].

Biological Assay

Representative compounds of Formula I of the present invention (referred to as test compounds) were tested for their activity using the assay and the method described below.

Example 121

General RORγ Binding Assay:

The RORγ binding of compounds of the present invention as described herein to RORγ was measured. For the radioligand binding assay, various concentrations of the test compounds were prepared (0.01 µM, 0.03 µM, 0.1 µM, 0.3 µM, 1 µM and 3 µM) and the samples were incubated with 200 ng of RORγt receptor protein in the presence of the [$^3$H]25-hydroxy cholesterol and the mixture was incubated at room temperature for 1 h. An extent of displacement of the radioligand was measured after harvesting the reaction mixture on filter plate reader using TopCount (Perkin Elmer) for radioactivity. The compounds of present invention were tested for RORγ binding using the above assay procedure and the results obtained are given in the below Table 1.

TABLE 1

| ROR binding of the compounds of present invention | | |
|---|---|---|
| Sr. No. | Example number | ROR binding (%) |
| 1 | Example 6 | +++ |
| 2 | Example 14 | ++ |
| 3 | Example 23 | ++ |
| 4 | Example 27 | ++ |
| 5 | Example 31 | ++ |
| 6 | Example 38 | ++ |
| 7 | Example 45 | ++ |
| 8 | Example 55 | ++ |
| 9 | Example 59 | +++ |
| 10 | Example 78 | +++ |
| 11 | Example 81 | +++ |
| 12 | Example 84 | ++ |
| 13 | Example 94 | ++ |

'+++' corresponds to more than 80% binding of the compounds of present invention
'++' corresponds to 50 to 70% binding of the compounds of present invention

CONCLUSION

The radioligand binding results demonstrate that the compounds of the present invention bind directly to RORγ. The RORγ binding was determined for the compounds of the present invention is indicative of RORγ modulating activity of the compounds of the present invention.

We claim:
1. A compound of Formula I,

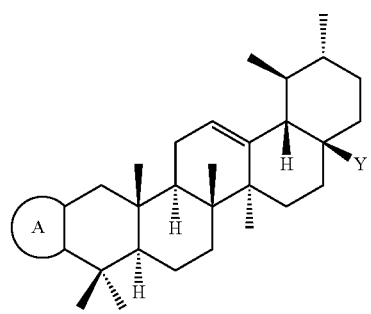

Formula I

123 or a stereoisomer, a tautomer, a pharmaceutically acceptable salt, a pharmaceutically acceptable solvate, a prodrug, an N-oxide, a S-oxide or a carboxylic acid isostere thereof;

Y is —COOR'; wherein R' is hydrogen or $(C_1-C_6)$alkyl, wherein $(C_1-C_6)$alkyl is unsubstituted or substituted with $(C_6-C_{10})$aryl;

Ring A is 5- to 14-membered heteroaryl selected from the group consisting of pyrimidinyl, pyridyl, quinazolinyl, pyrazolyl and thiazolyl;

wherein, said pyrimidinyl, pyridyl, quinazolinyl, or thiazolyl is unsubstituted or substituted with one or more groups of R, and wherein, said pyrazolyl is substituted with one or more groups of R, provided that when Ring A is pyrazolyl, then R excludes amino; wherein R is selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, 3- to 10-membered heterocyclyl, $(C_6-C_{10})$aryl, 5- to 14-membered heteroaryl, cyano, amino, —O—$(C_6-C_{10})$aryl, —$OR^a$, —$C(O)R^a$, —$C(O)OR^a$, —CH=NOH, —$C(O)NH_2$, —$C(O)NR^aR^b$, —$SR^a$, —$S(O)_mR^a$, —$S(O)_mNR^aR^b$, —$S(O)(NH)R^a$, —$N[(C_1-C_6)alkyl]R^a$, —$N[(C_1-C_6)alkyl]_2$, —$NHR^a$, —$N(R^a)$—$C(O)R^a$, —$N(R^a)$—$C(O)NR^aR^b$ and —$NR^aR^b$;

or two R groups present on adjacent carbon atoms of the ring A combine together to form an optionally substituted unsaturated or saturated carbocycle optionally containing one or two heteroatoms independently selected from the group consisting of N, O and S;

$R^a$ and $R^b$ are independently selected from the group consisting of hydrogen, halogen, hydroxy, $(C_1-C_6)$alkyl, halo$(C_1-C_6)$alkyl, —O—$(C_1-C_6)$alkyl, $(C_3-C_{10})$cycloalkyl, 3- to 10-membered heterocyclyl, $(C_6-C_{10})$aryl and 5- to 14-membered heteroaryl;

or $R^a$ and $R^b$ together with the nitrogen to which they are attached, can combine to form a 3- to 10-membered saturated or unsaturated heterocyclyl which contains one or two heteroatoms independently selected from the group consisting of N, O and S;

m is 1 or 2;

provided that when Ring A is pyrimidinyl, then one of the R groups is other than hydrogen; and provided that, when Ring A is pyrimidinyl substituted with a single hydroxy group, a single —SH group, or a single —$NH_2$ group, the pyrimidinyl moiety is further substituted with another non-hydrogen R group;

provided that when Ring A is pyrazolyl and R is attached on nitrogen atom of pyrazolyl ring then R is selected from the group consisting of

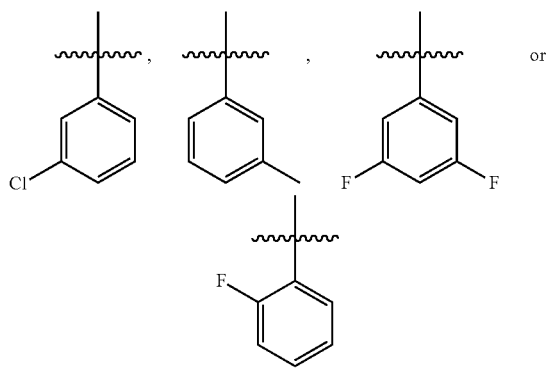

124 wherein

ℓ is point of attachment to nitrogen atom of pyrazolyl ring;

wherein:

$(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —$NH(C_1-C_6)$alkyl, —$N[(C_1-C_6)alkyl]_2$, —$C(O)(C_1-C_6)$alkyl, —$C(O)O(C_1-C_6)$alkyl, —$C(O)NH_2$, —$C(O)NH(C_1-C_6)$alkyl, —$C(O)N[(C_1-C_6)alkyl]_2$ and —$C(O)NHS(O)_2(C_1-C_6)$alkyl;

$(C_3-C_{10})$cycloalkyl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, amino and cyano;

carbocycle is 3- to 12-membered ring which is unsubstituted or substituted with one or more groups independently selected from the group consisting of $(C_1-C_6)$alkyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heteroaryl, heterocyclyl, cyano, amino, —$C(O)O(C_1-C_6)$alkyl, —$C(O)NR^aR^b$ and —$S(O)_2R^a$; wherein $R^a$ and $R^b$ are as defined above;

$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —$C(O)O(C_1-C_6)$alkyl, —$C(O)NR^aR^b$ and —$S(O)_2R^a$; wherein $R^a$ and $R^b$ are as defined above;

heterocyclyl is 3- to 10-membered ring which is unsubstituted or substituted with one or more groups independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —$C(O)OR^a$, —$C(O)NR^aR^b$ and —$S(O)_2R^a$; wherein $R^a$ and $R^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —$C(O)NR^aR^b$ and —$S(O)_2R^a$; wherein $R^a$ and $R^b$ are as defined above;

and halogen is selected from chlorine, bromine, iodine and fluorine.

2. The compound according to claim 1, wherein Y is —COOH; and Ring A is as defined in claim 1 or a stereoisomer, a tautomer or a pharmaceutically acceptable salt, a pharmaceutically acceptable solvate, a prodrug, an N-oxide, a S-oxide or a carboxylic acid isostere thereof.

3. The compound according to claim 1, wherein Y is —COOR'; wherein R' $(C_1-C_6)$alkyl, wherein $(C_1-C_6)$alkyl is unsubstituted or substituted with $(C_6-C_{10})$aryl; and Ring A is 5- to 14-membered heteroaryl selected from the group consisting of pyrimidinyl, pyridyl, quinazolinyl, pyrazolyl, and thiazolyl; wherein said pyrimidinyl, pyridyl, quinazolinyl, pyrazolyl, or thiazolyl is unsubstituted or substituted with one or more groups of R as defined in claim 1 or a stereoisomer, a tautomer or a pharmaceutically acceptable salt, a pharmaceutically acceptable solvate, a prodrug, an N-oxide, a S-oxide or a carboxylic acid isostere thereof.

4. The compound according to claim 1, represented by Formula Ia

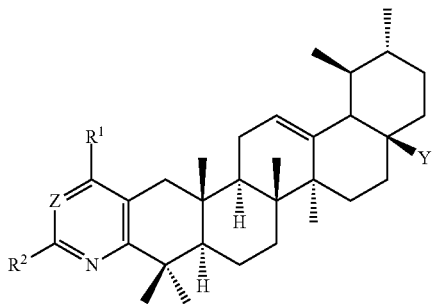

Formula Ia or a stereoisomer, a tautomer or a pharmaceutically acceptable salt, a pharmaceutically acceptable solvate, a prodrug, an N-oxide, a S-oxide or a carboxylic acid isostere thereof, wherein: Y is —COOR'; wherein R' is hydrogen or $(C_1$-$C_6)$alkyl, wherein $(C_1$-$C_6)$alkyl is unsubstituted or substituted with $(C_6$-$C_{10})$aryl;

$R^1$ is independently selected from the group consisting of hydrogen, halogen, hydroxy, $(C_1$-$C_6)$alkyl, halo$(C_1$-$C_6)$ alkyl, —O—$(C_1$-$C_6)$alkyl, —O—$(C_1$-$C_6)$haloalkyl, $(C_3$-$C_{10})$cycloalkyl, 3- to 10-membered heterocyclyl, $(C_6$-$C_{10})$aryl, 5- to 14-membered heteroaryl, cyano, amino, —C(O)NH$_2$, —C(O)NR$^a$R$^b$, —SR$^a$, —S(O)$_m$R$^a$, —S(O)$_m$NR$^a$R$^b$, —N[$(C_1$-$C_6)$alkyl]R$^a$, —N[$(C_1$-$C_6)$alkyl]$_2$, —NHR$^a$, —N(R$^a$)—C(O)R$^a$, —N(R$^a$)—C(O)NR$^a$R$^b$ and —NR$^a$R$^b$; wherein R$^a$ and R$^b$ are hydrogen or $(C_1$-$C_6)$alkyl; or R$^a$ and R$^b$ together with the nitrogen atom to which they are attached, can combine to form an unsaturated or saturated 3- to 10-membered heterocyclyl containing 1, 2 or 3 heteroatoms independently selected from the group consisting of N, O and S;

$R^2$ is independently selected from the group consisting of hydrogen, halogen, hydroxy, $(C_1$-$C_6)$alkyl, halo$(C_1$-$C_6)$ alkyl, $(C_3$-$C_6)$cycloalkyl, —O—$(C_1$-$C_6)$alkyl, —O—$(C_1$-$C_6)$haloalkyl, 3- to 10-membered heterocyclyl, $(C_6$-$C_{10})$aryl, 5- to 14-membered heteroaryl, cyano, amino, —SR$^a$, —S(O)$_m$R$^a$, —S(O)$_m$NR$^a$R$^b$, —N(R$^a$)—C(O)R$^a$, —N[$(C_1$-$C_6)$alkyl]R$^a$, —N[$(C_1$-$C_6)$alkyl]$_2$, —NHR$^a$ and —NR$^a$R$^b$; wherein R$^a$ and R$^b$ are independently selected from the group consisting of hydrogen, $(C_1$-$C_6)$alkyl, $(C_3$-$C_{10})$cycloalkyl or $(C_6$-$C_{10})$aryl; or R$^a$ and R$^b$ combine together with the nitrogen atom to which they are attached, can combine to form an unsaturated or saturated heterocyclyl which contains 1, 2 or 3 heteroatoms independently selected from the group consisting of N, O and S;

$R^3$ at each occurrence is independently selected from the group consisting of hydrogen, halogen, hydroxy, cyano, $(C_1$-$C_6)$alkyl, halo$(C_1$-$C_6)$alkyl, —O—$(C_1$-$C_6)$ alkyl, —O—$(C_1$-$C_6)$haloalkyl, $(C_3$-$C_6)$cycloalkyl, heterocyclyl, $(C_6$-$C_{10})$aryl, heteroaryl, —COOH, —CH$_2$OH, —C(O)R$^a$, —C(O)OR$^a$, —CH=N—OH and —C(O)NR$^a$R$^b$, wherein R$^a$ and R$^b$ are selected from the group consisting of hydrogen, hydroxy, $(C_1$-$C_6)$alkyl, —O—$(C_1$-$C_6)$alkyl, heterocyclyl and heteroaryl; or R$^a$ and R$^b$ together with the nitrogen atom to which they are attached, can combine to form an unsaturated or saturated heterocyclyl containing 1, 2 or 3 heteroatoms independently selected from the group consisting of N, O and S;

Z is —CR$^3$ or N;

when Z is N, one of the R$^1$ or R$^2$ is other than hydrogen; and when Z is N, and R$^2$ is OH, —SH, or —NH$_2$, then R$^1$ is a non-hydrogen substituent, when Z is —CR$^3$; R$^1$, R$^2$ and R$^3$ are as defined above; or R$^2$ and R$^3$ present on adjacent carbon atoms of the heteroaryl can combine to form a 3- to 6-membered saturated or unsaturated heterocyclyl containing one or two heteroatoms independently selected from the group consisting of O, N and S;

m is 1 or 2;

wherein said $(C_1$-$C_6)$alkyl is unsubstituted or substituted with one or more groups independently selected from the group consisting of halogen, hydroxy, $(C_1$-$C_6)$alkyl, halo$(C_1$-$C_6)$alkyl, $(C_2$-$C_8)$alkenyl, $(C_2$-$C_8)$alkynyl, —O—$(C_1$-$C_6)$alkyl, —O—$(C_1$-$C_6)$haloalkyl, $(C_3$-$C_{10})$cycloalkyl, $(C_6$-$C_{10})$aryl, heterocyclyl, heteroaryl, cyano, amino, —NH$(C_1$-$C_6)$alkyl, —N[$(C_1$-$C_6)$alkyl]$_2$, —C(O)($C_1$-$C_6)$alkyl, —C(O)O$(C_1$-$C_6)$alkyl, —C(O)NH$_2$, —C(O)NH$(C_1$-$C_6)$alkyl, —C(O)N[$(C_1$-$C_6)$alkyl]$_2$ and —C(O) NHS(O)$_2$$(C_1$-$C_6)$alkyl;

$(C_3$-$C_{10})$cycloalkyl is unsubstituted or substituted with one or more groups independently selected from the group consisting of halogen, hydroxy, $(C_1$-$C_6)$alkyl, halo$(C_1$-$C_6)$alkyl, —O—$(C_1$-$C_6)$alkyl, —O—$(C_1$-$C_6)$ haloalkyl, amino and cyano;

carbocycle is 3- to 12-membered ring which is unsubstituted or substituted with one or more groups independently selected from the group consisting of $(C_1$-$C_6)$ alkyl, halo$(C_1$-$C_6)$alkyl, hydroxy, halogen, $(C_1$-$C_6)$ alkoxy, halo$(C_1$-$C_6)$alkoxy, $(C_6$-$C_{10})$aryl, $(C_3$-$C_{10})$ cycloalkyl, heteroaryl, heterocyclyl, cyano, amino, —C(O)O$(C_1$-$C_6)$alkyl, —C(O)NR$^a$R$^b$ and —S(O)$_2$R$^a$; wherein R$^a$ and R$^b$ are as defined above;

$(C_6$-$C_{10})$aryl is unsubstituted or substituted with one or more groups independently selected from the group consisting of halogen, hydroxy, $(C_1$-$C_6)$alkyl, halo$(C_1$-$C_6)$alkyl, —O—$(C_1$-$C_6)$alkyl, —O—$(C_1$-$C_6)$haloalkyl, $(C_3$-$C_{10})$Cycloalkyl, $(C_6$-$C_{10})$aryl, heterocyclyl, heteroaryl, cyano, amino, —C(O)O$(C_1$-$C_6)$alkyl, —C(O) NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, $(C_1$-$C_6)$alkyl, halo$(C_1$-$C_6)$alkyl, —O—$(C_1$-$C_6)$alkyl, —O—$(C_1$-$C_6)$haloalkyl, $(C_3$-$C_{10})$ cycloalkyl, $(C_6$-$C_{10})$aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1$-$C_6)$alkyl, halo$(C_1$-$C_6)$alkyl, —O—$(C_1$-$C_6)$alkyl, —O—$(C_1$-$C_6)$haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

5. The compound according to claim 4, represented by Formula A

Formula A

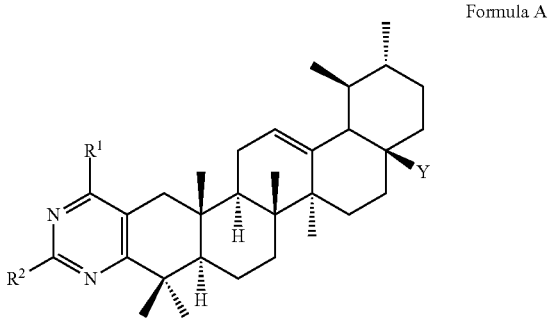

or a stereoisomer, a tautomer, a pharmaceutically acceptable salt, a pharmaceutically acceptable solvate, a prodrug, an N-oxide, a S-oxide or a carboxylic acid isostere thereof, wherein: Y is —COOR'; wherein R' is hydrogen or $(C_1-C_6)$alkyl, wherein $(C_1-C_6)$alkyl is unsubstituted or substituted with $(C_6-C_{10})$aryl and one of $R^1$ or $R^2$ is other than hydrogen; $R^1$ is independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, 3- to 10-membered heterocyclyl, $(C_6-C_{10})$aryl, 5- to 14-membered heteroaryl, cyano, amino, —C(O)NH$_2$, —C(O)NR$^a$R$^b$, —SR$^a$, —S(O)$_m$R$^a$, —S(O)$_m$NR$^a$R$^b$, —N[$(C_1-C_6)$alkyl]R$^a$, —N[$(C_1-C_6)$alkyl]$_2$, —NHR$^a$, —N(R$^a$)—C(O)R$^a$, —N(R$^a$)—C(O)NR$^a$R$^b$ and —NR$^a$R$^b$; wherein R$^a$ and R$^b$ are hydrogen or $(C_1-C_6)$alkyl; or R$^a$ and R$^b$ together with the nitrogen atom to which they are attached, can combine to form an unsaturated or saturated 3- to 10-membered heterocyclyl containing 1, 2 or 3 heteroatoms independently selected from the group consisting of N, O and S;

$R^2$ is independently selected from the group consisting of hydrogen, halogen, hydroxy, $(C_1-C_6)$alkyl, halo$(C_1-C_6)$alkyl, $(C_3-C_6)$cycloalkyl, —O—$(C_1-C_6)$alkyl, —O—$(C_1-C_6)$haloalkyl, 3- to 10-membered heterocyclyl, $(C_6-C_{10})$aryl, 5- to 14-membered heteroaryl, cyano, amino, —SR$^a$, —S(O)$_m$R$^a$, —S(O)$_m$NR$^a$R$^b$, —N(R$^a$)—C(O)R$^a$, —N[$(C_1-C_6)$alkyl]R$^a$, —N[$(C_1-C_6)$alkyl]$_2$, —NHR$^a$ and —NR$^a$R$^b$; wherein R$^a$ and R$^b$ are independently selected from the group consisting of hydrogen, $(C_1-C_6)$alkyl, $(C_3-C_{10})$cycloalkyl or $(C_6-C_{10})$aryl; or R$^a$ and R$^b$ combine together with the nitrogen atom to which they are attached, can combine to form an unsaturated or saturated heterocyclyl which contains 1, 2 or 3 heteroatoms independently selected from the group consisting of N, O and S; provided that when $R^2$ is OH, SH, or NH$_2$, then $R^1$ is a non-hydrogen substituent, m is 1 or 2;

wherein said $(C_1-C_6)$alkyl is unsubstituted or substituted with one or more groups independently selected from the group consisting of halogen, hydroxy, $(C_1-C_6)$alkyl, halo$(C_1-C_6)$alkyl, $(C_2-C_8)$alkenyl, $(C_2-C_8)$alkynyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —NH$(C_1-C_6)$alkyl, —N[$(C_1-C_6)$alkyl]$_2$, —C(O)$(C_1-C_6)$alkyl, —C(O)O$(C_1-C_6)$alkyl, —C(O)NH$_2$, —C(O)NH$(C_1-C_6)$alkyl, —C(O)N[$(C_1-C_6)$alkyl]$_2$ and —C(O)NHS(O)$_2$$(C_1-C_6)$alkyl;

$(C_3-C_{10})$Cycloalkyl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, amino and cyano;

carbocycle is 3- to 12-membered ring which is unsubstituted or substituted with one or more groups independently selected from the group consisting of $(C_1-C_6)$alkyl, halo$(C_1-C_6)$alkyl, hydroxy, halogen, $(C_1-C_6)$alkoxy, halo$(C_1-C_6)$alkoxy, $(C_6-C_{10})$aryl, $(C_3-C_{10})$cycloalkyl, heteroaryl, heterocyclyl, cyano, amino, —C(O)O$(C_1-C_6)$alkyl, —C(O)NR$^a$R$^b$ and —S(O)$_2$R$^a$; wherein R$^a$ and R$^b$ are as defined above;

$(C_6-C_{10})$aryl is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)O$(C_1-C_6)$alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, $(C_1-C_6)$alkyl, halo$(C_1-C_6)$alkyl, —O—$(C_1-C_6)$alkyl, —O—$(C_1-C_6)$haloalkyl, $(C_3-C_{10})$cycloalkyl, $(C_6-C_{10})$aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, $(C_1-C_6)$alkyl, halo$(C_1-C_6)$alkyl, —O—$(C_1-C_6)$alkyl, —O—$(C_1-C_6)$haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

6. The compound according to claim 5, Y is —COOR'; R' is hydrogen or $(C_1-C_6)$alkyl, wherein $(C_1-C_6)$alkyl is unsubstituted or substituted with $(C_6-C_{10})$aryl;

$R^1$ is halogen or hydroxy; and $R^2$ is hydrogen or —SR$^a$; wherein R$^a$ is hydrogen or $(C_1-C_6)$alkyl.

7. The compound according to claim 5, wherein Y is —COOR';

R' is hydrogen or $(C_1-C_6)$alkyl, wherein $(C_1-C_6)$alkyl is unsubstituted or substituted with $(C_6-C_{10})$aryl;

$R^1$ is hydroxy; and $R^2$ is hydrogen, halogen, hydroxy, $(C_1-C_6)$alkyl, halo$(C_1-C_6)$alkyl, or —O$(C_1-C_6)$alkyl.

8. The compound according to claim 5, Y is —COOR'; R' is hydrogen or $(C_1-C_6)$alkyl, wherein $(C_1-C_6)$alkyl is unsubstituted or substituted with $(C_6-C_{10})$aryl;

$R^1$ is, —N[$(C_1-C_6)$alkyl]R$^a$, —N[$(C_1-C_6)$alkyl]$_2$, —NH$(C_3-C_{10})$cycloalkyl, —NHR$^a$, —N(R$^a$)—C(O)R$^a$;

R$^a$ is hydrogen or $(C_1-C_6)$alkyl; wherein $(C_1-C_6)$alkyl is unsubstituted or substituted with 3- to 10-membered heterocyclyl containing 1, 2 or 3 heteroatoms independently selected from the group consisting of N, O and S, and $R^2$ is hydrogen.

9. The compound according to claim 5, wherein Y is —COOR';

R' is hydrogen or $(C_1-C_6)$alkyl, wherein $(C_1-C_6)$alkyl is unsubstituted or substituted with $(C_6-C_{10})$aryl;

$R^1$ is —NR$^a$R$^b$; wherein R$^a$ and R$^b$ are selected from hydrogen, halogen, $(C_1-C_6)$alkyl and halo$(C_1-C_6)$alkyl; wherein $(C_1-C_6)$alkyl is unsubstituted or substituted with 3- to 10-membered heterocyclyl;

R$^a$ and R$^b$ together with the nitrogen atom to which they are attached, can combine to form a heterocyclyl which contains 1, 2 or 3 heteroatoms independently selected from the group consisting of N, O and S, and R$^2$ is (C$_1$-C$_6$)alkyl.

10. The compound according to claim 4, represented by Formula B

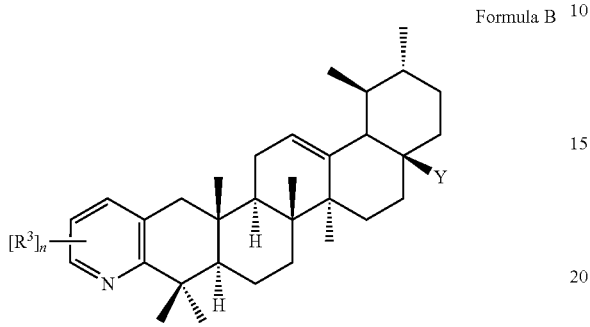

Formula B or a stereoisomer, a tautomer, a pharmaceutically acceptable salt, a pharmaceutically acceptable solvate, a prodrug, an N-oxide, a S-oxide or a carboxylic acid isostere thereof; wherein: Y is —COOR'; wherein R' is hydrogen or (C$_1$-C$_6$)alkyl, wherein (C$_1$-C$_6$)alkyl is unsubstituted or substituted with (C$_6$-C$_{10}$)aryl;

R$^3$ at each occurrence is independently selected from the group consisting of hydrogen, halogen, hydroxy, cyano, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_6$)cycloalkyl, (C$_6$-C$_{10}$)aryl, heteroaryl, 3- to 10-membered heterocyclyl, —COOH, —CH$_2$OH, —C(O)R$^a$, —C(O)OR$^a$, —CH=N—OH and —C(O)NR$^a$R$^b$; wherein R$^a$ and R$^b$ are selected from the group consisting of hydrogen, hydroxy, (C$_1$-C$_6$)alkyl, —O—(C$_1$-C$_6$)alkyl, heterocyclyl and heteroaryl; or R$^a$ and R$^b$ together with the nitrogen atom to which they are attached, can combine to form heteroaryl; or two R$^3$ groups present on adjacent carbon atoms of the heteroaryl ring can combine to form a heteroayrl containing one or two heteroatoms independently selected from the group consisting of N, O and S;

n is 1 or 2;

wherein said (C$_1$-C$_6$)alkyl is unsubstituted or substituted with one or more groups independently selected from the group consisting of halogen, hydroxy, (C$_1$-C$_6$)alkyl, halo(C$_1$-C$_6$)alkyl, (C$_2$-C$_8$)alkenyl, (C$_2$-C$_8$)alkynyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —NH(C$_1$-C$_6$)alkyl, —N[(C$_1$-C$_6$)alkyl]$_2$, —C(O)(C$_1$-C$_6$)alkyl, —C(O)O(C$_1$-C$_6$)alkyl, —C(O)NH$_2$, —C(O)NH(C$_1$-C$_6$)alkyl, —C(O)N[(C$_1$-C$_6$)alkyl]$_2$ and —C(O)NHS(O)$_2$(C$_1$-C$_6$)alkyl;

(C$_3$-C$_{10}$)Cycloalkyl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, amino and cyano;

carbocycle is 3- to 12-membered ring which is unsubstituted or substituted with one or more groups independently selected from the group consisting of (C$_1$-C$_6$)alkyl, halo(C$_1$-C$_6$)alkyl, hydroxy, halogen, (C$_1$-C$_6$)alkoxy, halo(C$_1$-C$_6$)alkoxy, (C$_6$-C$_{10}$)aryl, (C$_3$-C$_{10}$)cycloalkyl, heteroaryl, heterocyclyl, cyano, amino, —C(O)O(C$_1$-C$_6$)alkyl, —C(O)NR$^a$R$^b$ and —S(O)$_2$R$^a$; wherein R$^a$ and R$^b$ are as defined above;

(C$_6$-C$_{10}$)aryl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)O(C$_1$-C$_6$)alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above;

heteroaryl is 5- to 14-membered ring, which is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, heterocyclyl, heteroaryl, cyano, amino, —C(O)NR$^a$R$^b$ and —S(O)$_2$R$^a$; wherein R$^a$ and R$^b$ are as defined above;

and halogen is selected from chlorine, bromine, iodine and fluorine.

11. The compound according to claim 10, wherein Y is —COOR';
R' is hydrogen or (C$_1$-C$_6$)alkyl, wherein (C$_1$-C$_6$)alkyl is unsubstituted or substituted with (C$_6$-C$_{10}$)aryl;
R$^3$ at each occurrence is independently selected from the groups consisting of hydrogen, halogen, (C$_1$-C$_6$)alkyl, halo(C$_1$-C$_6$)alkyl, —C(O)R$^a$ and —CH$_2$OH;
R$^a$ is hydrogen or (C$_1$-C$_6$)alkyl; and n is 1 or 2.

12. The compound according to claim 10, wherein: Y is —COOR';
R' is hydrogen or (C$_1$-C$_6$)alkyl, wherein (C$_1$-C$_6$)alkyl is unsubstituted or substituted with (C$_6$-C$_{10}$)aryl;
R$^3$ at each occurrence is independently selected from one or more groups consisting of halogen, cyano, —O—(C$_1$-C$_6$)alkyl, (C$_1$-C$_6$)haloalkyl, —COOH, —C(O)OR$^a$, —C(O)R$^a$ and —CH=N—OH,
R$^a$ is hydrogen or (C$_1$-C$_6$)alkyl and n is 1 or 2.

13. The compound according to claim 10, wherein Y is —COOR';
R' is hydrogen or (C$_1$-C$_6$)alkyl, wherein (C$_1$-C$_6$)alkyl is unsubstituted or substituted with (C$_6$-C$_{10}$)aryl;
n is 2,
R$^3$ is halogen or —C(O)NR$^a$R$^b$; wherein R$^a$ and R$^b$ are hydrogen or (C$_1$-C$_6$)alkyl.

14. The compound according to claim 10, wherein: Y is —COOR';
R' is hydrogen or (C$_1$-C$_6$)alkyl, wherein (C$_1$-C$_6$)alkyl is unsubstituted or substituted with (C$_6$-C$_{10}$)aryl;
n is 2; and
two R$^3$ groups present on adjacent carbon atoms of a heteroaryl ring can combine to form a 3- to 6-membered saturated or unsaturated heterocyclyl containing 1, 2 or 3 heteroatoms independently selected from the group consisting of N, O and S, which is unsubstituted or substituted with one or more groups independently selected from the group consisting of hydrogen, halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)NR$^a$R$^b$ and —S(O)$_2$R$^a$; wherein R$^a$ and R$^b$ are as claimed in claim 10.

15. The compound according to claim 1, represented by Formula Ib

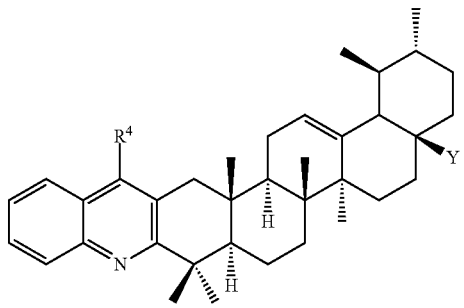

Formula Ib or a stereoisomer, a tautomer or a pharmaceutically acceptable salt, a pharmaceutically acceptable solvate, a prodrug, an N-oxide, a S-oxide or a carboxylic acid isostere thereof; wherein: Y is —COOR'; wherein R' is hydrogen or (C$_1$-C$_6$)alkyl, wherein (C$_1$-C$_6$)alkyl is unsubstituted or substituted with (C$_6$-C$_{10}$)aryl;

R$^4$ is hydrogen, halogen, hydroxy, (C$_1$-C$_6$)alkyl, (C$_1$-C$_6$)haloalkyl, —O—(C$_1$-C$_6$)alkyl, —O—(C$_6$-C$_{10}$)aryl, amino, —NHR$^a$, —N[(C$_1$-C$_6$)alkyl]R$^a$ or —NR$^a$R$^b$; wherein R$^a$ and R$^b$ are hydrogen or (C$_1$-C$_6$)alkyl;

R$^a$ and R$^b$ are independently selected from the group consisting of hydrogen, (C$_1$-C$_6$)alkyl and halo(C$_1$-C$_6$)alkyl; wherein (C$_1$-C$_6$)alkyl is unsubstituted or substituted with heterocyclyl containing 1, 2 or 3 heteroatoms independently selected from the group consisting of N, O and S;

wherein said
(C$_1$-C$_6$)alkyl is unsubstituted or substituted with one or more groups independently selected from the group consisting of halogen, hydroxy, (C$_1$-C$_6$)alkyl, halo(C$_1$-C$_6$)alkyl, (C$_2$-C$_8$)alkenyl, (C$_2$-C$_8$)alkynyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —NH(C$_1$-C$_6$)alkyl, —N[(C$_1$-C$_6$)alkyl]$_2$, —C(O)(C$_1$-C$_6$)alkyl, —C(O)O(C$_1$-C$_6$)alkyl, —C(O)NH$_2$, —C(O)NH(C$_1$-C$_6$)alkyl, —C(O)N[(C$_1$-C$_6$)alkyl]$_2$ and —C(O)NHS(O)$_2$(C$_1$-C$_6$)alkyl;

(C$_6$-C$_{10}$)aryl is unsubstituted or substituted with one or more groups independently selected from the group consisting of halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)O(C$_1$-C$_6$)alkyl, —C(O)NR$^a$R$^b$ and —S(O)$_2$R$^a$; wherein R$^a$ and R$^b$ are as defined above;

heterocyclyl is 3- to 10-membered ring which is unsubstituted or substituted with one or more groups independently selected from the group consisting of hydrogen, halogen, hydroxy, (C$_1$-C$_6$)alkyl, halo(C$_1$-C$_6$)alkyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —C(O)OR$^a$, —C(O)NR$^a$R$^b$ and —S(O)$_2$R$^a$; wherein R$^a$ and R$^b$ are as defined above; and halogen is selected from chlorine, bromine, iodine and fluorine.

16. The compound according to claim 15, wherein Y is —COOR';
R' is hydrogen or (C$_1$-C$_6$)alkyl, wherein (C$_1$-C$_6$)alkyl is unsubstituted or substituted with (C$_6$-C$_{10}$)aryl;
R$^4$ is hydrogen, halogen or —NR$^a$R$^b$;
R$^a$ and R$^b$ are hydrogen or (C$_1$-C$_6$)alkyl.

17. The compound according to claim 15, wherein: Y is —COOR';
R' is hydrogen or (C$_1$-C$_6$)alkyl, wherein (C$_1$-C$_6$)alkyl is unsubstituted or substituted with (C$_6$-C$_{10}$)aryl;
R$^4$ is —O—(C$_1$-C$_6$)alkyl, —O—(C$_6$-C$_{10}$)aryl or —NH(C$_1$-C$_6$)alkyl;
wherein (C$_1$-C$_6$)alkyl is unsubstituted or substituted with one or more groups independently selected from the group consisting of halogen, hydroxy, (C$_1$-C$_6$)alkyl, halo(C$_1$-C$_6$)alkyl, (C$_2$-C$_8$)alkenyl, (C$_2$-C$_8$)alkynyl, —O—(C$_1$-C$_6$)alkyl, —O—(C$_1$-C$_6$)haloalkyl, (C$_3$-C$_{10}$)cycloalkyl, (C$_6$-C$_{10}$)aryl, heterocyclyl, heteroaryl, cyano, amino, —NH(C$_1$-C$_6$)alkyl, —N[(C$_1$-C$_6$)alkyl]$_2$, —C(O)(C$_1$-C$_6$)alkyl, —C(O)O(C$_1$-C$_6$)alkyl, —C(O)NH$_2$, —C(O)NH(C$_1$-C$_6$)alkyl, —C(O)N[(C$_1$-C$_6$)alkyl]$_2$ and —C(O)NHS(O)$_2$(C$_1$-C$_6$)alkyl.

18. A compound represented by Formula Ic

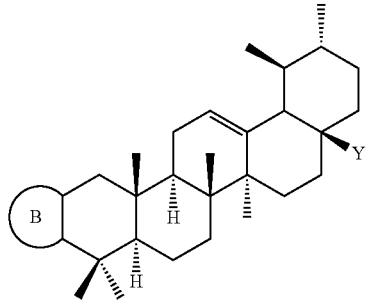

Formula Ic or a stereoisomer, a tautomer, a pharmaceutically acceptable salt, a pharmaceutically acceptable solvate, a prodrug, an N-oxide, a S-oxide or a carboxylic acid isostere thereof;
wherein, Y is —COOR'; wherein R' is hydrogen or (C$_1$-C$_6$)alkyl, wherein (C$_1$-C$_6$)alkyl is unsubstituted or substituted with (C$_6$-C$_{10}$)aryl;
Ring B is a 5-membered heteroaryl selected from the group consisting of

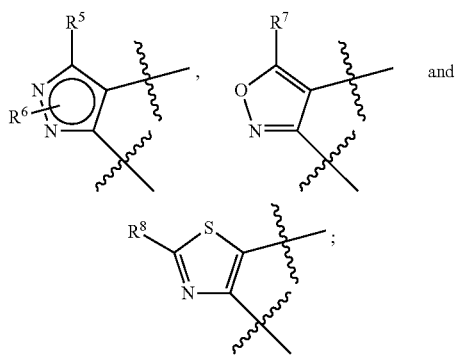

R$^5$ is hydrogen, (C$_1$-C$_6$)alkyl, —O—(C$_1$-C$_6$)alkyl, (C$_6$-C$_{10}$)aryl, heteroaryl or —S(R$^a$)$_m$, wherein R$^a$ is hydrogen or (C$_1$-C$_6$)alkyl;

R⁶ is hydrogen or (C₆-C₁₀)aryl, provided that when R⁵ is hydrogen, R⁶ is (C₆-C₁₀)aryl;

R⁷ is (C₁-C₆)alkyl or —O—(C₁-C₆)alkyl;

R⁸ is —NR$^a$R$^b$; wherein R$^a$ and R$^b$ are hydrogen or (C₁-C₆)alkyl;

wherein:

(C₁-C₆)alkyl is unsubstituted or substituted with one or more groups independently selected from the group consisting of halogen, hydroxy, (C₁-C₆)alkyl, halo(C₁-C₆)alkyl, (C₂-C₈)alkenyl, (C₂-C₈)alkynyl, —O—(C₁-C₆)alkyl, —O—(C₁-C₆)haloalkyl, (C₃-C₁₀)cycloalkyl, (C₆-C₁₀)aryl, heterocyclyl, heteroaryl, cyano, amino, —NH(C₁-C₆)alkyl, —N[(C₁-C₆)alkyl]₂, —C(O)(C₁-C₆)alkyl, —C(O)O(C₁-C₆)alkyl, —C(O)NH₂, —C(O)NH(C₁-C₆)alkyl, —C(O)N[(C₁-C₆)alkyl]₂ and —C(O)NHS(O)₂(C₁-C₆)alkyl;

(C₆-C₁₀)aryl is unsubstituted or substituted with one or more groups independently selected from the group consisting of halogen, hydroxy, (C₁-C₆)alkyl, halo(C₁-C₆)alkyl, —O—(C₁-C₆)alkyl, —O—(C₁-C₆)haloalkyl, (C₃-C₁₀)cycloalkyl, (C₆-C₁₀)aryl, heterocyclyl, heteroaryl, cyano, amino, —C(O)O(C₁-C₆)alkyl, —C(O)NR$^a$R$^b$ and —S(O)₂R$^a$; wherein R$^a$ and R$^b$ are as defined above;

heteroaryl is 5- to 14-membered ring, which is unsubstituted or substituted with one or more groups independently selected from the group consisting of halogen, hydroxy, (C₁-C₆)alkyl, halo(C₁-C₆)alkyl, —O—(C₁-C₆)alkyl, —O—(C₁-C₆)haloalkyl, heterocyclyl, heteroaryl, cyano, amino, —C(O)NR$^a$R$^b$ and —S(O)₂R$^a$; wherein R$^a$ and R$^b$ are as defined above;

and halogen is selected from chlorine, bromine, iodine and fluorine.

19. A compound selected from the group consisting of:

(1S,2R,4aS,6aS,6bR,8aR,14aR,14bR,16bS)-ethyl 13-hydroxy-11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16b S)-benzyl 13-hydroxy-11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16b S)-ethyl 13-hydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,12,14a-octamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a,12-dicarboxylic acid;

(1S,2R,4aS,6aS,6bR,8aR,14aR,14bR,16bS)-12-(methoxycarbonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-1,2,6a,6b,9,9,14a-heptamethyl-12-(methylcarbamoyl)-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-12-cyano-11-ethoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-11-chloro-12-cyano-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,15aR,15bR,17bS)-1,2,6a,6b,9,9,15a-heptamethyl-1,2,3,4,4a,5,6,6a,6b,7,8,8a,9,15,15a,15b,16,17b-octadecahydrochryseno[1,2-g]isoxazolo[5,4-b]quinoline-4a-carboxylic acid;

(1S,4aS,6aS,6bR,8aR,14aR,14bR,16b S)-12-formyl-1,6a,6b,9,9,14a-hexamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-13-hydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-11,13-dihydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-(4-methylpiperazin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-(piperazin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-(pyrrolidin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-methoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-(methylamino)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-(dimethylamino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,14a-heptamethyl-13-((2-morpholinoethyl)amino)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-hydroxy-1,2,6a,6b,9,9,11,14a-octamethyl-1,2,3,4,4a,5,6,6a,6b, 7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-methoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-ethoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-(dimethylamino)-1,2,6a,6b,9,9,11,14a-octamethyl-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,14aR,14bR,16bS)-1,2,6a,6b,9,9,11,14a-octamethyl-13-(methylamino)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-(diethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,11,14a-octamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,14aR,14bR,16bS)-1,2,6a,6b,9,9,11,14a-octamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,11,14a-octamethyl-13-(4-methylpiperazin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-(cyclohexylamino)-1,2,6a,6b,9,9,11,14a-octamethyl-1,2,3,4,4a,5,6,6a,6b,7,8,8a,9,14,14a,14b,15,16b-octadecahydro chryseno[1,2-g]quinazoline-4a-carboxylic acid;

(1S,2R,4aS,6aS,6bR,8aR,14aR,14bR,16bS)-1,2,6a,6b,9,9,11,14a-octamethyl-13-(piperazin-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-1,2,6a,6b,9,9,11,14a-octamethyl-13-morpholino-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,14aR,14bR,16bS)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-11-((2-carboxyethyl)amino)-1,2,6a,6b, 9,9,14a-heptamethyl-1,2,3,4,4a,5,6,6a,6b,7,8,8a,9,14,14a,14b,15,16b-octadecahydro chryseno[1,2-g]quinazoline-4a-carboxylic acid;

(1S,2R,4aS,6aS,6bR,8aR,14aR,14bR,16bS)-11-((2-methoxyphenoxy)methyl)-1,2,6a,6b,9,9,14a-heptamethyl-1,2,3,4,4a,5,6,6a,6b,7,8,8a,9,14,14a,14b,15,16b-octadeca hydro chryseno[1,2-g]quinazoline-4a-carboxylic acid;

(1S,2R,4aS,6aS,6bR,8aR,14aR,14bR,16b S)-11-amino-1,2,6a,6b,9,9,14a-heptamethyl-1,2,3,4,4a,5,6,6a,6b,7,8,8a,9,14,14a,14b,15,16b-octadecahydrochryseno[1,2-g] quinazoline-4a-carboxylic acid;

(1S,2R,4aS,6aS,6bR,8aR,14aR,14bR,16bS)-1,2,6a,6b,9,14a-heptamethyl-11-phenyl 1,2,3,4,4a,5,6,6a,6b,7,8,8a,9,14,14a,14b,15,16b-octadecahydrochryseno[1,2-g] quinazoline-4a-carboxylic acid;

(1S,2R,4aS,6aS,6bR,8aR,14aR,14bR,16bS)-1,2,6a,6b,9,9,14a-heptamethyl-11-morpholino-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,14aR,14bR,16bS)-1,2,6a,6b,9,9,14a-heptamethyl-11-(1H-pyrazol-1-yl)-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 11-(ethylthio)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,14a-heptamethyl-11-(methylsulfonyl)-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,14aR,14bR)-11-(ethylsulfonyl)-1,2,6a,6b,9,9,14a-hepta methyl-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,16aR,16bR,18bS)-1,2,6a,6b,9,9,16a-heptamethyl-1,2,3,4,4a, 5,6,6a,6b,7,8,8a,9,16,16a, 16b, 17,18b-octadecahydrochryseno[1,2-b]acridine-4a-carboxylic acid;

(1S,2R,4aS,6aS,6bR,8aR,16aR,16bR,18bS)-1,2,6a,6b,9,9,16a-heptamethyl-15-((3-morpholinopropyl)amino)-1,2,3,4,4a,5,6,6a,6b,7,8,8a,9,16,16a, 16b, 17,18b-octadecahydro chryseno[1,2-b]acridine-4a-carboxylic acid;

(1S,2R,4aS,6aS,6bR,8aR,16aR,16bR,18bS)-15-amino-1,2,6a,6b,9,9,16a-heptamethyl-1,2,3,4,4a,5,6,6a,6b,7,8,8a,9,16,16a, 16b, 17,18b-octadecahydrochryseno[1,2-b]acridine-4a-carboxylic acid;

(1S,2R,4aS,6aS,6bR,8aR,16aR,16bR,18bS)-1,2,6a,6b,9,9,16a-heptamethyl-15-phenoxy-1,2,3,4,4a,5,6,6a,6b,7,8,8a,9,16,16a, 16b,17,18b-octadecahydrochryseno[1,2-b] acridine-4a-carboxylic acid;

(1S,2R,4aS,6aS,6bR,8aR,14aR,14bR,16bS)-11-cyclopropyl-1,2,6a,6b,9,9,14a-hepta methyl-1,2,3,4,4a,5,6,6a,6b,7,8,8a,9,14,14a,14b,15,16b-octadecahydrochryseno [1,2-g]quinazoline-4a-carboxylic acid;

(1S,2R,4aS,6aS,6bR,8aR,14aR,14bR,16bS)-13-hydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16b S)-benzyl 13-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl, 11,13-dihydroxy-1,2,6a,6b,9,9,14a heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-ethyl 11,13-dihydroxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-13-morpholino-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-1,2,6a,6b,9,9,14a-heptamethyl-13-morpholino-1,2,3,4,4a,5,6,6a, 6b,7,8,8a,9,14,14a,14b,15,16b-octadecahydrochryseno[1,2-g]quinazoline-4a-carboxylic acid hydrochloride;

(1S,2R,4aS,6aS,6bR,8aR,14aR,14bR,16bS)-benzyl 1,2,6a,6b,9,9,14a-heptamethyl-13-(4-methylpiperazin-1-yl)-1,2,3,4,4a,5,6,6a,6b,7,8,8a,9,14,14a,14b,15,16b-octadecahydro chryseno[1,2-g]quinazoline-4a-carboxylate;

(1S,2R,4aS,6aS,6bR,8aR,14aR,14bR,16bS)-benzyl 13-(4-((benzyloxy)carbonyl)piperazin-1-yl)-1,2,6a,6b,9,9,14a-heptamethyl-1,2,3,4,4a,5,6,6a,6b,7,8,8a,9,14,14a,14b,15,16b-octadeca hydrochryseno[1,2-g]quinazoline-4a-carboxylate;

(1S,2R,4aS,6aS,6bR,8aR,14aR,14bR,16bS)-1,2,6a,6b,9,9,14a-heptamethyl-13-(piperazin-1-yl)-1,2,3,4,4a, 5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 1,2,6a,6b,9,9,14a-heptamethyl-13-(pyrrolidin-1-yl)-1,2,3,4,4a,5,6,6a,6b,7,8,8a,9,14,14a,14b,15,16b-octadecahydrochryseno [1,2-g]quinazoline-4a-carboxylate;

(1S,2R,4aS,6aS,6bR,8aR,14aR,14bR,16bS)-benzyl 13-methoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-13-(methylamino)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(dimethylamino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-hydroxy-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-chloro-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-13-(dimethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-13-(dimethylamino)-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylic acid hydrochloride;

(1S,2R,4aS,6aS,6bR,8aR,14aR,14bR,16bS)-benzyl 1,2,6a,6b,9,9,11,14a-octamethyl-13-(methylamino)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1,2,6a,6b,9,9,14a-heptamethyl-13-((2-morpholinoethyl)amino)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-methoxy-1,2,6a,6b,9,9,11,14a-octa methyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-ethoxy-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 13-(diethylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-13-(pyrrolidin-1-yl)-1,2,3,4,4a, 5,6,6a,6b,7,8,8a, 9,14,14a,14b,15,16b-octadecahydrochryseno [1,2-g]quinazoline-4a-carboxylate;

(1S,2R,4aS,6aS,6bR,8aR,14aR,14bR,16bS)-11-((2-carboxyethyl)amino)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 11-((2-methoxyphenoxy)methyl)-1,2,6a, 6b,9,9,14a-heptamethyl-1,2,3,4,4a,5,6,6a,6b,7,8,8a,9,14,14a,14b,15,16b-octadecahydro chryseno[1,2-g]quinazoline-4a-carboxylate;

(1S,2R,4aS,6aS,6bR,8aR,14aR,14bR,16bS)-benzyl 11-amino-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 11-cyclopropyl-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16b S)-benzyl 11-(ethylsulfonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR)-11-(ethylsulfonyl)-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylic acid;

(1S,2R,4aS,6aS,6bR,8aR,14aR,14bR,16bS)-benzyl 1,2,6a,6b,9,9,11,14a-octamethyl-13-(piperidin-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,11,14a-octamethyl-13-(4-methylpiperazin-1-yl)-1,2,3,4,4a,5,6,6a,6b,7,8,8a,9,14,14a,14b,15,16b-octadecahydrochryseno [1,2-g]quinazoline-4a-carboxylate;

(1S,2R,4aS,6aS,6bR,8aR,14aR,14bR,16bS)-benzyl 13-(cyclohexylamino)-1,2,6a,6b,9,9,11,14a-octamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-11-phenyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-11-morpholino-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16b S)-benzyl 13-(4-((benzyloxy)carbonyl) piperazin-1-yl)-1,2,6a,6b,9,9,11,14a-octamethyl-1,2,3,4,4a,5,6,6a,6b,7,8,8a,9,14, 14a,14b,15,16b-octadecahydrochryseno [1,2-g] quinazoline-4a-carboxylate;

(1S,2R,4aS,6aS,6bR,8aR,14aR,14bR,16bS)-benzyl 1,2,6a,6b,9,9,11,14a-octamethyl-13-morpholino-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 1,2,6a,6b,9,9,14a-heptamethyl-11-(1H-pyrazol-1-yl)-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16bS)-benzyl 11-mercapto-1,2,6a,6b,9,9,14a-heptamethyl-1,2,3,4,4a,5,6,6a,6b,7,8,8a,9,14,14a,14b,15,16b-octadecahydrochryseno[1,2-g]quinazoline-4a-carboxylate;

(1S,2R,4aS,6aS,6bR,8aR,14aR,14bR,16b S)-benzyl 11-chloro-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate;

(1S,2R,4aS,6aS,6bR,8aR,14aR,14bR,16bS)-benzyl 11-chloro-12-(hydroxymethyl)-1,2,6a,6b,9,9,14a-heptamethyl-1,2,3,4,4a,5,6,6a,6b,7,8,8a,9,14,14a,14b,15,16b octadecahydrochryseno[1,2-g]quinoline-4a-carboxylate;

(1S,4aS,6aS,6bR,8aR,14aR,14bR,16bS)-12-(hydroxymethyl)-1,6a,6b,9,9,14a-hexamethyl-1,2,3,4,4a,5,6,6a,6b,7,8,8a,9,14,14a,14b,15,16b-octadecahydrochryseno[1,2-g]quinoline-4a-carboxylic acid;

(1S,2R,4aS,6aS,6bR,8aR,14aR,14bR,16bS)-4a-benzyl-12-methyl-11-chloro-1,2,6a,6b,9,9,14a-heptamethyl-1,2,3,4,4a,5,6,6a,6b,7,8,8a,9,14,14a,14b,15,16b-octadecahydrochryseno [1,2-g]quinoline-4a,12-dicarboxylate;

(1S,2R,4aS,6aS,6bR,8aR,14aR,14bR,16b S)-4a-((benzyloxy)carbonyl)-11-chloro-1,2,6a,6b,9,9,14a-heptamethyl-1,2,3,4,4a,5,6,6a,6b,7,8,8a,9,14,14a,14b,15,16b-octadecahydrochryseno [1,2-g]quinoline-12-carboxylic acid;

(1S,2R,4aS,6aS,6bR,8aR,16aR,16bR,18b S)-benzyl 15-chloro-1,2,6a,6b,9,9,16a-heptamethyl-1,2,3,4,4a,5,6,6a,6b,7,8,8a,9,16,16a,16b, 17,18b-octadecahydrochryseno[1,2-b]acridine-4a-carboxylate;

(1S,2R,4aS,6aS,6bR,8aR,16aR,16bR,18bS)-15-amino-1,2,6a,6b,9,9,16a-heptamethyl-1,2,3,4,4a,5,6,6a,6b,7,8,8a,9,16,16a, 16b,17,18b-octadecahydrochryseno[1,2-b]acridine-4a-carboxylic acid;

(1S,2R,4aS,6aS,6bR,13 aR,13bR)-10-(2-fluorophenyl)-1,2,6a,6b,9,9,13a-heptamethyl-2,3,4,4a,5,6,6a,6b,7,8,8a,9,10,13,13a, 13b, 14,15b-octadecahydro-1H-chryseno [1,2-f]indazole-4a-carboxylic acid;

(1S,2R,4aS,6aS,6bR,13aR,13bR)-10-(3,5-difluorophenyl)-1,2,6a,6b,9,9,13a-heptamethyl-2,3,4,4a,5,6,6a,6b,7,8,8a,9,10,13,13a,13b,14,15b-octadecahydro-1H-chryseno[1,2-f]indazole-4a-carboxylic acid;

(1S,2R,4aS,6aS,6bR,8aR,14aR,14bR,16b S)benzyl 11chloro12((hydroxyimino)methyl) 1,2,6a,6b,9,9,14aheptamethyl1,2,3,4,4a,5,6,6a,6b,7,8,8a,9,14,14a,14b,15,16boctadecahydrochryseno[1,2-g]quinoline-4a-carboxylate;

(1S,2R,4aS,6aS,6bR,8aR,14aR,14bR,16b S)-benzyl 11-chloro-1,2,6a,6b,9,9,14a-heptamethyl-12-(methylcarbamoyl)1,2,3,4,4a,5,6,6a,6b,7,8,8a,9,14,14a,14b,15,16b-octadecahydro chryseno[1,2-g]quinoline-4a-carboxylate;

(1S,2R,4aS,6aS,6bR,8aR,14aR,14bR,16b S)-benzyl 12-carbamoyl-11-chloro-1,2,6a,6b,9,9,14a-heptamethyl-1,2,3,4,4a,5,6,6a,6b,7,8,8a,9,14,14a,14b,15,16b-octadecahydrochryseno [1,2-g]quinoline-4a-carboxylate;

(1S,2R,4aS,6aS,6bR,8aR,14aR,14bR,16bS)-1,2,3,4,4a,5,6,6a,6b,7,8,8a,9,14,14a,14b,15,16b-octadecahydro-1,2,6a,6b,9,9,14a-heptamethylchryseno[1,2-g]quinoline-4a, 12-dicarboxylic acid;

(1S,2R,4aS,6aS,6bR,8aR,15aR,15bR,17bS)-benzyl 1,2,6a,6b,9,9,15a-heptamethyl-1,2,3,4,4a,5,6,6a,6b,7,8,8a,9,15,15a,15b, 16,17b-octadecahydrochryseno[1,2-g]isoxazolo[5,4-b] quinoline-4a-carboxylate;

(1S,2R,4aS,6aS,6bR,8aR,14aR,14bR,16b S)-benzyl 11-chloro-12-cyano-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate;

(1S,2R,4aS,6aS,6bR,8aR,14aR,14bR,16b S)-benzyl 12-cyano-11-ethoxy-1,2,6a,6b,9,9,14a-heptamethyl-1,2,3,4,4a,5,6,6a,6b,7,8,8a,9,14,14a,14b,15,16b-octadecahydrochryseno[1,2-g]quinoline-4a-carboxylate;

(1S,2R,4aS,6aS,6bR,8aR,16aR,16bR,18bS)-benzyl 1,2,6a,6b,9,9,16a-heptamethyl-15-((3-morpholinopropyl) amino)-1,2,3,4,4a,5,6,6a,6b,7,8,8a,9,16,16a,16b, 17,18b-octadecahydro chryseno[1,2-b]acridine-4a-carboxylate;

(1S,2R,4aS,6aS,6bR,8aR,16aR,16bR,18bS)-benzyl 1,2,6a,6b,9,9,16a-heptamethyl-15-phenoxy-1,2,3,4,4a,5,6,6a,6b,7,8,8a,9,16,16a,16b, 17,18b-octadecahydrochryseno[1,2-b]acridine-4a-carboxylate;

(1S,2R,4aS,6aS,6bR,13aR,13bR)-10-(3-chlorophenyl)-1,2,6a,6b,9,9,13a-heptamethyl-2,3,4,4a,5,6,6a,6b,7,8,8a,9,10,13,13a,13b, 14,15b-octadecahydro-1H-chryseno [1,2-f]indazole-4a-carboxylic acid;

(1S,2R,6aS,6bR,8aR,13 aR,13bR)-methyl 1,2,6a,6b,9,9,13a-heptamethyl-12-(methylthio)-2,3,4,4a,5,6,6a,6b,7,8,8a,9,11,13,13a, 13b, 14,15b-octadecahydro-1H-chryseno [1,2-f]indazole-4a-carboxylate;

(1S,2R,6aS,6bR,8aR,13 aR,13bR)-benzyl 12-(4-methoxyphenyl)-1,2,6a,6b,9,9,13a-heptamethyl-2,3,4,4a,5,6,6a,6b,7,8,8a,9,11,12,12a,13,13a,13b,14,15b-icosahydro-1H-chryseno[1,2-f]indazole-4a-carboxylate;

(1S,2R,4aS,6aS,6bR,13aR,13bR)-1,2,6a,6b,9,9,13a-heptamethyl-10-(m-tolyl)-2,3,4,4a,5,6,6a,6b,7,8,8a,9,10,13,13a,13b, 14,15b-octadecahydro-1H-chryseno[1,2-f]indazole-4a-carboxylic acid;

(1S,2R,6aS,6bR,8aR,13aR,13bR)-1,2,6a,6b,9,9,13a-heptamethyl-1,2,3,4,4a,5,6,6a,6b,7,8,8a, 9,13,13a, 13b,14,15b-octadecahydropiceno[3,2-c]isoxazole-4a-carboxylic acid; and (1S,2R,6aS,6bR,8aR,13 aR,13bR)-benzyl 11-amino-1,2,6a,6b,9,9,13a-heptamethyl-1,2,3,4,4a, 5,6,6a,6b,7,8,8a,9,13,13a, 13b, 14,15b-octadecahydropiceno[3,2-d] thiazole-4a-carboxylate;

or a stereoisomer, a tautomer, a pharmaceutically acceptable salt or a solvate, a prodrug, an N-oxide, a S-oxide or a carboxylic acid isostere thereof.

20. A pharmaceutical compositions comprising the compound according to claim 1 or a stereoisomer, a tautomer or a pharmaceutically acceptable salt or a pharmaceutically acceptable solvate, a prodrug, an N-oxide, a S-oxide or a carboxylic acid isostere thereof and at least one pharmaceutically acceptable excipient.

21. A method for the treatment of a disease or a disorder mediated by RORγ and/or IL-17 in a subject in need thereof comprising administering to said subject a therapeutically effective amount of one or more compounds according to claim 1 or a stereoisomer, a tautomer, a pharmaceutically acceptable salt or a pharmaceutically acceptable solvate thereof.

22. The method according to claim 21, wherein the said disease or a disorder is selected from the group consisting of autoimmune disease or a disorder, inflammatory disease or a disorder, cancer and metabolic disease or a disorder.

\* \* \* \* \*